United States Patent
Khatri et al.

(10) Patent No.: US 10,533,224 B2
(45) Date of Patent: Jan. 14, 2020

(54) METHODS FOR DIAGNOSIS OF SEPSIS

(71) Applicant: The Board of Trustees of the Leland Stanford Junior University, Stanford, CA (US)

(72) Inventors: Purvesh Khatri, Menlo Park, CA (US); Timothy E. Sweeney, San Francisco, CA (US)

(73) Assignee: THE BOARD OF TRUSTEE OF THE LELAND STANFORD JUNIOR UNIVERSITY, Stanford, CA (US)

( * ) Notice: Subject to any disclaimer, the term of this patent is extended or adjusted under 35 U.S.C. 154(b) by 273 days.

(21) Appl. No.: 15/526,306

(22) PCT Filed: Mar. 12, 2016

(86) PCT No.: PCT/US2016/022233
§ 371 (c)(1),
(2) Date: May 11, 2017

(87) PCT Pub. No.: WO2016/145426
PCT Pub. Date: Sep. 15, 2016

(65) Prior Publication Data
US 2018/0291449 A1 Oct. 11, 2018

Related U.S. Application Data

(60) Provisional application No. 62/132,293, filed on Mar. 12, 2015.

(51) Int. Cl.
| | | |
|---|---|---|
| *C12Q 1/6883* | (2018.01) | |
| *G16B 25/00* | (2019.01) | |
| *G16H 50/20* | (2018.01) | |

(52) U.S. Cl.
CPC .......... *C12Q 1/6883* (2013.01); *G16B 25/00* (2019.02); *G16H 50/20* (2018.01); *C12Q 2600/106* (2013.01); *C12Q 2600/158* (2013.01); *Y02A 90/26* (2018.01)

(58) Field of Classification Search
CPC .............................................. C12Q 2600/158
See application file for complete search history.

(56) References Cited

U.S. PATENT DOCUMENTS

| | | |
|---|---|---|
| 2006/0056948 A1 | 3/2006 | Hossain et al. |
| 2009/0203534 A1 | 8/2009 | Hossain et al. |
| 2014/0141435 A1 | 5/2014 | Garrett et al. |
| 2015/0038351 A1 | 2/2015 | Wyrobek et al. |

FOREIGN PATENT DOCUMENTS

WO   WO 2014/201516 A2   12/2014

OTHER PUBLICATIONS

Wong et al. Identification of pediatric septic shock subclasses based on genome-wide expression profiling. BMC Medicine, vol. 7, 34, 2009, printed as pp. 1-12. (Year: 2009).*
Platform GPL570, Affymetrix Human Genome U133 Plus 2.0 Array, Public on Nov. 7, 2003, printed as pp. 1-3, including pp. 1-6 of Data Table Information. (Year: 2003).*
Hajian-Tilaki. Receiver operating characteristic (ROC) curve analysis for medical diagnostic test evaluation. Caspian Journal of Internal Medicine, vol. 4, No. 2, pp. 627-635, 2013. (Year: 2013).*
Siddiqui et al. Early versus late pre-intensive care unit admission broad spectrum antiboitics for severe sepsis in adults (Review). Cochrante Database of Systematic Reviews, Issue 10, No. CD007081, pp. i and 1-14, 2010. (Year: 2010).*
Kasamatsu et al., "Identification of candidate genes associated with salivary adenoid cystic carcinomas using combined comparative genomic hybridization and oligonucleotide microarray analyses", The International Journal of Biochemistry & Cell Biology, 2005, 37: 1869-1880.
Madsen-Bouterse et al., "The Transcriptome of the Fetal Inflammatory Response Syndrome", Am J Reprod Immunol., 2010, 63(1): 73-92. doi:10.1111/j.1600-0897.2009.00791.x.
Dix, et al., "Biomarker-based classification of bacterial and fungal whole-blood infections in a genome-wide expression study", Frontiers in Microbiology, 2015, 6(171): 1-11.
Maslove, et al., "Gene expression profiling in sepsis: Timing, tissue, and translational considerations", Trends Mol Med., 2014, 20(4): 204-213.

* cited by examiner

*Primary Examiner* — Jennifer Dunston
(74) *Attorney, Agent, or Firm* — James S. Keddie; Bozicevic, Field & Francis LLP

(57) ABSTRACT

Methods for diagnosis of sepsis are disclosed. In particular, the invention relates to the use of biomarkers for aiding diagnosis, prognosis, and treatment of sepsis, and to a panel of biomarkers that can be used to distinguish sepsis from noninfectious sources of inflammation, such as caused by traumatic injury, surgery, autoimmune disease, thrombosis, or systemic inflammatory response syndrome (SIRS).

6 Claims, 54 Drawing Sheets

Specification includes a Sequence Listing.

SEQUENCE LISTING

<160> NUMBER OF SEQ ID NOS: 11

<210> SEQ ID NO 1
<211> LENGTH: 3470
<212> TYPE: DNA
<213> ORGANISM: Homo sapiens

<400> SEQUENCE: 1

```
aaagctctgg gccccaggga ggaggctcag cacagagagt ggaaaacagc agaggtgaca        60
gagcagccgt gctcgaagcg ttcctggagc ccaagctctc ctccacaggt gaagacaggg       120
ccagcaggag acaccatggg gcacctctca gccccacttc acagagtgcg tgtaccctgg       180
caggggcttc tgctcacagc ctcacttcta accttctgga acccgcccac cactgcccag       240
ctcactactg aatccatgcc attcaatgtt gcagagggga aggaggttct tctccttgtc       300
cacaatctgc cccagcaact ttttggctac agctggtaca aaggggaaag agtggatggc       360
aaccgtcaaa ttgtaggata tgcaatagga actcaacaag ctaccccagg gcccgcaaac       420
agcggtcgag agacaatata ccccaatgca tccctgctga tccagaacgt cacccagaat       480
gacacaggat tctacaccct acaagtcata aagtcagatc ttgtgaatga agaagcaact       540
ggacagttcc atgtataccc ggagctgccc aagccctcca tctccagcaa caactccaac       600
cctgtggagg acaaggatgc tgtggccttc acctgtgaac ctgagactca ggacacaacc       660
tacctgtggt ggataaacaa tcagagcctc ccggtcagtc ccaggctgca gctgtccaat       720
ggcaacagga ccctcactct actcagtgtc acaaggaatg acacaggacc ctatgagtgt       780
gaaatacaga cccagtgag tgcgaaccgc agtgacccag tcaccttgaa tgtcacctat       840
ggcccggaca cccccaccat ttcccccttca gacacctatt accgtccagg ggcaaacctc       900
agcctctcct gctatgcagc ctctaaccca cctgcacagt actcctggct tatcaatgga       960
acattccagc aaagcacaca agagctcttt atccctaaca tcactgtgaa taatagtgga      1020
tcctataccc t gccacgccaa taactcagtc actggctgca acaggaccac agtcaagacg      1080
atcatagtca ctgagctaag tccagtagta gcaaagcccc aaatcaaagc cagcaagacc      1140
acagtcacag gagataagga ctctgtgaac ctgacctgct ccacaaatga cactggaatc      1200
tccatccgtt ggttcttcaa aaaccagagt ctccgtcct cggagaggat gaagctgtcc      1260
cagggcaaca ccaccctcag cataaaccct gtcaagaggg aggatgctgg gacgtattgg      1320
tgtgaggtct tcaacccaat cagtaagaac caaagcgacc ccatcatgct gaacgtaaac      1380
tataatgctc taccacaaga aaatggcctc tcacctgggg ccattgctgg cattgtgatt      1440
```

```
ggagtagtgg ccctggttgc tctgatagca gtagccctgg catgttttct gcatttcggg    1500
aagaccggca ggaccactcc aatgacccac ctaacaagat gaatgaagtt acttattcta    1560
ccctgaactt tgaagcccag caacccacac aaccaacttc agcctcccca tccctaacag    1620
ccacagaaat aatttattca gaagtaaaaa agcagtaatg aaacctgtcc tgctcactgc    1680
agtgctgatg tatttcaagt ctctcaccct catcactagg agattccttt cccctgtagg    1740
ggtagagggg tggggacaga aacaactttc tcctactctt ccttcctaat aggcatctcc    1800
aggctgcctg gtcactgccc ctctctcagt gtcaatagat gaaagtacat gggagtctg     1860 taggaaaccc aaccttcttg tcattgaaat ttggcaaagc tgactttggg aaagagggac    1920
cagaacttcc cctcccttcc ccttttccca acctggactt gttttaaact tgcctgttca    1980
gagcactcat tccttcccac ccccagtcct gtcctatcac tctaattcgg atttgccata    2040
gccttgaggt tatgtccttt tccattaagt acatgtgcca ggaaacaaga gagagagaaa    2100
gtaaaggcag taatgccttc tcctatttct ccaaagcctt gtgtgaactc accaaacaca    2160
agaaaatcaa atatataacc aatagtgaaa tgccacacct ttgtccactg tcagggttgt    2220
ctacctgtag gatcagggtc taagcacctt ggtgcttagc tagaatacca cctaatcctt    2280
ctggcaagcc tgtcttcaga gaacccacta gaagcaacta ggaaaatcac ttgccaaaat    2340
ccaaggcaat tcctgatgga aaatgcaaaa gcacatatat gttttaatat ctttatgggc    2400
tctgttcaag gcagtgctga gagggagggg ttatagcttc aggagggaac cagcttctga    2460
taaacacaat ctgctaggaa cttgggaaag gaatcagaga gctgcccttc agcgattatt    2520
taaattattg ttaaagaata cacaatttgg ggtattggga ttttctcct tttctctgag     2580 acattccacc atttaatt ttgtaactgc ttatttatgt gaaagggtt attttactt        2640 agcttagcta tgtcagccaa tccgattgcc ttaggtgaaa gaaaccaccg aaatccctca    2700
ggtcccttgg tcaggagcct ctcaagattt ttttgtcag aggctccaaa tagaaaataa     2760
gaaaaggttt tcttcattca tggctagagc tagatttaac tcagtttcta ggcacctcag    2820
accaatcatc aactaccatt ctattccatg tttgcacctg tgcattttct gtttgccccc    2880
attcactttg tcaggaaacc ttggcctctg ctaaggtgta tttggtcctt gagaagtggg    2940
agcaccctac agggacacta tcactcatgc tggtggcatt gtttacagct agaaagctgc    3000
actggtgcta atgccccttg gggaaatggg gctgtgagga ggaggattat aacttaggcc    3060
tagcctcttt taacagcctc tgaaatttat cttttcttct atggggtcta taaatgtatc    3120
ttataataaa aaggaaggac aggaggaaga caggcaaatg tacttctcac ccagtcttct    3180
acacagatgg aatctctttg gggctaagag aaaggtttta ttctatattg cttacctgat    3240
ctcatgttag gcctaagagg ctttctccag gaggattagc ttggagttct ctatactcag    3300
gtacctcttt cagggttttc taaccctgac acggactgtg catactttcc ctcatccatg    3360
ctgtgctgtg ttatttaatt tttccctggct aagatcatgt ctgaattatg tatgaaaatt    3420
attctatgtt tttataataa aaataatata tcagacatcg aaaaaaaaaa               3470
```

<210> SEQ ID NO 2
<211> LENGTH: 1370
<212> TYPE: DNA
<213> ORGANISM: Homo sapiens

<400> SEQUENCE: 2

```
ctttcaccct gggctgcggc tctgaggctg ccgtggccat ggagctctgg aagctgggct     60
gggggaggaa gcctggtggc tctgacctcc cctggaggcg aaggaggccc agccatgaca    120
```

```
ctcttaacgg atgccacgcc gctggtgaag gagccccatc ccctgcctct ggtcccacgt      180
ccctggttcc tccctagcct ctttgctgcc ttcaatgtgg tgctgctggt cttttcagt      240
ggcctcttct tcgcattccc ttgcaggtgg ctggctcaga acggggagtg ggcctttcct      300
gttatcacag gctccctctt tgtccttacc ttcttcagtc ttgtttcact caacttctca      360
gaccctggca tcttacatca aggctccgct gagcagggcc ccttgacggt gcacgtggtg      420
tgggtgaacc acggggcctt ccgctgcaa tggtgtccaa agtgctgctt ccaccgcccg      480
ccccggactt accactgccc tggtgcaac atctgtgtgg aggactttga ccaccactgc      540
aagtgggtca ataactgcat cggtcaccgc aacttccgct tcttcatgct gcttgtcctg      600
tccctgtgcc tctactcggg cgccatgctg gtcacctgtc tcatcttcct ggtgcgcaca      660
acccacctgc ccttctccac cgacaaggcc atcgccatcg tggtggccgt gtccgccgcg      720
ggcctcctgg tgccgctgtc cctcctgctg ctgatccagg cactgtccgt gagctcggcc      780
gaccgcacct acaagggcaa gtgcagacac cttcagggat acaacccctt cgaccagggc      840
tgtgccagca actggtattt aacaatttgt gcaccactgg acccaagta catggctgaa      900
gctgtccagc tgcagagagt ggtggggcct gactggacat ccatgccgaa tctgcaccct      960
ccaatgtccc cctctgctct caacccccca gccccaacct ctgggtccct acaaagcagg     1020
gaagggaccc ccggggcgtg gtgaggctgc agctctccag gagttccaca cgggcccagt     1080
gctgcccctg ctgctgcagg agcccccagg cgaggttcgg ccttcctctc gccctgtgc      1140
acccggagat gccacagca ccagcacctg agctcacctc cgaacccgcc tcctgaaccc     1200
gcctcctgaa cctgcctcct tacctcccac ttcctgagcc ctgagtggaa gcctttctgt     1260
gccttgccct ttgcccactc ccctggtggg actgccaaga ccctcaatgc ccattaaata     1320
ctcttgcctg cctcttaaaa aaaaaaaaaa aaaaaaaaaa aaaaaaaaa                  1370
```

<210> SEQ ID NO 3
<211> LENGTH: 1476
<212> TYPE: DNA
<213> ORGANISM: Homo sapiens

<400> SEQUENCE: 3

```
caacggggc tggaacccgg cgccgagagt agagaaaagg ggcctctggt gaccgcccct       60
acctggcatc cctctaaccc aggaggagcg tggggaaagg ggctgtgggc ctctcgggga     120
gcgagctgcg ggtagcggcg cactgggtac aggcgcgcgc ttggctgtcg cctctgccgc     180
tgtgtttggg aggactcgaa ctggcgccag gaaatattag gaagctgtga ttttcaaagc     240
taattatgaa aacatttatc attggaatca gtggacatga gccccaggtt aaaacacgct     300
ttcaataaat gactgaatcg agaagtgcct ccctcccgtg tgatctcctc gatgctgcaa     360
aactagatct aaagaggagt aactcagtgc cccttctcct ggacttcaca gtccggtcag     420
aagagacaaa taactggcct gttgtgataa gctacagcag acctcccagc tggccccag      480
gtggagagag atggggaaaa ggaggcatcg cagaggaaat gtgatttcat gtgtgacaaa     540
cagtggcaaa acaacactgg ctaagaattt gcagaaacac ctcccaaatt gcagtgtcat     600
atctcaggat gatttcttca agccagagtc tgagatagag acagataaaa atggattttt     660
gcagtacgat gtgcttgaag cacttaacat ggaaaaaatg atgtcagcca tttcctgctg     720
gatgaaaagc gcaagacact ctgtggtatc aacagaccag gaaagtgctg aggaaattcc     780
cattttaatc atcgaaggtt ttcttctttt taattataag cccccttgaca ctatatggaa     840
```

| | |
|---|---:|
| tagaagctat ttcctgacta ttccatatga agaatgtaaa aggaggagga gtacaagggt | 900 |
| ctatcagcct ccagactctc cgggatactt tgatggccat gtgtggccca tgtatctaaa | 960 |
| gtacagacaa gaaatgcagg acatcacatg gaagttgtg tacctggatg aacaaaatc | 1020 |
| tgaagaggac ctcttttttgc aagtatatga agatctaata caagaactag caaagcaaaa | 1080 |
| gtgtttgcaa gtgacagcat aaagacggaa cacaacaaat ccttcctgaa gtgaattagg | 1140 |
| aaactccaag gagtaattta agaaccttca ccaagataca atgtatactg tggtacaatg | 1200 |
| acagccattg tttcatatgt ttgatttta ttgcacatgg ttttcccaac atgtggaaca | 1260 |
| ataaatatcc atgccaatgg acaggactgt accttagcaa gttgctccct ctccagggag | 1320 |
| cgcatagata cagcagagct cacagtgagt cagaaagtct ccactttctg aacatagctc | 1380 |
| tataacaatg attgtcaaac ttttctaact ggagctcaga gtaagaaata aagattacat | 1440 |
| cacaatccaa aaaaaaaaaa aaaaaaaaaa aaaaaa | 1476 |

<210> SEQ ID NO 4
<211> LENGTH: 2311
<212> TYPE: DNA
<213> ORGANISM: Homo sapiens

<400> SEQUENCE: 4

| | |
|---|---:|
| cagaaggagg aagaagggcc ctgctggtca cacaggaccc agtctgcggt gggggttttc | 60 |
| ccgccaccgc cccgccctcc ctggggcccc cacctcaccc tctcctggca cccttcaccg | 120 |
| tcaacctgtc gggccgggtc tgagcaggtc tggaggtggg cggggagccc tggcctcccc | 180 |
| acctcctccc gtccccaccc tgttcccagc actcaagcct tgccaccgcc gagccgggct | 240 |
| tcctgggtgt ttcaggcaag gaagtctagg tccctggggg gtgaccccca aggaaaaggc | 300 |
| agcctccctg cgcacccggt tgccggagc cctctccagg gccggctggg ctggggttg | 360 |
| ccctggccag caggggcccg ggggcgatgc cacccggtgc cgactgaggc caccgcacca | 420 |
| tggcccgctc gctgacctgg cgctgctgcc cctggtgcct gacggaggat gagaaggccg | 480 |
| ccgcccgggt ggaccaggag atcaacagga tcctcttgga gcagaagaag caggaccgcg | 540 |
| gggagctgaa gctgctgctt ttgggccag gcgagagcgg gaagagcacc ttcatcaagc | 600 |
| agatgcggat catccacggc gccggctact cggaggagga gcgcaagggc ttccggcccc | 660 |
| tggtctacca gaacatcttc gtgtccatgc gggccatgat cgaggccatg gagcggctgc | 720 |
| agattccatt cagcaggccc gagagcaagc accacgctag cctggtcatg agccaggacc | 780 |
| cctataaagt gaccacgttt gagaagcgct acgctgcggc catgcagtgg ctgtggaggg | 840 |
| atgccggcat ccgggcctgc tatgagcgtc ggcgggaatt ccacctgctc gattcagccg | 900 |
| tgtactacct gtcccacctg gagcgcatca ccgaggaggg ctacgtcccc acagctcagg | 960 |
| acgtgctccg cagccgcatg cccaccactg gcatcaacga gtactgcttc tccgtgcaga | 1020 |
| aaaccaacct gcgggatcgt gacgtcgggg gccagaagtc agagcgtaag aaatggatcc | 1080 |
| attgtttcga gaacgtgatc gccctcatct acctggcctc actgagtgaa tacgaccagt | 1140 |
| gcctggagga gaacaaccag gagaaccgca tgaaggagag cctcgcattg tttgggacta | 1200 |
| tcctggaact accctggttc aaaagcacat ccgtcatcct cttctcaac aaaaccgaca | 1260 |
| tcctggagga gaaaatcccc acctcccacc tggctaccta ttttcccagt ttccagggcc | 1320 |
| ctaagcagga tgctgaggca gccaagaggt tcatcctgga catgtacacg aggatgtaca | 1380 |
| ccgggtgcgt ggacgccccc gagggcagca agaagggcgc acgatcccga cgcctcttca | 1440 |
| gccactacac atgtgccaca gacacacaga acatccgcaa ggtcttcaag gacgtgcggg | 1500 |

```
actcggtgct cgcccgctac ctggacgaga tcaacctgct gtgacccagg ccccacctgg      1560
ggcaggcggc accggcgggc gggtggggag tgggagtggc tgcagggacc cctagtgtcc      1620
ctggtctatc tctccagcct cggcccacac gcaagggagt cggggggacgg acggcccgct     1680 gctggccgct ctcttctctg cctctcacca ggacagccgc cccccagggt actcctgccc      1740
ttgcttgact cagtttccct cctttgaaag ggaaggagca aaacggccat tgggatgcc       1800 agggtggatg aaaaggtgaa gaaatcaggg gattgaggac ttgggtgggt gggcatctct      1860
caggagcccc atctccgggc gtgtcacctc ctgggcaggg ttctgggacc ctctgtgggt     1920
gacgcacacc ctgggatggg gctagtagag ccttcaggcg ccttcgggcg tggactctgg      1980
cgcactctag tggacaggag aaggaacgcc ttccaggaac ctgtggacta ggggtgcagg      2040
gacttccctt tgcaagggt aacagaccgc tggaaaacac tgtcactttc agagctcggt       2100
ggctcacagc gtgtcctgcc ccggtttgcg gacgagagaa atcgcggccc acaagcatcc      2160
ccccatccct tgcaggctgg gggctgggca tgctgcatct taacctttg tatttattcc       2220 ctcaccttct gcagggctcc gtgcgggctg aaattaaaga tttcttagag gctgcgtcgc     2280
cagcgtcctg tttaaaaaaa aaaaaaaaaa a                                    2311

<210> SEQ ID NO 5
<211> LENGTH: 953
<212> TYPE: DNA
<213> ORGANISM: Homo sapiens

<400> SEQUENCE: 5
caagagagag agagagcgtg caagccccaa agcgagcgac atgtcccttt ggggagcagt       60
ccctctgcac cccagagtga ggaggacgca ggggtcagag gtggctacag ggcaggcaga     120
ggaggcacct gtaggggtg gtgggctggt ggcccaggag aagtcaggaa gggagcccag      180
ctggtgacaa gagagcccag aggtgcctgg ggctgagtgt gagagcccgg aagatttcag     240
ccatgcctca cagctccgac agcagtgact ccagcttcag ccgctctcct cccctggca     300 aacaggactc atctgatgat gtgagaagag ttcagaggag ggagaaaaat cgtattgccg    360
cccagaagag ccgacagagg cagacacaga aggccgacac cctgcacctg gagagcgaag    420
acctggagaa acagaacgcg gctctacgca aggagatcaa gcagctcaca gaggaactga    480
agtacttcac gtcggtgctg aacagccacg agccctgtg ctcggtgctg gccgccagca     540
cgccctcgcc ccccgaggtg gtgtacagcg cccacgcatt ccaccaacct catgtcagct    600
ccccgcgctt ccagccctga gcttccgatg cggggagagc agagcctcgg gaggggcaca    660
cagactgtgg cagagctgcg cccatcccgc agaggcccct gtccacctgg agacccggag     720
acagaggcct ggacaaggag tgaacacggg aactgtcacg actggaaggg cgtgaggcct     780
cccagcagtg ccgcagcgtt tcgaggggcg tgtgctggac cccaccactg tgggttgcag     840
gcccaatgca gaagagtatt aagaaagatg ctcaagtccc atggcacaga gcaaggcggg    900
cagggaacgg ttatttttct aaataaatgc tttaaaagaa aaaaaaaaa aaa             953

<210> SEQ ID NO 6
<211> LENGTH: 1985
<212> TYPE: DNA
<213> ORGANISM: Homo sapiens

<400> SEQUENCE: 6
actgtggcta agtgtgggga ccagacagga ctcgtggaga catccaggtg ctgaagcctt       60
```

```
cagctactgt ctcagttttt tgaagtttag caatggcgtc tttctctgct gagaccaatt        120
caactgacct actctcacag ccatggaatg agcccccagt aattctctcc atggtcattc        180
tcagccttac ttttttactg ggattgccag gcaatgggct ggtgctgtgg gtggctggcc        240
tgaagatgca gcggacagtg aacacaattt ggttcctcca cctcacctta gcggacctcc        300
tctgctgcct ctccttgccc ttctcgctgg ctcacttggc tctccaggga cagtggccct        360
acggcaggtt cctatgcaag ctcatcccct ccatcattgt cctcaacatg tttgccagtg        420
tcttcctgct tactgccatt agcctggatc gctgtcttgt ggtattcaag ccaatctggt        480
gtcagaatca tcgcaatgta gggatggcct gctctatctg tggatgtatc tgggtggtgg        540
cttttgtgat gtgcattcct gtgttcgtgt accgggaaat cttcactaca gacaaccata        600
atagatgtgg ctacaaattt ggtctctcca gctcattaga ttatccagac ttttatggag        660
atccactaga aaacaggtct cttgaaaaca ttgttcagcc gcctggagaa atgaatgata        720
ggttagatcc ttcctctttc caaacaaatg atcatccttg gacagtcccc actgtcttcc        780
aacctcaaac atttcaaaga ccttctgcag attcactccc taggggttct gctaggttaa        840
caagtcaaaa tctgtattct aatgtatttta aacctgctga tgtggtctca cctaaaatcc        900
ccagtgggtt tcctattgaa gatcacgaaa ccagcccact ggataactct gatgcttttc        960
tctctactca tttaaagctg ttccctagcg cttctagcaa ttccttctac gagtctgagc       1020
taccacaagg tttccaggat tattacaatt taggccaatt cacagatgac gatcaagtgc       1080
caacacccct cgtggcaata acgatcacta ggctagtggt gggtttcctg ctgccctctg       1140
ttatcatgat agcctgttac agcttcattg tcttccgaat gcaaaggggc cgcttcgcca       1200
agtctcagag caaaaccttt cgagtggccg tggtggtggt ggctgtcttt cttgtctgct       1260
ggactccata ccacattttt ggagtcctgt cattgcttac tgacccagaa actcccttgg       1320
ggaaaactct gatgtcctgg gatcatgtat gcattgctct agcatctgcc aatagttgct       1380
ttaatccctt cctttatgcc ctcttgggga aagattttag gaagaaagca aggcagtcca       1440
ttcagggaat tctggaggca gccttcagtg aggagctcac acgttccacc cactgtccct       1500
caaacaatgt catttcagaa agaaatagta caactgtgtg aaaatgtgga gcagccaaca       1560 agcagggget cttaggcaat cacatagtga agtttataa gaggatgaag tgatatggtg       1620
agcagcggac ttcaaaaact gtcaaagaat caatccagcg gttctcaaac ggtacacaga       1680
ctattgacat cagcatcacc tagaaacttg ttagaaatgc aaattctcaa gccgcatccc       1740
agacttgctg aatcggaatc tctgggggtt gggacccagc aagggcactt aacaaaccct       1800
cgtttctgat taatgctaaa tgtaagaatc attgtaaaca ttagttctat ttctatccca       1860
aactaagcta tgtgaaataa gagaagctac tttgttttta aatgatgttg aatatttgtc       1920
gatatttcca tcattaaatt tttccttagc attgtaaaaa aaaaaaaaaa aaaaaaaaa        1980 aaaaa                                                                  1985

<210> SEQ ID NO 7
<211> LENGTH: 4243
<212> TYPE: DNA
<213> ORGANISM: Homo sapiens

<400> SEQUENCE: 7
gaaaaacctt acacggaggg aagcgggatc agcacccaac gctgaacatt tgttttaacc         60
gctgcagaca tctggatccc tcagttactg atagtatagc tattgatagc cagaaggcaa        120
cttcctttat acaaggattc cagtatggtt ttcagtggaa acaaagggct tcacagagaa        180
```

```
gatactctgg atgaatattt tgaatatgat gcagaggagt tcttggtctc tttggccttg    240
ctgataacag aaggacgaac acctgaatgt tctgtaaaag gtcgaacaga aagctttcat    300
tgccctccag cacagtcttg ttacccagta actaccaaac atgaatgtag tgacaagctg    360
gcccagtgcc gccaagccag acgaactagg tctgaggtca cattgttgtg aagaataac    420 cttccaatca tggtggaaat gatgctacta ccagactgct gctacagcga tgatgggccc    480
accacagagg gaattgatct aaatgatcct gcgattaagc aagatgcatt attattagaa    540
agatggatct tggagccagt tcctcgacag aatggtgacc gatttattga agagaagacg    600
cttctgttgg ctgtccgctc atttgtgttt ttttctcagt taagtgcatg ctgagtgtt    660 tctcatggtg ctattccacg aaatattctc tacagaatca gtgctgctga tgtagaccta    720
cagtggaatt tttcacagac tccaattgag catgtgtttc ctgttcccaa tgtttctcac    780
aatgttgcct tgaaagtcag tgttcagtcc ttgcccagac aatctaatta ccagttttg    840 acgtgcagta ttcacactaa tattggcctt tatgagaaaa gaattcaaca acataaactt    900
aaaactcatc agcaccataa cccaaatgaa gcagaacaat gtggtacaaa cagttcacag    960
cgtctgtgta gcaaacaaac ttggaccatg gcacctgaaa gtgtgttaca tgcaaaaagt    1020
ggcccaagtc cagaatatac tgcagctgtc aaaaatatca actatatccc aggcactggc    1080
agtaaatctg accatgggac atctcaagcc aatattctag gctttagtgg tataggtgat    1140
ataaaatcac aagaaacatc agtgagaact ttaaaatcat tttcaatggt tgattccagt    1200
atctctaacc gccagagttt ctggcagtca gctggtgaga ctaacccttt aataggctct    1260
ttaattcagg agcggcaaga aatcattgca agaattgccc aacatttgat tcattgtgat    1320
ccaagcactt cacatgtttc tggacgtcca tttaatactc aagagtctag ttcactccat    1380
tcaaaacttt tccgggtttc acaagaaaat gagaacgtgg gaaaaggtaa agaagctttc    1440
tccatgactt ttggtagtcc agagtttagt tccccagaag acaccaatga ggggaaaatt    1500
cgactaaaac cagaaactcc tcgaagtgaa acttgtattt ctaatgactt ttattctcat    1560
atgcctgttg gagagactaa tcctttgata ggctctttac tccaggagcg gcaagatgtt    1620
attgcaagga ttgctcaaca cttggagcac attgatccaa cagcatcaca tatccccgg    1680 cagtcattca acatgcatga ctccagttcg gttgcatcta agtgtttag gagttcatat    1740 gaagacaaaa atttgttgaa gaaaaataag gatgagtcct cagtttccat ttctcacaca    1800
aaatgttcct tgttaggaga catcagtgat gggaaaaact tagtacctaa taaatgtttt    1860 acttcttta aaaataatag taaagaaaag tgttctttga acatcaaac aagaaatcag    1920 tgtcagaaca atcctagtga aatcatccaa agtacgtatc aggagacaca gaacaaaagt    1980
tctagtttat caacttcctc aatttttgtct cagcacaaag aaaataactt agatttgaca    2040
agcagattca aggagcaaga aatgagcaat ggaattgata acagtattc aaattgcacc    2100 actattgaca aacagatttg tacaaataag tataaggaaa aaataataaa tgagaactat    2160
aatccaaaat tctttggcaa tcttcagtct gatgattcca aaaaaatga ctcaaaaata    2220 aaagttactg tgttggaaat gtctgaatat ttgaacaaat atgaaagcat gtcctcaaat    2280
aaagactcaa aaaggcctaa gacatgtgag caaaatactc aacttaatag catagagaat    2340
tatctcaata agataatga aggtttcaaa tgtaaaaagt cagaccaatt aaaaaatgaa    2400
caagataagc aagaagatcc aactaatgaa aaatcccaaa actattctca gagaagaagt    2460
ataaaagact gtttgtctac atgtgagcaa ccaaaaaata cagaggtatt gaggactaca    2520
```

| | |
|---|---|
| ctgaaacatt caaatgtgtg gcgaaaacat aattttcatt ccttggatgg aacttcaacc | 2580 |
| agagcctttc atcctcaaac tggattgcct cttctttcaa gccctgttcc tcaaagaaaa | 2640 |
| acacaatcag gttgctttga tctggattct tcattactac atctgaaaag cttctcatct | 2700 |
| agaagtcctc gaccatgttt aaacattgaa gatgatccag atattcatga aaaaccattt | 2760 |
| ttgagttcta gtgctccacc tataacaagt cttagtctcc taggaaattt tgaggaatct | 2820 |
| gtcttgaact atcgtttcga tcctctcggc attgttgatg gttttactgc cgaggtaggg | 2880 |
| gcaagtggtg ctttctgccc cacacatttg actcttccag ttgaagtgtc attctacagt | 2940 |
| gtttcagatg acaatgctcc ctctccttat atgggtgtga ttactttaga gtcccttggt | 3000 |
| aaaaggggtt atcgagtacc tccttcagga acaatacaag tgaccttatt taatcctaat | 3060 |
| aagactgtgg tgaagatgtt tgttgtgata tatgatttac gagatatgcc agccaatcat | 3120 |
| cagacattcc tacgacaaag aacttttttct gtacctgtta acaagaagt gaagagaagt | 3180 |
| gttaataaag agaacatccg acacacagaa gaacggttat tacgctacct catacatctg | 3240 |
| aggttccaga gttctaaatc tggaaagatc tacctccata gagacgtacg gctcctgttc | 3300 |
| tctagaaagt caatggaggt tgatagcggt gctgcatatg aactcaaatc ttacactgaa | 3360 |
| tcaccaacaa accctcagtt ttcaccaaga tgttgataag gagtgatgat ttaaagtatt | 3420 |
| tactcagtac ccaagtttgc aagtaaaaat tagcatagaa tggagtgtac caaattaaca | 3480 |
| atcaggagag tggattctct cctgttatcc tggaccagtt tttatgaaag gattcctgaa | 3540 |
| atgaaatcca tatattccat gtagactgga aaaactcatg tcctaatcct ttttgtactg | 3600 |
| ttgaaaccac ttcattggac atgttgcaat agcaaaaccc ccagttagat tagtgtttac | 3660 |
| acattttctc agttatttaa tatttaatgt tttccttaat actcaagtga tgtttgtctc | 3720 |
| tagtgttcta atgtagcaca aatcctatgt aaaatcatac tatgtatttt tgacattaat | 3780 |
| gttgaaatca aatatatgca caagtcttta attttgtgta atgtgttaag tgctgttcat | 3840 |
| ttaagttatt gaaaatgaga ataaaatgtt gagcttcttt aaaagtaaca cactatgcaa | 3900 |
| gcatgtgtac ttttttatatc tctcatgttt agttttttata acaccatatc caggttgcta | 3960 |
| tctcacatag tagtcccttta acatattgta ttagcagtgc aatgtggact aagctgcttc | 4020 |
| actttccctt tgcaagttca gatcatcatg cccattcata gccaggattc cttatcccca | 4080 |
| aaacagttct attttttcctt aatcactact atagagtctt tacattaaat tactgtcgta | 4140 |
| tgctagataa tttttctcaaa ttgttaaaag aatatgtact ttggaaacaa attagtattt | 4200 |
| atattgtaaa tatattcaaa aaaaactaaa aaaaaaaaaa aaa | 4243 |

<210> SEQ ID NO 8
<211> LENGTH: 2805
<212> TYPE: DNA
<213> ORGANISM: Homo sapiens

<400> SEQUENCE: 8

| | |
|---|---|
| ctccttgcac gggccggccc agcttccccg cccctggcgt ccgctccctc ccgctcgcag | 60 |
| cttacttaac ctggcccggg cggcggaggc gctctcactt ccctggagcc gcccgcttgc | 120 |
| ccgtcggtcg ctagctcgct cggtgcgcgt cgtcccgctc catggcgctc ttcgtgcggc | 180 |
| tgctggctct cgccctggct ctggccctgg gcccgccgc gaccctggcg gtcccgcca | 240 |
| agtcgcccta ccagtggtg ctgcagcaca gcaggctccg gggccgccag cacggcccca | 300 |
| acgtgtgtgc tgtgcagaag gttattggca ctaataggaa gtacttcacc aactgcaagc | 360 |
| agtggtacca aggaaaatc tgtggcaaat caacagtcat cagctacgag tgctgtcctg | 420 |

```
gatatgaaaa ggtccctggg gagaagggct gtccagcagc cctaccactc tcaaacctttt    480 acgagaccct gggagtcgtt ggatccacca ccactcagct gtacacggac cgcacggaga    540
agctgaggcc tgagatggag gggcccggca gcttcaccat cttcgcccct agcaacgagg    600
cctgggcctc cttgccagct gaagtgctgg actccctggt cagcaatgtc aacattgagc    660
tgctcaatgc cctccgctac catatggtgg gcaggcgagt cctgactgat gagctgaaac    720
acggcatgac cctcacctct atgtaccaga attccaacat ccagtccac cactatccta     780 atgggattgt aactgtgaac tgtgcccggc tgctgaaagc cgaccaccat gcaaccaacg    840
gggtggtgca cctcatcgat aaggtcatct ccaccatcac caacaacatc cagcagatca    900
ttgagatcga ggaccctttt gagacccttc gggctgctgt ggctgcatca gggctcaaca    960
cgatgcttga aggtaacggc cagtacacgc ttttggcccc gaccaatgag gccttcgaga   1020
agatccctag tgagactttg aaccgtatcc tgggcgaccc agaagccctg agagacctgc   1080
tgaacaacca catcttgaag tcagctatgt gtgctgaagc catcgttgcg gggctgtctg   1140
tagagaccct ggagggcacg acactggagg tgggctgcag cggggacatg ctcactatca   1200 acggaaggc gatcatctcc aataaagaca tcctagccac caacgggtg atccactaca     1260 ttgatgagct actcatccca gactcagcca agacactatt tgaattggct gcagagtctg   1320
atgtgtccac agccattgac cttttcagac aagccggcct cggcaatcat ctctctggaa   1380
gtgagcggtt gaccctcctg gctcccctga attctgtatt caaagatgga acccctccaa   1440
ttgatgccca tacaaggaat ttgcttcgga accacataat taaagaccag ctggcctcta   1500
agtatctgta ccatggacag accctggaaa ctctgggcgg caaaaaactg agagtttttg   1560
tttatcgtaa tagcctctgc attgagaaca gctgcatcgc ggcccacgac aagaggggga   1620
ggtacgggac cctgttcacg atggaccggg tgctgacccc cccaatgggg actgtcatgg   1680
atgtcctgaa gggagacaat cgctttagca tgctggtagc tgccatccag tctgcaggac   1740
tgacggagac cctcaaccgg gaaggagtct acacagtctt tgctcccaca aatgaagcct   1800
tccgagccct gccaccaaga gaacggagca gactcttggg agatgccaag gaacttgcca   1860
acatcctgaa ataccacatt ggtgatgaaa tcctggttag cggaggcatc ggggccctgg   1920
tgcggctaaa gtctctccaa ggtgacaagc tggaagtcag cttgaaaaac aatgtggtga   1980
gtgtcaacaa ggagcctgtt gccgagcctg acatcatggc cacaaatggc gtggtccatg   2040
tcatcaccaa tgttctgcag cctccagcca acagacctca ggaaagaggg gatgaacttg   2100
cagactctgc gcttgagatc ttcaaacaag catcagcgtt ttccagggct tcccagaggt   2160
ctgtgcgact agcccctgtc tatcaaaagt tattagagag gatgaagcat tagcttgaag   2220
cactacagga ggaatgcacc acggcagctc tccgccaatt tctctcagat ttccacagag   2280 actgttttgaa tgttttcaaa accaagtatc acactttaat gtacatgggc cgcaccataa   2340
tgagatgtga gccttgtgca tgtggggag gagagagagaga atgtactttt ttaaatcatg   2400 ttcccctaa acatggctgt taacccactg catgcagaaa cttggatgtc actgcctgac   2460
attcacttcc agagaggacc tatcccaaat gtggaattga ctgcctatgc caagtccctg   2520
gaaaaggagc ttcagtattg tggggctcat aaaacatgaa tcaagcaatc cagcctcatg   2580
ggaagtcctg gcacagtttt tgtaaagccc ttgcacagct ggagaaatgg catcattata   2640
agctatgagt tgaaatgttc tgtcaaatgt gtctcacatc tacacgtggc ttggaggctt   2700
ttatggggcc ctgtccaggt agaaaagaaa tggtatgtag agcttagatt tccctattgt   2760
```

| gacagagcca tggtgtgttt gtaataataa aaccaaagaa acata | 2805 |

<210> SEQ ID NO 9
<211> LENGTH: 2334
<212> TYPE: DNA
<213> ORGANISM: Homo sapiens

<400> SEQUENCE: 9

| gcagagaaaa ctcccgaagc cagggaggtg gcttggaagc gcctcagacc atattgggga | 60 |
| cgtctggcag ccagaggcgc cgaaccccgc cccgcgtgc tctgggcatc ccgggggagc | 120 |
| gccccggcct gcggctgccg ccacagctcc cgagcccggg gccccggctg cccgccacca | 180 |
| ttgaccccg gcccgcagcc cagtgtcctg ctaggcctcc aaccggccgg ggagccacat | 240 |
| ccggcgtgtc ccaccgccg caccacgctc ccgagctccc ccgcggcctg gagtggtgcg | 300 |
| ccccggcccc gccccctgac gccggtgagg gggcgtggcc ccgtcacgtg acggggagtg | 360 |
| acctcgccgc cgggcgccat ggagcttcg gaccggaag tggcgccctg gctcgcggc | 420 |
| ggtgccgcgg ggatggcggg agccggagct ggagccgag ctcgcggcgg agcggcggcg | 480 |
| ggggtcgagg ctcgagctcg cgatccaccg cccgcgcacc gcgcacatcc tcgccaccct | 540 |
| cggcctgcgc ctcagccctc ggcccgcagg atggatggcg gtcaggggg cctgggtct | 600 |
| ggggacaacg ccccgaccac tgaggctctt ttcgtggcac tgggcgcggg cgtgacggcg | 660 |
| ctcagccatc ccctgctcta cgtgaagctg ctcatccagg tgggtcatga gccgatgccc | 720 |
| cccacccttg ggaccaatgt gctggggagg aaggtcctct atctgccgag cttcttcacc | 780 |
| tacgccaagt acatcgtgca agtggatggt aagatagggc tgttccgagg cctgagtccc | 840 |
| cggctgatgt ccaacgccct ctctactgtg actcggggta gcatgaagaa ggttttccct | 900 |
| ccagatgaga ttgagcaggt ttccaacaag gatgatatga agacttccct gaagaaagtt | 960 |
| gtgaaggaga cctcctacga tgatgatg cagtgtgtgt cccgcatgtt ggcccacccc | 1020 |
| ctgcatgtca tctcaatgcg ctgcatggtc cagtttgtgg acggaggc caagtacagt | 1080 |
| ggtgtgctga gctccattgg gaagattttc aaagaggaag gctgctggg attcttcgtt | 1140 |
| ggattaatcc ctcacctcct gggcgatgtg gttttcttgt ggggctgtaa cctgctggcc | 1200 |
| cacttcatca atgcctacct ggtggatgac agcgtgagtg acaccccagg ggggctggga | 1260 |
| aacgaccaga atccaggttc ccagttcagc caggccctgg ccatccggag ctataccaag | 1320 |
| ttcgtgatgg ggattgcagt gagcatgctg acctacccct tcctgctagt tggcgacctc | 1380 |
| atggctgtga caactgcgg gctgcaagct gggctccccc cttactcccc agtgttcaaa | 1440 |
| tcctggattc actgctggaa gtacctgagt gtgcagggcc agctcttccg aggctccagc | 1500 |
| ctgctttttcc gccgggtgtc atcaggatca tgctttgccc tggagtaacc tgaatcatct | 1560 |
| aaaaaacacg gtctcaacct ggccaccgtg ggtgaggcct gaccaccttg ggacacctgc | 1620 |
| aagacgactc caacccaaca acaaccagat gtgctccagc ccagccgggc ttcagttcca | 1680 |
| tatttgccat gtgtctgtcc agatgtgggg ttgagcgggg gtggggctgc acccagtgga | 1740 |
| ttgggtcacc cggcagacct agggaaggtg aggcgaggtg gggagttggc agaatcccca | 1800 |
| tacctcgcag atttgctgag tctgtcttgt gcagagggcc agagaatggc ttatgggggc | 1860 |
| ccaggttgga tggggaaagg ctaatgggt cagaccccac ccgtctacc cctccagtca | 1920 |
| gcccagcgcc catcctgcag ctcagctggg agcatcattc tcctgctttg tacatagggt | 1980 |
| gtggtccct ggcacgtggc caccatcatg tctaggccta tgctaggagg caaatggcca | 2040 |
| ggctctgcct gtgttttct caacactact tttctgatat gagggcagca cctgcctctg | 2100 |

```
aatgggaaat catgcaacta ctcagaatgt gtcctcctca tctaatgctc atctgtttaa    2160
tggtgatgcc tcgcgtacag gatctggtta cctgtgcagt tgtgaatacc cagaggttgg    2220
gcagatcagt gtctctagtc ctacccagtt ttaaagttca tggtaagatt tgacctcatc    2280
tcccgcaaat aaatgtattg gtgatttgga gtttttaaaa aaaaaaaaaa aaaa          2334
```

<210> SEQ ID NO 10
<211> LENGTH: 3950
<212> TYPE: DNA
<213> ORGANISM: Homo sapiens

<400> SEQUENCE: 10

```
atgtcacatc tggtggaccc tacatcagga gacttgccag ttagagacat agatgctata     60
cctctggtgc taccagcctc aaaaggtaag aatatgaaaa ctcaaccacc cttgagcagg    120
atgaaccggg aggaattgga ggacagtttc tttcgacttc gcgaagatca catgttggtg    180
aaggagcttt cttggaagca acaggatgag atcaaaaggc tgaggaccac cttgctgcgg    240
ttgaccgctg ctggccggga cctgcgggtc gcggaggagg cggcgccgct ctcggagacc    300
gcaaggcgcg ggcagaaggc gggatggcgg cagcgcctct ccatgcacca gcgcccccag    360
atgcaccgac tgcaagggca tttccactgc gtcggccctg ccagccccg ccgcgcccag     420 cctcgcgtcc aagtgggaca cagacagctc cacacagccg gtgcaccggt gccggagaaa    480
cccaagaggg ggccaaggga caggctgagc tacacagccc ctccatcgtt taaggagcat    540
gcgacaaatg aaaacagagg tgaagtagcc agtaaaccca gtgaacttgt ttctggttct    600
aacagcataa tttctttcag cagtgtcata agtatggcta acccattgg tctatgcatg     660 cctaacagtg cccacatcat ggccagcaat accatgcaag tggaagagcc acccaagtct    720
cctgagaaaa tgtggcctaa agatgaaaat tttgaacaga gaagctcatt ggagtgtgct    780
cagaaggctg cagagcttcg agcttccatt aaagagaagg tagagctgat tcgacttaag    840
aagctcttac atgaaagaaa tgcttcattg gttatgacaa agcacaatt aacagaagtt     900 caagaggcat acgaaccctt gctccagaag aatcagggaa tcctgagtgc agcccatgag    960
gccctcctca gcaagtgaa tgagctcagg gcagagctga aggaagaaag caagaaggct    1020
gtgagcttga agagccaact ggaagatgtg tctatcttgc agatgactct gaaggagttt    1080
caggagagag ttgaagattt ggaaaaagaa cgaaaattgc tgaatgacaa ttatgacaaa    1140
ctcttagaaa gcatgctgga cagcagtgac agctccagtc agcccactg gagcaacgag     1200 ctcatagcgg aacagctaca gcagcaagtc tctcagctgc aggatcagct ggatgctgag    1260
ctggaggaca agagaaaagt tttacttgag ctgtccaggg agaaagccca aaatgaggat    1320
ctgaagcttg aagtcaccaa catacttcag aagcataaac aggaagtaga gctcctccaa    1380
aatgcagcca caatttccca acctcctgac aggcaatctg aaccagccac tcacccagct    1440
gtattgcaag agaacactca gatcgagcca agtgaaccca aaaccaaga agaaaagaaa    1500 ctgtcccagg tgctaaatga gttgcaagta tcacacgcag agaccacatt ggaactagaa    1560
aagaccaggg acatgcttat tctgcagcgc aaaatcaacg tgtgttatca ggaggaactg    1620
gaggcaatga tgacaaaagc tgacaatgat aatagagatc acaaagaaaa gctggagagg    1680
ttgactcgac tactagacct caagaataac cgtatcaagc agctggaagg tatttttaaga    1740 agccatgacc ttccaacatc tgaacagctc aaagatgttg cttatggcac ccgaccgttg    1800
tcgttatgtt tggaaacact gccagcccat ggagatgagg ataaagtgga tatttctctg    1860
```

```
ctgcatcagg gtgagaatct tttttgaactg cacatccacc aggccttcct gacatctgcc   1920
gccctagctc aggctggaga tacccaacct accactttct gcacctattc cttctatgac   1980
tttgaaaccc actgtacccc attatctgtg gggccacagc ccctctatga cttcacctcc   2040
cagtatgtga tggagacaga ttcgcttttc ttacactacc ttcaagaggc ttcagcccgg   2100
cttgacatac accaggccat ggccagtgaa cacagcactc ttgctgcagg atggatttgc   2160
tttgacaggg tgctagagac tgtggagaaa gtccatggct tggccacact gattggagct   2220
ggtggagaag agttcggggt tctagagtac tggatgaggc tgcgtttccc cataaaaccc   2280
agcctacagg cgtgcaataa acgaaagaaa gcccaggtct acctgtcaac cgatgtgctt   2340
ggaggccgga aggcccagga agaggagttc agatcggagt cttgggaacc tcagaacgag   2400
ctgtggattg aaatcaccaa gtgctgtggc ctccggagtc gatggctggg aactcaaccc   2460
agtccatatg ctgtgtaccg cttcttcacc ttttctgacc atgacactgc catcattcca   2520
gccagtaaca cccctactt tagagaccag gctcgattcc cagtgcttgt gacctctgac   2580
ctggaccatt atctgagacg ggaggccttg tctatacatg tttttgatga tgaagactta   2640
gagcctggct cgtatcttgg ccgagcccga gtgcctttac tgcctcttgc aaaaaatgaa   2700
tctatcaaag gtgattttaa cctcactgac cctgcagaga aacccaacgg atctattcaa   2760
gtgcaactgg attggaagtt tccctacata ccccctgaga gcttcctgaa accagaagct   2820
cagactaagg ggaaggatac caaggacagt tcaaagatct catctgaaga ggaaaaggct   2880
tcatttcctt cccaggatca gatggcatct cctgaggttc ccattgaagc tggccagtat   2940
cgatctaaga gaaaacctcc tcatggggga gaaagaaagg agaaggagca ccaggttgtg   3000
agctactcaa gaagaaaaca tggcaaaaga ataggtgttc aaggaaagaa tagaatggag   3060
tatcttagcc ttaacatctt aaatggaaat acaccagagc aggtgaatta cactgagtgg   3120
aagttctcag agactaacag cttcataggt gatggcttta aaaatcagca cgaggaagag   3180
gaaatgacat tatcccattc agcactgaaa cagaaggaac ctctacatcc tgtaaatgac   3240
aaagaatcct ctgaacaagg ttctgaagtc agtgaagcac aaactaccga cagtgatgat   3300
gtcatagtgc cacccatgtc tcagaaatat cctaaggcag attcagagaa gatgtgcatt   3360
gaaattgtct ccctggcctt ctacccagag gcagaagtga tgtctgatga aacataaaa   3420 caggtgtatg tggagtacaa attctacgac ctacccttgt cggagacaga gactccagtg   3480
tccctaagga agcctagggc aggagaagaa atccactttc actttagcaa ggtaatagac   3540
ctggacccac aggagcagca aggccgaagg cggtttctgt tcgacatgct gaatggacaa   3600
gatcctgatc aaggacattt aaagtttaca gtggtaagtg atcctctgga tgaagaaaag   3660
aaagaatgtg aagaagtggg atatgcatat cttcaactgt ggcagatcct ggagtcagga   3720
agagatattc tagagcaaga gctagacatt gttagccctg aagatctggc taccccaata   3780
ggaaggctga aggtttccct tcaagcagct gctgtcctcc atgctattta caaggagatg   3840
actgaagatt tgttttcatg aaggaacaag tgctattcca atctaaaagt ctctgaggga   3900
accatagtaa aaagtctctt ataaagttag cttgctataa catgaaaaaa   3950
```

<210> SEQ ID NO 11
<211> LENGTH: 4055
<212> TYPE: DNA
<213> ORGANISM: Homo sapiens

<400> SEQUENCE: 11

```
gtcacagaag actacttggg ttcatggtct ctaatatttc aaacaggagc tcccttttagc    60
```

```
gagtccttct tttcctgact gcagctcttt tcattttgcc atcctttcc agctccatga      120 tggttctgca ggtttctgcg gccccccgga cagtggctct gacggcgtta ctgatggtgc      180
tgctcacatc tgtggtccag ggcagggcca ctccagagaa ttacctttc cagggacggc      240 aggaatgcta cgcgtttaat gggacacagc gcttcctgga gagatacatc tacaaccggg      300
aggagttcgc gcgcttcgac agcgacgtgg gggagttccg ggcggtgacg gagctggggc      360
ggcctgctgc ggagtactgg aacagccaga aggacatcct ggaggagaag cgggcagtgc      420
cggacaggat gtgcagacac aactacgagc tgggcgggcc catgaccctg cagcgccgag      480
tccagcctag ggtgaatgtt tccccctcca agaaggggcc cttgcagcac acaaccctgc      540
ttgtctgcca cgtgacggat ttctacccag gcagcattca agtccgatgg ttcctgaatg      600
gacaggagga aacagctggg gtcgtgtcca ccaacctgat ccgtaatgga gactggacct      660
tccagatcct ggtgatgctg gaaatgaccc cccagcaggg agatgtctac acctgccaag      720
tggagcacac cagcctggat agtcctgtca ccgtggagtg gaaggcacag tctgattctg      780
cccggagtaa gacattgacg ggagctgggg gcttcgtgct ggggctcatc atctgtggag      840
tgggcatctt catgcacagg aggagcaaga agttcaacg aggatctgca taaacagggt      900
tcctgagctc actgaaaaga ctattgtgcc ttaggaaaag catttgctgt gtttcgttag      960
catctggctc caggacagac cttcaacttc caaattggat actgctgcca agaagttgct     1020
ctgaagtcag tttctatcat tctgctcttt gattcaaagc actgtttctc tcactgggcc     1080
tccaaccatg ttcccttctt cttagcacca caaataatca aaacccaaca tgactgtttg     1140
ttttccttta aaaatatgca ccaaatcatc tctcatcact tttctctgag ggttttagta     1200
gacagtagga gttaataaag aagttcattt tggtttaaac ataggaaaga agagaaccat     1260
gaaaatgggg atatgttaac tattgtataa tggggcctgt tacacatgac actcttctga     1320
attgactgta tttcagtgag ctgccccaa atcaagttta gtgccctcat ccatttatgt     1380
ctcagaccac tattcttaac tattcaatgg tgagcagact gcaaatctgc ctgataggac     1440
ccatattccc acagcactaa ttcaacatat accttactga gagcatgttt tatcattacc     1500
attaagaagt taaatgaaca tcagaattta aaatcataaa tataatctaa tacactttaa     1560
ccatttcttt tgtgtgccat cacaaatact ccttaaccaa atacggcttg gacttttgaa     1620
tgcatccaat agacgtcatt tgtcgtctaa gtctgcattc atccaccagc ctaggcctcc     1680
tgtcttaatt ttcatacaga cagaaatgac tccccactgg ggaaagagca agcaataca      1740 tgtagcactc ttttcaaac actggtcttt ttttttttct taacaatcca acattgttat     1800
gtgttttgcg tctcatattg acaccttttg gtcaaggtag aggacatgtt tgttgtaagc     1860 tttcttttc gtgtagagga tggattcttc actcctgata cacacaatca gtgcacagca     1920
gctctcttat acatccagtt gatgccttca gtctccctgg cttcttacaa gcatcttctg     1980
ggccttgtgt gtccctgggc acctgtccct ggtcaattcc cgaaagctac tgtgctcctc     2040
ttgcccatct ccccttgcaa ataatatctt ccatcggggg accggcttcc tccaatttca     2100
ggagaggtgg ggctgaaggc acagacttgg gcgtcactgg cacagatata agtaaataca     2160
gctggagtct gcagagaggc tggactgagt caggagtcga ggaaagagaa gccacacaca     2220
aggacaacca atcatgtttc tcataatctt cttaacctag ggaataggac acaatcattt     2280
tttcttttta aaacatcttt atccctgatc agcctcattt cctcaaaaac tataaaggaa     2340
aatgctgctg acttgttttt gcgtagtaat ttcagctgtc acataataag ctaaggaaga     2400
```

```
cagtatatag taaataagga ccctttatct gtcttatttt cccttttggc ttcacaggaa    2460
acttgtgaga aacctatgca gcataaaatt aatatgattt caatccaggg attcaacgat    2520
ggaaggaggt catgagaata gcagaaagtc ttcaaatcga gatcattatg aaatcctcag    2580
acccagagca cataaatcct accctcagag tcactgagca gttaacatta caaattacaa    2640
accatatcca gtcagagtca ttctctttcc tgcttgtctc ctgtactcat gttacaggtt    2700
agggcagtac cccgagtgga gtgaacaatc tctggactaa cacttgtcag gatcagaagc    2760
tgaggtatct gcacccacat tacaggaaca ggatatgtgc tcctagggaa ctgagggtgt    2820
caggagatga ggaatgtccc tggagtcaca gaaagaaggt atcagatgtg tctcactctg    2880
acatatgcag gtgtttatga aactctggga tttctaagga aggatgcagt gcagagacag    2940
gtcccagagg agacaagagc tgagagacca tccaaactgg gaccaccttg tcactagact    3000
tcaaattttc aatattgata gagtgttttc taagagtcag gcccttcgt gagtgctatg     3060 tgcagcagga tcaaaggcag ccaggaggta gaggagtctt gaggtacatc agtcattgga    3120
gttgaagagc agagattcaa aggaaagttg gaactggagc tttaaaggag atgtgaagtg    3180
ggtgactcaa cctctgactc agaaaaattg atacctgcag aagaaaaaac ccggcgggct    3240
taggactccc agctgagtgt tgtatcctcc atccctttcc acctggtccc ttcattttct    3300 accctcaca gttccctaac gagaaggtgg tccacccaac agacaacact gcctcagatg     3360
gttatcaagg ggtaccctaa gaagaaatca tctcaccctc tctttgtccc catttgtcaa    3420
gtagcagtga ggccgagcca ggggatggtg aaagtggaag gaggtgggag ttgggcatcg    3480
ggtgtgaaga tgctcttgaa aggggtttta ataaccactt gctaccaggc cagtgaacac    3540
ttaccatagt tgatgccttt tgagcatgtt gcattgtaaa ctgtccctga aattactgtg    3600
cacttggctt atgggatgaa acatcctcct agttcttttg tctctcagct tctctgaagt    3660
ctcattgagc accttctctt caatttcttt tacacagtaa gaataggatc agctgtgcta    3720
aactaacaaa tacccagata tccaggtttg gctcatgtta cacgtccaaa gtaagtcatg    3780
caggaagctc tgctcatcat cgtactcagg aagtcaggct gacagtcttt ctcctgcaca    3840
tctgctccca gaacctcccc agcagaatga agggaaccta agaatttatt cactggcttt    3900
taatgatccc tcctagaaag aacacacttc tcgcatttca tttccaatg taaatcatat     3960 ggctgcaact aacttcaaat aagtgggaat acttgaaggt ggaaaacatt taagaagtac    4020
acactaaata aataataaaa tacttctaca agaga                                4055
```

METHODS FOR DIAGNOSIS OF SEPSIS

STATEMENT REGARDING FEDERALLY SPONSORED RESEARCH OR DEVELOPMENT

This invention was made with Government support under contracts AI057229, AI109662, and LM007033 awarded by the National Institutes of Health. The Government has certain rights in the invention.

SEQUENCE LISTING

The sequencing listing entitled STAN-1391 SEQ-LIST-.txt, created on May 11, 2017 of size 38 KB is hereby incorporated by reference.

TECHNICAL FIELD

The present invention pertains generally to methods for diagnosis of sepsis. In particular, the invention relates to the use of biomarkers for aiding diagnosis, prognosis, and treatment of sepsis, and more specifically to biomarkers that can be used to distinguish sepsis from noninfectious sources of inflammation, such as caused by traumatic injury, surgery, autoimmune disease, thrombosis, or systemic inflammatory response syndrome (SIRS).

BACKGROUND

Sepsis, a syndrome of systemic inflammation in response to infection, kills approximately 750,000 people in the United States every year (Angus et al. (2001) Crit Care Med 29:1303-1310). It is also the single most expensive condition treated in the US, costing the healthcare system more than $24 billion annually (Lagu et al. (2012) Crit Care Med 40:754-761); Torio and Andrews (2013) National Inpatient Hospital Costs: The Most Expensive Conditions by Payer, 2011 (Statistical Brief #160, Agency for Healthcare Research and Quality, Rockville, Md., August 2013). Prompt diagnosis and treatment of sepsis is crucial to reducing mortality, with every hour of delay increasing mortality risk (Gaieski et al. (2010) Crit Care Med 38:1045-1053; Ferrer et al. (2014) Crit Care Med 42:1749-1755). Sepsis is defined by the presence of systemic inflammatory response syndrome (SIRS), in addition to a known or suspected source of infection (Dellinger et al. (2013) Intensive Care Med 39:165-228). However, SIRS is not specific for sepsis, as sterile inflammation can arise as a nonspecific response to trauma, surgery, thrombosis, and other noninfectious insults. Thus, sepsis can be difficult to distinguish clinically from systemic inflammation caused by non-infectious sources, such as tissue trauma (Coburn et al. JAMA (2012) 308:502-511). There is no 'gold standard' blood test for distinguishing patients with infections at time of diagnosis, before results become available from standard microbiological cultures. One of the most common biomarkers of infection, procalcitonin, has a summary area under the receiver operating characteristic curve (AUC) of 0.78 (range 0.66-0.90) (Tang et al. (2007) Lancet Infect Dis 7:210-217; Uzzan et al. (2006) Crit Care Med 34:1996-2003; Cheval et al. (2000) Intensive Care Med 26 Suppl 2:S153-158; Ugarte et al. (1999) Crit Care Med 27:498-504). Several groups have evaluated whether cytokine or gene expression arrays can accurately diagnose sepsis; however, due to the highly variable nature of host response and human genetics, no robust diagnostic signature has been found (Cobb et al. (2009) Ann Surg 250:531-539; Xiao et al. (2011) J Exp Med 208:2581-2590; Pankla et al. (2009) Genome Biol 10:R127; Tang et al. (2009) Crit Care Med 37:882-888; Wong (2012) Crit Care 16:204; Johnson et al. (2007) Ann Surg 245:611-621). Indeed, "finding the 'perfect' sepsis marker has been one of the most elusive dreams in modern medicine" (Vega et al. (2009) Crit Care Med 37:1806-1807).

Both infections and tissue trauma activate many of the same innate immune receptor families, such as the Toll-like receptors and NOD-like receptors, and consequently, activate largely overlapping transcriptional pathways. Thus, distinguishing conserved downstream effects attributable solely to infections has been exceedingly difficult. Recent work has shown that there are pattern recognition receptors potentially specific to pathogen response, such as the c-type lectin, CEACAM, and siglec receptor families (Geijtenbeek et al. (2009) Nat Rev Immunol 9:465-479; Crocker (2007) Nat Rev Immunol 7:255-266; Kuespert et al. (2006) Curr Opin Cell Biol 18:565-571). Hence, it may be possible that an infection-specific immune response could be differentiated from sterile inflammation.

The ongoing search for new therapies for sepsis, and for new prognostic and diagnostic biomarkers, has generated several dozen microarray-based genome-wide expression studies over the past decade, variously focusing on diagnosis, prognosis, pathogen response, and underlying sepsis pathophysiology (Johnson et al., supra; Maslove et al. (2014) Trends Mol Med. 20(4):204-213). Despite tremendous gains in the understanding of gene expression in sepsis, few insights have translated to improvements in clinical practice. Importantly, many of these studies have been deposited into public repositories such as the NIH Gene Expression Omnibus (GEO) and ArrayExpress, and thus there is now a wealth of publically available data on sepsis. In particular, there are several studies comparing patients with sepsis to patients with non-infectious inflammation (such as SIRS) that occurs after major surgery, traumatic injury, or in non-sepsis-related ICU admission (thrombosis, respiratory failure, etc.).

One dataset in particular, the Inflammation and Host Response to Injury Program (Glue Grant) (Cobb et al. (2005) Proc Natl Acad Sci USA 102:4801-4806), has yielded several important findings about the effects of time on gene expression after trauma and in sepsis. One part of the Glue Grant longitudinally examined gene expression in patients after severe traumatic injuries. Several groups have examined these data with respect to time; notable findings are that (1) more than 80% of expressed genes show differential expression after traumatic injury (Xiao et al., supra), (2) different clusters of genes recover over markedly different time periods (Seok et al. (2013) Proc Natl Acad Sci USA 110:3507-3512), (3) differing scenarios of inflammation such as trauma, burns, and endotoxicosis exhibit similar gene expression changes (Seok et al., supra), and (4) the extent to which post-trauma gene expression profiles differ from those of healthy patients, and their degree of gene expression recovery over time, are correlated with clinical outcomes (Desai et al. (2011) PLoS Med 8:e1001093; Warren et al. (2009) Mol Med 15:220-227). There is thus growing understanding of the importance of the changes that underlie recovery from trauma, and their impact on specific clinical outcomes.

There remains a need for sensitive and specific diagnostic tests for sepsis that can distinguish sepsis from noninfectious sources of inflammation, such as caused by traumatic injury and SIRS.

SUMMARY

The invention relates to the use of biomarkers for diagnosis of sepsis. In particular, the inventors have discovered biomarkers that can be used to diagnose sepsis and to distinguish sepsis from noninfectious sources of systemic inflammation, such as caused by traumatic injury, surgery, autoimmune disease, thrombosis, or systemic inflammatory response syndrome (SIRS). These biomarkers can be used alone or in combination with one or more additional biomarkers or relevant clinical parameters in prognosis, diagnosis, or monitoring treatment of sepsis.

Biomarkers that can be used in the practice of the invention include polynucleotides comprising nucleotide sequences from genes or RNA transcripts of genes, including but not limited to, CEACAM1, ZDHHC19, C9orf95, GNA15, BATF, C3AR1, KIAA1370, TGFBI, MTCH1, RPGRIP1, and HLA-DPB1.

In certain embodiments, a panel of biomarkers is used for diagnosis of sepsis. Biomarker panels of any size can be used in the practice of the invention. Biomarker panels for diagnosing sepsis typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In one embodiment, the biomarker panel comprises a plurality of biomarkers for diagnosing sepsis, wherein the plurality of biomarkers comprises one or more polynucleotides comprising a nucleotide sequence from a gene or an RNA transcript of a gene selected from the group consisting of CEACAM1, ZDHHC19, C9orf95, GNA15, BATF, C3AR1, KIAA1370, TGFBI, MTCH1, RPGRIP1, and HLA-DPB1. In certain embodiments, the biomarker panel comprises at least 11 biomarkers. In one embodiment the biomarker panel comprises a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide.

In one aspect, the invention includes a method for diagnosing sepsis in a subject. The method comprises a) measuring the level of a plurality of biomarkers in a biological sample derived from the subject; and b) analyzing the levels of the biomarkers in conjunction with respective reference value ranges for the plurality of biomarkers, wherein differential expression of one or more biomarkers in the biological sample compared to reference value ranges of the biomarkers for a non-infected control subject indicate that the subject has sepsis. The reference value ranges can represent the levels of one or more biomarkers found in one or more samples of one or more subjects without sepsis (e.g., healthy subject or non-infected subject). Alternatively, the reference values can represent the levels of one or more biomarkers found in one or more samples of one or more subjects with sepsis. In certain embodiments, the levels of the biomarkers are compared to time-matched reference values ranges for non-infected or infected/septic subjects.

In certain embodiments, the invention includes a method for diagnosing sepsis in a subject using a biomarker panel described herein. The method comprises: a) collecting a biological sample from the subject; b) measuring each biomarker of the biomarker panel in the biological sample; and c) comparing the measured values of each biomarker with respective reference value ranges for the biomarkers, wherein differential expression of the biomarkers of the biomarker panel in the biological sample compared to reference values of the biomarkers for a control subject indicate that the subject has sepsis.

In one embodiment, the invention includes a method for diagnosing sepsis in a subject, the method comprising: a) collecting a biological sample from the subject; b) measuring levels of expression of CEACAM1, ZDHHC19, C9orf95, GNA15, BATF, C3AR1, KIAA1370, TGFBI, MTCH1, RPGRIP1, and HLA-DPB1 biomarkers in the biological sample; and c) analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the subject has sepsis.

In another embodiment, the invention includes a method for diagnosing sepsis in a subject comprising determining a sepsis score for the subject based on the levels of the biomarkers according to the following formula:

$$\sqrt[6]{(CEACAM1 * ZDHHC19 * C9orf95 * GNA15 * BATF * C3AR1)} - 5/6 \sqrt[5]{(KIAA1370 * TGFBI * MTCH1 * RPGRIP1 * HLA - DPB1)},$$

wherein a higher sepsis score for the subject compared to reference value ranges for a non-infected control subject indicates that the subject has sepsis.

Methods of the invention, as described herein, can be used to distinguish a diagnosis of sepsis for a subject from noninfectious sources of inflammation, such as caused by traumatic injury, surgery, autoimmune disease, thrombosis, or systemic inflammatory response syndrome (SIRS).

The biological sample may comprise, for example, whole blood, buffy coat, plasma, serum, peripheral blood mononucleated cells (PBMCS), band cells, neutrophils, monocytes, or T cells.

Biomarker polynucleotides (e.g., coding transcripts) can be detected, for example, by microarray analysis, polymerase chain reaction (PCR), reverse transcriptase polymerase chain reaction (RT-PCR), Northern blot, or serial analysis of gene expression (SAGE).

In another aspect, the invention includes a method of determining an infection Z-score for a subject suspected of having sepsis, the method comprising: a) collecting a biological sample from the subject; b) measuring the levels of a plurality of sepsis biomarkers in the biological sample; and c) determining the infection Z-score for the biomarkers by subtracting the geometric mean of the expression levels of all biomarkers that are underexpressed compared to control reference values for the biomarkers from the geometric mean of the expression levels of all biomarkers that are overexpressed compared to control reference values for the biomarkers, and multiplying the difference by the ratio of the number of biomarkers that are overexpressed to the number of biomarkers that are underexpressed compared to control reference values for the biomarkers.

In certain embodiments, the infection Z-score is calculated from the expression levels of a plurality of biomarkers comprising one or more polynucleotides comprising a nucleotide sequence from a gene or an RNA transcript of a gene selected from the group consisting of CEACAM1, ZDHHC19, C9orf95, GNA15, BATF, C3AR1, KIAA1370, TGFBI, MTCH1, RPGRIP1, and HLA-DPB1. In one embodiment, the plurality of biomarkers comprises a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide.

In another aspect, the invention includes a method of treating a subject having sepsis, the method comprising: a) diagnosing the subject with sepsis according to a method described herein; and b) administering a therapeutically effective amount of broad spectrum antibiotics to the subject if the subject has a positive sepsis diagnosis.

In another aspect, the invention includes a method of treating a subject suspected of having sepsis, the method comprising: a) receiving information regarding the diagnosis of the subject according to a method described herein; and b) administering a therapeutically effective amount of broad spectrum antibiotics to the subject if the patient has a positive sepsis diagnosis.

In certain embodiments, subject data is analyzed by one or more methods including, but not limited to, multivariate linear discriminant analysis (LDA), receiver operating characteristic (ROC) analysis, principal component analysis (PCA), ensemble data mining methods, cell specific significance analysis of microarrays (csSAM), and multi-dimensional protein identification technology (MUDPIT) analysis.

In another embodiment, the invention includes a method for evaluating the effect of an agent for treating sepsis in a subject using a biomarker panel described herein, the method comprising: analyzing the measured value of each biomarker of the biomarker panel in samples derived from the subject before and after the subject is treated with the agent in conjunction with respective reference value ranges for each biomarker.

In another embodiment, the invention includes a method for monitoring the efficacy of a therapy for treating sepsis in a subject using a biomarker panel described herein, the method comprising: analyzing the measured value of each biomarker of the biomarker panel in samples derived from the subject before and after the subject undergoes said therapy, in conjunction with respective reference value ranges for each biomarker.

In another embodiment, the invention includes a method for monitoring the efficacy of a therapy for treating sepsis in a subject, the method comprising: measuring levels of expression of CEACAM1, ZDHHC19, C9orf95, GNA15, BATF, C3AR1, KIAA1370, TGFBI, MTCH1, RPGRIP1, and HLA-DPB1 biomarkers in a first sample derived from the subject before the subject undergoes the therapy and a second sample derived from the subject after the subject undergoes the therapy, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers in the second sample compared to the levels of expression of the biomarkers in the first sample indicate that the subject is worsening, and decreased levels of expression of the CEACAM1, ZDHHC19, C9orf95, GNA15, BATF, and C3AR1 biomarkers and increased levels of expression of the KIAA1370, TGFBI, MTCH1, RPGRIP1, and HLA-DPB1 biomarkers in the second sample compared to the levels of expression of the biomarkers in the first sample indicate that the subject is improving.

In another aspect, the invention includes a kit for diagnosing sepsis in a subject. The kit may include a container for holding a biological sample isolated from a human subject suspected of having sepsis, at least one agent that specifically detects a sepsis biomarker; and printed instructions for reacting the agent with the biological sample or a portion of the biological sample to detect the presence or amount of at least one sepsis biomarker in the biological sample. The agents may be packaged in separate containers. The kit may further comprise one or more control reference samples and reagents for performing PCR or microarray analysis for detection of biomarkers as described herein.

In certain embodiments, the kit includes agents for detecting polynucleotides of a biomarker panel comprising a plurality of biomarkers for diagnosing sepsis, wherein one or more biomarkers are selected from the group consisting of a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide. In one embodiment, the kit includes agents for detecting biomarkers of a biomarker panel comprising a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide. Furthermore, the kit may include agents for detecting more than one biomarker panel, such as two or three biomarker panels, which can be used alone or together in any combination, and/or in combination with clinical parameters for diagnosis of sepsis.

In certain embodiments, the kit comprises a microarray for analysis of a plurality of biomarker polynucleotides. In one embodiment, the kit comprises a microarray comprising an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

In another aspect, the invention includes an assay comprising: a) measuring at least one biomarker in a biological sample collected from a subject suspected of having sepsis; and b) comparing the measured value of the at least one biomarker in the biological sample with reference values for the biomarker for a control subject, wherein differential expression of the at least one biomarker in the biological sample compared to the reference values indicate that the subject has sepsis. The biological sample may comprise, for example, whole blood, buffy coat, plasma, serum, peripheral blood mononucleated cells (PBMCS), band cells, neutrophils, monocytes, or T cells. In one embodiment, the assay further comprises determining an infection Z-score for the subject.

In one embodiment, the invention includes an assay comprising: a) measuring each biomarker of a biomarker panel, described herein, in a biological sample collected from a subject suspected of having sepsis; and b) comparing the measured value of each biomarker of the biomarker panel in the biological sample with reference values for each biomarker for a control subject, wherein differential expression of the biomarkers in the biological sample compared to the reference values indicate that the subject has sepsis. The biological sample may comprise, for example, whole blood, buffy coat, plasma, serum, peripheral blood mononucleated cells (PBMCS), band cells, neutrophils, monocytes, or T cells. The assay may further comprise determining an infection Z-score for the subject.

In other embodiments, measuring at least one biomarker comprises performing microarray analysis, polymerase chain reaction (PCR), reverse transcriptase polymerase chain reaction (RT-PCR), a Northern blot, or a serial analysis of gene expression (SAGE). In one embodiment, microarray analysis is performed with a microarray comprising an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

In another aspect, the invention includes a diagnostic system comprising a storage component (i.e., memory) for storing data, wherein the storage component has instructions for determining the diagnosis of the subject stored therein; a computer processor for processing data, wherein the computer processor is coupled to the storage component and configured to execute the instructions stored in the storage component in order to receive patient data and analyze patient data according to an algorithm; and a display component for displaying information regarding the diagnosis of the patient. The storage component may include instructions for calculating an infection Z-score or sepsis score, as described herein (see Examples 1 and 2). Additionally, the storage component may further include instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis.

In certain embodiments, the invention includes a computer implemented method for diagnosing a patient suspected of having sepsis, the computer performing steps comprising: a) receiving inputted patient data comprising values for the level of a plurality of sepsis biomarkers in a biological sample from the patient; b) analyzing the level of a plurality of sepsis biomarkers and comparing with respective reference value ranges for the sepsis biomarkers; c) calculating an infection Z-score or sepsis score for the patient based on the levels of the sepsis biomarkers; d) calculating the likelihood that the patient has sepsis based on the value of the infection Z-score; and e) displaying information regarding the diagnosis of the patient.

In certain embodiments, the inputted patient data comprises values for the levels of at least 11 sepsis biomarkers in a biological sample from the patient. For example, the inputted patient data may comprises values for the levels of a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide.

In another embodiment, the invention includes a computer implemented method for diagnosing a patient suspected of having sepsis, the computer performing steps comprising: a) receiving inputted patient data comprising values for levels of expression of CEACAM1, ZDHHC19, C9orf95, GNA15, BATF, C3AR1, KIAA1370, TGFBI, MTCH1, RPGRIP1, and HLA-DPB1 biomarkers in a biological sample from the patient; b) analyzing the level of each biomarker and comparing with respective reference value ranges for each biomarker; c) calculating a sepsis score for the patient based on the levels of expression of the biomarkers according to the following formula:

$$\sqrt[6]{(CEACAM1 * ZDHHC19 * C9orf95 * GNA15 * BATF * C3AR1)} - 5/6 \sqrt[5]{(KIAA1370 * TGFBI * MTCH1 * RPGRIP1 * HLA - DPB1)};$$

d) calculating the likelihood that the patient has sepsis based on the value of the sepsis score, wherein a higher sepsis score for the patient compared to reference value ranges for a non-infected control subject indicates that the patient has sepsis; and e) displaying information regarding the diagnosis of the patient.

These and other embodiments of the subject invention will readily occur to those of skill in the art in view of the disclosure herein.

BRIEF DESCRIPTION OF THE FIGURES

FIG. 1A shows that sterile SIRS/trauma and sepsis patients appear to be largely separable in the transcriptomic space, with only a minimal non-separable set. FIG. 1B shows the same labelled PCA with labels updated to reflect patients in recovery from non-infectious SIRS/trauma, and patients with hospital-acquired sepsis; the 'late' group (>48 hours after hospital admission) is much harder to separate. N=1094 combined from 15 studies.

FIG. 3A shows ROC curves separating sterile SIRS/ICU/trauma patients from those with sepsis in the discovery datasets. FIG. 3B shows ROC curves separating trauma patients with infections from time-matched trauma patients without infection in the Glue Grant neutrophil validation datasets. Glue Grant (FIG. 3C) buffy coat discovery and (FIG. 3D) neutrophil validation samples, after >1 day since injury, show average infection Z-scores for non-infected patients versus patients within +/−24 hours of diagnosis. In both cases there is a significant effect due to both time and infection status. Boxplots of infection Z-score by time since injury are shown for (FIG. 3E) buffy coat discovery and (FIG. 3F) neutrophil validation samples: patients never infected are compared to patients >5 days prior to infection, 5-to-1 days prior to infection, +/−1 day of diagnosis (cases), and 2-to-5 days after infection diagnosis. JT trend test was significant (p<0.01) for an increasing trend from never infected to +/−1 day of infection for each time point after admission.

FIG. 4D shows ROC curves comparing patients within +/−1 day of diagnosis (dark gray points in FIGS. 4A-4C) with time-matched non-infected Glue Grant patients. See Table 5 for further dataset details.

FIG. 5A shows infection Z-scores for all n=446 patients, which were combined in a single violin plot; error bars show middle quartiles. P-values calculated with Wilcoxon rank-sum test. FIG. 5B shows separate ROC curves for each of the 8 datasets discriminating sepsis patients from healthy controls. Mean ROC AUC=0.98. See Table 6 for further dataset details.

FIG. 6B also shows a boxplot of the distributions of Z-scores.

FIG. 7A shows that healthy patients, SIRS/Trauma patients and sepsis patients appear to be largely separable in the transcriptomic space, with only a minimal non-separable set. FIG. 7B shows the same labelled PCA with labels updated to reflect patients in recovery from non-infectious SIRS/Trauma, and patients with hospital-acquired sepsis; the 'late' group (>48 hours after hospital admission) is much harder to separate. N=1316 combined from 15 studies.

FIGS. 9E-9I show violin plots for the datasets included in the discovery multi-cohort analysis for Glue Grant Buffy Coat cohorts, comparing non-infected trauma patients to sepsis patients at matched time points, including [1,3) (FIG. 9E), [3,6) (FIG. 9F), [6,10) (FIG. 9G), [10,18) (FIG. 9H), and [18,24) (FIG. 9I). Error bars show middle quartiles. P-values are computed using Wilcoxon rank-sum test.

FIG. 10A shows ROC curves for each of the four sampled time bins. FIG. 10B shows boxplots of infection Z-score by time since injury. Patients never infected are compared to patients >5 days prior to infection, 5-to-1 days prior to infection, within +/−1 day of diagnosis (cases), and 2-to-5 days post infection.

FIG. 11A shows ROC curves for each of the four sampled time bins. FIG. 11B shows boxplots of infection Z-score by time since injury. Patients never infected are compared to patients >5 days prior to infection, 5-to-1 days prior to infection, within +/−1 day of diagnosis (cases), and 2-to-5 days post infection.

FIG. 12A shows logistic regression models for Glue Grant patients with both SIRS data and microarray data available. SIRS criteria are represented as binary variables. The first model shows SIRS criteria in combination; the second model adds the infection Z-score. Significance codes: p<0.001 '*'; 0.01 ''; 0.05 '*'. FIG. 12B shows boxplots of predicted log odds of infection for patients as output by the logistic regression models in FIG. 12A.

FIG. 14A shows violin plots; error bars show middle quartiles. Patients with autoimmune inflammation vs. those with sepsis tested with Wilcoxon rank-sum test. FIG. 14B shows a ROC plot of autoimmune patients or healthy controls versus septic patients.

FIG. 18A shows the 11-gene score. FIG. 18B shows the FAIM3:PLAC8 ratio. FIG. 18C shows the Septicyte Lab.

FIG. 19A shows the 11-gene score. FIG. 19B shows the FAIM3:PLAC8 ratio. FIG. 19C shows the Septicyte Lab.

DETAILED DESCRIPTION

Figure 1A:
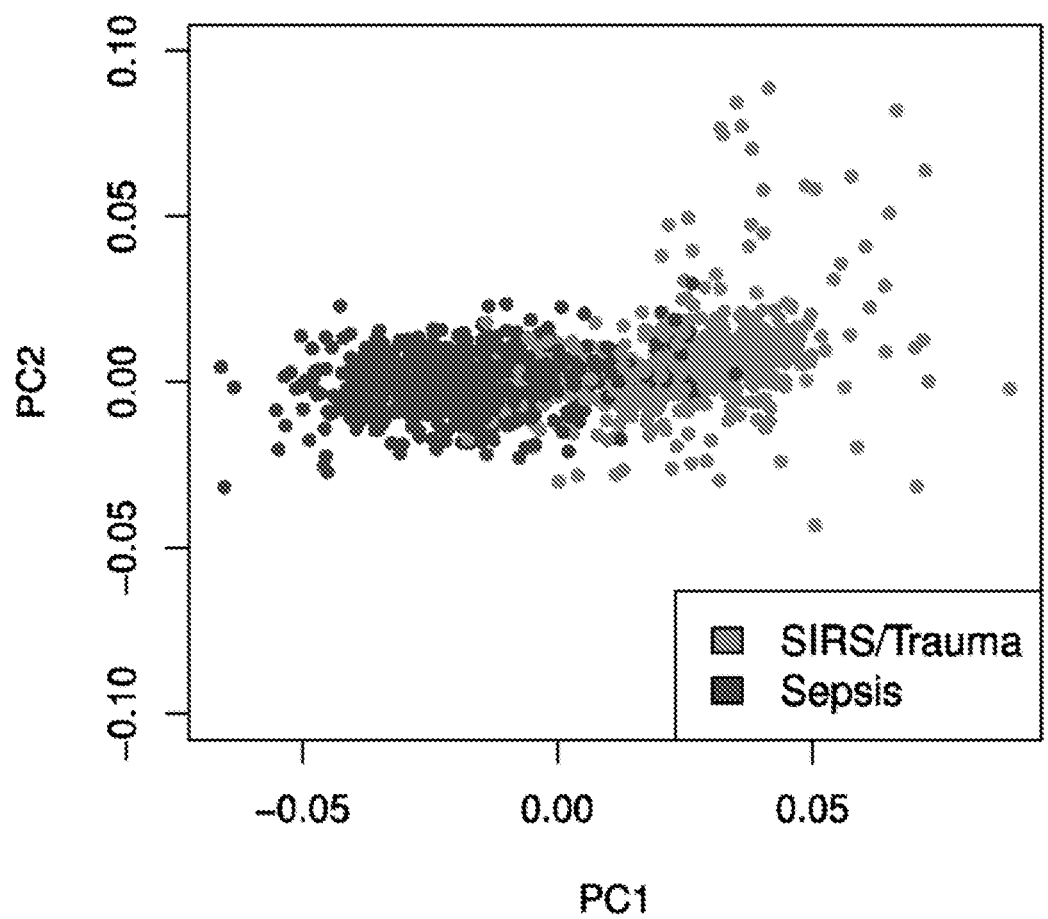
FIGS. 1A and 1B show a labelled principal components analysis (PCA) comparing sterile SIRS/trauma patients versus sepsis patients.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., J. R. Brown *Sepsis: Symptoms, Diagnosis and Treatment* (Public Health in the 21st Century Series, Nova Science Publishers, Inc., 2013); *Sepsis and Non-infectious Systemic Inflammation: From Biology to Critical Care* (J. Cavaillon, C. Adrie eds., Wiley-Blackwell, 2008); *Sepsis: Diagnosis, Management and Health Outcomes* (Allergies and Infectious Diseases, N. Khardori ed., Nova Science Pub Inc., 2014); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

A "biomarker" in the context of the present invention refers to a biological compound, such as a polynucleotide which is differentially expressed in a sample taken from patients having sepsis as compared to a comparable sample taken from control subjects (e.g., a person with a negative diagnosis, normal or healthy subject, or non-infected subject). The biomarker can be a nucleic acid, a fragment of a nucleic acid, a polynucleotide, or an oligonucleotide that can be detected and/or quantified. Sepsis biomarkers include polynucleotides comprising nucleotide sequences from genes or RNA transcripts of genes, including but not limited to, CEACAM1, ZDHHC19, C9orf95, GNA15, BATF, C3AR1, KIAA1370, TGFBI, MTCH1, RPGRIP1, and HLA-DPB1.

The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation, hydroxylation, oxidation, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), and any other type of polynucleotide which is an N- or C-glycoside of a purine or pyrimidine base. There is no intended distinction in length between the terms "polynucleotide," "oligonucleotide," "nucleic acid" and "nucleic acid molecule," and these terms are used interchangeably.

The phrase "differentially expressed" refers to differences in the quantity and/or the frequency of a biomarker present in a sample taken from patients having, for example, sepsis as compared to a control subject or non-infected subject. For example, a biomarker can be a polynucleotide which is present at an elevated level or at a decreased level in samples of patients with sepsis compared to samples of control subjects. Alternatively, a biomarker can be a polynucleotide which is detected at a higher frequency or at a lower frequency in samples of patients with sepsis compared to samples of control subjects. A biomarker can be differentially present in terms of quantity, frequency or both.

A polynucleotide is differentially expressed between two samples if the amount of the polynucleotide in one sample is statistically significantly different from the amount of the polynucleotide in the other sample. For example, a polynucleotide is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polynucleotide is differentially expressed in two sets of samples if the frequency of detecting the polynucleotide in samples of patients' suffering from sepsis, is statistically significantly higher or lower than in the control samples. For example, a polynucleotide is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A "similarity value" is a number that represents the degree of similarity between two things being compared. For example, a similarity value may be a number that indicates the overall similarity between a patient's expression profile using specific phenotype-related biomarkers and reference value ranges for the biomarkers in one or more control samples or a reference expression profile (e.g., the similarity to a "sepsis" expression profile or a "sterile inflammation" expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

As used herein, a "biological sample" refers to a sample of tissue, cells, or fluid isolated from a subject, including but not limited to, for example, blood, buffy coat, plasma, serum, blood cells (e.g., peripheral blood mononucleated cells (PBMCS), band cells, neutrophils, monocytes, or T cells), fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

A "test amount" of a biomarker refers to an amount of a biomarker present in a sample being tested. A test amount can be either an absolute amount (e.g., µg/ml) or a relative amount (e.g., relative intensity of signals).

A "diagnostic amount" of a biomarker refers to an amount of a biomarker in a subject's sample that is consistent with a diagnosis of sepsis. A diagnostic amount can be either an absolute amount (e.g., µg/ml) or a relative amount (e.g., relative intensity of signals).

A "control amount" of a biomarker can be any amount or a range of amount which is to be compared against a test amount of a biomarker. For example, a control amount of a biomarker can be the amount of a biomarker in a person without sepsis. A control amount can be either in absolute amount (e.g., µg/ml) or a relative amount (e.g., relative intensity of signals).

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) Nature 349:293-299; and U.S. Pat. No. 4,816,567); F(ab')$_2$ and F(ab) fragments; F$_v$ molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, e.g., Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, e.g., Riechmann et al. (1988) Nature 332:323-327; Verhoeyan et al. (1988) Science 239: 1534-1536; and U.K. Patent Publication No. GB 2,276,169, published 21 Sep. 1994); and, any functional fragments obtained from such molecules, wherein such fragments retain specific-binding properties of the parent antibody molecule.

"Detectable moieties" or "detectable labels" contemplated for use in the invention include, but are not limited to, radioisotopes, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding β-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The invention relates to the use of biomarkers either alone or in combination with clinical parameters for diagnosis of sepsis. In particular, the inventors have discovered a panel of biomarkers whose expression profile can be used to diagnose sepsis and to distinguish sepsis from noninfectious sources of systemic inflammation, such as caused by traumatic injury, surgery, autoimmune disease, thrombosis, or systemic inflammatory response syndrome (see Example 1).

A. Biomarkers

Biomarkers that can be used in the practice of the invention include polynucleotides comprising nucleotide sequences from genes or RNA transcripts of genes, including but not limited to, CEACAM1, ZDHHC19, C9orf95, GNA15, BATF, C3AR1, KIAA1370, TGFBI, MTCH1, RPGRIP1, and HLA-DPB1. Differential expression of these biomarkers is associated with sepsis and therefore expression profiles of these biomarkers are useful for diagnosing sepsis and distinguishing sepsis from non-infectious inflammatory conditions, such as caused by traumatic injury, surgery, autoimmune disease, thrombosis, or systemic inflammatory response syndrome (SIRS).

Accordingly, in one aspect, the invention provides a method for diagnosing sepsis in a subject, comprising measuring the level of a plurality of biomarkers in a biological sample derived from a subject suspected of having sepsis, and analyzing the levels of the biomarkers and comparing with respective reference value ranges for the biomarkers, wherein differential expression of one or more biomarkers in the biological sample compared to one or more biomarkers in a control sample indicates that the subject has sepsis. When analyzing the levels of biomarkers in a biological sample, the reference value ranges used for comparison can represent the level of one or more biomarkers found in one or more samples of one or more subjects without sepsis (i.e., normal or non-infected control samples). Alternatively, the reference values can represent the level of one or more biomarkers found in one or more samples of one or more subjects with sepsis. In certain embodiments, the levels of the biomarkers are compared to time-matched reference values for non-infected or infected/septic subjects.

The biological sample obtained from the subject to be diagnosed is typically whole blood, buffy coat, plasma, serum, or blood cells (e.g., peripheral blood mononucleated cells (PBMCS), band cells, neutrophils, monocytes, or T cells), but can be any sample from bodily fluids, tissue or cells that contain the expressed biomarkers. A "control" sample, as used herein, refers to a biological sample, such as a bodily fluid, tissue, or cells that are not diseased. That is, a control sample is obtained from a normal or non-infected subject (e.g. an individual known to not have sepsis). A biological sample can be obtained from a subject by conventional techniques. For example, blood can be obtained by venipuncture, and solid tissue samples can be obtained by surgical techniques according to methods well known in the art.

In certain embodiments, a panel of biomarkers is used for diagnosis of sepsis. Biomarker panels of any size can be used in the practice of the invention. Biomarker panels for diagnosing sepsis typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, or at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a panel of biomarkers for diagnosing sepsis comprising one or more polynucleotides comprising a nucleotide sequence from a gene or an RNA transcript of a gene selected from the group consisting of CEACAM1, ZDHHC19, C9orf95, GNA15, BATF, C3AR1, KIAA1370, TGFBI, MTCH1, RPGRIP1, and HLA-DPB1. In one embodiment, the panel of biomarkers comprises a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide.

In certain embodiments, an infection Z-score is used for diagnosis of sepsis. The infection Z-score is calculated by subtracting the geometric mean of the expression levels of all measured biomarkers that are underexpressed compared to control reference values for the biomarkers from the geometric mean of the expression levels of all measured biomarkers that are overexpressed compared to control reference values for the biomarkers, and multiplying the difference by the ratio of the number of biomarkers that are overexpressed to the number of biomarkers that are underexpressed compared to control reference values for the biomarkers. A higher infection Z-score for the subject compared to reference value ranges for non-infected control subjects indicates that the subject has sepsis (see Example 1).

In other embodiments, a sepsis score is used for diagnosis of sepsis. A sepsis score for a patient can be calculated based on the levels of expression of CEACAM1, ZDHHC19, C9orf95, GNA15, BATF, C3AR1, KIAA1370, TGFBI, MTCH1, RPGRIP1, and HLA-DPB1 biomarkers according to the following formula:

$$\sqrt[6]{(CEACAM1 * ZDHHC19 * C9orf95 * GNA15 * BATF * C3AR1)} - 5/6 \sqrt[5]{(KIAA1370 * TGFBI * MTCH1 * RPGRIP1 * HLA-DPB1)}.$$

A higher sepsis score for a subject compared to reference value ranges for non-infected control subjects indicates that the subject has sepsis (see Example 2).

In another aspect, the invention includes an assay comprising: a) measuring each biomarker of a biomarker panel, described herein, in a biological sample collected from a subject suspected of having sepsis; and b) comparing the measured value of each biomarker of the biomarker panel in the biological sample with reference values for each biomarker for a control subject, wherein differential expression of the biomarkers in the biological sample compared to the reference values indicate that the subject has sepsis. In certain embodiments, the assay further comprises determining an infection Z-score, as described herein.

The methods described herein may be used to determine if a patient having systemic inflammation should be treated for sepsis. For example, a patient is selected for treatment for sepsis if the patient has a positive sepsis diagnosis based on a biomarker expression profile or an infection Z-score or sepsis score, as described herein.

In one embodiment, the invention includes a method of treating a subject having sepsis, the method comprising: a) diagnosing the subject with sepsis according to a method described herein; and b) administering a therapeutically effective amount of broad spectrum antibiotics to the subject if the subject has a positive sepsis diagnosis.

In another embodiment, the invention includes a method of treating a subject suspected of having sepsis, the method comprising: a) receiving information regarding the diagnosis of the subject according to a method described herein; and b) administering a therapeutically effective amount of broad spectrum antibiotics to the subject if the patient has a positive sepsis diagnosis.

In another embodiment, the invention includes a method for monitoring the efficacy of a therapy for treating sepsis in a subject, the method comprising: measuring levels of expression of CEACAM1, ZDHHC19, C9orf95, GNA15, BATF, C3AR1, KIAA1370, TGFBI, MTCH1, RPGRIP1, and HLA-DPB1 biomarkers in a first sample derived from the subject before the subject undergoes the therapy and a second sample derived from the subject after the subject undergoes the therapy, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers in the second sample compared to the levels of expression of the biomarkers in the first sample indicate that the subject is worsening, and decreased levels of expression of the CEACAM1, ZDHHC19, C9orf95, GNA15, BATF, and C3AR1 biomarkers and increased levels of expression of the KIAA1370, TGFBI, MTCH1, RPGRIP1, and HLA-DPB1 biomarkers in the second sample compared to the levels of expression of the biomarkers in the first sample indicate that the subject is improving. The method may further comprise calculating a sepsis score for the subject, wherein a higher sepsis score for the second sample compared to the sepsis score for the first sample indicates that the subject is worsening, and a lower sepsis score for the second sample compared to the sepsis score for the first sample indicates that the subject is improving.

B. Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites) that are indicative of the expression level of the biomarker. The methods for measuring biomarkers in a sample have many applications. For example, one or more biomarkers can be measured to aid in the diagnosis of sepsis, to determine the appropriate treatment for a subject, to monitor responses in a subject to treatment, or to identify therapeutic compounds that modulate expression of the biomarkers in vivo or in vitro.

Detecting Biomarker Polynucleotides

In one embodiment, the expression levels of the biomarkers are determined by measuring polynucleotide levels of the biomarkers. The levels of transcripts of specific biomarker genes can be determined from the amount of mRNA, or polynucleotides derived therefrom, present in a biological sample. Polynucleotides can be detected and quantitated by a variety of methods including, but not limited to, microarray analysis, polymerase chain reaction (PCR), reverse transcriptase polymerase chain reaction (RT-PCR), Northern blot, and serial analysis of gene expression (SAGE). See, e.g., Draghici *Data Analysis Tools for DNA Microarrays*, Chapman and Hall/CRC, 2003; Simon et al. *Design and Analysis of DNA Microarray Investigations*, Springer, 2004; *Real-Time PCR: Current Technology and Applications*, Logan, Edwards, and Saunders eds., Caister Academic Press, 2009; Bustin *A-Z of Quantitative PCR* (IUL Biotechnology, No. 5), International University Line, 2004; Velculescu et al. (1995) Science 270: 484-487; Matsumura et al. (2005) Cell. Microbiol. 7: 11-18; *Serial Analysis of Gene Expression (SAGE): Methods and Protocols (Methods in Molecular Biology)*, Humana Press, 2008; herein incorporated by reference in their entireties.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., sepsis).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm$^2$ and 25 cm$^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., *PCR Protocols: A Guide To Methods And Applications*, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length.

In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual,* 3rd Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 $cm^2$. The polynucleotide probes are attached to the support covalently at either the 3' or the 5' end of the polynucleotide.

Biomarker polynucleotides which may be measured by microarray analysis can be expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or a fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)$^+$ RNA are well known in the art, and are described generally, e.g., in Sambrook, et al., *Molecular Cloning: A Laboratory Manual* (3rd Edition, 2001). RNA can be extracted from a cell of interest using guanidinium thiocyanate lysis followed by CsCl centrifugation (Chirgwin et al., 1979, Biochemistry 18:5294-5299), a silica gel-based column (e.g., RNeasy (Qiagen, Valencia, Calif.) or StrataPrep (Stratagene, La Jolla, Calif)), or using phenol and chloroform, as described in Ausubel et al., eds., 1989, *Current Protocols In Molecular Biology*, Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. RNA can be fragmented by methods known in the art, e.g., by incubation with $ZnCl_2$, to generate fragments of RNA.

In one embodiment, total RNA, mRNA, or nucleic acids derived therefrom, are isolated from a sample taken from a sepsis patient. Biomarker polynucleotides that are poorly expressed in particular cells may be enriched using normalization techniques (Bonaldo et al., 1996, Genome Res. 6:791-806).

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise polynucleotide molecules from a normal biological sample (i.e., control sample, e.g., blood from a subject not having sepsis) or from a sepsis reference biological sample, (e.g., blood from a subject having sepsis).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization With Nucleic Acid Probes*, Elsevier Science Publishers B.V.; and Kricka, 1992, *Nonisotopic Dna Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy.

In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

In one embodiment, the invention includes a microarray comprising an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

Polynucleotides can also be analyzed by other methods including, but not limited to, northern blotting, nuclease protection assays, RNA fingerprinting, polymerase chain reaction, ligase chain reaction, Qbeta replicase, isothermal amplification method, strand displacement amplification, transcription based amplification systems, nuclease protection (Si nuclease or RNAse protection assays), SAGE as well as methods disclosed in International Publication Nos. WO 88/10315 and WO 89/06700, and International Applications Nos. PCT/US87/00880 and PCT/US89/01025; herein incorporated by reference in their entireties.

A standard Northern blot assay can be used to ascertain an RNA transcript size, identify alternatively spliced RNA transcripts, and the relative amounts of mRNA in a sample, in accordance with conventional Northern hybridization techniques known to those persons of ordinary skill in the art. In Northern blots, RNA samples are first separated by size by electrophoresis in an agarose gel under denaturing conditions. The RNA is then transferred to a membrane, cross-linked, and hybridized with a labeled probe. Nonisotopic or high specific activity radiolabeled probes can be used, including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Isotopes that can be used include, but are not limited to $^{3}$H, $^{14}$C, $^{32}$P, $^{35}$S, $^{36}$Cl, $^{35}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing Si nuclease. The single-stranded, antisense probe must typically be completely homologous to target RNA to prevent cleavage of the probe:target hybrid by nuclease.

Serial Analysis Gene Expression (SAGE) can also be used to determine RNA abundances in a cell sample. See, e.g., Velculescu et al., 1995, Science 270:484-7; Carulli, et al., 1998, Journal of Cellular Biochemistry Supplements 30/31: 286-96; herein incorporated by reference in their entireties. SAGE analysis does not require a special device for detection, and is one of the preferable analytical methods for simultaneously detecting the expression of a large number of transcription products. First, poly A$^{+}$ RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif, USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Analysis of Biomarker Data

Biomarker data may be analyzed by a variety of methods to identify biomarkers and determine the statistical significance of differences in observed levels of biomarkers between test and reference expression profiles in order to evaluate whether a patient has sepsis or systemic inflammation arising from a noninfectious source, such as traumatic injury, surgery, autoimmune disease, thrombosis, or systemic inflammatory response syndrome (SIRS). In certain embodiments, patient data is analyzed by one or more methods including, but not limited to, multivariate linear discriminant analysis (LDA), receiver operating characteristic (ROC) analysis, principal component analysis (PCA), ensemble data mining methods, significance analysis of microarrays (SAM), cell specific significance analysis of microarrays (csSAM), spanning-tree progression analysis of density-normalized events (SPADE), and multi-dimensional protein identification technology (MUDPIT) analysis. (See, e.g., Hilbe (2009) Logistic Regression Models, Chapman & Hall/CRC Press; McLachlan (2004) Discriminant Analysis and Statistical Pattern Recognition. Wiley Interscience; Zweig et al. (1993) Clin. Chem. 39:561-577; Pepe (2003) The statistical evaluation of medical tests for classification and prediction, New York, N.Y.: Oxford; Sing et al. (2005) Bioinformatics 21:3940-3941; Tusher et al. (2001) Proc. Natl. Acad. Sci. U.S.A. 98:5116-5121; Oza (2006) Ensemble data mining, NASA Ames Research Center, Moffett Field, Calif., USA; English et al. (2009) J. Biomed. Inform. 42(2):287-295; Zhang (2007) Bioinformatics 8: 230; Shen-Orr et al. (2010) Journal of Immunology 184: 144-130; Qiu et al. (2011) Nat. Biotechnol. 29(10):886-891; Ru et al. (2006) J. Chromatogr. A. 1111(2):166-174, Jolliffe Principal Component Analysis (Springer Series in Statistics, $2^{nd}$ edition, Springer, N.Y., 2002), Koren et al. (2004) IEEE Trans Vis Comput Graph 10:459-470; herein incorporated by reference in their entireties.)

C. Kits

In yet another aspect, the invention provides kits for diagnosing sepsis, wherein the kits can be used to detect the biomarkers of the present invention. For example, the kits can be used to detect any one or more of the biomarkers described herein, which are differentially expressed in samples of a sepsis patient and healthy or non-infected subjects. The kit may include one or more agents for detection of biomarkers, a container for holding a biological sample isolated from a human subject suspected of having sepsis; and printed instructions for reacting agents with the biological sample or a portion of the biological sample to detect the presence or amount of at least one sepsis biomarker in the biological sample. The agents may be packaged in separate containers. The kit may further comprise one or more control reference samples and reagents for performing an immunoassay or microarray analysis.

In certain embodiments, the kit comprises agents for measuring the levels of at least eleven biomarkers of interest. For example, the kit may include agents for detecting biomarkers of a panel comprising a CEACAM1 polynucleotide, a ZDHHC19 polynucleotide, a C9orf95 polynucleotide, a GNA15 polynucleotide, a BATF polynucleotide, a C3AR1 polynucleotide, a KIAA1370 polynucleotide, a TGFBI polynucleotide, a MTCH1 polynucleotide, a RPGRIP1 polynucleotide, and a HLA-DPB1 polynucleotide. In addition, the kit may include agents for detecting more than one biomarker panel, such as two or three biomarker panels, which can be used alone or together in any combination, and/or in combination with clinical parameters for diagnosis of sepsis.

In certain embodiments, the kit comprises a microarray for analysis of a plurality of biomarker polynucleotides. An exemplary microarray included in the kit comprises an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing sepsis.

The kits of the invention have a number of applications. For example, the kits can be used to determine if a subject has sepsis or some other inflammatory condition arising from a noninfectious source, such as traumatic injury, surgery, autoimmune disease, thrombosis, or systemic inflammatory response syndrome (SIRS). In another example, the kits can be used to determine if a patient should be treated for sepsis, for example, with broad spectrum antibiotics. In another example, kits can be used to monitor the effectiveness of treatment of a patient having sepsis. In a further example, the kits can be used to identify compounds that modulate expression of one or more of the biomarkers in in vitro or in vivo animal models to determine the effects of treatment.

D. Diagnostic System and Computerized Methods for Diagnosis of Sepsis

In a further aspect, the invention includes a computer implemented method for diagnosing a patient suspected of having sepsis. The computer performs steps comprising: receiving inputted patient data comprising values for the levels of one or more sepsis biomarkers in a biological sample from the patient; analyzing the levels of one or more sepsis biomarkers and comparing with respective reference value ranges for the sepsis biomarkers; calculating an infection Z-score or sepsis score for the patient; calculating the likelihood that the patient has sepsis; and displaying information regarding the diagnosis of the patient. In certain embodiments, the inputted patient data comprises values for the levels of a plurality of sepsis biomarkers in a biological sample from the patient. In one embodiment, the inputted patient data comprises values for the levels CEACAM1, ZDHHC19, C9orf95, GNA15, BATF, C3AR1, KIAA1370, TGFBI, MTCH1, RPGRIP1, and HLA-DPB1 polynucleotides.

Figure 16:
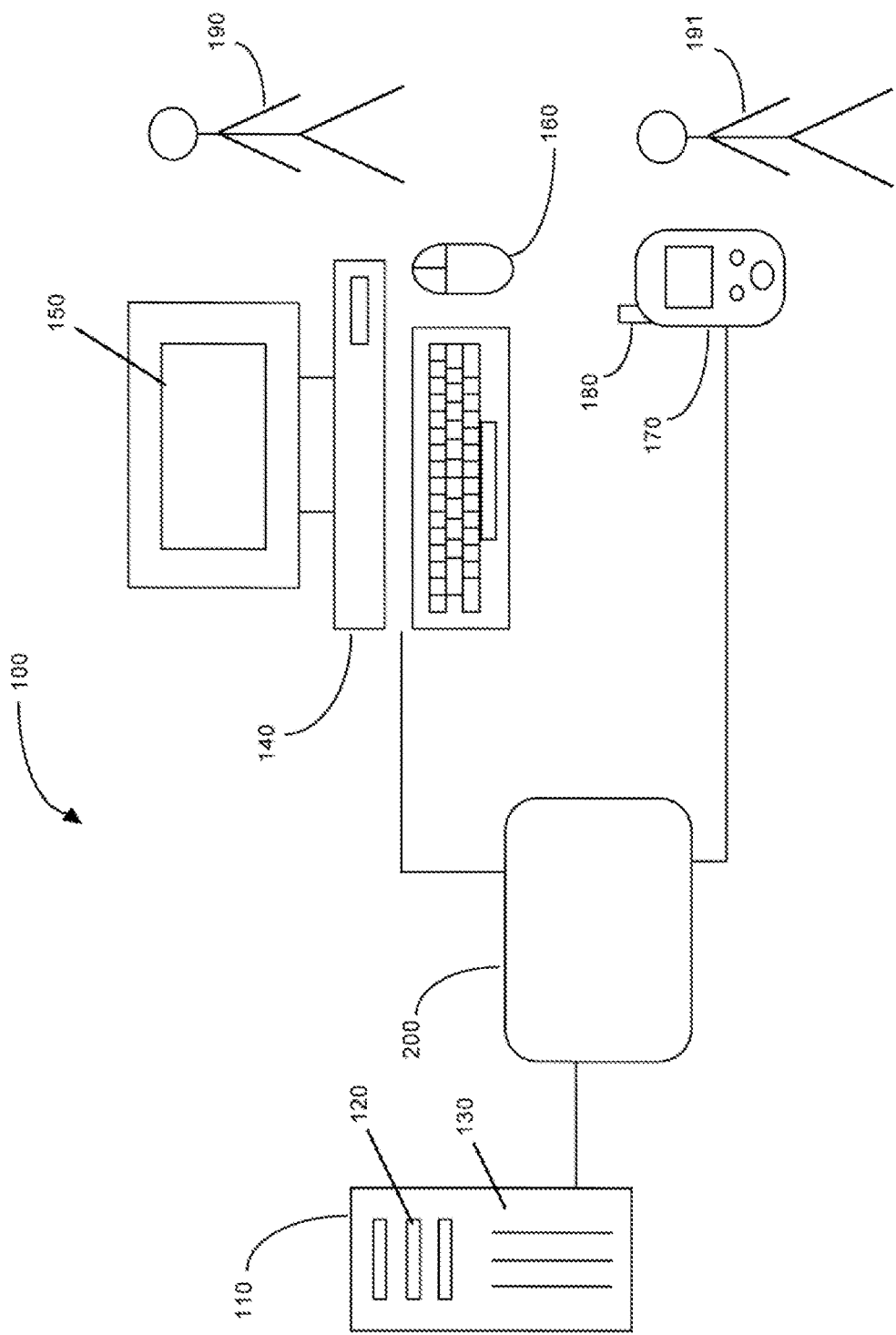
FIG. 16 shows a schematic diagram of a diagnostic system.

In a further aspect, the invention includes a diagnostic system for performing the computer implemented method, as described. As shown in FIG. 16, a diagnostic system 100 includes a computer 110 containing a processor 130, a storage component (i.e., memory) 120, a display component 150, and other components typically present in general purpose computers. The storage component 120 stores information accessible by the processor 130, including instructions that may be executed by the processor 130 and data that may be retrieved, manipulated or stored by the processor.

The storage component includes instructions for determining the diagnosis of the subject. For example, the storage component includes instructions for calculating an infection Z-score or sepsis score for the subject based on biomarker expression levels, as described herein (see Examples 1 and 2). In addition, the storage component may further comprise instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis. The computer processor 130 is coupled to the storage component 120 and configured to execute the instructions stored in the storage component in order to receive patient data and analyze patient data according to one or more algorithms. The display component 150 displays information regarding the diagnosis of the patient.

The storage component 120 may be of any type capable of storing information accessible by the processor, such as a hard-drive, memory card, ROM, RAM, DVD, CD-ROM, USB Flash drive, write-capable, and read-only memories. The processor 130 may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor 130 in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In one aspect, computer 110 is a server communicating with one or more client computers 140, 170. Each client computer may be configured similarly to the server 110, with a processor, storage component and instructions. Each client computer 140, 170 may be a personal computer, intended for use by a person 190-191, having all the internal components normally found in a personal computer such as a central processing unit (CPU), display 150 (for example, a monitor displaying information processed by the processor), CD-ROM, hard-drive, user input device (for example, a mouse, keyboard, touch-screen or microphone) 160, speakers, modem and/or network interface device (telephone, cable or otherwise) and all of the components used for connecting these elements to one another and permitting them to communicate (directly or indirectly) with one another. Moreover, computers in accordance with the systems and methods described herein may comprise any device capable of processing instructions and transmitting data to and from humans and other computers including network computers lacking local storage capability.

Although the client computers 140 and 170 may comprise a full-sized personal computer, many aspects of the system and method are particularly advantageous when used in connection with mobile devices capable of wirelessly exchanging data with a server over a network such as the Internet. For example, client computer 170 may be a wireless-enabled PDA such as a Blackberry phone, Apple iPhone, or other Internet-capable cellular phone. In such regard, the user may input information using a small keyboard, a keypad, a touch screen, or any other means of user input. The computer may have an antenna 180 for receiving a wireless signal.

The server 110 and client computers 140, 170 are capable of direct and indirect communication, such as over a network 200. Although only a few computers are depicted in FIG. 16, it should be appreciated that a typical system can include a large number of connected computers, with each different computer being at a different node of the network 200. The network, and intervening nodes, may comprise various combinations of devices and communication protocols including the Internet, World Wide Web, intranets, virtual private networks, wide area networks, local networks, cell phone networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. Server 110 may be a web server.

Although certain advantages are obtained when information is transmitted or received as noted above, other aspects of the system and method are not limited to any particular manner of transmission of information. For example, in some aspects, information may be sent via a medium such as a disk, tape, flash drive, DVD, or CD-ROM. In other aspects, the information may be transmitted in a non-electronic format and manually entered into the system. Yet further, although some functions are indicated as taking place on a server and others on a client, various aspects of the system and method may be implemented by a single computer having a single processor.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

A Comprehensive Time-Course-Based Multi-Cohort Analysis of Sepsis and Sterile Inflammation Reveals a Robust Diagnostic Gene Set Introduction We hypothesized that only time-matched comparisons, such as those that compare SIRS/trauma to sepsis at the same clinical time-points, would yield genes robustly diagnostic of sepsis. We carried out a comprehensive, time-course-based multi-cohort analysis of the publically available gene expression data in sepsis to identify a conserved 11-gene set that can robustly distinguish non-infectious inflammation (such as SIRS, trauma, and ICU admissions) from inflammation due to acute infections, as in sepsis. This 11-gene set had excellent diagnostic power in the discovery cohorts, and was then validated in 15 independent cohorts.

Results

Comprehensive Search and Labelled Principal Components Analysis (PCA) Visualizations We identified 27 independent gene expression datasets that satisfied our criteria in GEO and ArrayExpress, from which a total of 2,903 microarrays were included (Pankla et al. (2009) Genome Biol 10:R127; Tang et al. (2009) Crit Care Med 37:882-888; Cvijanovich et al. (2008) Physiol Genomics 34:127-134; Shanley et al. (2007) Mol Med 13:495-508; Wong et al. (2007) Physiol Genomics 30:146-155; Wong et al. (2009) Crit Care Med 37:1558-1566; Wong et al. (2010) Pediatr Crit Care Med 11:349-355; Wong et al. (2011) Crit Care Med 39:2511-2517; Almansa et al. (2014) J Crit Care 29:307-309; Bermejo-Martin et al. (2010) Crit Care 14:R167; Martin-Loeches et al. (2012) Med Intensiva 36:257-263; Tamayo et al. (2012) J Crit Care 27:616-622; Hu et al. (2013) Proc Natl Acad Sci USA 110:12792-12797;

Parnell et al. (2012) Crit Care 16:R157; Sutherland et al. (2011) Crit Care 15:R149; Tang et al. (2006) J Cereb Blood Flow Metab 26:1089-1102; Tang et al. (2007) Am J Respir Crit Care Med 176:676-684; Ahn et al. (2013) PLoS One 8:e48979; Dolinay et al. (2012) Am J Respir Crit Care Med 185:1225-1234; Berdal et al. (2011) J Infect 63:308-316; Berry et al. (2010) Nature 466:973-977; Fredriksson et al. (2008) PLoS One 3:e3686; McDunn et al. (2008) PLoS One 3:e1564; Chung et al. (2006) J Am Coll Surg 203:585-598; Parnell et al. (2011) PLoS One 6:e17186; and Emonts, Ph.D. thesis, Erasmus University Rotterdam, (2008); herein incorporated by reference in their entireties). These 27 datasets comprised only 22 independent cohorts, as the six datasets from the Genomics of Pediatric SIRS/Septic Shock Investigators (GPSSSI) were combined into a single cohort containing 219 patients with SIRS or sepsis (Cvijanovich et al., supra; Shanley et al., supra; Wong et al. (2007), supra; Wong et al. (2009), supra; Wong et al. (2010), supra; Wong et al. (2011), supra). Many of the samples used were from the Glue Grant trauma datasets, which have a total of 333 patients sampled at up to 8 time-points (1301 samples used here) after traumatic injury. These 27 datasets contain cohorts of children and adults, men and women, with a mix of community-acquired and hospital acquired sepsis, sampled from whole blood, neutrophils, and PBMCs.

Figure 1B:
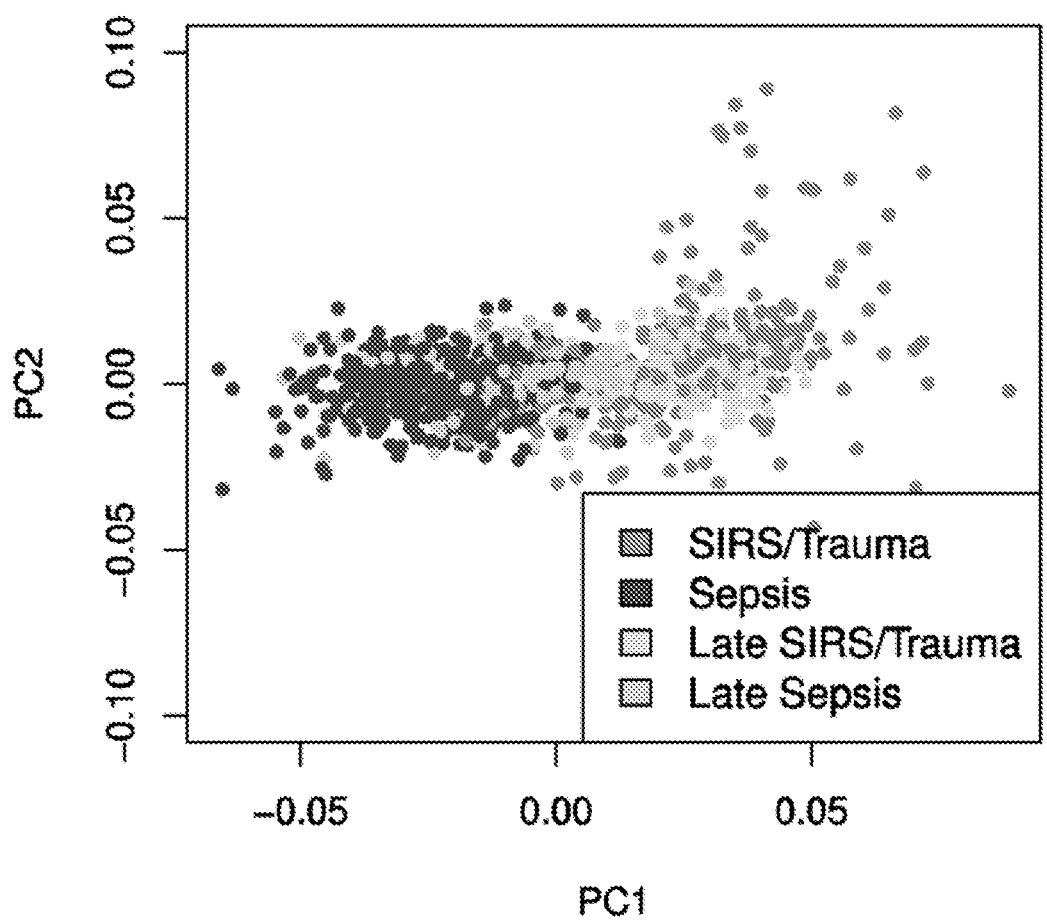
Figure 2A:
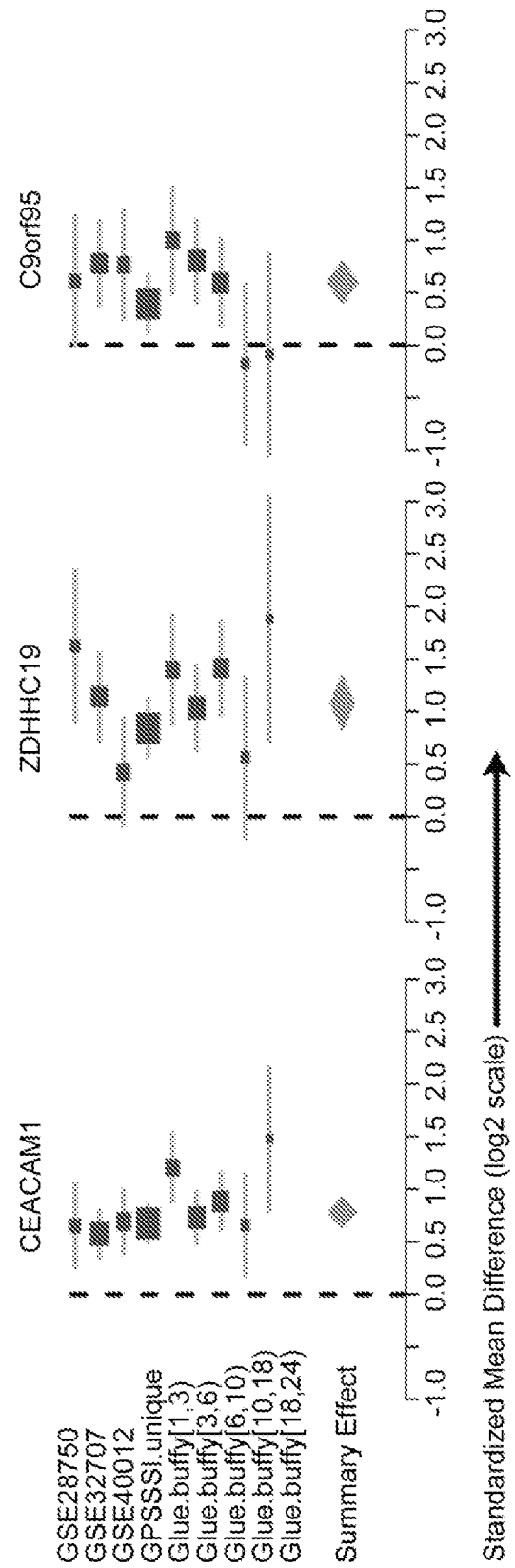
FIGS. 2A-2D show effects of size of the 11 gene set. Forest plots are shown for random effects model estimates of effect size of the positive genes, comparing SIRS/trauma/ICU to infection/sepsis patients, in each of the discovery cohorts.
Figure 2B:
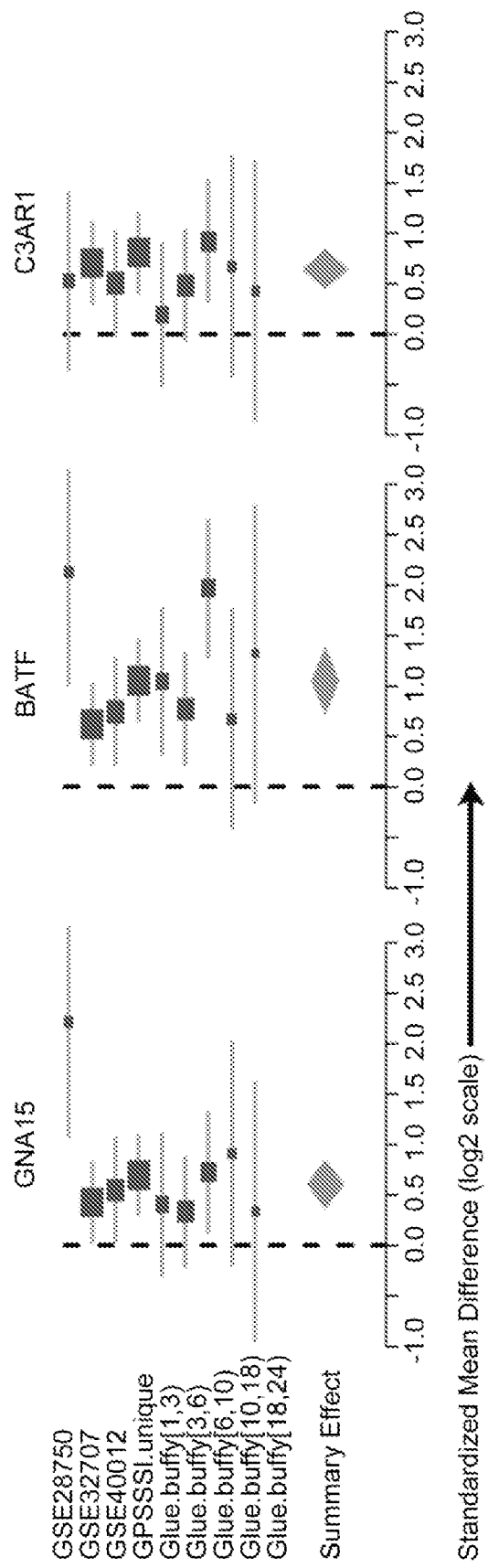
Figure 2C:
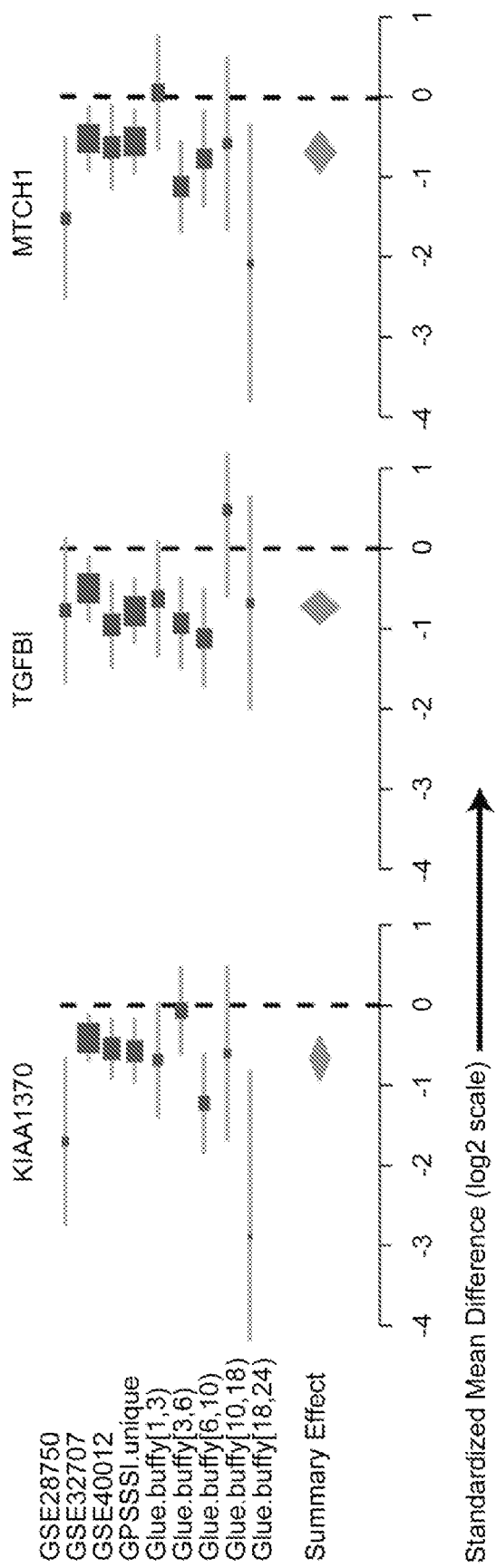
Figure 2D:
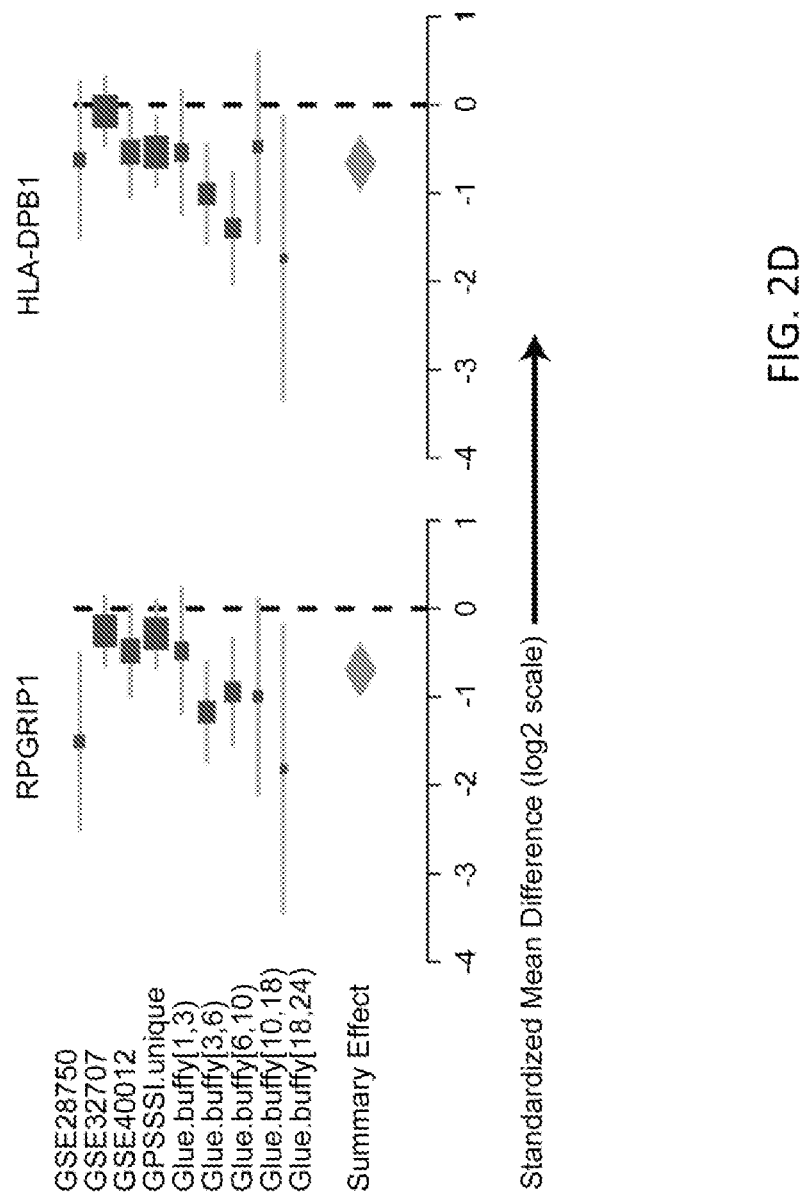
Figure 7A:
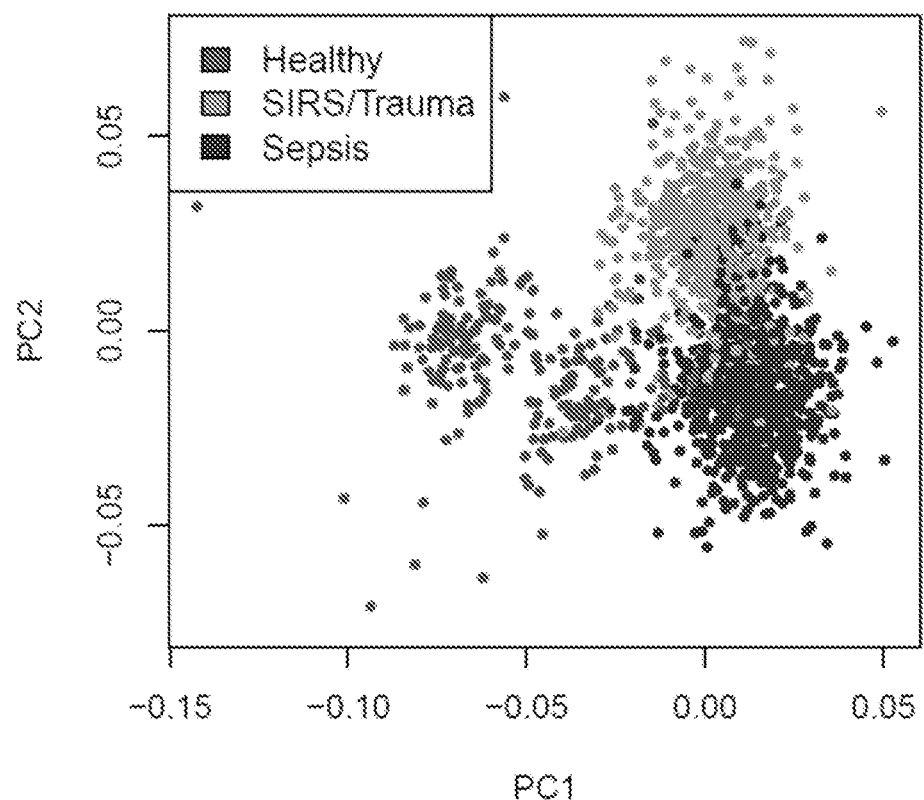
FIGS. 7A and 7B show labelled PCA comparing healthy patients versus SIRS/Trauma patients versus sepsis patients.
Figure 7B:
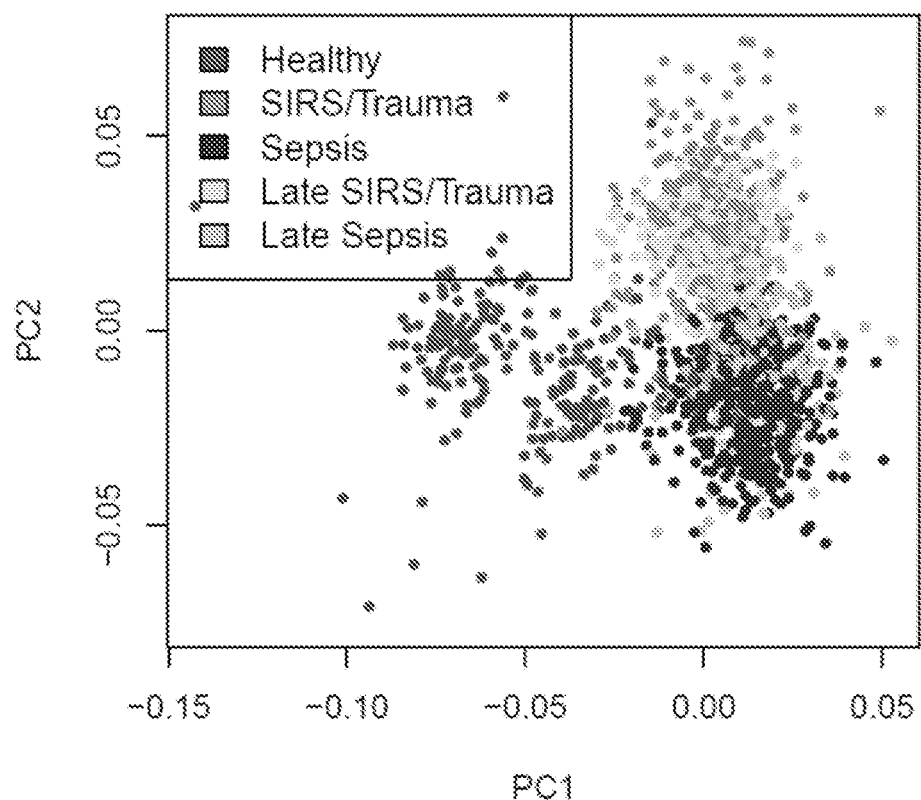

First, we sought to use the simplest possible methods to see whether non-infected SIRS/trauma patients and sepsis/infection patients could be separated by gene expression. We thus co-normalized all available datasets comparing SIRS/trauma with sepsis/infection in a single matrix. Labeled PCA (using 168 genes identified by 10-fold cross-validated Lasso-penalized logistic regression) showed that SIRS/trauma patients can be separated from sepsis patients with modest overlap (FIG. 1A). Next, we labeled each sample as "early" (within 48 hours of admission) or "late" (more than 48 hours of admission). The majority of the non-separable samples were the 'late' samples (FIG. 1B). This finding remained true even when we included healthy patients as a separate class (FIG. 7). Prior work has shown that gene expression after trauma, burns, or endotoxemia changes non-linearly over time (Cobb et al., supra; Xiao et al., supra; Seok et al., supra; Desai et al., supra; and McDunn et al., supra). This continuous change in expression after initial insult could explain the inability to distinguish non-infected SIRS/trauma from sepsis in the 'late' samples if all time-points are treated as equal.

Therefore, we sought to get a qualitative sense of whether gene expression during the hospital course after injury is similar among different cohorts. We included all peripheral blood datasets that examined gene expression longitudinally over time after admission for non-septic events. We used CUR matrix decomposition to identify the 100 genes that were most orthogonal to each other, and used these to perform labelled PCA with classes determined by days post-injury. Reassuringly, the gene expression group at each time-point was closest to the time-points by which it was bounded (for example, the days [1,2] group was preceded by days [0,1) and followed by days [2,3)). Furthermore, changes in expression over time explained most variance in the datasets, as evidenced by the different day-groups changing in each of the first three labeled principal components. In summary, our analysis showed that the changes in gene expression after trauma/ICU admissions (1) proceed in a nonlinear fashion over time, and (2) show similar changes over time across datasets.

Time-Matched Multi-Cohort Analysis

Since changes in gene expression after admission for trauma explain a large amount of variance in the dataset, and since these changes proceed nonlinearly, direct comparisons of a patient at admission with that same patient several days later at the time of infection would be confounded by 'normal' changes in expression due to recovery from the inciting event, as well as any 'abnormal' changes due to the hospital-acquired infection. It would be extremely difficult to disentangle these changes, if not impossible. Consequently, comparisons that do not take clinical time into account will not yield biomarkers that can robustly discriminate infected from non-infected patients (FIG. 1). Therefore, we focused only on infection datasets that also included a time-matched non-infected cohort (to allow for direct time-matched comparisons). We thus separated the datasets into two groups: (1) datasets comparing patients at hospital admission for trauma, surgery, or critical illness versus patients at admission to the hospital for sepsis (GSE28750 (Sutherland et al., supra), GSE32707 (Dolinay et al., supra), GSE40012 (Parnell et al., supra), and the GPSSSI Unique combined datasets (n=408 samples) (Cvijanovich et al., supra; Shanley et al., supra; Wong et al. (2007), supra; Wong et al. (2009), supra; Wong et al. (2010), supra; and Wong et al. (2011), supra), and (2) the Glue Grant datasets containing patients with hospital-acquired infections and day-matched non-infected patients, from which we used only patients in the buffy coat sample cohort (Table 1). The Glue Grant trauma cohorts were sampled at roughly 0.5, 1, 4, 7, 14, 21, and 28 days since injury; these cohorts were thus divided into their sampling time bins, creating subgroups in which patients diagnosed with an infection in a given time bin can be compared to non-infected patients in the same time bin. For the buffy coat samples, there were at least 10 patients present in five time bins, and these were thus taken for further study. Thus, we used a total of 9 cohorts comparing time-matched SIRS/trauma to sepsis/infection, comprising 663 samples (326 SIRS/trauma controls and 337 sepsis/infection cases; Table 2 shows the cohorts in the multi-cohort analysis.

Figure 3A:
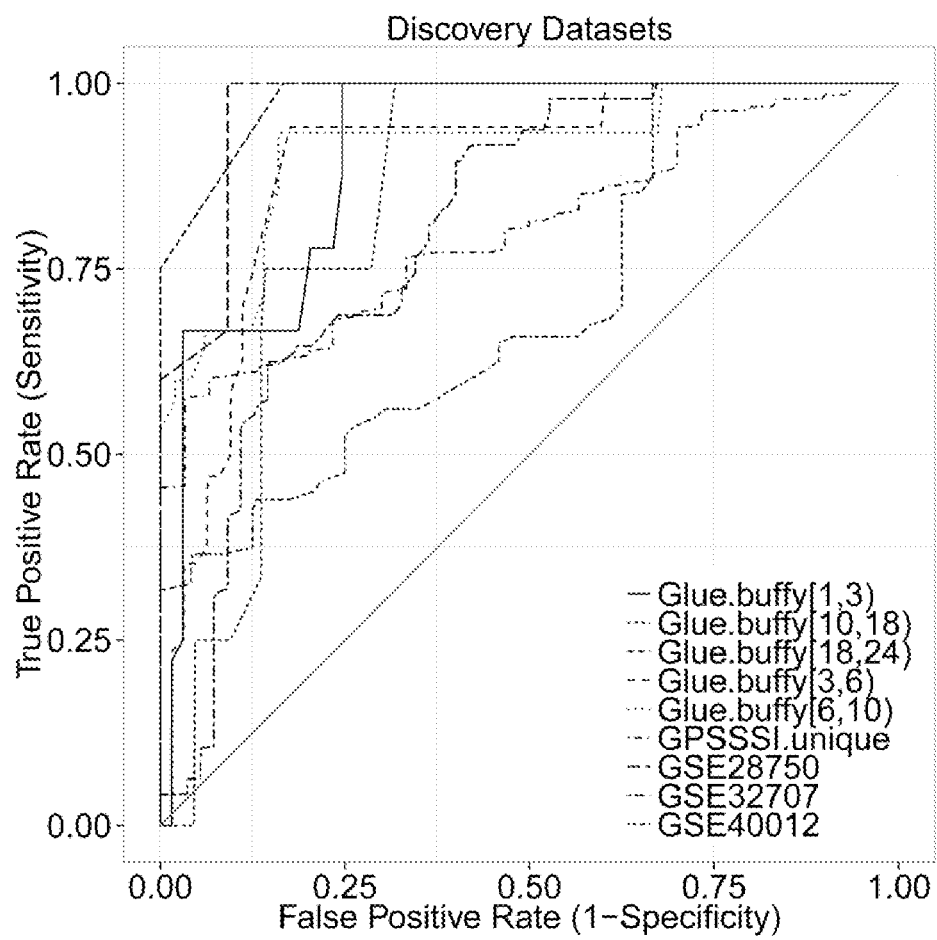
FIGS. 3A-3F show results of the 11-gene set in the discovery and neutrophils validation datasets.

We then applied our previously described (Khatri et al. (2013) J Exp Med 210:2205-2221; herein incorporated by reference in its entirety) multi-cohort gene expression analysis framework to compare SIRS/trauma with sepsis/infection, including all 9 cohorts in a leave-onedataset-out fashion. The output from this analysis underwent a three-step thresholding process (false discovery rate (FDR) <1% for both pooled effect size and Fischer's method, inter-dataset heterogeneity p>0.01, and absolute summary effect size fold change >1.5), which yielded 82 genes differentially expressed between SIRS/trauma and sepsis patients across all time-points (summary statistics for all 82 genes shown in Table 8). To obtain the most parsimonious set of significant genes that best discriminates between classes, we carried out a greedy forward search to identify which combination of the 82 genes produced the best improvements in AUC across all discovery datasets. Here discrimination is based on an 'infection Z-score' that combines gene expression levels (using the difference of geometric means between positive and negative genes) into a standardized score for each sample in each dataset. This yielded a final set of 11 genes (6 over- and 5 under-expressed in sepsis; Table 3 and FIG. 2). The mean ROC AUC of this 11 gene set in the 9 discovery cohorts was 0.87 (range 0.70-0.98; FIG. 3A and FIG. 9).

Glue Grant Sorted-Cell Cohort Validation

The Glue Grant trauma cohorts have two independent sub-cohorts; one is the buffy coat cohort (samples processed 2004-2006 on Affymetrix array GPL570), the other is the sorted-cells cohort, which included neutrophils, monocytes, and T-cells (samples processed 2008-2011 on custom Glue Grant-Human (GGH) arrays). These cohorts are separate patients, separated in time, and profiled using different technologies. While there inclusion criteria and enrolling sites are largely the same, they are otherwise independent. We thus validated our 11-gene signature in the sorted-cell Glue Grant cohorts. Here we split the sorted-cell cohorts into the same time-bins as the discovery buffy-coat cohorts, and treated each time-bin separately.

Figure 3B:
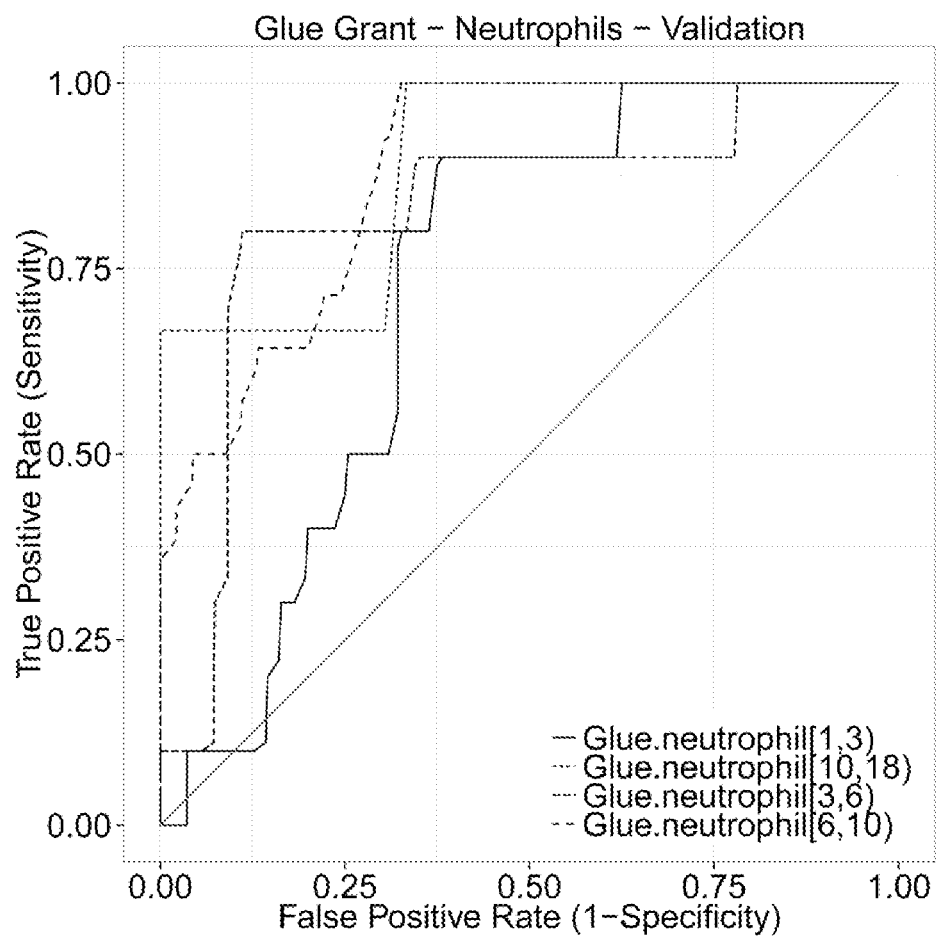
Figure 8:
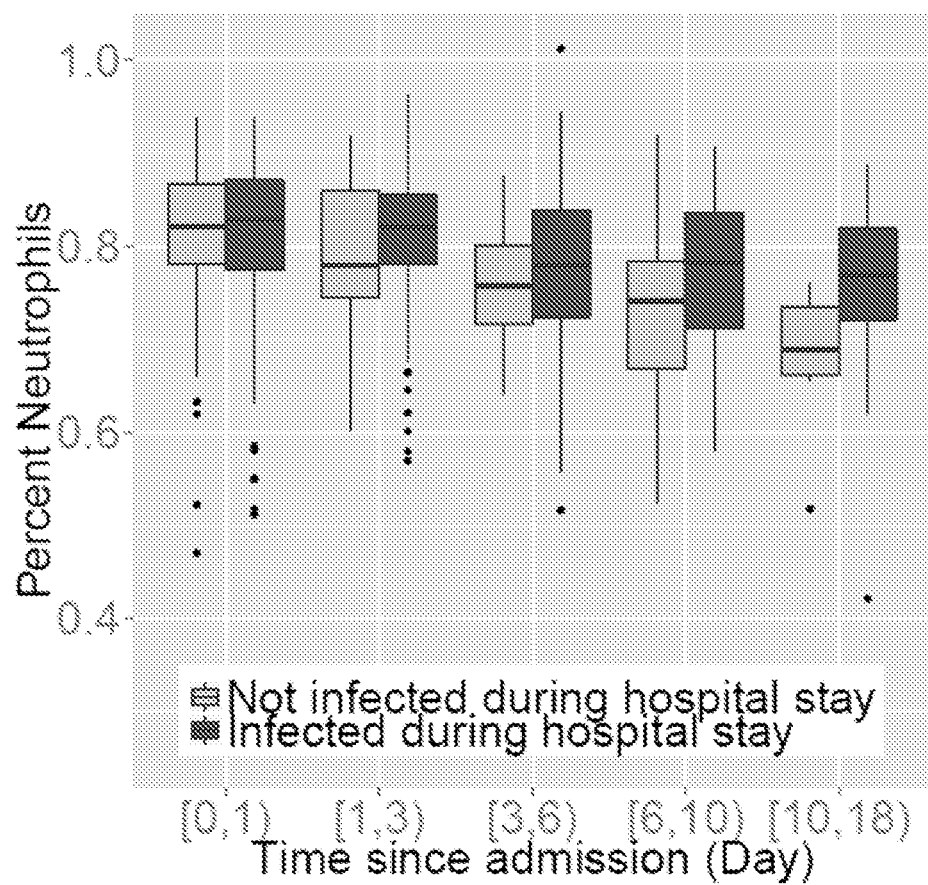
FIG. 8 shows the neutrophil percentage for the Glue Grant patients with both complete blood count and microarray data. Median neutrophil percentage is between 75-85% for all time points. Patients who were ever infected during their hospital stay are compared to patients never infected during their hospital stay.
Figure 9A:
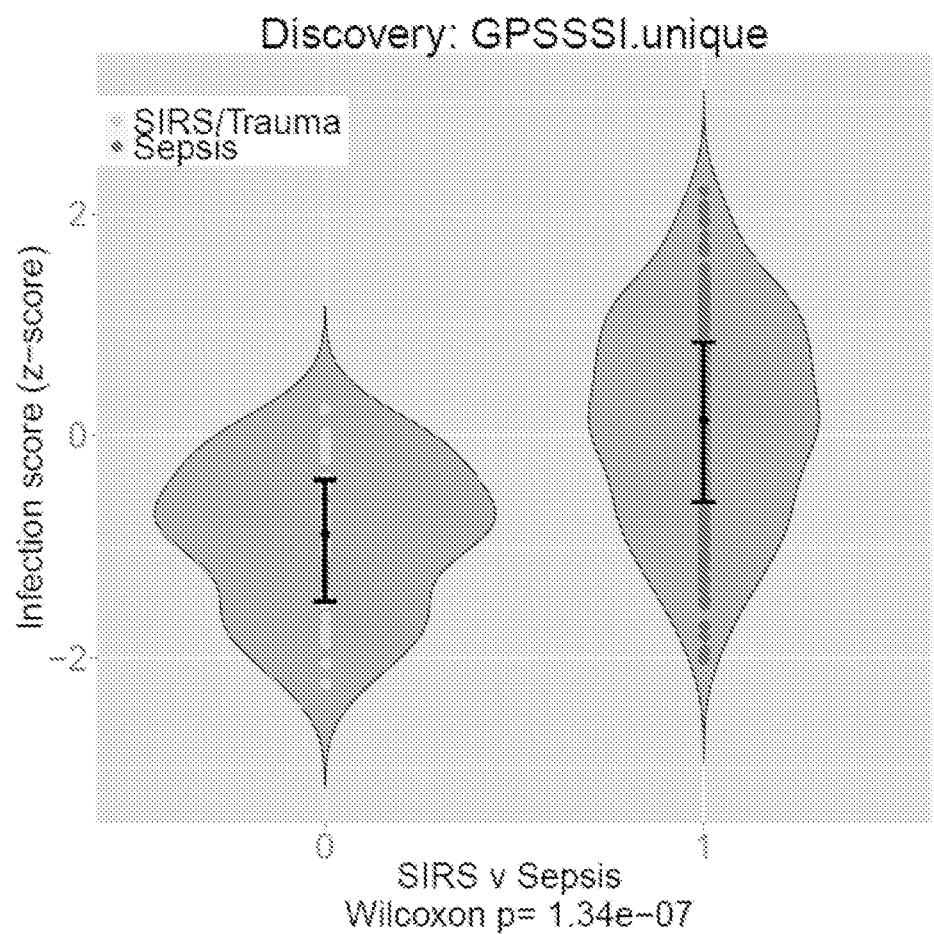
FIGS. 9A-9I show violin plots for the datasets that were included in the discovery multi-cohort analysis, including GPSSSI Unique (FIG. 9A), GSE28750 (FIG. 9B), GSE32707 (FIG. 9C), and GSE40012 (FIG. 9D). Shown are the datasets comparing SIRS/ICU/trauma to sepsis patients at admission. Error bars show middle quartiles. P-values are computed using Wilcoxon rank-sum test.
Figure 9B:
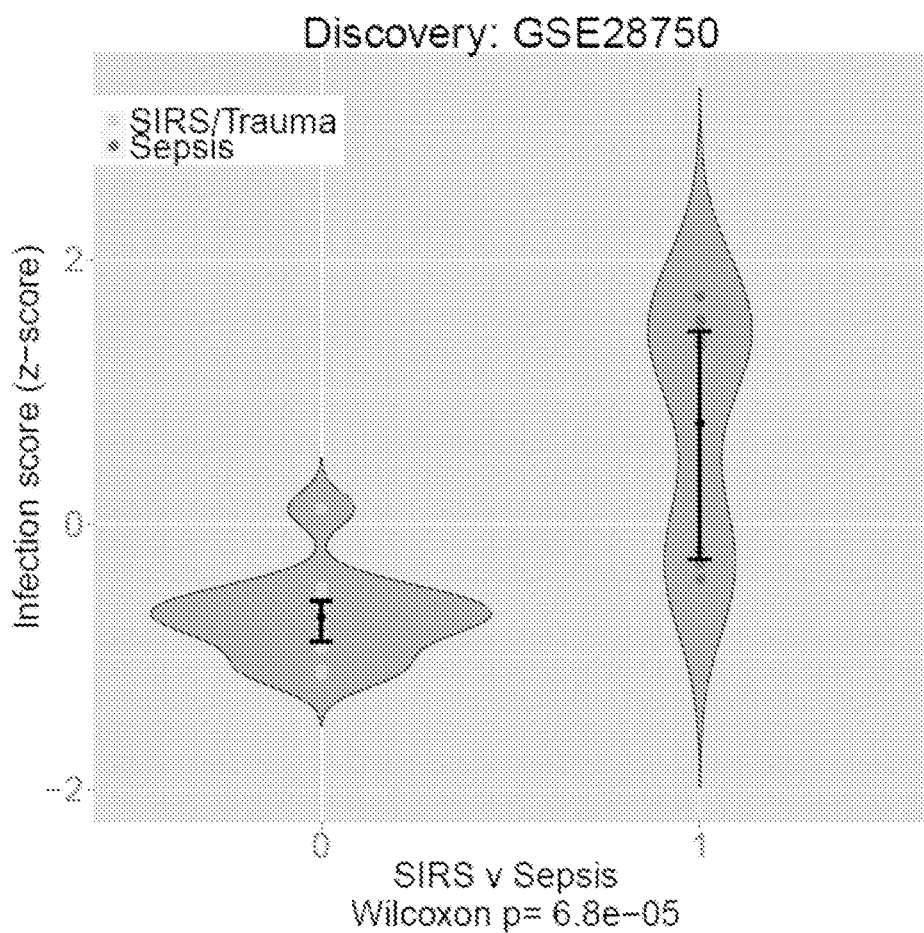
Figure 9C:
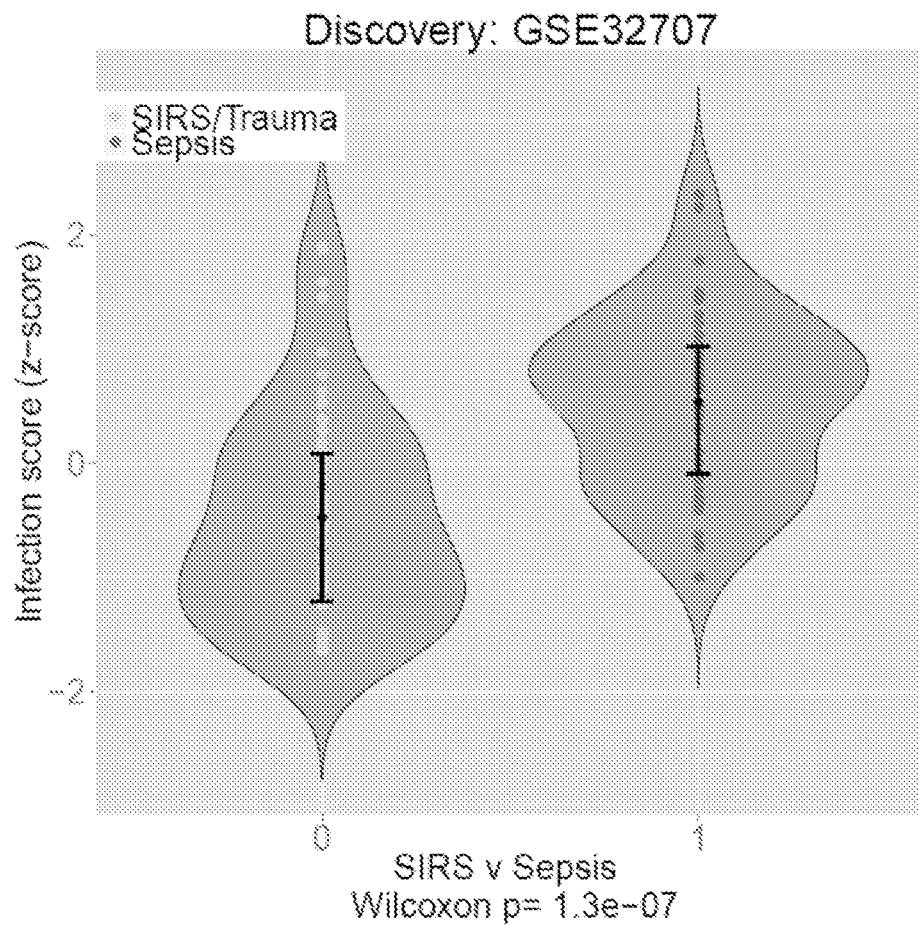
Figure 9D:
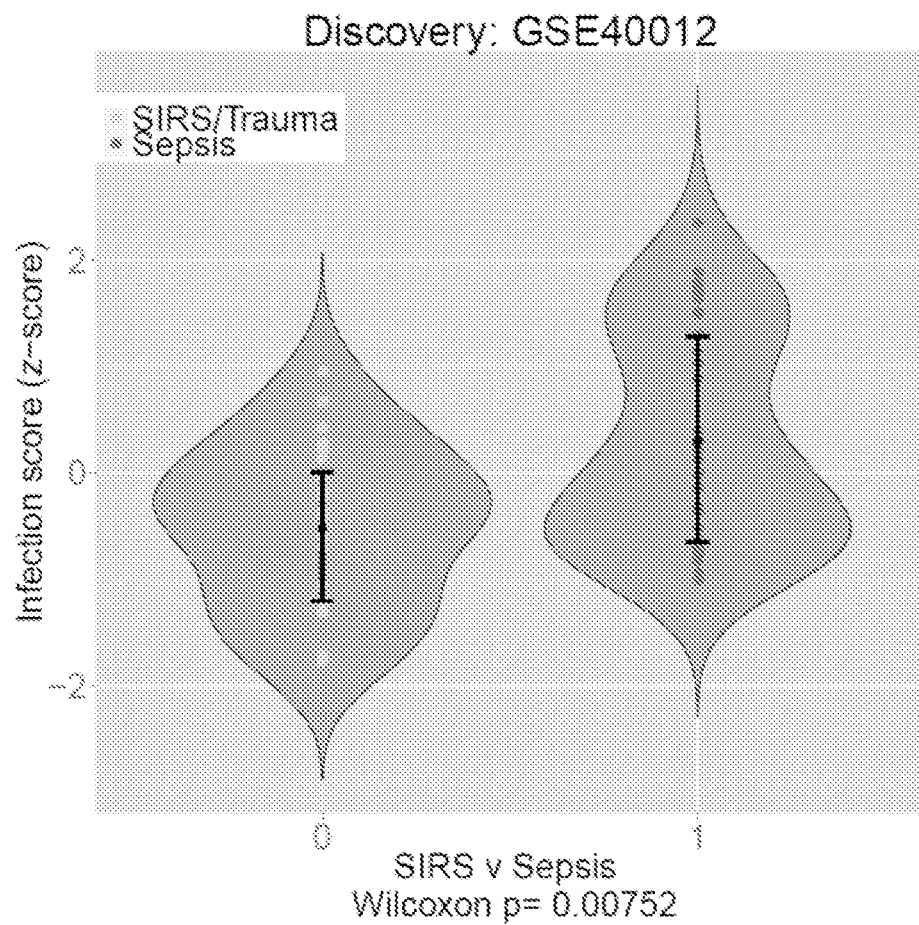
Figure 9E:
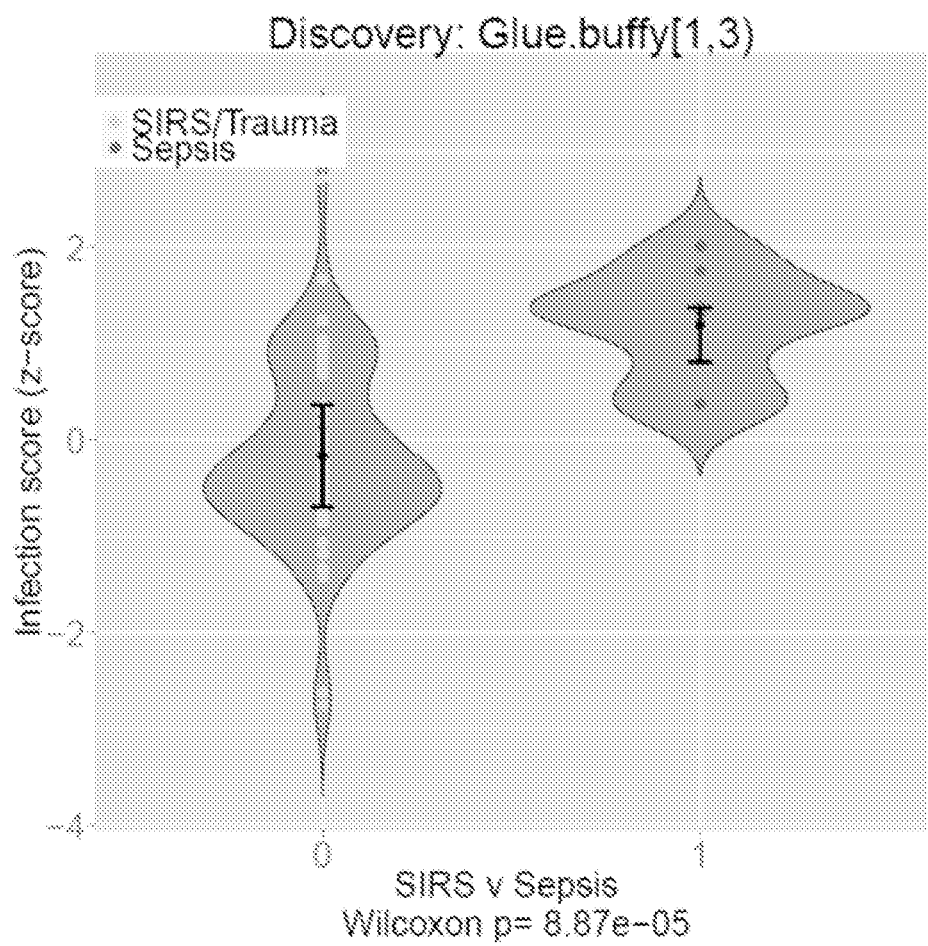
Figure 9F:
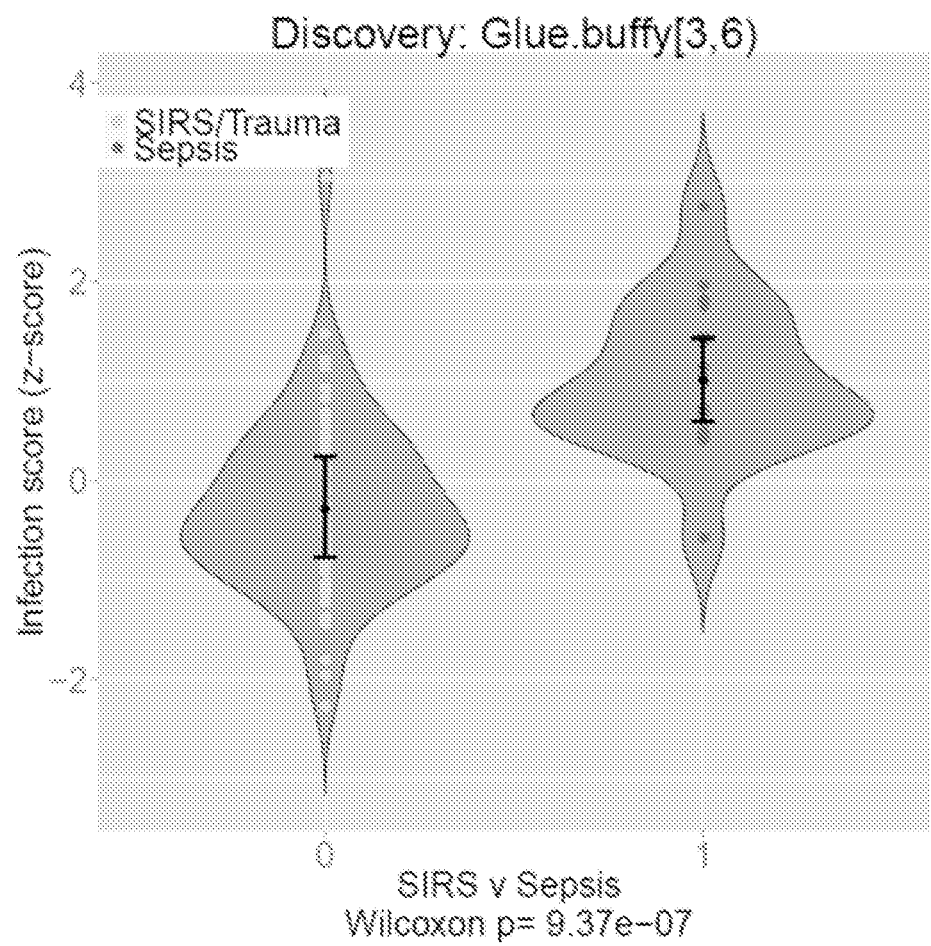
Figure 9G:
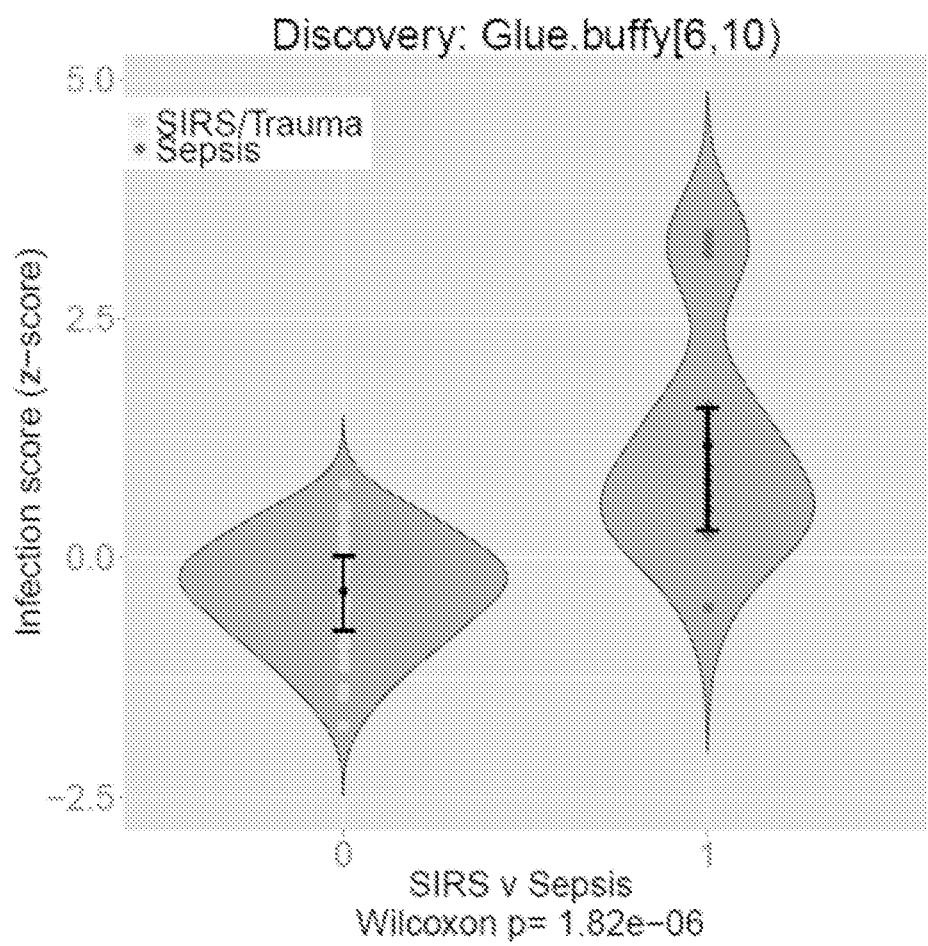
Figure 9H:
Figure 9I:
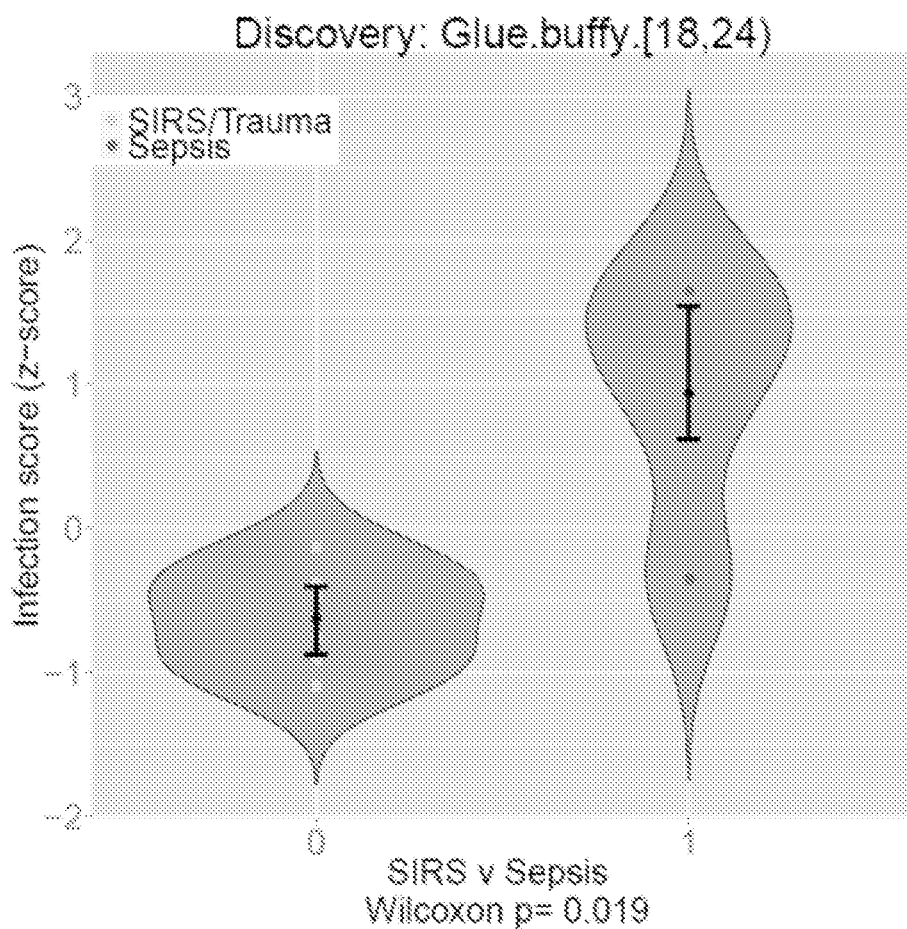
Figure 10A:
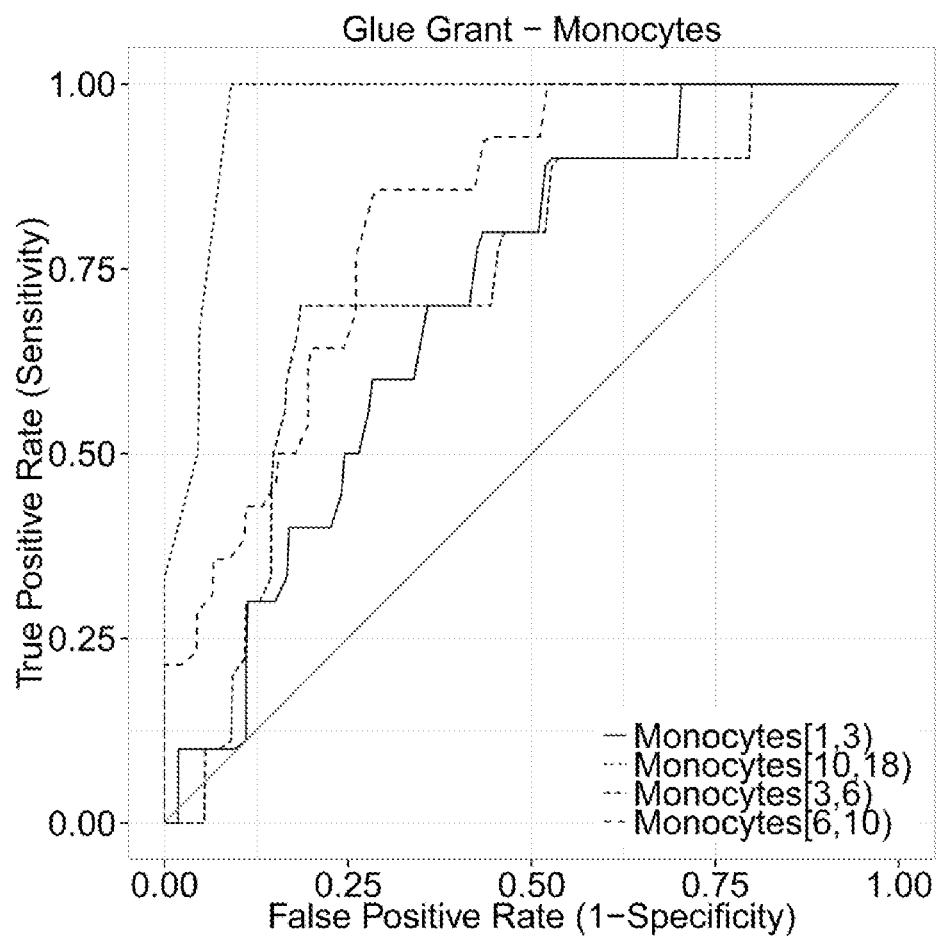
FIGS. 10A and 10B show performance of the infection Z-score in the sorted monocytes from the Glue Grant cohort. These are the same patients as the neutrophils validation cohort in FIGS. 3B, 3D, and 3F.
Figure 11A:
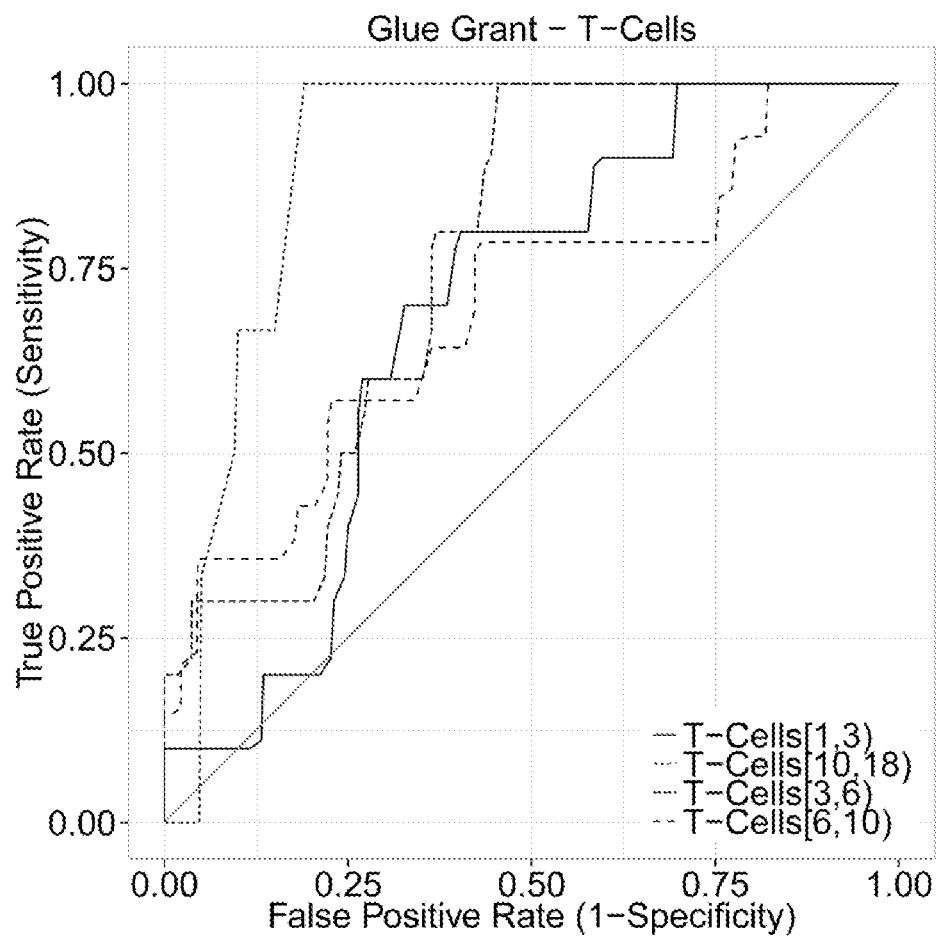
FIGS. 11A and 11B show performance of the infection Z-score in the sorted T-cells from the Glue Grant cohort. These are the same patients as the neutrophils validation cohort in FIGS. 3B, 3D, and 3F.

From the sorted-cells sub-cohort, we expected the neutrophil set to perform most similarly to a whole-blood sample, as neutrophils make up 75-85% of the total leukocyte pool after trauma in both infected and non-infected patients (and hence most of the gene expression present in peripheral blood) (FIG. 8). Indeed, the 11-gene set performed very well at separating time-matched non-infected trauma patients from septic trauma patients (4 cohorts, 218 samples; mean AUC 0.83, range 0.73-0.89) (FIG. 3B). Surprisingly, the 11-gene set also showed discriminatory power in the monocytes and T-cells from these same patients (monocytes AUC range 0.71-0.97, T-cells AUC range 0.69-0.9) (FIGS. 10A, 11A). Since we excluded any sorted-cell datasets from the multi-cohort analysis, we did not expect diagnostic capability in these cell types. Interestingly, in the sorted-cells cohort, AUC increases with greater time since initial trauma; this may suggest that inflammation due to infection is easier to discriminate as the 'genomic storm' of traumatic injury begins to recover.

Examination of the 11-Gene Set in the Glue Grant Cohorts

Figure 3C:
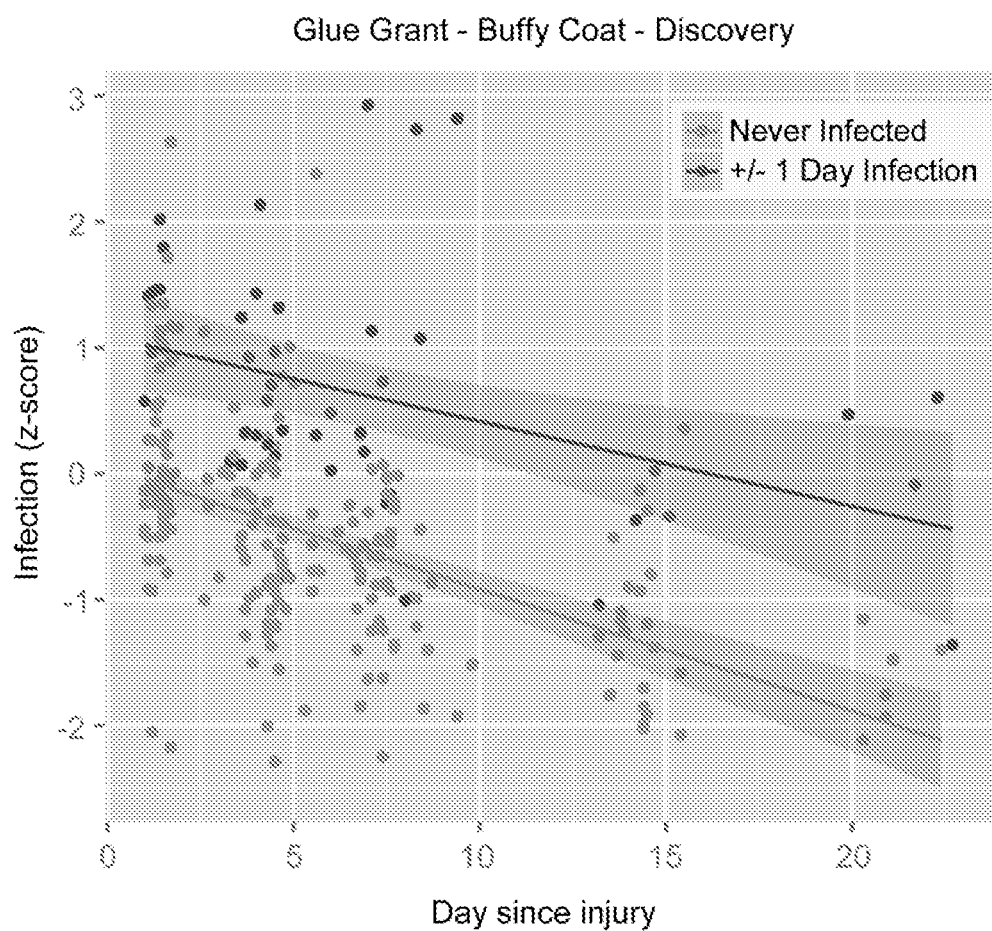
Figure 3D:
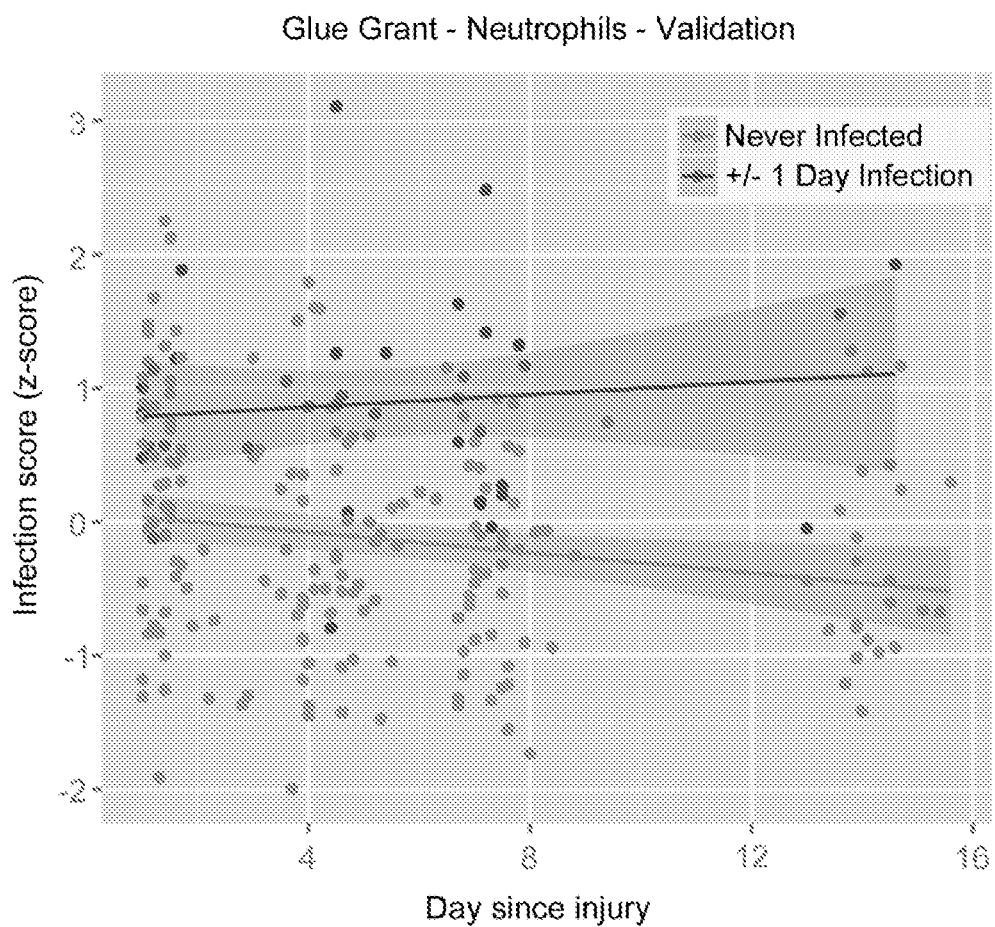

As expected, in the Glue Grant buffy coat cohort, patients within +/−24 hours of diagnosis of infection have significantly higher infection Z-scores at all time-points as compared to time-matched patients without infection; this was validated in the neutrophils cohort (repeated-measures ANOVA $p<0.0001$; FIGS. 3C-3D, Table 9A). Comparison of the infection Z-score by time since injury in the buffy coat cohort shows a significant decline over time (repeated measures ANOVA change over time $p<0.0001$), but there appears to be a lesser (though still significant) effect in the neutrophils validation cohort (repeated measures ANOVA change over time $p<0.05$) (FIGS. 3C-3D, Table 9A). The interaction of group with time since injury was not significant in either discovery or validation cohorts, suggesting that the decline in infection Z-scores over time for both groups is likely due to recovery from traumatic injury resulting in reduced inflammation (Table 9A).

Figure 3E:
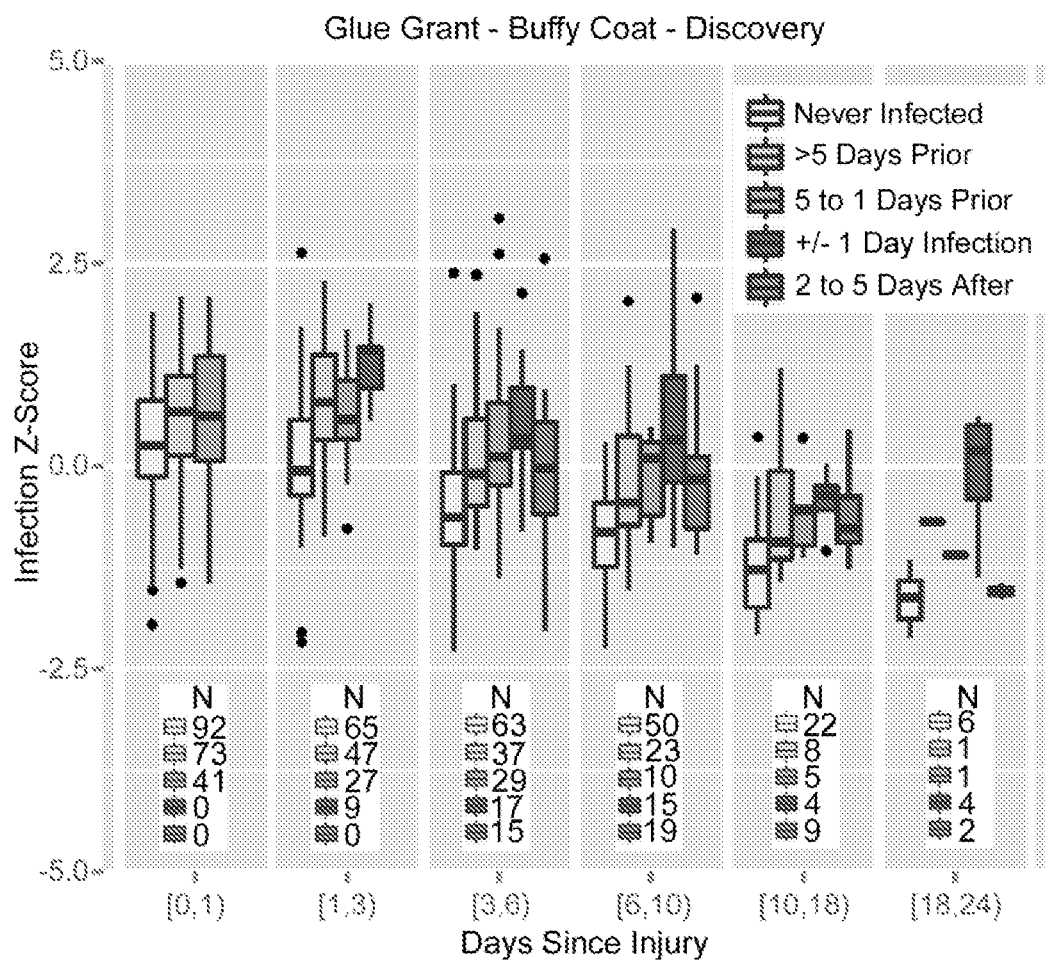
Figure 3F:
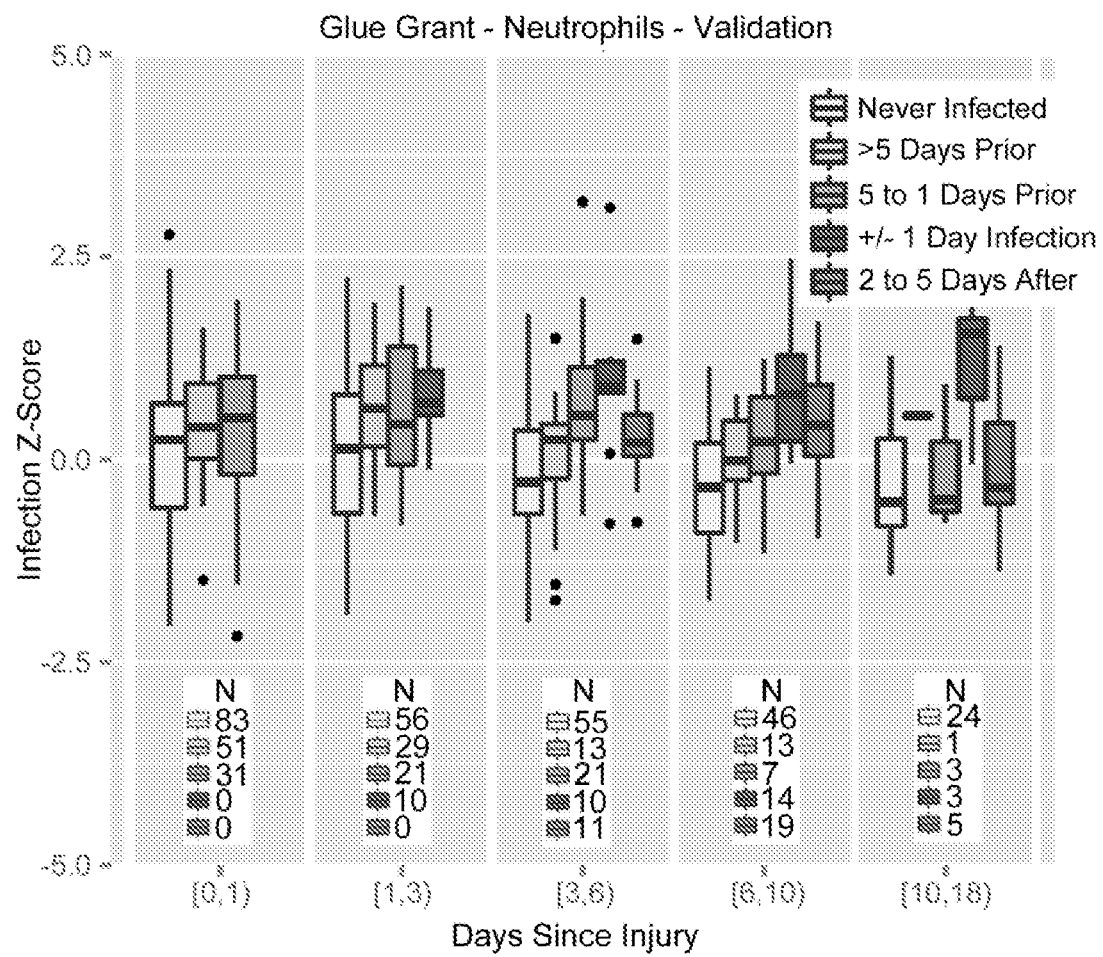
Figure 4A:
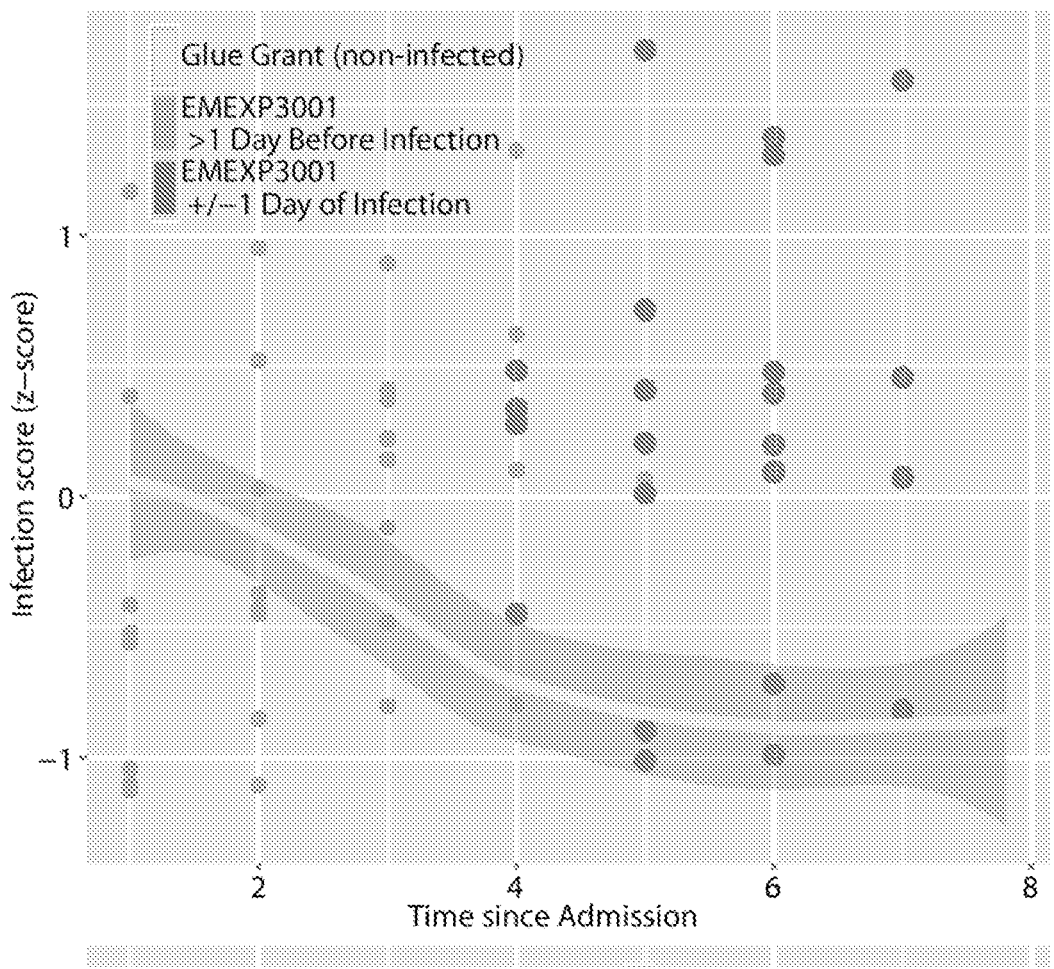
FIGS. 4A-4D show no-controls datasets of trauma/ICU patients that develop VAP. These datasets did not include non-infected patients, so they were empiric-Bayes co-normalized with time-matched Glue Grant patients. The gray line shows the Glue Grant loess curve for (FIG. 4A) EMEXP3001, (FIG. 4B) GSE6377, and (FIG. 4C) GSE12838 neutrophil and whole blood samples. In all cases, only the first 8 days since admission are shown, and patients are censored >1 day after diagnosis of infection.
Figure 4B:
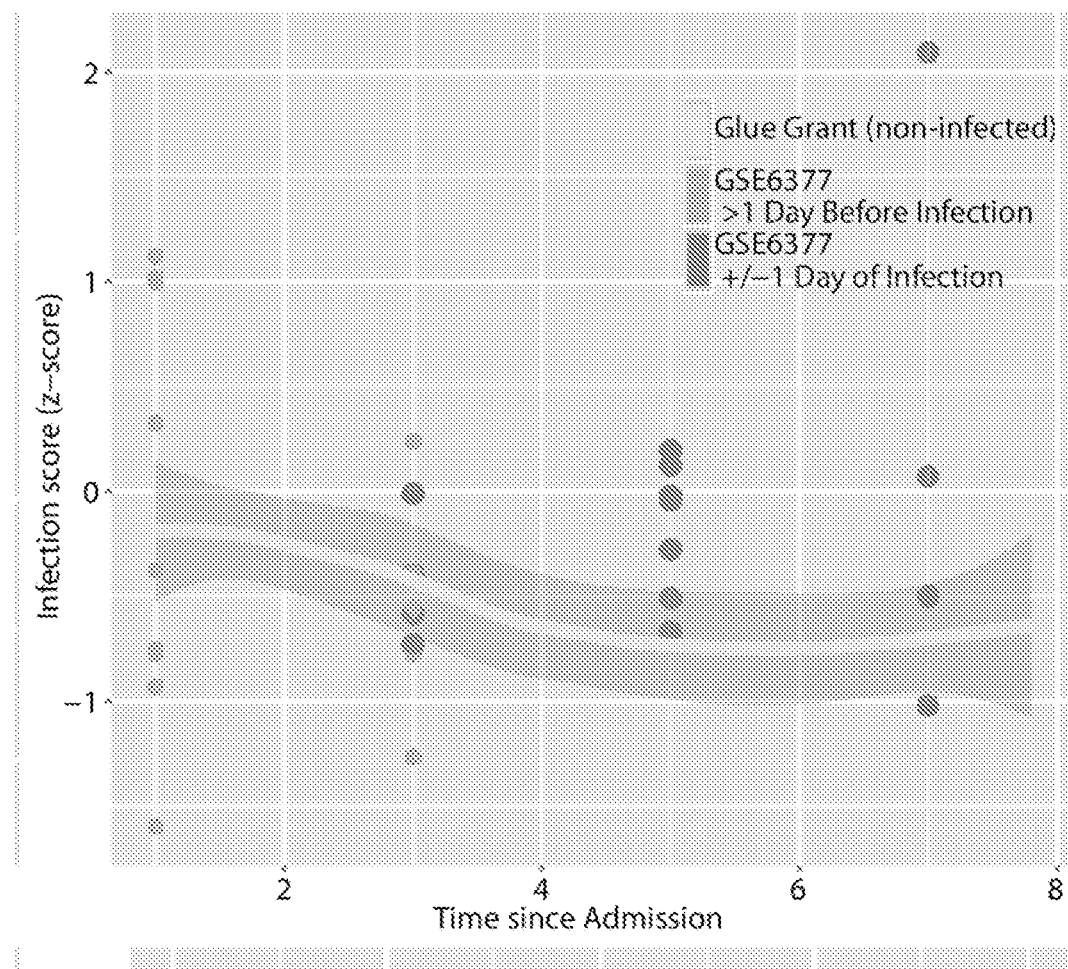
Figure 4C:
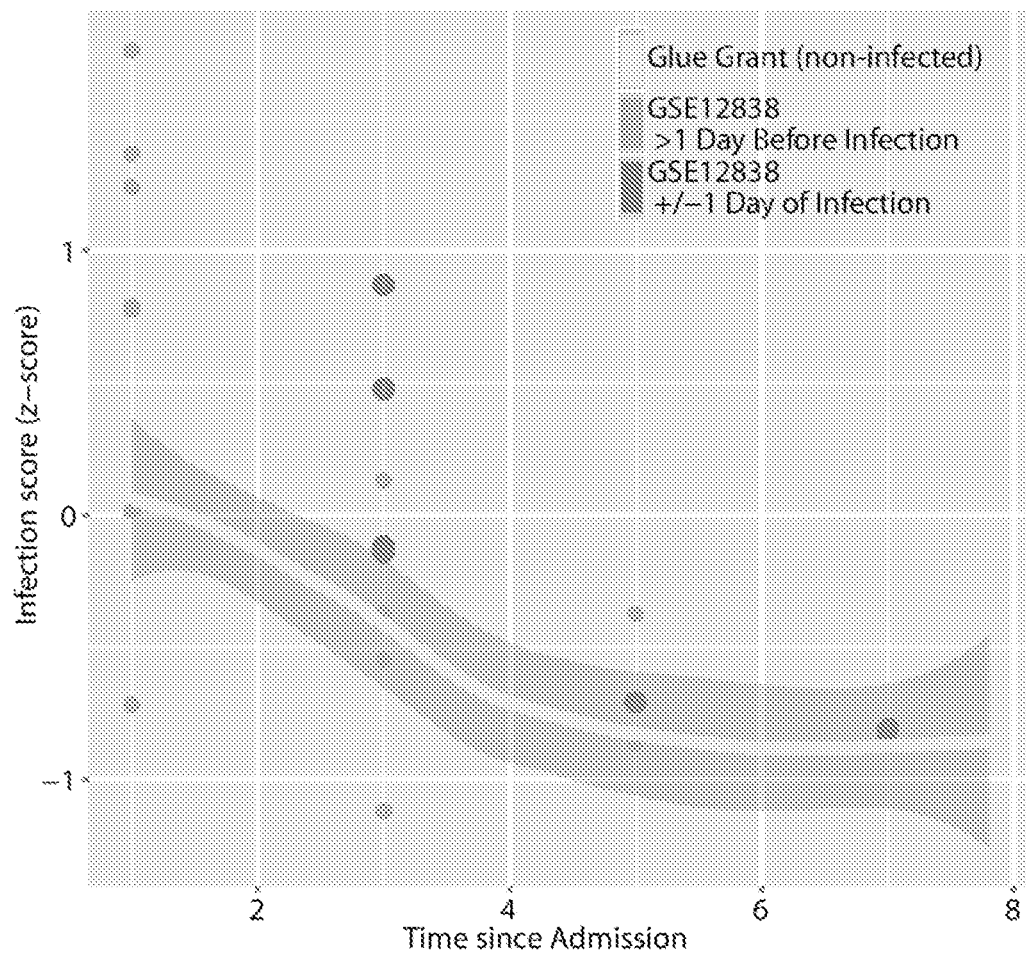
Figure 4D:
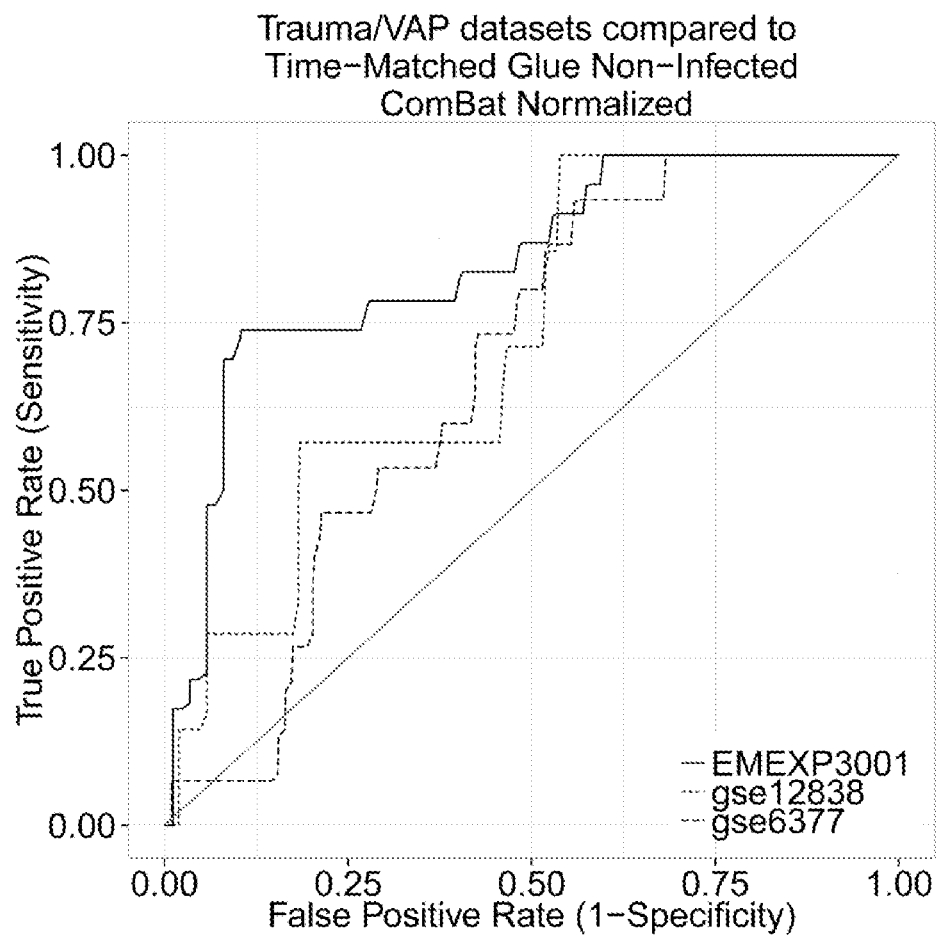
Figure 10B:
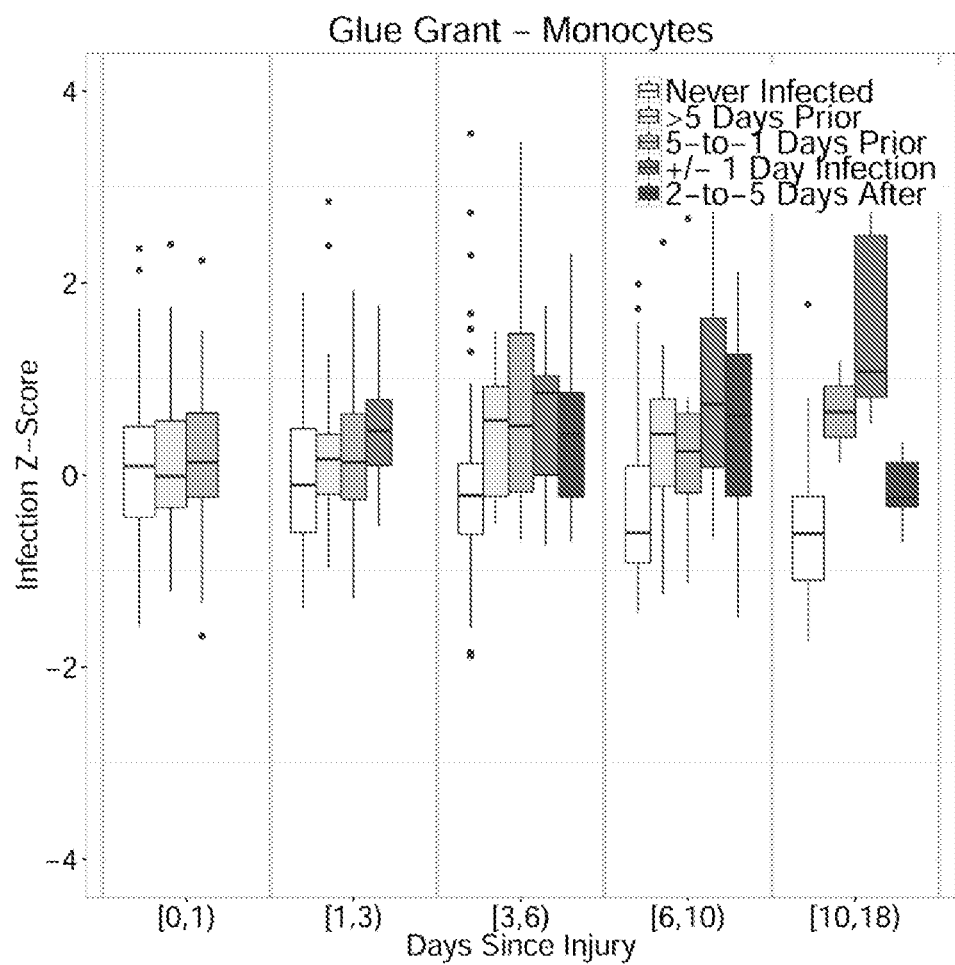
Figure 11B:
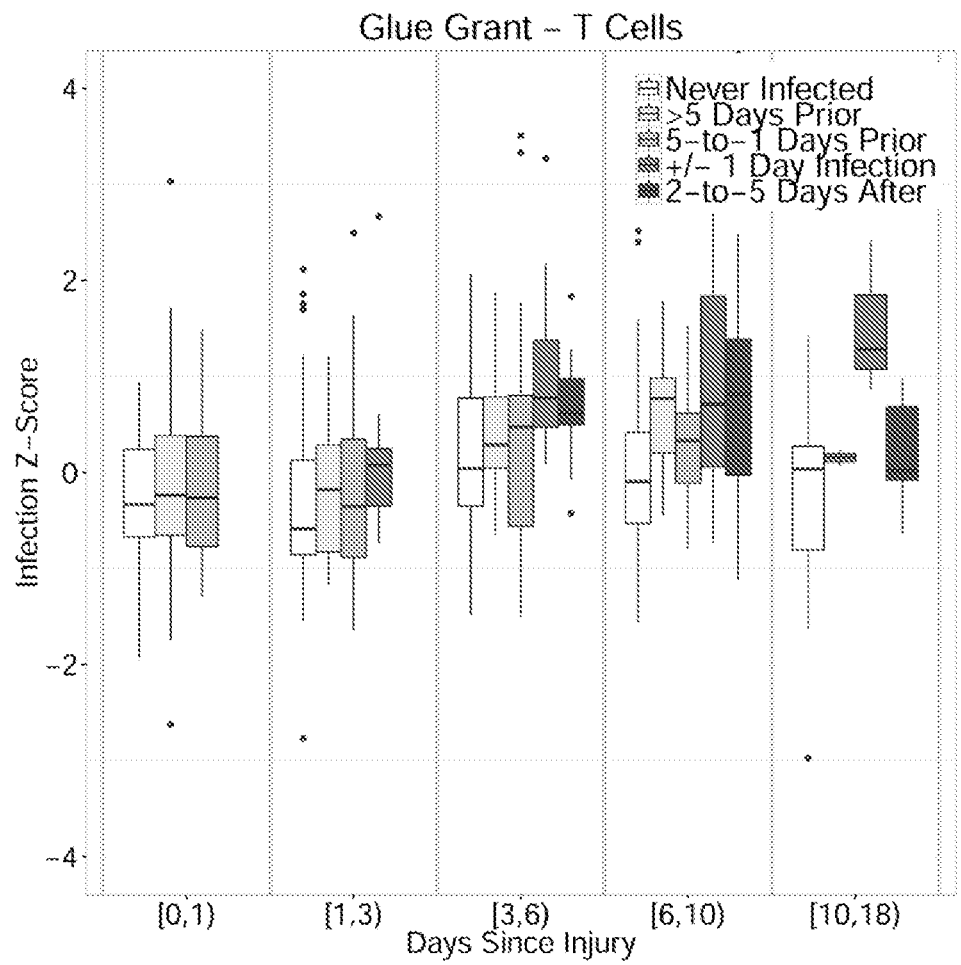

Next, we analyzed how infection Z-scores changed in infected patients before and after diagnosis of infection (samples that were not included in identifying the 11-gene set). We grouped the samples from patients who were ever diagnosed with infection on the same hospital stay into four groups according to their time from diagnosis of infection (either greater than 5 days prior to infection, 5-to-1days prior to infection, within +/−1 day of diagnosis of infection, or 2-to-5 days after diagnosis of infection, where no group besides the +/−1 day of diagnosis of infection was included in the multi-cohort analysis for discovery of the 11-gene set). We further divided these groups into bins according to days since injury. Within each time-bin, the infection Z-scores for the diagnostic groups increased significantly as they progressed towards infection for both the discovery buffy coat cohort and the validation neutrophils cohort (Jonckheere trend (JT) test $p<0.01$; FIGS. 3E-3F). Furthermore, in all cohorts, the infection Z-score declined in the groups that were 2-5 days after infection diagnosis, when patients were beginning to recover from infection, presumably due to antibiotic treatment. This may also explain the increase in diagnostic power as time increases since initial injury. We emphasize that the resulting 'peak' in infection Z-score around the time of infection diagnosis validates the association of the infection Z-score with clinical infection, because neither the >5 days prior cohorts, the 1-5 days prior cohorts, nor the 2-5 after cohorts were included in the multi-cohort analysis, but still show the hypothesized trends in both the discovery buffy coat cohort and the validation neutrophils cohort. Similar results were seen in the monocytes and T-cells samples (same patients as the neutrophils validation cohorts; FIGS. 10B, 11B).

Interestingly, the infection Z-scores for patients that were later infected during their hospital stays were significantly higher in buffy coat samples at the time of admission than the patients never infected during their hospital admission ($p<0.01$; neutrophils validation group $p=0.05$; FIGS. 3E-3F). One possibility is that there was a baseline difference in injury severity, and that this might influence the infection Z-score. Severely injured patients are known to be more susceptible to infection (Osborn et al. (2004) Crit Care Med 32:2234-2240). In order to test this hypothesis, we used linear regression of eventual hospital-acquired infection status, injury severity score, and their interaction to predict infection Z-score as the independent variable (Table 9B). Both eventual hospital-acquired infection status and injury severity score were independently significant in predicting infection Z-score at admission, indicating that injury severity alone does not explain these effects. The interaction term was significant and negative in both the discovery buffy coat cohort and the validation neutrophils cohort samples, perhaps suggesting that higher infection Z-score at admission may indicate greater susceptibility to later infection. Further studies are needed to examine this observation.

Clinical Utility in the Glue Grant

Figure 12A:
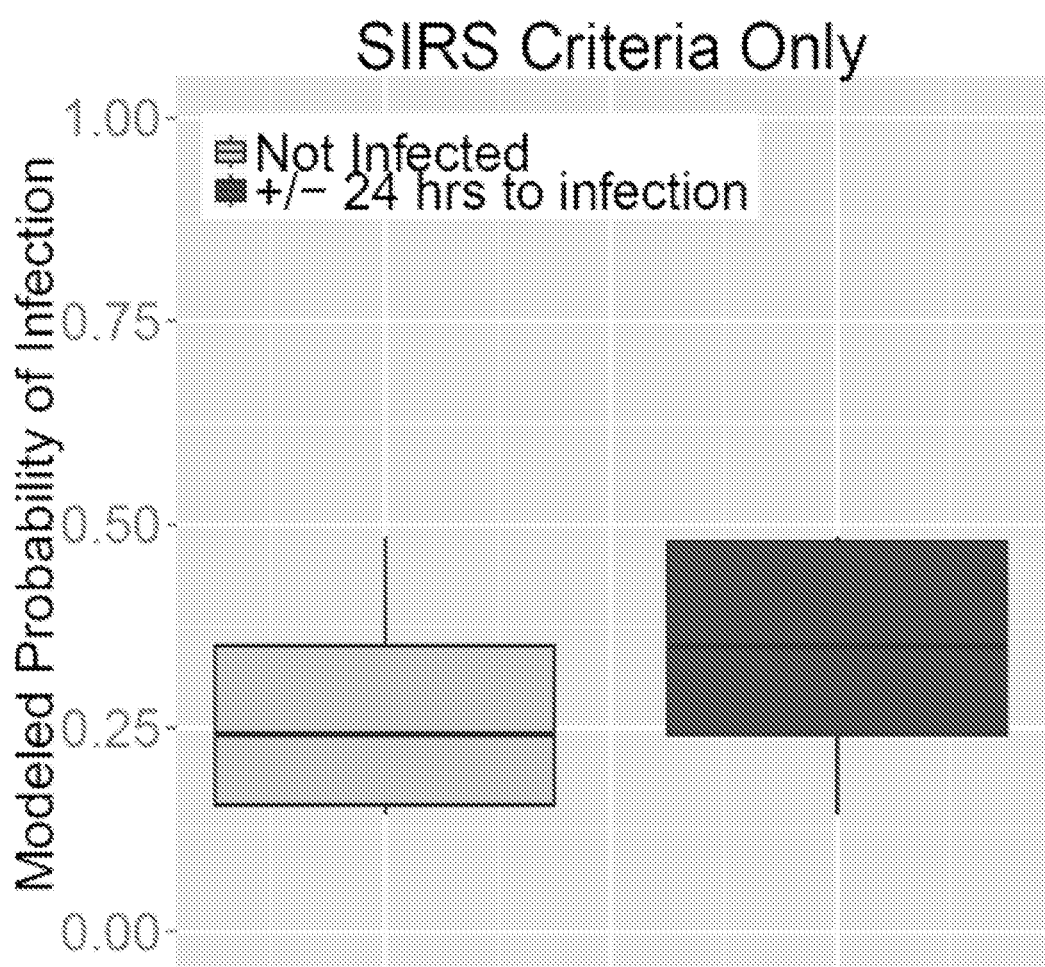
FIGS. 12A and 12B show linear models of SIRS criteria and the infection Z-score.
Figure 12B:
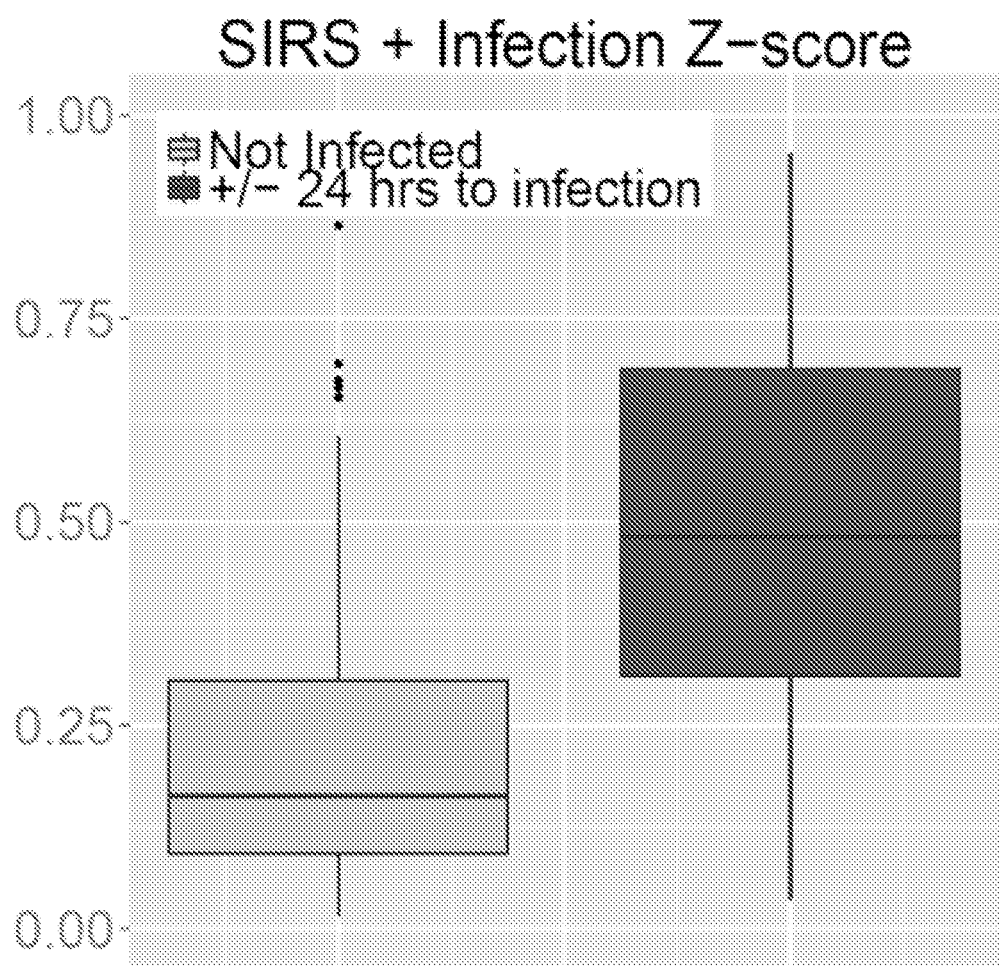
Figure 13A:
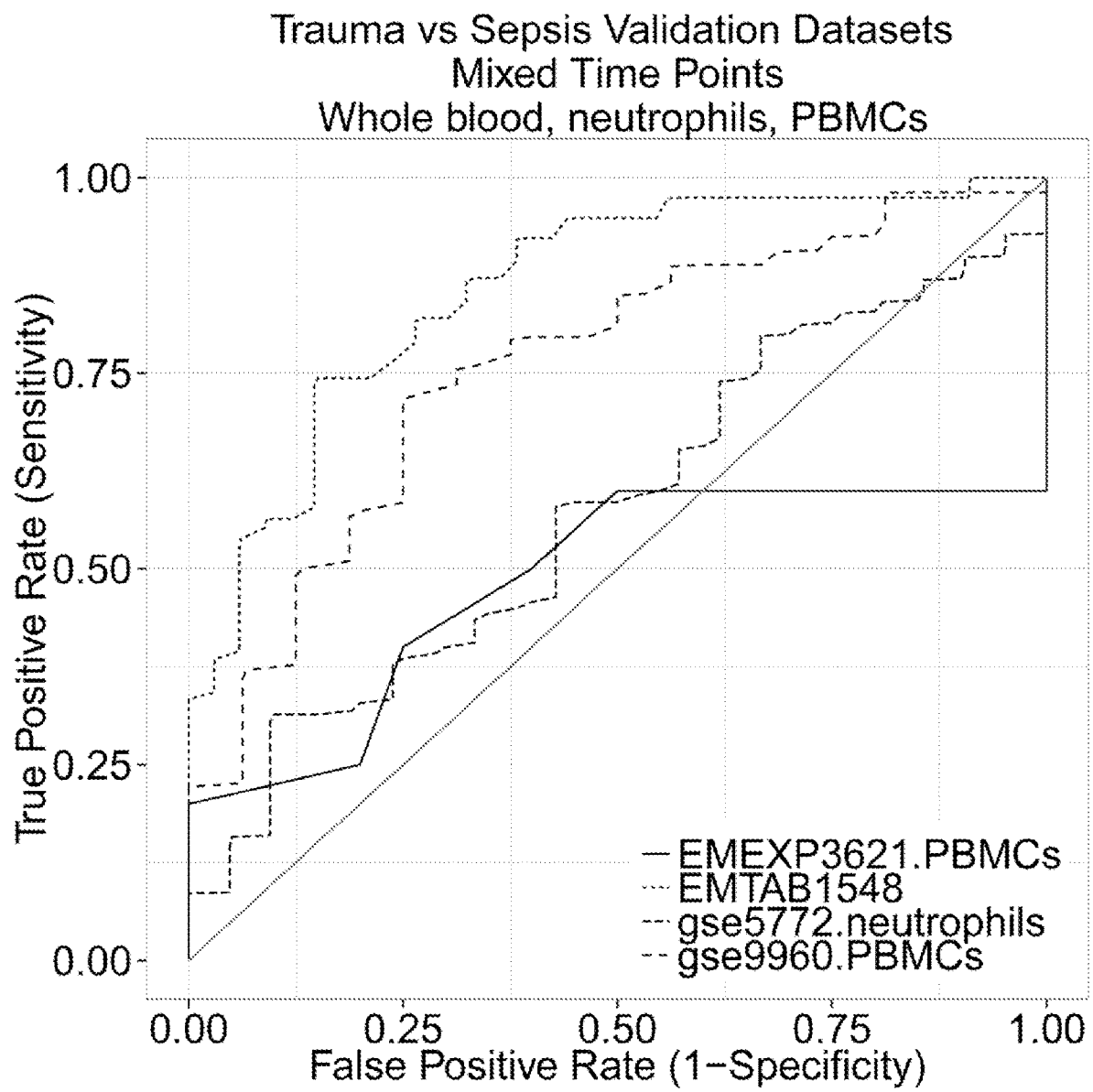
FIG. 13A shows the infection Z-score in non-time-matched datasets. Four datasets compared SIRS/ICU/trauma patients to sepsis patients at non-matched time points. These datasets tested neutrophils (GSE5772, N=93), whole blood (EMTAB1548, N=73), and PBMCs (GSE9960, N=30; EMEXP3621, N=10). See Table 7 for further dataset details.
Figure 13B:
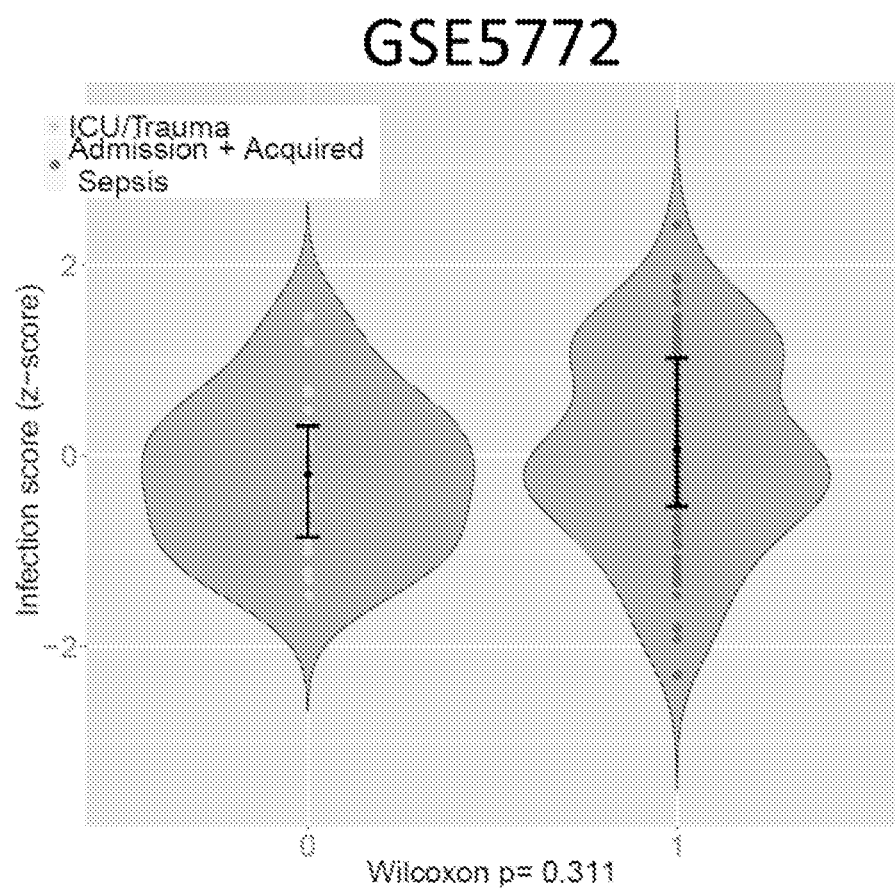
FIGS. 13B-13E show infection Z-scores in non-time-matched datasets. Violin plots are shown for the non-matched time-point datasets including GSE5772 (FIG. 13B), GSE9960 (FIG. 13C), EMTAB1548 (FIG. 13D), and EMEXP3621 (FIG. 13E). Error bars show middle quartiles. Tested with Wilcoxon rank-sum test.
Figure 13C:
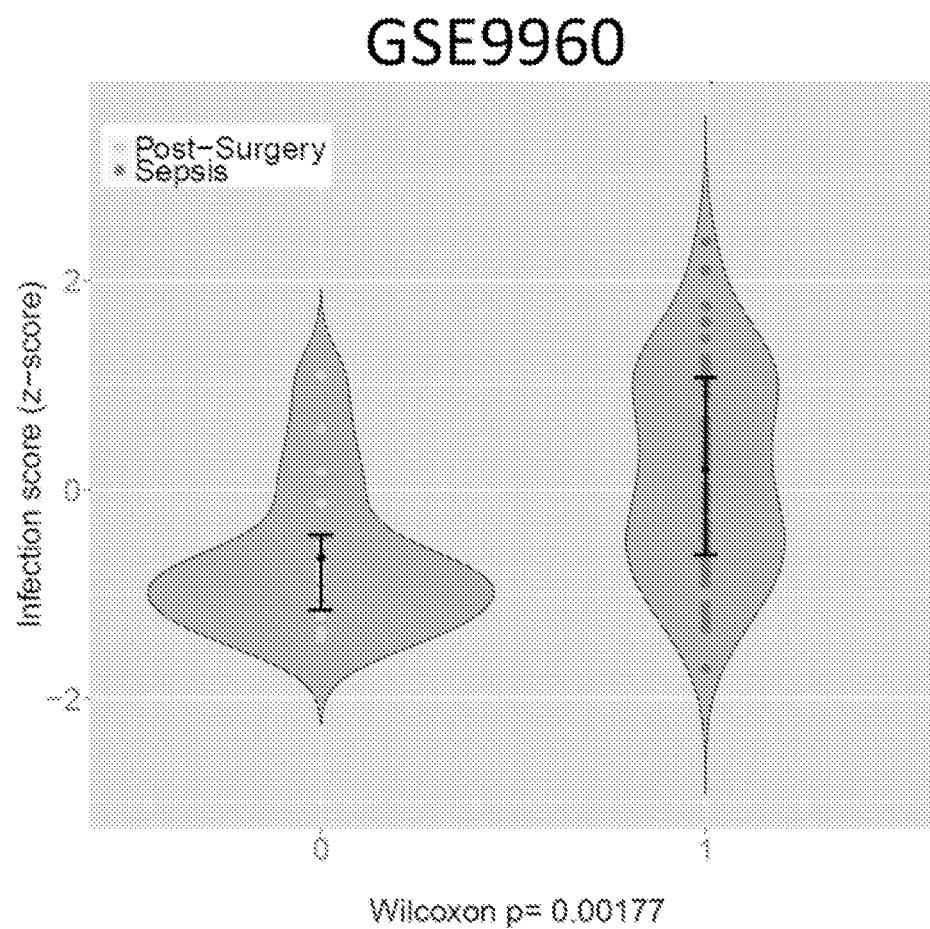
Figure 13D:
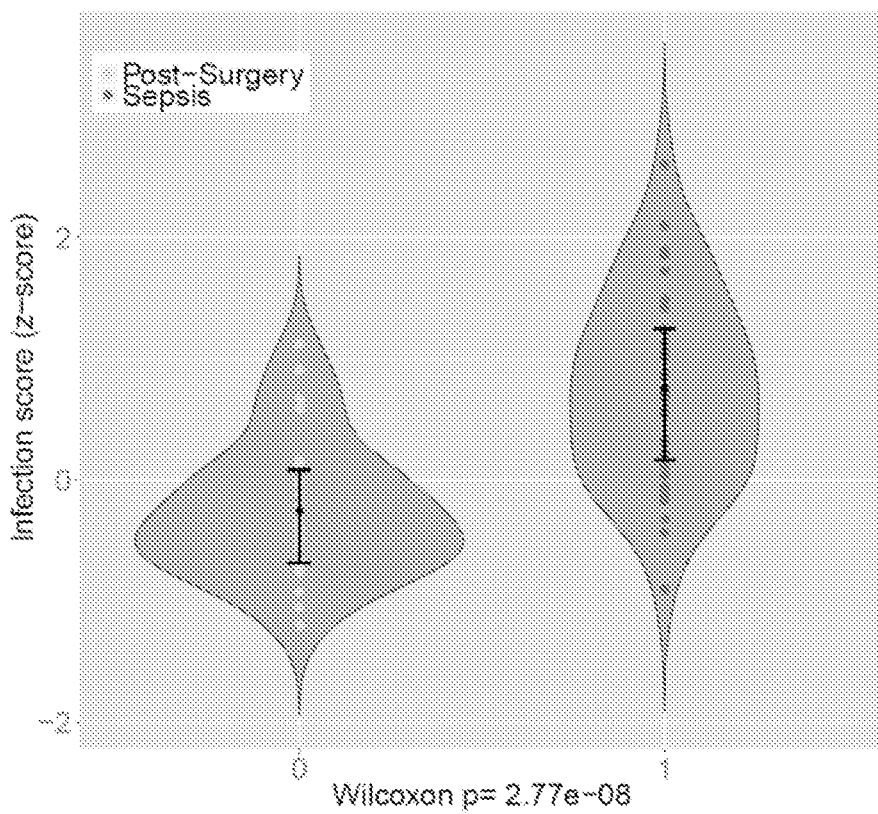
Figure 13E:
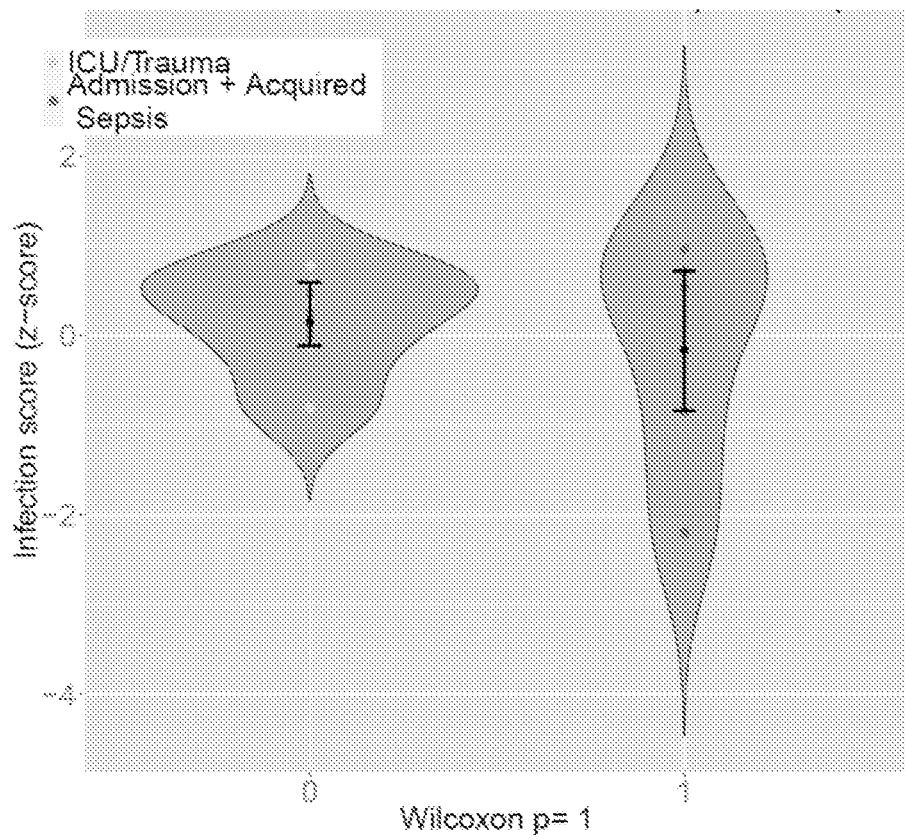

To test whether the infection Z-score might add to clinical determinations of infection, we compared logistic regression using SIRS criteria alone to that using SIRS criteria plus our infection Z-score in discriminating Glue Grant trauma patients (both buffy coat and neutrophils cohorts) with and without infection. The logistic regression model using SIRS criteria alone had an AUC of 0.64, while SIRS criteria plus the infection Z-score had an overall AUC (using a single coefficient for infections at all time-points) of 0.81 (FIG. 12). The continuous net reclassification index (NRI) is a measure of how many patients would be correctly re-classified by improving a disease marker; here the continuous NRI of adding the infection Z-score to SIRS alone was 0.90 (95% CI 0.62-1.17), where a continuous NRI greater than 0.6 is associated with 'strong' improvement in prediction (Pencina et al. (2012) Stat Med 31:101-113).

Independent Validation of the Infection Z-Score

Next, we validated our score in three independent longitudinal cohorts that included only trauma or ICU patients that eventually acquired infections: GSE6377 (McDunn et al., supra), GSE12838, and EMEXP3001 (Martin-Loeches et al., supra) (Table 4). All three cohorts followed patients from the day of admission to at least through the day of infection diagnosis (mostly ventilator-associated pneumonia, VAP). Because all patients in each of the three cohorts acquired infections, they did not have time-matched non-infected controls. To compare the validation cohort infection cases with non-infected trauma patients, we used Glue Grant buffy coat non-infected controls. We internally normalized each cohort using housekeeping genes, and then co-normalized with the Glue Grant buffy coat patients using empiric-Bayes batch correction. Then, we compared the validation cohorts to the Glue Grant non-infected patients at matched time-points as a variable reference. Comparing trauma/ICU patients to a time-matched baseline is necessary because our earlier findings (FIGS. 3C-3F) showed a change over time in infection Z-score in the non-infected patients (Table 9A). The three independent longitudinal trauma/ICU cohorts show that patients within +/−1 day of infection are generally separable from time-matched non-infected Glue Grant patients, with ROC AUCs ranging from 0.68-0.84 (FIG. 4).

Figure 5A:
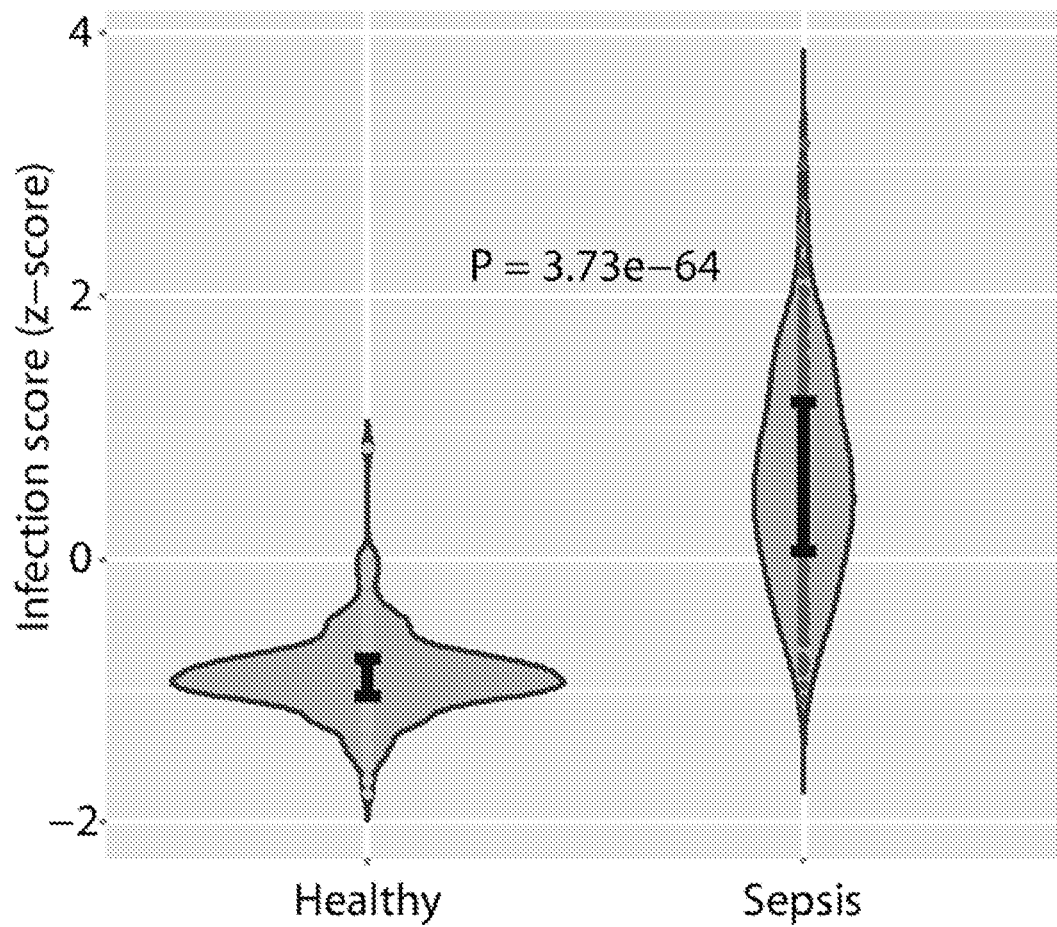
FIGS. 5A and 5B show discrimination of healthy versus sepsis patients. Eight independent validation datasets that met inclusion criteria (peripheral whole blood or neutrophils, sampled within 48 hours of sepsis diagnosis) were tested with the infection Z-score.
Figure 5B:
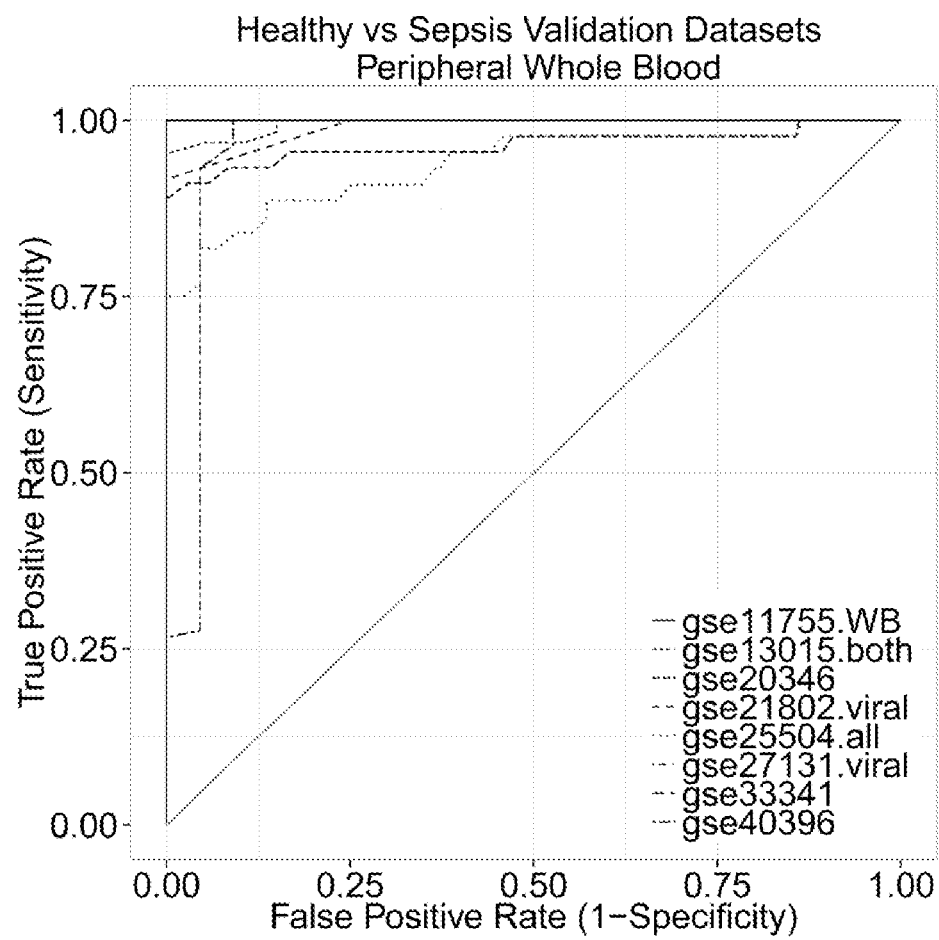

We further validated the 11-gene set in 8 additional independent datasets that compared healthy patients to those with bacterial or viral sepsis at admission using whole blood samples (total N=446: GSE11755 (Emonts et al., supra), GSE13015 (Pankla et al., supra), GSE20346 (Parnell et al., supra), GSE21802 (Bermejo-Martin et al., supra), GSE25504 (Smith et al. (2014) Nat Commun 5:4649), GSE27131 (Berdal et al., supra), GSE33341 (Ahn et al., supra), and GSE40396 (Hu et al., supra), Table 5). The infection Z-scores for all 8 datasets were combined in a single violin plot, showing excellent separation (Wilcoxon p<1e-63, FIG. 5A). The mean ROC for separating healthy and septic patients is 0.98 (range: 0.94-1.0, FIG. 5B).

Our results provide strong evidence that the infection Z-score declines over time since admission/injury in whole blood, buffy coat, neutrophils, and monocytes. We have also shown that non-time-matched comparison yields inaccurate classification of infection, especially for late acquired infections in SIRS/trauma patients. Hence, comparing infection Z-scores of SIRS/trauma patients at admission with those of late-acquired sepsis/infection patients would be an inaccurate measure of diagnostic power. However, because the effect of the decrease in infection Z-score over time is relatively monotonous, comparison of admission SIRS/trauma/surgery patients with late-acquired sepsis/infection would provide a lower limit on detection ROC AUC for the infection Z-scores. In other words, because the infection Z-score decreases over time, if the non-infected patients tested at admission had been sampled later (at matched times to the sepsis patients), their infection Z-scores would be lower at that later time (and hence more easily separable from the higher infection Z-scores in the septic patients). Using this inference, we examined four independent datasets that compared SIRS/trauma/surgery patients either to the same patients later in their hospital course at onset of sepsis, or to a mixed cohort of patients with community-acquired and hospital-acquired sepsis. These datasets studied whole blood (EMTAB1548 (Almansa et al., supra)), neutrophils (GSE5772 (Tang et al. (2007), supra)), and PBMCs (GSE9960 (Tang et al. (2009), supra)); EMEXP3621(Vassiliou et al. (2013) Crit Care 17:R199)) (Table 6). In each of these four datasets, the infection Z-score separated late acquired infections from admission SIRS or trauma, with ROC AUCs ranging from 0.48-0.76 in PBMCs to 0.86 in whole blood (FIG. 13). We emphasize that these AUCs are expected to be lower due to their time-mismatched comparison, and are essentially the lower limits of what properly time-matched infection Z-scores would be in each of these cell compartments.

Figure 14A:
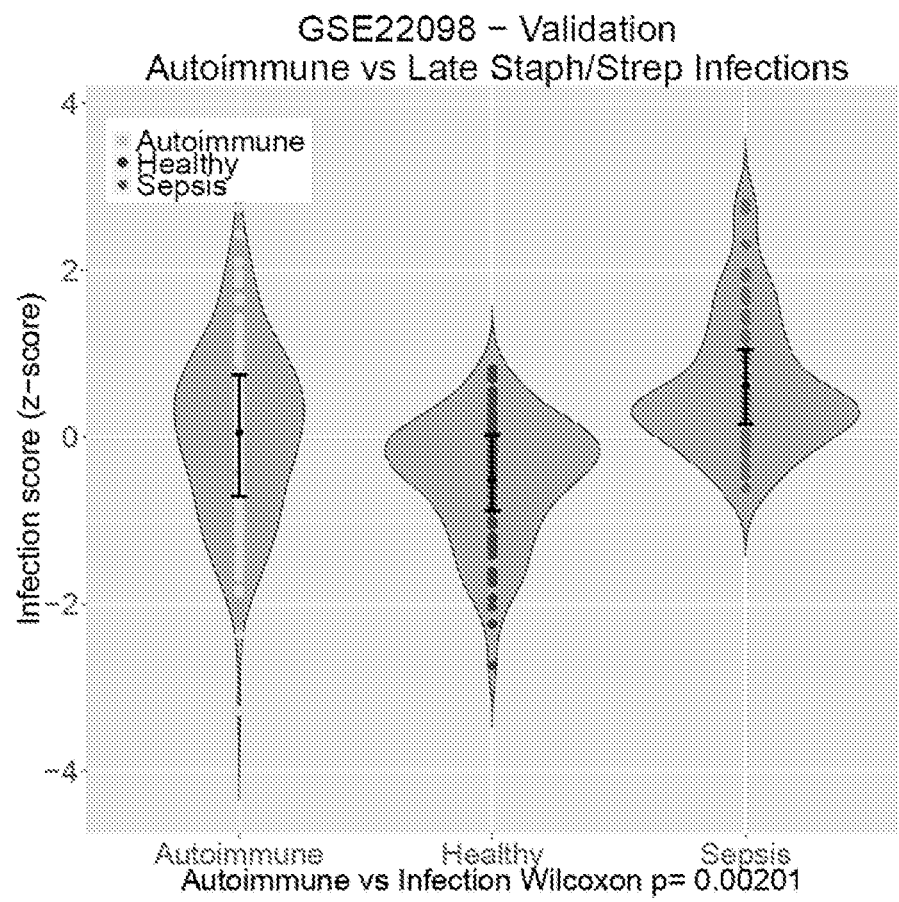
FIGS. 14A and 14B show a comparison of the infection Z-scores in patients with acute infections to healthy controls and patients with autoimmune diseases. GSE22098 compares healthy controls to patients with acute autoimmune inflammation or acute infections. The infection Z-score shows good discrimination of infection from both healthy patients and those with autoimmune inflammation.
Figure 14B:
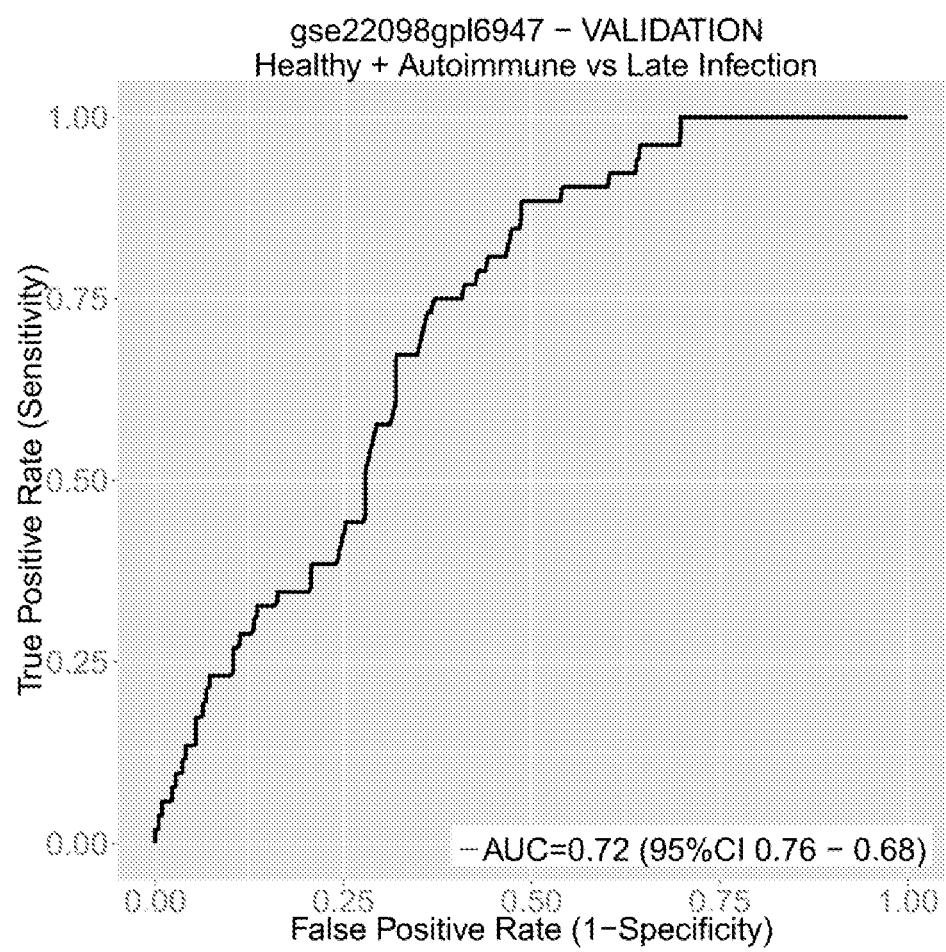

Finally, we examined our 11-gene set in one dataset comparing healthy patients or those with autoimmune inflammation to acute bacterial infections after diagnosis confirmation (GSE22098, n=274) (Berry et al., supra; Allantaz et al. (2007) J Exp Med 204:2131-2144). Exact sampling times are not available, but typically confirmation of infection take 24-72 hours, so these infection samples are expected to show lower Z-scores than at the time of diagnosis. Still, the infection Z-score is able to discriminate healthy and autoimmune inflammation patients from those with acute infections (ROC AUC 0.72; FIG. 14). Considering that cohorts studying autoimmune inflammation were not included in our discovery, this provides validation of the specificity of the infection Z-score for infectious inflammation.

The Effect of Infection Type on Infection Z-Score

In order to examine whether there were any infection-type-specific differences in the infection Z-score, we compared patients infected with Gram positive vs. Gram negative bacteria, as well as those infected with viral infections to those with bacterial infections. The Glue Grant patients were not analyzed as there were too few time-matched infection patients in each sub-cohort. Four datasets had information on Gram positive versus Gram negative infection, and four had data on bacterial vs viral infections; in neither case was there a clear trend of differences in infection Z-score based on infection subtype (Table 10).

Gene Set Pathway Evaluation and Transcription Factor Analysis

Having validated the 11-gene set, we examined whether any mechanism might explain why these genes were acting in concert. We analyzed the 11-gene set with Ingenuity Pathway Analysis, which showed that several of the genes are under control by IL-6 and JUN (FIG. 16). All 11 genes identified by the multi-cohort analysis were loaded into both EncodeQT and PASTAA (chosen for a mix of experimental results and in silico transcription factor predictions). EncodeQT found only one significant transcription factor among the 6 positive genes (Max), and none for the negative genes (EncodeQT Q-value≤0.01, Table 10A). PASTAA showed enrichment for well-known pro-inflammatory transcription factors, such as Nf-KB member c-Rel, Stat5, and Interferon Response Factors (IRFs) 1 and 10 (Table 10B). However, since these two methods for transcription factor analysis did not agree on an enriched set of factors, no obvious conclusions can be drawn.

Figure 6A:
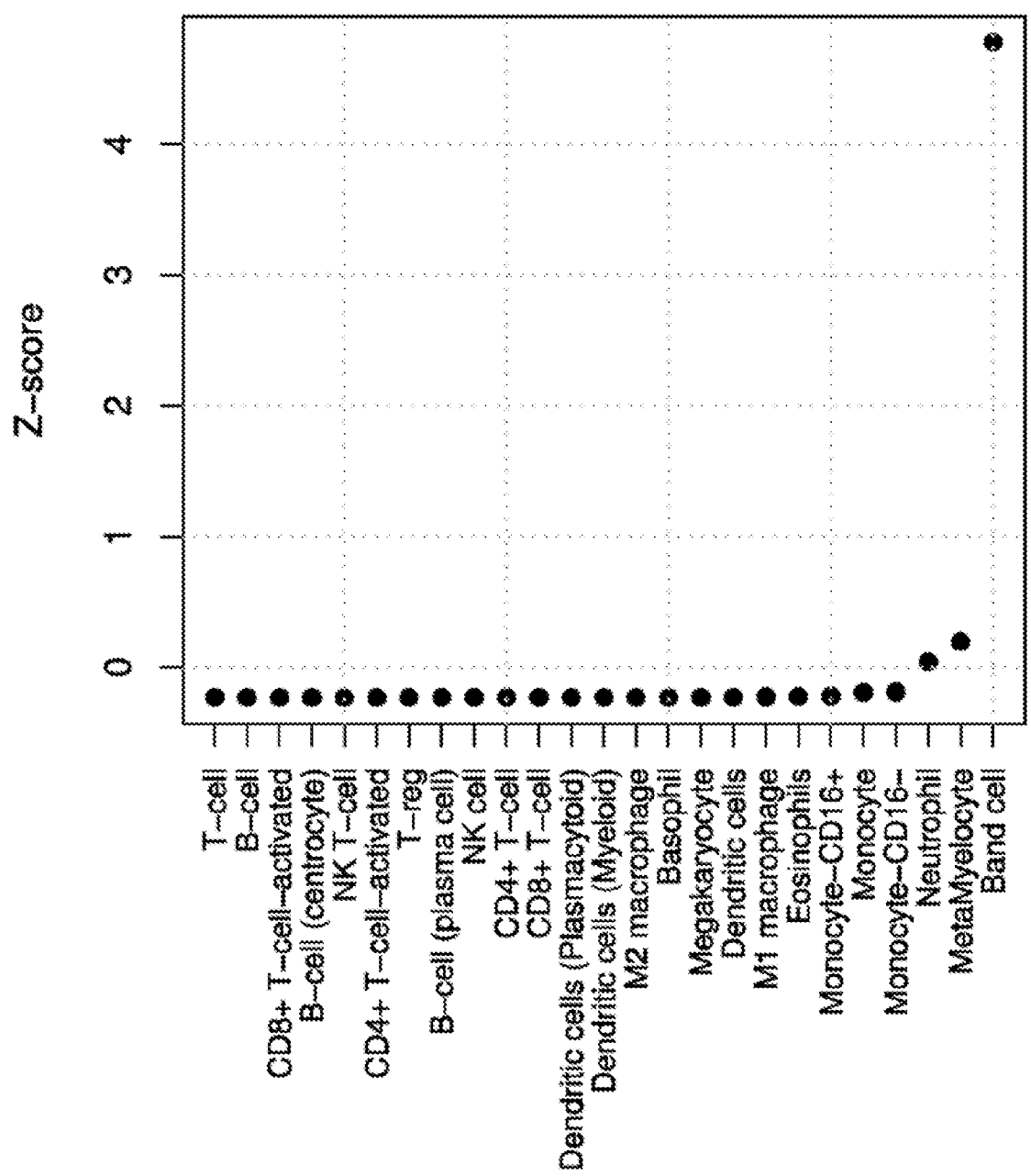
FIGS. 6A and 6B show cell-type enrichment analyses. Shown are standardized enrichment scores (Z-scores, black dots) for human immune cell types for both (FIG. 6A) the entire set of 82 genes found to be significant in multi-cohort analysis, and (FIG. 6B) the 11-gene set found after forward search (subset of the 82 genes).
Figure 6B:
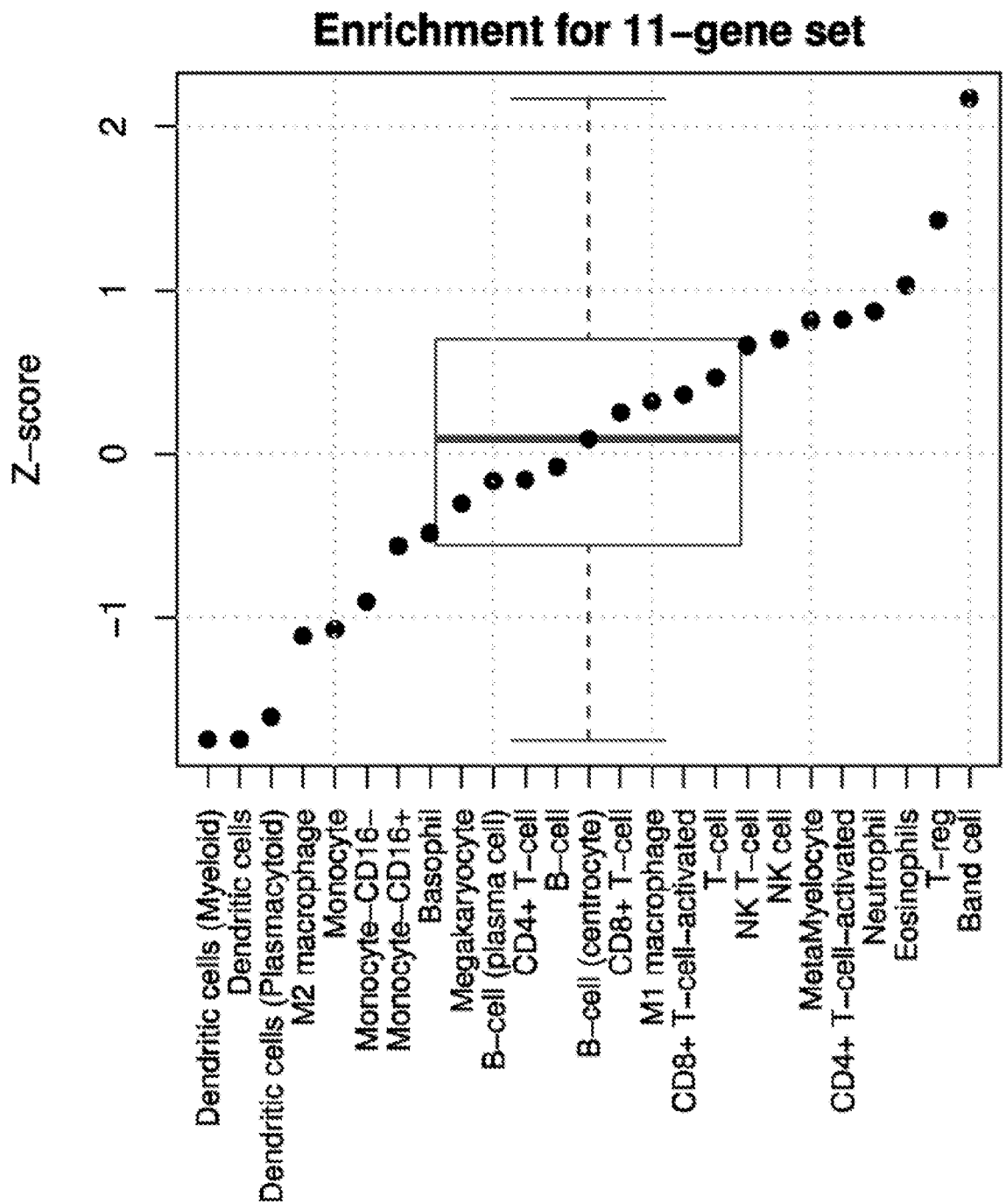

Since there was no obvious network driver found, we next studied whether the genes were enriched in certain immune cell types that might explain their relation to sepsis. We searched GEO for human immune-cell-type-specific gene expression profiles, and found 277 samples from 18 datasets matching our criteria. We aggregated these into broad immune cell type signatures using mean gene expression scores. We then calculated standardized enrichment scores using the same method as the Infection Z-score (difference of geometric means between positive and negative genes). We did this both for the initial set of 82 genes found to be significantly enriched in the multi-cohort analysis, and for the 11-gene set found after forward search (the genes that make the Infection Z-score) (FIG. 6). The set of all 82 significant genes was found to be highly enriched in band cells only (>4 standard deviations above the mean, p<1e-6). Interestingly, the 11-gene set was significantly enriched for band cells (>2 standard deviations above the mean, p=0.015) in band cells but also showed up-regulation in T-regulatory cells and down-regulation in dendritic cells. This suggests that one driving force in differential gene expression between sterile SIRS and sepsis is the presence of band cells; however, the best set of genes for diagnosis contains information possibly incorporating multiple cell-type shifts at once.

Discussion

The changes in gene expression after trauma and during sepsis have been described as a 'genomic storm' (Xiao et al. (2011) J Exp Med 208:2581-2590). The dozens of studies that we examined here have reported valuable insights into changes in gene expression that occur in response to SIRS, trauma, surgery, and sepsis; however, none of the prior single-study analyses has yet produced a common-use clinical tool to reduce the morbidity and mortality associated with sepsis. We used an integrated, multi-cohort analysis, based on a growing understanding of the time-dependent changes in gene expression, to distinguish gene expression in SIRS/trauma from that in sepsis. From this we found an 11-gene set that is optimized for diagnostic capability, which we validated in 15 independent cohorts. With further prospective clinical validation, this 11-gene set could assist with clinical sepsis diagnosis, which could, in turn, have a major impact on patient care.

Both infectious and non-infectious inflammation can lead to SIRS through activation of the same innate immune pathways (TLRs, RLRs, NLRs, etc.), so the 'typical' pro-inflammatory genes and cytokines (such as TNF and the interleukins) are generally expressed in both sterile and infectious inflammation (Newton et al. (2012) Cold Spring Harb Perspect Biol 4). For instance, one recent study showed high correlation in gene expression between sterile inflammation (Glue Grant burns cohort) and four independent sepsis datasets, with as much as 93% of the genes changing in the same direction in the two conditions (Seok et al. (2013) Proc Natl Acad Sci USA 110:3507-3512). Thus, a standard hypothesis-driven approach in the search of biomarkers specifically differentially expressed between sterile SIRS and sepsis is unlikely to succeed, given that the 'standard' suite of cytokines and chemokines known to be expressed in sepsis are mostly also activated in sterile SIRS. However, several protein families such as the lectins and CEACAMs have been shown to have specificity only for pathogen-associated molecular patterns, thus giving rise to the possibility of infection-specific innate immune signaling pathways (Geijtenbeek et al. (2009) Nat Rev Immunol 9:465-479; Crocker et al. (2007) Nat Rev Immunol 7:255-266; Kuespert et al. (2006) Curr Opin Cell Biol 18:565-571). We thus took a data-driven, unbiased approach searching specifically for genes that are homogeneously statistically differentially expressed between sterile SIRS/trauma patients and sepsis patients across multiple cohorts.

We systematically identified all publically available microarray-based genome-wide expression studies in SIRS, trauma, critical illness, acute infections, and sepsis, and sorted through all datasets to identify those that compared non-infected SIRS, ICU, or trauma patients to patients with acute infections or sepsis. Time post-injury is known to be an important factor in gene expression after trauma (Xiao et al., supra; Seok et al., supra; Desai et al., supra; McDunn et al., supra). Across multiple independent cohorts, we showed that changes in gene expression over time are non-linear but follow a similar trajectory. Furthermore, the normal recovery from trauma induces large changes in gene expression over time. Therefore, a comparison of gene expression at or near the time of injury with a later time point in the same patient (such as at time of diagnosis of infection) will yield a large number of differentially expressed genes solely due to the recovery process. It is thus very difficult to identify relatively small changes in gene expression due to infection from the large changes caused by recovery. Therefore, we restricted our discovery cohorts to only those studies that compared SIRS/trauma and sepsis/infection patients at matched time points. However, unlike trauma or surgery, sepsis has no easily defined 'start', since infections take time to manifest. We thus used as cases patients within 48 hours of admission for sepsis or within +/−24 hours from diagnosis of infection, as these are the times at which infectious signs and symptoms are present, and a clinical diagnosis is necessary. We used a multi-cohort analysis approach (Khatri et al. (2013) J Exp Med 210:2205-2221; Chen et al. (2014) Cancer Res 74:2892-2902) to compare SIRS/trauma and sepsis/infection patients in a time-matched manner, including 663 samples from 9 patient cohorts. We then used a forward search, optimizing a sample size-weighted ROC AUC, to select a parsimonious set of statistically significant genes (FDR<1%, absolute summary effect size>1.5 fold) optimized for discriminatory power. An infection Z-score, defined as the geometric mean of the 11-gene set, had a mean ROC AUC of 0.87 in the discovery cohorts for distinguishing SIRS/trauma from sepsis/infection patients.

We validated this gene set in an independent group of patients from the Glue Grant. The mean AUC for distinguishing sepsis from non-infectious inflammation was 0.83 in the neutrophils validation cohort, with a clear trend towards better diagnostic power with greater time since initial injury. Although we expect the whole-blood transcriptional profiles to be largely driven by neutrophils, the signal in sorted cells will certainly differ from whole blood. Thus, use of sorted cells instead of whole blood for diagnosis is expected to result in lower discriminatory power. Despite this limitation, the infection Z-scores performed comparably in validation cohorts, especially at three or more days since initial injury, when initial traumatic inflammation wanes and hospital-acquired infections manifest (Hietbrink et al. (2013) Shock 40:21-27).

Using the extensive clinical phenotype data available for patients in the Glue Grant, we illustrated several important points about the application of the infection Z-score. First, the infection Z-score showed a decline over time since injury that was similar in both infected and non-infected patients. We also showed that using the time-variable non-infected baseline in the Glue Grant as reference thresholds allowed us to discriminate septic patients from non-infected trauma patients in three independent longitudinal cohorts with ROC AUCs ranging from 0.68-0.84. Thus, for maximal discriminatory power, if the infection Z-score were to be tested prospectively in a longitudinal study, the diagnostic thresholds would need to be a function of the time since initial injury. Second, the infection Z-scores increased over the days prior to infection, peaked within the +/−1 day surrounding the time of infection diagnosis, and decreased afterwards (presumably due to treatment of infection). This observation raises the possibility that earlier diagnosis or stratification of patients at risk of developing sepsis may be possible using the 11-gene set, although further studies are required. In particular, we note that the early rise in infection Z-score that precedes a clinical diagnosis of infection is not a false positive but an 'early positive' result. Finally, the infection Z-score was higher at admission in patients with higher injury severity score (ISS); initial infection Z-score thus depends on both ISS and relative time to clinical infection. However, trauma patients within 24 hours of admission are not usually suspected to have non-obvious infection (other than open wounds, peritoneal contamination, etc.), and so we would not expect the infection Z-score to be of clinical utility in this group anyway.

In the Glue Grant buffy coat cohort, for those patients who had all four SIRS markers available, SIRS binary parameters performed poorly in discriminating patients at time of infection from non-infected patients (ROC AUC 0.64). SIRS criteria plus the infection Z-score with a global cutoff (i.e., not broken into separate time-bins) increased the discriminatory power (ROC AUC 0.81), with a continuous NRI of 0.9. However, SIRS is only one of several criteria used to diagnose sepsis. Procalcitonin is a well-studied biomarker for differentiating sepsis from SIRS; two meta-analyses of procalcitonin both showed summary ROC AUCs of 0.78 (range 0.66-0.90) (Tang et al. (2007) Lancet Infect Dis 7:210-217; Uzzan et al. (2006) Crit Care Med 34:1996-2003; Cheval et al. (2000) Intensive Care Med 26 Suppl 2:S153-158; Ugarte et al. (1999) Crit Care Med 27:498-504). The average AUC in our discovery cohorts was 0.87, and the time-matched neutrophils validation cohort had a mean AUC of 0.83, both of which are thus at least comparable to procalcitonin. We emphasize, however, that each of these markers need not be used in isolation. None of the publically available datasets included procalcitonin levels at time of diagnosis of sepsis. Thus, any prospective study of the infection Z-score should include both traditional and new biomarkers, to test both for better diagnostic performance using biomarker combinations and for head-to-head comparisons.

We validated the infection Z-score in several additional external datasets, which included three longitudinal cohorts of ICU/trauma patients that developed VAP/VAT; eight cohorts of healthy patients compared to bacterial or viral sepsis; four cohorts of admission SIRS/trauma patients compared to patients at mixed or later time-points using whole blood, neutrophils, PBMCs; and one cohort of patients with autoimmune inflammation compared to patients with acute infection. The infection Z-score had discriminatory power in every publically available dataset that matched our inclusion criteria. Moreover, the infection Z-score does not have systematic trends with regard to infection type (Gram positive versus Gram negative and bacterial versus viral) across those datasets for which infection type information is available. We emphasize that, based on the finding that the baseline infection Z-score decreases over time since injury in the Glue Grant data, a comparison of admission SIRS/trauma to a later time-point in any of these compartments will have worse diagnostic power than would a time-matched study. Thus the discriminatory power of the infection Z-score in the four independent non-time-matched cohorts may be a lower bound on the true discriminatory power in the respective blood compartments.

Some of the genes in the sepsis-specific 11-gene set have been previously associated with sepsis or infections, such as CEACAM1, C3AR1, GNA15 and HLA-DPB1 (Madsen-Bouterse et al. (2010) Am J Reprod Immunol 63:73-92; Wong et al. (2012) Crit Care 16:R213; Kwan et al. (2013) PLoS One 8:e60501). The regulatory control of these genes may be enriched for pro-inflammatory factors such as IL-6, JUN, c-Rel, Stat5, and IRF 1/10 based on in silico analyses, but no single common factor explained the network. The gene sets found here may be better explained by cell-type enrichment analyses. We show that band cells and the myeloid cell line are highly enriched for the whole set of 82 genes found to be significantly differentially expressed between sterile SIRS and sepsis. The finding of enrichment in band cells is particularly intriguing, as bands have previously been shown to help differentiate sterile SIRS and sepsis (Cavallazzi et al. (2010) J Intensive Care Med 25:353-357; Drifte et al. (2013) Crit Care Med 41:820-832). Further, there is very high variability in band counts both by automatic blood counters and by hand (Cornbleet et al. (2002) Clin Lab Med 22:101-136; van der Meer et al. (2006) Eur J Haematol 76:251-254), and no good serum marker exists. However, the 11-gene set may be better at distinguishing sepsis from sterile SIRS at least in part because it also includes information on increased T-regulatory cells and decreased dendritic cells, both of which have previously been implicated in sepsis (Saito et al. (2008) Tohoku J Exp Med 216:61-68; Venet et al. (2008) J Leukoc Biol 83:523-535; Grimaldi et al. (2011) Intensive Care Med 37:1438-1446). The connection between the 11-gene set and different immune cell types may help explain some sepsis biology, but certainly these 11 genes require further study.

The potential translation of the current study to clinical use rests on two factors. First, both the 11-gene set and the protein products of these genes will need to be tested prospectively in a time-matched manner. Protein assays currently have a faster response time than PCRs, though a number of advances in PCR technology have brought time to results down towards the range of clinical applicability (Park et al. (2011) Biotechnol Adv 29:830-839; Poritz et al. (2011) PLoS One 6, e26047). Second, our results showed that the changes in gene expression due to normal recovery from a traumatic event (such as injury or surgery) mean that time must be properly accounted for in any gene expression study of acute illness. Our search found several studies that examine time course after SIRS/trauma (GSE6377, GSE12838, GSE40012, EMEXP3001) and several that examine the time course since onset of sepsis/infection (GSE20346, GSE2713, GSE40012, EMEXP3850). However, we found only one publically available microarray study (the Glue Grant) that examined a cohort of patients over time for which some of the cohort develops infection and some do not. Thus, based on our results, we recommend that future studies of sepsis diagnostics should be designed with longitudinal cohorts both with and without infection, to enable appropriate time-matched comparisons (Johnson et al. (2007) Ann Surg 245:611-621; Maslove et al. (2014) Trends Mol Med. 20(4):204-213).

Overall, our comprehensive analysis of publically available gene expression data in SIRS/trauma and sepsis has yielded a parsimonious 11-gene set with excellent discriminatory power in both the discovery cohorts and in 15 independent cohorts. Optimizing a clinical assay for this gene set to get results within a window of clinical relevance should be feasible. Further study will be needed both to confirm our clinical findings in a prospective manner, and to investigate the molecular pathways upstream of these genes.

Methods

Study Design

The purpose of this study was to use an integrated multi-cohort meta-analysis framework to analyze multiple gene expression datasets to identify a set of genes that can separate patients with sterile inflammation from patients with infectious inflammation. This framework has been described previously (Khatri et al. (2013) J Exp Med 210: 2205-2221; Chen et al. (2014) Cancer Res 74:2892-2902).

Search

Two public gene expression microarray repositories (NIH GEO, ArrayExpress) were searched for all human datasets that matched any of the following search terms: sepsis, SIRS, trauma, shock, surgery, infection, pneumonia, critical, ICU, inflammatory, nosocomial. Datasets that compared either healthy controls or patients with non-infectious inflammation (SIRS, trauma, surgery, autoimmunity) to patients with acute infections and/or sepsis were kept for further study. Datasets that utilized endotoxin injection as a model for SIRS or sepsis were not included.

Multi-Cohort Analysis

A multi-cohort meta-analysis comparing gene expression in non-infected SIRS/trauma patients versus patients with infections or sepsis was completed. All datasets with comparisons of SIRS/trauma patients to septic/infected patients at the same time-point were selected for inclusion in the multi-cohort analysis; thus, comparisons of patients at admission to those with sepsis at a later time-point were excluded (see justification for this model in the Results). The admission datasets were limited to samples from patients within 48 hours of admission. The Glue Grant trauma datasets were split into time bins of days since injury, excluding the initial 24 hours after admission (see Supplemental Methods). Each of these time bins were treated as separate datasets in the multi-cohort analysis, where time-matched never-infected patients are compared to patients within +/−24 hours of diagnosis of infection (infection as defined above). Patients more than 24 hours after diagnosis of infection are thus censored in this comparison. This method allows for detection of deviation due to infection from the 'standard' changes in gene expression over time due to recovery from trauma.

Figure 15:
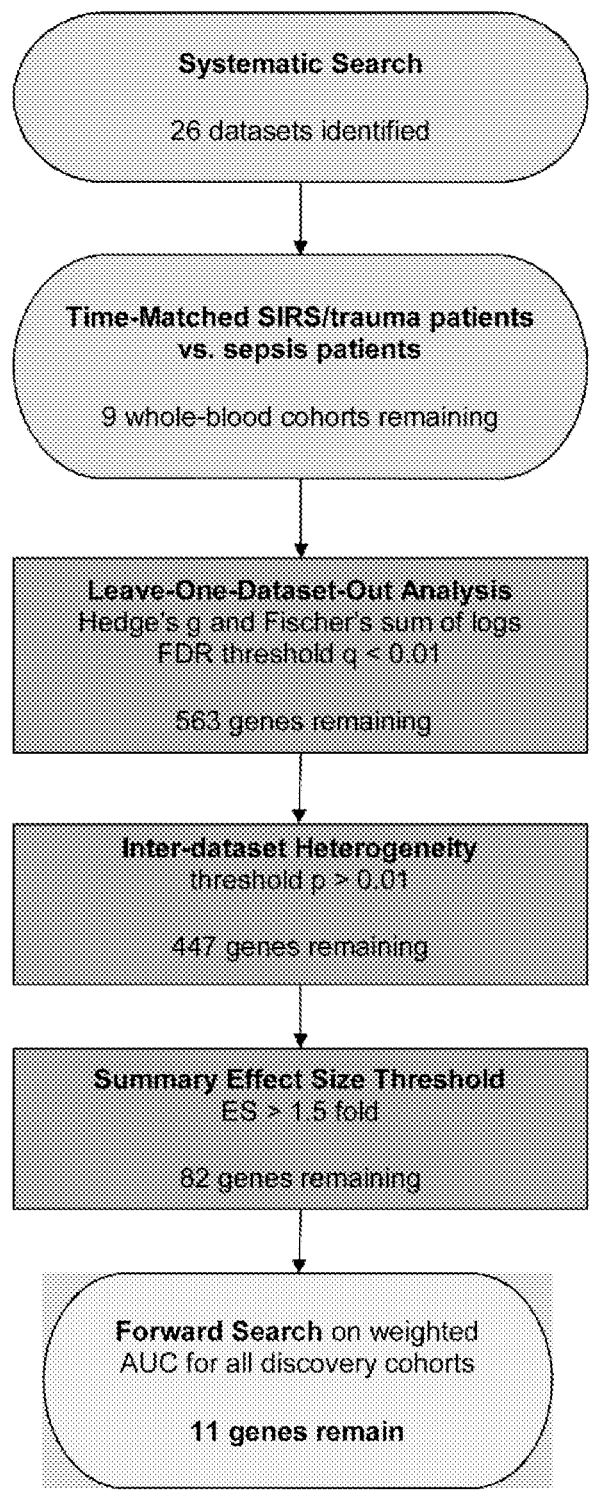
FIG. 15 shows a schematic of the entire integrated multi-cohort analysis.

After selecting the input datasets, we applied two meta-analysis methods; one combining effect sizes using Hedges' g; the other using Fisher's sum of logs method combining p-values (see schematic in FIG. 15). Given n datasets, this method is applied n times in a leave-one-dataset-out fashion. A false discovery rate (FDR) threshold was set (0.01), and genes with a q-value below the FDR threshold in both the effect size and the Fischer's sum of log analyses at every round of the leave-one-out analysis were selected. The genes were then subjected to a dataset heterogeneity test, such that in a test for heterogeneity across all input datasets, a p-value greater than 0.01 was required for each gene; this removes genes that show significantly different effects across different datasets. Next, all genes with a summary effect size <1.5 fold were thrown out. Finally, all genes found to be statistically significant in the multi-cohort analysis according to all three of the above criteria (Table 8) were subjected to a greedy forward search model, where, starting with the most significant gene, all remaining genes are added to the gene score one at a time, and the gene with the greatest increase in discriminatory ability is added to the final gene list.

Supplemental Methods

Dataset Details

Six of the publicly available whole blood datasets were from the Genomics of Pediatric SIRS/Septic Shock Investigators (GPSSSI) (Cvijanovich et al. (2008) Physiol Genomics 34:127-134; Shanley et al. (2007) Mol Med 13:495-508; Wong et al. (2007) Physiol Genomics 30:146-155; Wong et al. (2009) Crit Care Med 37:1558-1566; Wong et al. (2010) Pediatr Crit Care Med 11:349-355; Wong et al. (2011) Crit Care Med 39:2511-2517). These datasets contain overlapping samples, for which Hector Wong provided a key of the unique patients. Those unique patients were then gcRMA normalized together and treated as a single dataset (GPSSSI Unique).

In addition to the publicly-available datasets, we used the Inflammation and Host Response to Injury Program (Glue Grant) trauma datasets (Cobb et al., supra). The Glue Grant datasets consist of separate trauma patient cohorts sampled for either the entire buffy coat, or sorted cells (neutrophils, monocytes, T-cells). Inclusion criteria are described elsewhere (Desai et al., supra). Patients were sampled at the following days after admission: 0.5, 1, 4, 7, 14, 21, 28 days. The Glue Grant trauma cohort patients were classified as 'infected' if they had a nosocomial infection (pneumonia, urinary tract infection, catheter-related bloodstream infection, etc.), a surgical infection (excluding superficial wound infections), or underwent surgery for perforated viscus; infection definitions can be found at gluegrant.org/common-lyreferencedpubs.htm. For meta-analyses, samples drawn within +/−24 hours of the day of diagnosis of infection were included as infection cases. Time-points with fewer than 20 patients were not included in the multi-cohort analysis. The Glue Grant also contains burn patients, but these were not included due to the difficulty of distinguishing clinically relevant infections from colonized burn wounds. Use of the Glue Grant was approved by both the Glue Grant Consortium and the Stanford University IRB (protocol 29798).

Gene Expression Normalization

All Affymetrix datasets were downloaded as CEL files and re-normalized using gcRMA (R package affy). Output from Agilent chips and custom arrays analyzed on GenePix scanners were background corrected, within-arrays loess normalized, and then between-arrays quantile normalized (R package limma) (G. Smyth, in Bioinformatics and Computational Biology Solutions Using R and Bioconductor, C. V. Gentleman R, Dudoit S, Irizarry R and Huber W (eds.), Ed. (Springer, N.Y., 2005), pp. pp. 397-420). Illumina datasets were quantile normalized. The Glue Grant sorted-cell datasets were analyzed using custom arrays (GGH-1, GGH-2); these were normalized as previously described and used in their post-processed state (Xu et al. (2011) Proc Natl Acad Sci USA 108:3707-3712). For all gene analyses, the mean of probes for common genes was set as the gene expression level. All probeto-gene mappings were downloaded from GEO from the most current SOFT files on Dec. 14, 2014.

Labelled PCA Method

The labelled principal components analysis (PCA) method is an implementation of the constrained optimization described in equations 6 and 7 in section 4.1 of Koren and Carmel (IEEE Trans Vis Comput Graph (2004) 10:459-470). This optimization computes a linear transformation of the data that maximizes the pairwise distance between points in different labelled classes of the data while maintaining the constraint that the transformed data are orthogonal to each other. This orthogonal constraint is slightly different to the constraint employed by PCA, which demands that the transformed basis is mutually orthogonal, not the transformed data itself. While PCA is a projection scheme, labelled PCA is a general form of a linear transformation due to this difference in constraint.

Call X the original dataset, with m rows (data points) and n columns (each data point has n elements). Y is an m by 1 matrix that has a different listing for each class. In other words, Y (i) equals Y (j) if and only if elements i and j are part of the same labelled class. L is a symmetrical m by m matrix whose (i,j) entry is −1, unless Y (i) equals Y (j). In this latter case, the entry is 0. Finally, all diagonal entries (where i equals j) are filled so that row i sums to 0. Koren and Carmel prove in Lemma 3.2 that the eigenvectors of transpose (X)*L*X provide a mapping that maximizes the pairwise distance between points in different labelled classes of the data. However, this transformation remains a projection scheme, which means that these eigenvectors are orthogonal to each other. This latter result limits the utility of the transformed data, but is more generalizable. The general linear projection used in this paper instead finds the vectors v that solve the equation $Av=\lambda Bv$, where A is transpose (X)*L*X, and B is transpose (X)*X. Although more expressive, this method is not as robust as the labelled PCA projection scheme, however, since solutions to this generalized form require that B is not singular. Since B is not the identity matrix, the old orthogonal constraint used in projections does not have to hold. Instead, solutions to this form require the basis is mutually orthogonal with respect to the covariance basis of the original data.

Labelled PCA Applications

Labelled PCA method is described in the Supplemental Methods. All datasets that contain a comparison of non-infectious SIRS, ICU, or trauma patients to sepsis patients were converted from probes to genes, and then bound into a single large matrix and quantile normalized. Genes not present in all datasets were thrown out. Patients with sepsis at any time (either on admission or hospital-acquired) were grouped in a single class, and Lasso-penalized regression was applied to separate sterile SIRS patients from sepsis patients (R package glmnet). Labelled PCA was carried out using the genes selected by the penalized regression, on the classes of sterile SIRS versus sepsis. The same graph was then re-labelled to show which samples are from hospital-acquired (or late) sterile SIRS or sepsis patients. The same set of genes from the penalized regression was then used in labelled PCA to compare healthy, sterile SIRS, and sepsis patients. This same graph was then re-labelled to show which samples are from hospital-acquired or late sterile SIRS or sepsis patients.

To examine the effects of time on gene expression in SIRS/trauma and infection, all datasets that include serial measurements over time were selected. From the Glue Grant datasets, only buffy coat arrays were included, so as not to overwhelm the signal from the other datasets. The selected datasets were converted from probes to genes, and then bound into a single large matrix and quantile normalized. Genes not present in all datasets were thrown out. To reduce the gene set in an unbiased manner, CUR matrix decomposition was used to select the top 100 genes with the greatest orthogonality in the combined datasets (R package rCUR) (Bodor et al. (2012) BMC Bioinformatics 13:103). Labelled PCA was then carried out with each time point used as a different class (split at 1, 2, 3, 4, 5, 6, 10, 20, and 40 days). The resulting PCA was graphed in 3D, colored by time point, and a short video of rotations of the 3D space was captured using R package rgl.

Infection Z-score

Genes that were found to be significant after multi-cohort analysis were separated according to whether their effects were positive or negative (where 'positive' means a positive effect size in sepsis as compared to SIRS/trauma, and 'negative' means a negative effect size in sepsis as compared to SIRS/trauma). The class discrimination power of these gene sets was then tested using a single gene score. The gene score used is the geometric mean of the gene expression level for all positive genes minus the geometric mean of the gene expression level of all negative genes multiplied by the ratio of counts of positive to negative genes. This was calculated for each sample in a dataset, and the scores for each dataset were then standardized to yield a Z-score (infection Z-score'). Genes not present in an entire dataset were excluded; genes missing for individual samples were set to 1. To obtain an infection Z-score for datasets with negative gene expression values (two-channel arrays), the entire dataset was scaled by the minimum value present in the dataset, to ensure all values were positive (since the geometric mean yields imaginary values for negative input).

Class discriminatory power was examined comparing the infection Z-scores for classes of interest in each examined dataset. The infection Z-score ranges were examined with violin plots, and, since they cannot be assumed to have normal distributions, are shown with 25%-75% interquartile range and compared using Wilcoxon rank-sum test. ROC curves of the infection Z-score were constructed comparing classes of interest (such as sterile SIRS compared to sepsis), and the total ROC area under the curve (AUC) is shown, along with a 95% confidence interval.

Forward Search

To obtain a parsimonious gene set that discriminates SIRS/trauma patients and septic/infected patients, all genes found to be statistically significant in the multi-cohort analysis were subjected to a greedy forward search model, where, starting with the most significant gene in the data set, all remaining genes are added to the gene score one at a time, and the gene with the greatest increase in discriminatory ability is added to the final gene list. Here, discriminatory ability was defined as a weighted ROC AUC, wherein the infection Z-score is tested in each discovery dataset, and the resulting AUC is multiplied by the total number of samples in the dataset. The function then maximizes the sum of weighted AUCs across all discovery datasets for each step. In this way, excellent class discrimination in a small dataset does not outweigh modest gains in class discrimination in a very large dataset. The function stops at an arbitrarily defined threshold; we used a stopping threshold of one (such that when the function cannot find a gene that will increase the total discovery weight AUCs of the current infection Z-score by more than one, it will terminate). This final resulting gene set is thus maximized for discriminatory power in the discovery cohorts, though is not optimized as a global maximum. The probe-level data for the genes remaining after forward search is shown in Table 8.

Discovery Cohort Examinations

The final gene score was used to compute infection Z-scores in each discovery dataset. The admission datasets were analyzed separately and separate ROC plots plotted. For the hospital-acquired (Glue Grant) datasets, infection scores were standardized (converted into Z-scores) once for the whole cohort as opposed to normalizing the different time-bins separately to show changes over time in the same patients. The infection Z-scores were then analyzed for significance using repeated-measures analysis of variance. ROC curves were plotted for the individual time-bins treated as separate datasets in the multi-cohort analysis.

For the Glue Grant datasets two time-course analyses of infection Z-score were carried out for both the buffy coat and neutrophil datasets. First, the average infection Z-score was compared over time using linear regression for patients within +/−24 hours of infection and for non-infected patients. Repeated-measures analysis of variance was used to compare infected and non-infected groups to each other and to test for the significance of changes over time. Next, boxplots were constructed for each time window, such that the infection Z-score for the patients in that time window who were never infected were compared to patients at >5 days prior to their day of diagnosis with infection, 5-1 days prior to diagnosis, or +/−24 hours of diagnosis. For each time point (except for the 0-1 day window), the trend in infection Z-score across the different groups was tested with the Jonckheere trend (JT) test. The infection Z-scores at the admission time point ([0,1)) were tested as the outcomes variable in multiple linear regression, examining the contributory effects of both injury severity score and time to infection.

Validation

The final gene set was tested in several validation cohorts completely separate from the discovery cohorts. The sorted-cells cohort of the Glue Grant were broken into time-bins, and AUCs were calculated separately for each time bin. Note that no infections with +/−1 day of diagnosis were captured in this cohort after 18 days post injury, so the [18,24) day bin is never shown.

The validation cohorts included three datasets that examined trauma patients over time (GSE6377, GSE12838, and EMEXP3001), all of whom developed infections (mostly ventilator-associated pneumonia (VAP)). These datasets do not include controls, and so they were compared to the Glue Grant non-infected patients as a baseline. These three validation datasets and the Glue Grant buffy coat non-infected samples were first linearly scaled by a factor of the geometric mean of four housekeeping genes (GAPDH, ACTN1, RPL9, KARS) (Vandesompele et al. (2002) Genome Biol 3:RESEARCH0034). The datasets were then joined on overlapping genes, and batch-corrected between datasets using the ComBat empiric Bayes batch-correction tool, with parametric priors (R Package sva) (Leek et al. (2012) Bioinformatics 28:882-883). The ComBat correction was controlled for day after injury (so that relative differences between days stay relatively different). The infection Z-score was then calculated for the joined datasets, and the validation datasets were plotted against the loess curve from the non-infected Glue Grant cohort. Patients within +/−24 hours of their diagnosis of infection in the validation datasets were then compared to day-matched ComBat-co-normalized non-infected Glue Grant buffy coat patients, and ROC curves were constructed.

All of other datasets found in the initial search that allow for comparison between healthy or SIRS/trauma and sepsis patients were used for simple class discrimination validation. All datasets conducted on whole blood or neutrophils are shown. Studies carried out in PBMCs were selected for only those that examined SIRS/trauma and sepsis patients. Datasets using PBMC samples that did not include both a sterile SIRS group and a sepsis group were excluded. All peripheral blood healthy vs sepsis patient datasets were grouped into a single violin plot and tested jointly for separation (Wilcoxon rank-sum) since they were all being used to make the same comparison. ROC curves were carried out on each individual dataset separately to show the discriminatory capability of the infection Z-scores within each dataset.

Glue Grant SIRS Evaluation

To evaluate the effectiveness of SIRS as a screening criteria for infection in the Glue Grant cohort, all patients were classified as either non-infected, or within +/−24 hours of infection, with infection as defined above. Patients were censored >24 hours after infection diagnosis. SIRS criteria were defined according to standard international guidelines (Temperature<36C or >38C, respiratory rate>20 or PaCO2<32, total WBC<4,000 or >12,000, and HR>90). Patients missing any criteria were excluded. Each criterion was stored as a binary variable for each patient for each day. Logistic regression was run on the data both with and without inclusion of the Z-score, and ROC AUC was calculated for both models. The two models were then compared using the continuous net reclassification index (R package PredictABEL).

Gene Set Evaluation

The final gene set was evaluated for transcription factor binding sites using two online tools, EncodeQT (Auerbach et al. (2013) Bioinformatics 29:1922-1924) and PASTAA (Roider et al. (2009) Bioinformatics 25:435-442). Positive and negative genes were evaluated separately, since they are hypothesized to be under separate regulatory control. The EncodeQT tool was used with 5000 upstream and 5000 downstream base pairs from transcription start site. A similar analysis was carried out with PASTAA, examining the region −200 base pairs from transcription start site, examining only those factors which were conserved for both mouse and human. The top ten significant transcription factors were recorded for both analyses.

Cell-Type Enrichment Tests

GEO was searched for gene expression profiles of clinical samples of relevant immune cell types. The search was limited to only samples run on Affymetrix platforms, to ensure platform effect homogeneity. All datasets used were downloaded in RAW format and gcRMA normalized separately. For each sample, the mean of multiple probes mapping to the same gene was taken as the gene value. Genes not present in all samples were thrown out. For multiple samples all corresponding to the same cell type, the mean of the samples was taken as the final value, thus creating a single vector for each cell type. To obtain a Z-score for a gene set in each cell type vector, the geometric mean of the 'positive' genes' expression is taken, and from it is subtract the geometric mean of the 'negative' genes' expression, times the ratio of negative genes to positive genes (same procedure as for the infection Z-score). These scores are then standardized across all cell types, such that the score represents the number of standard deviations away from the group mean. This thus represents how enriched a given gene set is in a given cell type, relative to other tested cell types.

A total of 18 GEO datasets that matched criteria were used: GSE3982 (Jeffrey et al. (2006) Nat Immunol 7:274-283), GSE5099 (Martinez et al. (2006) J Immunol 177:7303-7311), GSE8668 (Radom-Aizik et al. (2008) J Appl Physiol 104:236-243), GSE11292 (He et al. (2012) Mol Syst Biol 8:624), GSE12453 (Giefing et al. (2013) PLoS One 8:e84928), GSE13987 (Meyers et al. (2009) J Immunol 182:5400-5411), GSE14879 (Eckerle et al. (2009) Leukemia 23:2129-2138), GSE15743 (Stegmann et al. (2010) Gastroenterology 138:1885-1897), GSE16020 (Vinh et al. (2010) Blood 115:1519-1529), GSE16836 (Ancuta et al. (2009) BMC Genomics 10:403), GSE24759 (Novershtern et al. (2011) Cell 144:296-309), GSE28490 (Allantaz et al. (2012) PLoS One 7:e29979), GSE28491 (Allantaz et al., supra), GSE31773 (Tsitsiou et al. (2012) J Allergy Clin Immunol 129:95-103), GSE34515 (Frankenberger et al. (2012) Eur J Immunol 42:957-974), GSE38043 (Huen et al. (2013) Int J Cancer 133:373-382), GSE39889 (Malcolm et al. (2013) PLoS One 8:e57402), GSE42519 (Rapin et al. (2014) Blood 123:894-904), GSE49910 (Mabbott et al. (2013) BMC Genomics 14:632).

Two gene sets were tested in this manner: both the entire set of genes found to be significant after the initial multicohort analysis, and the subset of genes found to be most diagnostic after forward search. Their corresponding figures show the Z-score (enrichment for the given gene set) in each cell subtype (black dots), as well as a box plot for the overall distribution of Z-scores (any outliers shown as open circles).

Statistics and R

All computation and calculations were carried out in the R language for statistical computing (version 3.0.2). Significance levels for p-values were set at 0.05, and analyses were two-tailed, unless specified otherwise.

TABLE 1

Publically available gene expression datasets comparing SIRS/ICU/trauma to sepsis/infections.

| Dataset | Year | Submitting Author | Paper Reference Number | Control Used Here | Condition Used Here | Sample Type Used | Platform | Timepoints Present in Dataset (Days) |
|---|---|---|---|---|---|---|---|---|
| GPSSSI Unique | 2006-2011 | Wong | 27-32 | Pediatric ICU-SIRS | Sepsis and Septic Shock (bacterial infections only) | Whole Blood | GPL570 | 1-3 |
| GSE28750 | 2011 | Sutherland | 39 | 24 h-post-'major surgery' | community-acquired sepsis | Whole Blood | GPL570 | Admission |
| GSE32707 | 2012 | Dolinay | 43 | MICU patients +/− SIRS, nonseptic | Sepsis, Sepsis + ARDS | Whole Blood | GPL10558 | 0 & 7 |
| GSE40012 | 2012 | Parnell | 38 | SIRS (66% Trauma) | Sepsis from CAP (bacterial infections only) | Whole Blood | GPL6947 | Days 1-5 for both SIRS and Sepsis |
| Glue Grant-Trauma-Buffy Coat | 2004-2006 | Multiple | 23-26 | Trauma | Trauma with infection | Buffy Coat | GPL570 | 0.5, 1, 4, 7, 14, 21, 28 |

CAP, community-acquired pneumonia.
ARDS, acute respiratory distress syndrome.

TABLE 2

All datasets used in the multi-cohort analysis. The numbers following the Glue Grant cohort titles indicates days since infection in the given cohort (for instance, [1, 3) is patients from 1-3 days since injury).

| | Cohort | SIRS/Trauma Controls (n) | Sepsis/Infection Cases (n) | Total (n) |
|---|---|---|---|---|
| Admission Comparisons | GSE28750 | 11 | 10 | 21 |
| | GSE32707 | 55 | 48 | 103 |
| | GSE40012 | 24 | 41 | 65 |
| | GPSSSI Unique | 30 | 189 | 219 |
| Hospital-Acquired Comparisons (Glue Grant buffy coat cohorts) | Glue Grant buffy coat [1, 3) | 65 | 9 | 74 |
| | Glue Grant buffy coat [3, 6) | 63 | 17 | 80 |
| | Glue Grant buffy coat [6, 10) | 50 | 15 | 65 |
| | Glue Grant buffy coat [10, 18) | 22 | 4 | 26 |
| | Glue Grant buffy coat [18, 24) | 6 | 4 | 10 |
| Total Used in Multi-cohort analysis | | 326 | 337 | 663 |

TABLE 3

The 11 gene set that separates SIRS/trauma from sepsis. Included are meta-analysis effect sizes, errors, and heterogeneity analyses.

| Gene Symbol | Full Name | Pooled Effect Size | Pooled Effect Size Standard Error | Effect Size P-Value | Effect Size Q-Value | Sum-of-Logs Q-Value | Cochran's Q | Tau squared | Inter-study heterogeneity p-Value |
|---|---|---|---|---|---|---|---|---|---|
| CEACAM1 | carcinoembryonic antigen-related cell adhesion molecule 1 | 0.778 | 0.073 | 1.9E−26 | 6.5E−22 | 7.2E−14 | 16.43 | 0.023 | 0.037 |
| ZDHHC19 | zinc finger, DHHC-type containing 19 | 1.083 | 0.130 | 6.6E−17 | 3.3E−13 | 7.1E−22 | 18.36 | 0.078 | 0.019 |
| C9orf95 | nicotinamide riboside kinase 1 | 0.598 | 0.102 | 4.6E−09 | 1.4E−06 | 2.9E−12 | 12.64 | 0.032 | 0.125 |
| GNA15 | guanine nucleotide binding protein (G protein), alpha 15 | 0.603 | 0.119 | 4.0E−07 | 4.3E−05 | 4.7E−08 | 10.66 | 0.030 | 0.222 |

TABLE 3-continued

The 11 gene set that separates SIRS/trauma from sepsis. Included are meta-analysis effect sizes, errors, and heterogeneity analyses.

| Gene Symbol | Full Name | Pooled Effect Size | Pooled Effect Size Standard Error | Effect Size P-Value | Effect Size Q-Value | Sum-of-Logs Q-Value | Cochran's Q | Tau squared | Inter-study heterogeneity p-Value |
|---|---|---|---|---|---|---|---|---|---|
| BATF | basic leucine zipper transcription factor, ATF-like | 1.053 | 0.163 | 9.4E−11 | 6.2E−08 | 1.6E−19 | 17.49 | 0.115 | 0.025 |
| C3AR1 | complement component 3a receptor 1 | 0.643 | 0.097 | 3.7E−11 | 3.0E−08 | 9.3E−08 | 3.99 | 0.000 | 0.858 |
| KIAA1370 | family with sequence similarity 214, member A | −0.664 | 0.148 | 7.8E−06 | 4.5E−04 | 2.1E−10 | 18.79 | 0.095 | 0.016 |
| TGFBI | transforming growth factor, beta-induced, 68 kDa | −0.730 | 0.108 | 1.2E−11 | 1.1E−08 | 2.0E−10 | 9.12 | 0.013 | 0.333 |
| MTCH1 | mitochondrial carrier 1 | −0.686 | 0.135 | 4.1E−07 | 4.3E−05 | 7.9E−10 | 13.04 | 0.058 | 0.111 |
| RPGRIP1 | retinitis pigmentosa GTPase regulator interacting protein 1 | −0.694 | 0.156 | 8.5E−06 | 4.7E−04 | 5.2E−09 | 16.93 | 0.103 | 0.031 |
| HLA-DPB1 | major histocompatibility complex, class II, DP beta 1 | −0.659 | 0.157 | 2.6E−05 | 1.1E−03 | 8.6E−09 | 17.38 | 0.107 | 0.026 |

TABLE 4

| Dataset | Year | Submitting Author | Paper Reference Number | Control Used Here | Condition Used Here | Sample Type Used | Platform | Days Since Injury | N, control | N, case |
|---|---|---|---|---|---|---|---|---|---|---|
| Glue Grant Sorted Cells | 2008-2011 | Multiple | | Trauma patients without infection | Trauma patients +/− 24 hours from diagnosis of infection | Neutrophils, Monocytes, T-Cells | GGH-1, GGH-2 (GPL11320) | [1, 3) [3, 6) [6, 10) [10, 18) | 56 55 46 24 | 10 10 14 3 |

TABLE 5

Publically available gene expression time-course datasets of trauma patients that develop infections.

| Dataset | Year | Submitting Author | Paper Reference Number | Control Used Here | Condition Used Here | Sample Type Used | Platform | N, control | N, case | Samples Used Here | Timepoints Present in Dataset |
|---|---|---|---|---|---|---|---|---|---|---|---|
| GSE6377 | 2008 | Cobb | 47 | None | ICU patients with eventual VAP | Buffy Coat | GPL201 | 0 | 11 | 99 | 1-21 days |
| GSE12838 | 2008 | Cobb | N/A | None | ICU patients with eventual VAP | Buffy Coat, Neutrophils | GPL570 | 0 | 4 | 60 | 1-11 days |
| E-MEXP-3001 | 2011 | Lopez | 35 | None | ICU patients with acquired VAP or VAT | Whole Blood | A-Agil-28 (GPL6480) | 0 | 8 | 56 | 1-7 days |

VAP, ventilator-associated pneumonia;
VAT, ventilator-associated tracheobronchitis.

TABLE 6

Publically available gene expression datasets in whole blood or neutrophils comparing healthy patients to septic patients.

| Dataset | Year | Submitting Author | Paper Reference Number | Control Used Here | Condition Used Here | Sample Type Used | Platform | N, control | N, case | Timepoints Present in Dataset |
|---|---|---|---|---|---|---|---|---|---|---|
| GSE11755 | 2008 | Emonts | 50 | Healthy Children | Children w/ meningococcal sepsis | Whole Blood | GPL570 | 3 | 8 | 0, 0.33, 1, 3 |
| GSE13015 | 2008 | Chaussabel | 14 | Healthy or Type 2 Diabetes | Community-acquired or nosocomial sepsis | Whole Blood | GPL6106, GPL69467 | 20 | 63 | Mixed, admission or sepsis onset |
| GSE20346 | 2011 | Parnell | 49 | Pre/Post-Flu Vaccine | Bacterial pneumonia, Severe influenza | Whole Blood | GPL6947 | 36 | 45 | 5-Jan |
| GSE21802 | 2011 | Bermejo-Martin | 34 | Healthy | Flu + ARDS | Whole Blood | GPL6102 | 4 | 12 | 'Early' vs. 'Late' Sepsis |
| GSE25504 | 2014 | Smith | | Healthy neonates | Neonates with bacterial infection | Whole Blood | GPL570, GPL6947, GPL13667 | 44 | 44 | Infection onset |
| GSE27131 | 2011 | Berdal | 44 | Healthy | Severe Flu A | Whole Blood | GPL6244 | 7 | 14 | 0-6 |
| GSE33341 | 2011 | Ahn | 42 | Healthy | Sepsis from Bacterial CAP | Whole Blood | GPl571 | 43 | 51 | Admission |
| GSE40396 | 2013 | Hu | 37 | Healthy Children after surgery | Children with infection + fever | Whole Blood | GPL10558 | 22 | 30 | Admission |

TABLE 7

Publically available gene expression datasets comparing sterile SIRS/trauma/autoimmunity patients to later or non-time-matched sepsis/infection patients.

| Dataset | Year | Submitting Author | Paper Reference Number | Control Used Here | Condition Used Here | Sample Type Used | Platform | N, control | N, case | Timepoints Present in Dataset |
|---|---|---|---|---|---|---|---|---|---|---|
| GSE5772 | 2007 | Tang | 41 | ICU non-sepsis (43% trauma) | sepsis-early + late | Neutrophils | GPL4274 | 23 | 70 | Mixed, admission or sepsis onset |
| GSE9960 | 2009 | Tang | 15 | ICU non-sepsis | sepsis | Monocytes | GPL570 | 16 | 54 | Mixed, admission or sepsis onset |
| GSE22098 | 2007-2010 | Chaussabel | | Healthy Controls & Autoimmunity | Infections after diagnosis | Whole Blood | GPL6947 | | | Autoimmunity during systemic phase; Infections after diagnosis confirmation |
| E-MEXP-3621 | 2012 | Harokopos | 54 | Trauma at Admission | Trauma at Onset of Sepsis | Monocytes | A-Affy-37 (GPL571) | 5 | 5 | Admission vs. onset of Sepsis |
| E-MTAB-1548 | 2014 | Almansa | 33 | Post-surgery (avg 2 days) | sepsis after surgery (avg 4 days) | Whole Blood | A-MEXP-2183 (GPL10332) | 34 Post-Surg | 39 | Post-Surgery (avg 2 days), Onset of Sepsis (avg 4 days) |

TABLE 8

Summary statistics for the 82 genes that passed significance, heterogeneity, and effect-size filtering after multi-cohort analysis.

| gene symbol | n studies | summary | se summary | tau2 | p value | Q | df | pval het | p fdr |
|---|---|---|---|---|---|---|---|---|---|
| ADAMTS3 | 9 | 0.648269 | 0.143917 | 0.07797 | 6.65E−06 | 14.83131 | 8 | 0.06251 | 0.000391 |
| ANKRD22 | 9 | 0.704397 | 0.068995 | 0 | 1.80E−24 | 3.023063 | 8 | 0.932902 | 3.14E−20 |
| ANXA3 | 9 | 0.718406 | 0.166894 | 0.12894 | 1.67E−05 | 19.21339 | 8 | 0.013759 | 0.00079 |
| AP3B2 | 9 | 0.691257 | 0.125869 | 0.074155 | 3.98E−08 | 18.56155 | 8 | 0.017389 | 7.22E−06 |
| ARL8A | 9 | 0.702502 | 0.156795 | 0.106433 | 7.45E−06 | 17.26336 | 8 | 0.027481 | 0.00043 |
| B3GNT8 | 9 | 0.615648 | 0.131508 | 0.052681 | 2.85E−06 | 12.60337 | 8 | 0.126245 | 0.000201 |
| BATF | 9 | 1.053446 | 0.162675 | 0.115021 | 9.43E−11 | 17.49358 | 8 | 0.025361 | 6.20E−08 |
| BPI | 9 | 0.648548 | 0.118551 | 0.029549 | 4.48E−08 | 10.58983 | 8 | 0.22604 | 7.93E−06 |
| BST1 | 9 | 0.591544 | 0.118229 | 0.029239 | 5.63E−07 | 10.57953 | 8 | 0.22668 | 5.64E−05 |

TABLE 8-continued

Summary statistics for the 82 genes that passed significance, heterogeneity, and effect-size filtering after multi-cohort analysis.

| | | | | | | | | | |
|---|---|---|---|---|---|---|---|---|---|
| C1orf162 | 9 | 0.675288 | 0.144756 | 0.078314 | 3.09E−06 | 14.83231 | 8 | 0.062489 | 0.000213 |
| C3AR1 | 9 | 0.642508 | 0.097145 | 0 | 3.74E−11 | 3.985702 | 8 | 0.858411 | 2.97E−08 |
| C9orf103 | 9 | 0.79588 | 0.146305 | 0.082027 | 5.33E−08 | 15.10186 | 8 | 0.057195 | 9.02E−06 |
| C9orf95 | 9 | 0.598498 | 0.102092 | 0.032317 | 4.56E−09 | 12.63991 | 8 | 0.124855 | 1.37E−06 |
| CCR1 | 9 | 0.617951 | 0.114205 | 0.052764 | 6.27E−08 | 15.60038 | 8 | 0.04847 | 1.01E−05 |
| CD177 | 9 | 0.859005 | 0.155738 | 0.103421 | 3.47E−08 | 18.17687 | 8 | 0.019939 | 6.51E−06 |
| CD63 | 9 | 0.715795 | 0.145235 | 0.07892 | 8.28E−07 | 14.84659 | 8 | 0.062198 | 7.87E−05 |
| CD82 | 9 | 0.712222 | 0.153324 | 0.105659 | 3.40E−06 | 19.9932 | 8 | 0.010362 | 0.000229 |
| CEACAM1 | 9 | 0.777702 | 0.073068 | 0.022592 | 1.87E−26 | 16.42612 | 8 | 0.036672 | 6.52E−22 |
| CLEC5A | 9 | 0.742933 | 0.098047 | 0 | 3.53E−14 | 7.6215 | 8 | 0.471288 | 8.20E−11 |
| DHRS9 | 9 | 0.588827 | 0.091062 | 0.039325 | 1.00E−10 | 19.65994 | 8 | 0.011702 | 6.49E−08 |
| EMR1 | 9 | 0.631226 | 0.137919 | 0.064062 | 4.72E−06 | 13.60366 | 8 | 0.092699 | 0.000295 |
| FAM89A | 9 | 0.683704 | 0.070109 | 0.001367 | 1.81E−22 | 8.215543 | 8 | 0.412704 | 2.10E−18 |
| FCER1G | 9 | 0.825093 | 0.113017 | 0.048372 | 2.86E−13 | 14.77229 | 8 | 0.063727 | 4.75E−10 |
| FCGR1B | 9 | 0.656424 | 0.083424 | 0 | 3.59E−15 | 6.900977 | 8 | 0.547353 | 1.26E−11 |
| FES | 9 | 0.619202 | 0.117056 | 0.027305 | 1.22E−07 | 10.3985 | 8 | 0.238162 | 1.69E−05 |
| FFAR3 | 9 | 0.625449 | 0.135784 | 0.060488 | 4.10E−06 | 13.3059 | 8 | 0.101749 | 0.000265 |
| FIG4 | 9 | 0.607879 | 0.117383 | 0.027801 | 2.24E−07 | 10.43819 | 8 | 0.235607 | 2.70E−05 |
| GNA15 | 9 | 0.603381 | 0.119077 | 0.030288 | 4.04E−07 | 10.65968 | 8 | 0.221738 | 4.33E−05 |
| GPR84 | 9 | 0.892627 | 0.120993 | 0.030557 | 1.61E−13 | 10.57938 | 8 | 0.22669 | 2.81E−10 |
| HK3 | 9 | 0.736906 | 0.15041 | 0.090003 | 9.62E−07 | 15.78283 | 8 | 0.045596 | 8.75E−05 |
| HP | 9 | 0.917673 | 0.138462 | 0.062412 | 3.41E−11 | 13.2873 | 8 | 0.102339 | 2.77E−08 |
| IL10 | 9 | 0.585979 | 0.127675 | 0.057993 | 4.44E−06 | 14.7083 | 8 | 0.065072 | 0.00028 |
| IL18R1 | 9 | 0.589237 | 0.133191 | 0.056256 | 9.69E−06 | 12.9634 | 8 | 0.113115 | 0.000531 |
| KCNE1 | 9 | 0.644633 | 0.076133 | 0 | 2.51E−17 | 5.362592 | 8 | 0.718211 | 1.51E−13 |
| LCN2 | 9 | 0.70721 | 0.135145 | 0.058578 | 1.67E−07 | 13.09133 | 8 | 0.108746 | 2.15E−05 |
| LIN7A | 9 | 0.691051 | 0.109274 | 0.042661 | 2.55E−10 | 14.05438 | 8 | 0.080359 | 1.46E−07 |
| OSCAR | 9 | 0.653819 | 0.124504 | 0.051008 | 1.51E−07 | 13.8118 | 8 | 0.086805 | 1.98E−05 |
| OSTalpha | 9 | 0.867976 | 0.136737 | 0.060402 | 2.18E−10 | 13.1769 | 8 | 0.105906 | 1.29E−07 |
| P2RX1 | 9 | 0.601662 | 0.097231 | 0 | 6.10E−10 | 7.903705 | 8 | 0.442933 | 2.72E−07 |
| PADI2 | 9 | 0.617007 | 0.104176 | 0.048808 | 3.17E−09 | 17.62447 | 8 | 0.024225 | 1.01E−06 |
| PECR | 9 | 0.646105 | 0.122849 | 0.068752 | 1.45E−07 | 17.8734 | 8 | 0.022196 | 1.92E−05 |
| PLAC8 | 9 | 0.914226 | 0.133684 | 0.064878 | 7.99E−12 | 15.16198 | 8 | 0.056071 | 7.72E−09 |
| PLB1 | 9 | 0.624304 | 0.101509 | 0.031745 | 7.74E−10 | 12.59051 | 8 | 0.126737 | 3.33E−07 |
| PNPLA1 | 9 | 0.661921 | 0.110402 | 0.02961 | 2.03E−09 | 11.37858 | 8 | 0.181157 | 7.00E−07 |
| PPM1M | 9 | 0.601672 | 0.14071 | 0.070244 | 1.90E−05 | 14.1845 | 8 | 0.077081 | 0.000875 |
| PSTPIP2 | 9 | 0.601434 | 0.106478 | 0.011848 | 1.62E−08 | 9.046349 | 8 | 0.338401 | 3.51E−06 |
| RETN | 9 | 0.846118 | 0.138226 | 0.061624 | 9.28E−10 | 13.23063 | 8 | 0.104157 | 3.76E−07 |
| RGL4 | 9 | 0.727597 | 0.097757 | 0 | 9.85E−14 | 5.163271 | 8 | 0.739991 | 1.91E−10 |
| S100A12 | 9 | 0.822032 | 0.154856 | 0.099381 | 1.11E−07 | 16.53376 | 8 | 0.035347 | 1.55E−05 |
| SEPHS2 | 9 | 0.655956 | 0.152148 | 0.095162 | 1.62E−05 | 16.32158 | 8 | 0.038002 | 0.000773 |
| SETD8 | 9 | 0.620324 | 0.106869 | 0.052338 | 6.46E−09 | 18.25896 | 8 | 0.019367 | 1.83E−06 |
| SGSH | 9 | 0.617383 | 0.121888 | 0.066408 | 4.08E−07 | 17.50436 | 8 | 0.025265 | 4.34E−05 |
| SIGLEC9 | 9 | 0.778995 | 0.150995 | 0.090956 | 2.48E−07 | 15.8002 | 8 | 0.045331 | 2.91E−05 |
| SLC26A8 | 9 | 0.661594 | 0.127735 | 0.063947 | 2.23E−07 | 18.16165 | 8 | 0.020047 | 2.69E−05 |
| SPPL2A | 9 | 0.626134 | 0.136141 | 0.062284 | 4.24E−06 | 13.50619 | 8 | 0.09558 | 0.000273 |
| SQRDL | 9 | 0.663981 | 0.12316 | 0.037073 | 7.00E−08 | 11.24886 | 8 | 0.187993 | 1.09E−05 |
| TCN1 | 9 | 0.590797 | 0.104398 | 0.00911 | 1.52E−08 | 8.805806 | 8 | 0.358942 | 3.40E−06 |
| ZDHHC19 | 9 | 1.082518 | 0.129588 | 0.077549 | 6.63E−17 | 18.36049 | 8 | 0.01868 | 3.30E−13 |
| ZDHHC3 | 9 | 0.605151 | 0.086784 | 0.029399 | 3.10E−12 | 15.30001 | 8 | 0.053568 | 3.38E−09 |
| ARHGEF18 | 9 | −0.70898 | 0.169784 | 0.138608 | 2.97E−05 | 20.06666 | 8 | 0.010087 | 0.001268 |
| CACNA2D3 | 9 | −0.64833 | 0.109938 | 0.015972 | 3.70E−09 | 9.394217 | 8 | 0.310139 | 1.15E−06 |
| CNNM3 | 9 | −0.58818 | 0.120969 | 0.040958 | 1.16E−06 | 12.19782 | 8 | 0.142593 | 0.000102 |
| GLO1 | 9 | −0.58606 | 0.097388 | 0 | 1.77E−09 | 6.320283 | 8 | 0.611403 | 6.42E−07 |
| GRAMD1C | 9 | −0.68641 | 0.110473 | 0.01627 | 5.19E−10 | 9.411211 | 8 | 0.308802 | 2.44E−07 |
| HACL1 | 9 | −0.60233 | 0.126366 | 0.042383 | 1.87E−06 | 11.71196 | 8 | 0.164526 | 0.000148 |
| HLA-DPB1 | 9 | −0.65892 | 0.156786 | 0.10708 | 2.64E−05 | 17.38174 | 8 | 0.026371 | 0.001142 |
| KIAA1370 | 9 | −0.66377 | 0.148487 | 0.095204 | 7.81E−06 | 18.78508 | 8 | 0.016052 | 0.000446 |
| KLHDC2 | 9 | −0.7076 | 0.098039 | 0 | 5.29E−13 | 7.407563 | 8 | 0.493364 | 8.39E−10 |
| METAP1 | 9 | −0.5853 | 0.097402 | 0 | 1.87E−09 | 7.655966 | 8 | 0.467777 | 6.70E−07 |
| MRPS35 | 9 | −0.62742 | 0.107996 | 0.013274 | 6.26E−09 | 9.160226 | 8 | 0.32896 | 1.79E−06 |
| MTCH1 | 9 | −0.68598 | 0.135413 | 0.058253 | 4.07E−07 | 13.03704 | 8 | 0.110581 | 4.34E−05 |
| NOC3L | 9 | −0.59889 | 0.097342 | 0 | 7.63E−10 | 6.778439 | 8 | 0.560715 | 3.32E−07 |
| ODC1 | 9 | −0.68104 | 0.127217 | 0.044613 | 8.63E−08 | 11.88186 | 8 | 0.156553 | 1.29E−05 |
| PRKRIR | 9 | −0.62305 | 0.109061 | 0.015161 | 1.11E−08 | 9.332856 | 8 | 0.314999 | 2.62E−06 |
| RPGRIP1 | 9 | −0.69388 | 0.155858 | 0.102714 | 8.51E−06 | 16.92937 | 8 | 0.030853 | 0.000474 |
| RPUSD4 | 9 | −0.59638 | 0.097168 | 0 | 8.37E−10 | 6.368051 | 8 | 0.606078 | 3.56E−07 |
| SETD1B | 9 | −0.5977 | 0.139034 | 0.068864 | 1.72E−05 | 14.10538 | 8 | 0.07906 | 0.000807 |
| TBC1D4 | 9 | −0.60254 | 0.114465 | 0.052354 | 1.41E−07 | 15.52911 | 8 | 0.049638 | 1.89E−05 |
| TGFBI | 9 | −0.72996 | 0.107749 | 0.012798 | 1.25E−11 | 9.115395 | 8 | 0.332655 | 1.05E−08 |
| TOMM20 | 9 | −0.69877 | 0.118071 | 0.062035 | 3.25E−09 | 17.88411 | 8 | 0.022112 | 1.02E−06 |
| UBE2Q2 | 9 | −0.58758 | 0.097879 | 0.000743 | 1.94E−09 | 8.065668 | 8 | 0.427082 | 6.88E−07 |
| WDR75 | 9 | −0.60831 | 0.138795 | 0.066488 | 1.17E−05 | 13.79844 | 8 | 0.087173 | 0.00061 |

TABLE 8-continued

Summary statistics for the 82 genes that passed significance, heterogeneity, and effect-size filtering after multi-cohort analysis.

| gene symbol | F Stat up | F Pval up | F stat down | F pval down | F Qval up | F Qval down |
|---|---|---|---|---|---|---|
| ADAMTS3 | 87.38284 | 4.25E-11 | 6.01495 | 0.996136 | 4.80E-09 | 1 |
| ANKRD22 | 100.4755 | 1.81E-13 | 1.08229 | 1 | 3.88E-11 | 1 |
| ANXA3 | 94.41522 | 2.31E-12 | 1.448082 | 1 | 3.71E-10 | 1 |
| AP3B2 | 91.26694 | 8.55E-12 | 1.170627 | 1 | 1.17E-09 | 1 |
| ARL8A | 92.45977 | 5.21E-12 | 1.203348 | 1 | 7.69E-10 | 1 |
| B3GNT8 | 84.85925 | 1.19E-10 | 4.280585 | 0.999614 | 1.21E-08 | 1 |
| BATF | 154.598 | 9.46E-24 | 0.293516 | 1 | 1.65E-19 | 1 |
| BPI | 86.28391 | 6.67E-11 | 2.613547 | 0.99999 | 7.26E-09 | 1 |
| BST1 | 77.70947 | 2.15E-09 | 1.215268 | 1 | 1.53E-07 | 1 |
| C1orf162 | 90.18378 | 1.34E-11 | 1.807791 | 1 | 1.71E-09 | 1 |
| C3AR1 | 79.13497 | 1.21E-09 | 1.848442 | 0.999999 | 9.34E-08 | 1 |
| C9orf103 | 103.9087 | 4.24E-14 | 0.692697 | 1 | 1.07E-11 | 1 |
| C9orf95 | 107.4787 | 9.26E-15 | 9.532782 | 0.946095 | 2.88E-12 | 1 |
| CCR1 | 80.84841 | 6.09E-10 | 3.026479 | 0.99997 | 5.11E-08 | 1 |
| CD177 | 121.6406 | 2.06E-17 | 0.32395 | 1 | 1.93E-14 | 1 |
| CD63 | 92.60416 | 4.91E-12 | 1.230922 | 1 | 7.31E-10 | 1 |
| CD82 | 108.0404 | 7.28E-15 | 1.689182 | 1 | 2.37E-12 | 1 |
| CEACAM1 | 118.0288 | 9.87E-17 | 1.316686 | 1 | 7.17E-14 | 1 |
| CLEC5A | 102.1517 | 8.92E-14 | 0.355484 | 1 | 2.09E-11 | 1 |
| DHRS9 | 84.21748 | 1.55E-10 | 3.233439 | 0.999951 | 1.52E-08 | 1 |
| EMR1 | 82.87146 | 2.68E-10 | 1.278954 | 1 | 2.46E-08 | 1 |
| FAM89A | 109.2253 | 4.39E-15 | 1.63419 | 1 | 1.56E-12 | 1 |
| FCER1G | 112.3815 | 1.13E-15 | 0.608485 | 1 | 5.26E-13 | 1 |
| FCGR1B | 93.22392 | 3.79E-12 | 0.387371 | 1 | 5.79E-10 | 1 |
| FES | 83.81039 | 1.83E-10 | 2.271224 | 0.999997 | 1.76E-08 | 1 |
| FFAR3 | 81.95591 | 3.89E-10 | 1.787622 | 1 | 3.43E-08 | 1 |
| FIG4 | 81.2461 | 5.18E-10 | 2.111909 | 0.999998 | 4.44E-08 | 1 |
| GNA15 | 81.07701 | 5.55E-10 | 1.382475 | 1 | 4.72E-08 | 1 |
| GPR84 | 125.5959 | 3.66E-18 | 0.122918 | 1 | 4.25E-15 | 1 |
| HK3 | 98.86862 | 3.57E-13 | 1.492149 | 1 | 7.03E-11 | 1 |
| HP | 130.1515 | 4.96E-19 | 0.217584 | 1 | 9.10E-16 | 1 |
| IL10 | 79.59046 | 1.01E-09 | 2.358741 | 0.999996 | 7.92E-08 | 1 |
| IL18R1 | 77.97628 | 1.93E-09 | 2.039255 | 0.999999 | 1.41E-07 | 1 |
| KCNE1 | 90.16343 | 1.35E-11 | 1.418853 | 1 | 1.72E-09 | 1 |
| LCN2 | 95.83204 | 1.28E-12 | 1.497105 | 1 | 2.21E-10 | 1 |
| LIN7A | 102.0331 | 9.38E-14 | 1.583338 | 1 | 2.17E-11 | 1 |
| OSCAR | 96.49838 | 9.66E-13 | 1.272787 | 1 | 1.70E-10 | 1 |
| OSTalpha | 117.464 | 1.26E-16 | 0.18605 | 1 | 8.79E-14 | 1 |
| P2RX1 | 77.33706 | 2.49E-09 | 2.562773 | 0.999992 | 1.72E-07 | 1 |
| PADI2 | 97.58179 | 6.13E-13 | 3.64118 | 0.999881 | 1.15E-10 | 1 |
| PECR | 96.60666 | 9.23E-13 | 2.68429 | 0.999988 | 1.63E-10 | 1 |
| PLAC8 | 129.0282 | 8.13E-19 | 0.166514 | 1 | 1.42E-15 | 1 |
| PLB1 | 88.34826 | 2.85E-11 | 2.460701 | 0.999994 | 3.33E-09 | 1 |
| PNPLA1 | 94.13861 | 2.59E-12 | 1.611789 | 1 | 4.14E-10 | 1 |
| PPM1M | 76.72304 | 3.19E-09 | 1.483244 | 1 | 2.12E-07 | 1 |
| PSTPIP2 | 78.6251 | 1.49E-09 | 0.989724 | 1 | 1.13E-07 | 1 |
| RETN | 117.1262 | 1.46E-16 | 0.323468 | 1 | 9.79E-14 | 1 |
| RGL4 | 96.77518 | 8.60E-13 | 0.457406 | 1 | 1.54E-10 | 1 |
| S100A12 | 110.5822 | 2.45E-15 | 1.153413 | 1 | 9.85E-13 | 1 |
| SEPHS2 | 84.2591 | 1.52E-10 | 1.03841 | 1 | 1.50E-08 | 1 |
| SETD8 | 98.64859 | 3.91E-13 | 5.179065 | 0.998553 | 7.66E-11 | 1 |
| SGSH | 88.57382 | 2.60E-11 | 2.932124 | 0.999977 | 3.06E-09 | 1 |
| SIGLEC9 | 104.9377 | 2.73E-14 | 0.544755 | 1 | 7.57E-12 | 1 |
| SLC26A8 | 99.37806 | 2.88E-13 | 1.618236 | 1 | 5.77E-11 | 1 |
| SPPL2A | 79.19584 | 1.18E-09 | 1.025124 | 1 | 9.15E-08 | 1 |
| SQRDL | 86.94967 | 5.07E-11 | 0.811722 | 1 | 5.69E-09 | 1 |
| TCN1 | 77.88568 | 2.00E-09 | 1.321941 | 1 | 1.45E-07 | 1 |
| ZDHHC19 | 168.2246 | 2.03E-26 | 1.078125 | 1 | 7.06E-22 | 1 |
| ZDHHC3 | 120.0334 | 4.14E-17 | 4.85356 | 0.99907 | 3.13E-14 | 1 |
| ARHGEF18 | 1.1909 | 1 | 90.30675 | 1.27E-11 | 1 | 1.83E-09 |
| CACNA2D3 | 1.439578 | 1 | 86.30028 | 6.62E-11 | 1 | 7.19E-09 |
| CNNM3 | 3.703486 | 0.999865 | 78.88287 | 1.34E-09 | 1 | 8.64E-08 |
| GLO1 | 1.224842 | 1 | 75.96508 | 4.31E-09 | 1 | 2.26E-07 |
| GRAMD1C | 0.248515 | 1 | 92.54547 | 5.03E-12 | 1 | 8.80E-10 |
| HACL1 | 1.289179 | 1 | 81.68863 | 4.33E-10 | 1 | 3.49E-08 |
| HLA-DPB1 | 1.65281 | 1 | 85.77693 | 8.20E-11 | 1 | 8.56E-09 |
| KIAA1370 | 1.651519 | 1 | 96.60836 | 9.22E-13 | 1 | 2.14E-10 |
| KLHDC2 | 0.289342 | 1 | 97.63983 | 5.98E-13 | 1 | 1.53E-10 |
| METAP1 | 1.536127 | 1 | 76.52258 | 3.45E-09 | 1 | 1.89E-07 |
| MRPS35 | 1.262215 | 1 | 84.65131 | 1.30E-10 | 1 | 1.28E-08 |
| MTCH1 | 2.017978 | 0.999999 | 92.8469 | 4.43E-12 | 1 | 7.94E-10 |
| NOC3L | 1.720305 | 1 | 78.04294 | 1.88E-09 | 1 | 1.15E-07 |
| ODC1 | 3.023994 | 0.999971 | 95.2574 | 1.62E-12 | 1 | 3.47E-10 |
| PRKRIR | 2.126397 | 0.999998 | 84.0165 | 1.68E-10 | 1 | 1.59E-08 |

TABLE 8-continued

Summary statistics for the 82 genes that passed significance, heterogeneity, and effect-size filtering after multi-cohort analysis.

| | | | | | | |
|---|---|---|---|---|---|---|
| RPGRIP1 | 0.714397 | 1 | 87.23139 | 4.52E−11 | 1 | 5.20E−09 |
| RPUSD4 | 1.250779 | 1 | 76.49836 | 3.49E−09 | 1 | 1.90E−07 |
| SETD1B | 2.383355 | 0.999995 | 74.7257 | 7.05E−09 | 1 | 3.44E−07 |
| TBC1D4 | 1.277458 | 1 | 79.65881 | 9.83E−10 | 1 | 6.87E−08 |
| TGFBI | 3.877609 | 0.999811 | 96.80662 | 8.48E−13 | 1 | 2.02E−10 |
| TOMM20 | 2.961433 | 0.999975 | 119.9027 | 4.38E−17 | 1 | 8.48E−14 |
| UBE2Q2 | 2.259608 | 0.999997 | 77.0402 | 2.81E−09 | 1 | 1.59E−07 |
| WDR75 | 2.401615 | 0.999995 | 83.69362 | 1.92E−10 | 1 | 1.77E−08 |

TABLE 9

Linear models of infection score in the Glue Grant data.
(A) Repeated-measures ANOVA of Glue Grant cohorts examining the effects of time since injury and infection status on infection Z-score.
(B) Linear regression of admission timepoint (Day 0-to-1 since injury) infection score data on injury severity score and infection status.

A. Repeated-measures ANOVA

| | DF | Sum Sq | Mean Sq | F value | P value | |
|---|---|---|---|---|---|---|
| Buffy Coat - DISCOVERY SET | | | | | | |
| Time since injury | 1 | 38.84 | 38.84 | 65.182 | 2.85E−14 | *** |
| Infection Status | 1 | 59.83 | 59.83 | 100.413 | <2e−16 | *** |
| Time:Infection status | 1 | 0.97 | 0.97 | 1.635 | 0.202 | |
| Residuals | 251 | 149.56 | 0.6 | | | |
| Neutrophils - VALIDATION SET | | | | | | |
| Time since injury | 1 | 3.33 | 3.33 | 4.822 | 2.92E−02 | * |
| Infection Status | 1 | 32.32 | 32.32 | 46.743 | 8.32E−11 | *** |
| Time:Infection status | 1 | 1.41 | 1.41 | 2.044 | 0.1543 | |
| Residuals | 214 | 147.99 | 0.69 | | | |

B. Linear Regression

| | Estimate | Std Error | T stat | P value | |
|---|---|---|---|---|---|
| Buffy Coat - DISCOVERY SET | | | | | |
| (Intercept) | −0.281325 | 0.188184 | −1.495 | 0.13639 | |
| Injury Severity Score (ISS) | 0.020229 | 0.006067 | 3.33 | 0.00101 | ** |
| Eventual Infection | 0.913283 | 0.275058 | 3.32 | 0.00106 | ** |
| ISS:Eventual Infection | −0.019907 | 0.008214 | −2.423 | 0.0162 | * |

Residual standard error: 0.7764 on 215 degrees of freedom
F-statistic: 7.484 on 3 and 215 DF, p-value: 8.673e−05

Neutrophils - VALIDATION SET

| | Estimate | Std Error | T stat | P value | |
|---|---|---|---|---|---|
| (Intercept) | −0.740711 | 0.241641 | −3.07 | 0.00253 | ** |
| Injury Severity Score (ISS) | 0.029675 | 0.007585 | 3.91 | 0.000132 | *** |
| Eventual Infection | 1.1357 | 0.372217 | 3.051 | 0.002645 | ** |
| ISS:Eventual Infection | −0.030582 | 0.011067 | −2.763 | 0.006353 | ** |

Residual standard error: 0.8582 on 170 degrees of freedom
F-statistic: 6.19 on 3 and 170 DF, p-value: 0.0005129

Significance levels: P less than: 0.001 '*' 0.01 '' 0.05 '*'.

TABLE 10

Comparison of infection Z-score across infection types. Shown are the infection classes present in the studied datasets for which n >20 within 1 day of infection diagnosis. Student's t-tests were used for comparisons, p <0.05 was considered significant.

Gram Positive versus Gram Negative

| Study | N, Gram Negative | N, Gram Positive | Gram Negative Mean Score | Gram Positive Mean Score | T Statistic | DF | P value | Outcome |
|---|---|---|---|---|---|---|---|---|
| GSE9960 | 18 | 17 | 0.32 | 0.12 | 0.58 | 33.0 | 0.5672 | Not different |
| GSE13015-gpl6106 | 32 | 13 | 0.64 | −0.13 | 3.10 | 31.0 | 0.0041 | Higher Gram Pos |
| GSE33341 | 19 | 32 | 0.83 | 0.77 | 0.34 | 42.4 | 0.7336 | Not different |
| GPSSSI Unique | 56 | 87 | 0.26 | 0.61 | −2.44 | 128.1 | 0.0162 | Higher Gram Neg |

TABLE 10-continued

Comparison of infection Z-score across infection types. Shown are the infection classes present in the studied datasets for which n >20 within 1 day of infection diagnosis. Student's t-tests were used for comparisons, p <0.05 was considered significant.

Bacterial versus Viral

| Study | N, Bacterial Infection | N, Viral Infection | Bacterial Infection Mean Score | Viral Infection Mean Score | T Statistic | DF | P value | Outcome |
|---|---|---|---|---|---|---|---|---|
| GSE20346 | 26 | 19 | 0.64 | 0.56 | 0.29 | 39.3 | 0.7770 | Not different |
| GSE40012 | 74 | 25 | 0.48 | 0.52 | −0.22 | 76.4 | 0.8230 | Not different |
| GSE40396 | 8 | 35 | 1.07 | 0.25 | 2.67 | 12.7 | 0.0194 | Bacterial Higher |
| GPSSSI Unique | 143 | 16 | 0.47 | 0.04 | 1.74 | 17.9 | 0.0994 | Not different |

TABLE 11A

Output from EncodeQT. The 6 positive and 5 negative genes were analyzed separately using default settings. Q-Values are derived from Benjamini-Hochberg corrected hypergeometric test.

ENCODEQT-POSITIVE GENES

| Factor | Total Genes with Factor | +/−5000 bp POSITIVE Observed Genes | Q-value | POSITIVE Factor Rank |
|---|---|---|---|---|
| Max | 14735 | 6 | 0.00E+00 | 1 |

ENCODEQT-NEGATIVE GENES

| Factor | Total Genes with Factor | +/−5000 bp NEGATIVE Observed Genes | Q-value | NEGATIVE Factor Rank |
|---|---|---|---|---|

No Significant Transcription Factor Interactions Found (q < .05)

TABLE 11B

Output from PASTAA. The 6 positive and 5 negative genes were analyzed separately using −200 basepairs from transcription start site, searching over conserved human/mouse sequences. P-values are from the hypergeometric test.

PASTAA - Positive Genes, −200 bp from TSS, conserved human/mouse

| Rank | Matrix | Transcription Factor | Association Score | P-Value |
|---|---|---|---|---|
| 1 | ZBRK1_01 | N/A | 3.353 | 1.28E−03 |
| 2 | PAX_Q6 | Pax-1, Pax-2 | 2.967 | 3.70E−03 |
| 3 | IRF_Q6_01 | Irf-1, Irf-10 | 2.72 | 6.74E−03 |
| 4 | CREL_01 | C-rel | 2.647 | 7.42E−03 |
| 5 | GATA4_Q3 | Gata-4 | 2.522 | 1.02E−02 |
| 6 | PAX4_03 | Pax-4a | 2.522 | 1.02E−02 |
| 7 | PPAR_DR1_Q2 | Ppar-alpha, Ppar-beta | 2.521 | 1.02E−02 |
| 8 | STAT5A_04 | Stat5a | 2.503 | 1.02E−02 |
| 9 | PTF1BETA_Q6 | N/A | 2.372 | 1.43E−02 |
| 10 | MYB_Q3 | C-myb | 2.371 | 1.43E−02 |

TABLE 11B-continued

Output from PASTAA. The 6 positive and 5 negative genes were analyzed separately using −200 basepairs from transcription start site, searching over conserved human/mouse sequences. P-values are from the hypergeometric test.

PASTAA - Negative Genes, −200 bp from TSS, conserved human/mouse

| Rank | Matrix | Transcription Factor | Association Score | P-Value |
|---|---|---|---|---|
| 1 | KAISO_01 | N/A | 3.264 | 1.28E−03 |
| 2 | PAX5_01 | Pax-5 | 3.236 | 1.28E−03 |
| 3 | TCF11_01 | Lcr-f1 | 3.066 | 1.78E−03 |
| 4 | STRA13_01 | Stra13 | 2.823 | 4.06E−03 |
| 5 | HNF4ALPHA_Q6 | Hnf-4, Hnf-4alpha | 2.473 | 9.47E−03 |
| 6 | ARNT_02 | Arnt | 2.346 | 1.31E−02 |
| 7 | USF_Q6 | Usf1, Usf2a | 2.346 | 1.31E−02 |
| 8 | PAX4_01 | Pax-4a | 2.221 | 1.70E−02 |
| 9 | TFIII_Q6 | Tfii-i | 2.22 | 1.70E−02 |
| 10 | AP1_Q6_01 | Fosb, Fra-1 | 2.204 | 1.70E−02 |

REFERENCES

1. D. C. Angus, W. T. Linde-Zwirble, J. Lidicker, G. Clermont, J. Carcillo, M. R. Pinsky, Epidemiology of severe sepsis in the United States: analysis of incidence, outcome, and associated costs of care. Crit Care Med 29, 1303-1310 (2001).
2. T. Lagu, M. B. Rothberg, M. S. Shieh, P. S. Pekow, J. S. Steingrub, P. K. Lindenauer, Hospitalizations, costs, and outcomes of severe sepsis in the United States 2003 to 2007. Crit Care Med 40, 754-761 (2012).
3. C. A. Torio, R. A. Andrews. (Agency for Healthcare Research and Quality, Rockville, Md., August 2013).
4. D. F. Gaieski, M. E. Mikkelsen, R. A. Band, J. M. Pines, R. Massone, F. F. Furia, F. S. Shofer, M. Goyal, Impact of time to antibiotics on survival in patients with severe sepsis or septic shock in whom early goal-directed therapy was initiated in the emergency department. Crit Care Med 38, 1045-1053 (2010).
5. R. Ferrer, I. Martin-Loeches, G. Phillips, T. M. Osborn, S. Townsend, R. P. Dellinger, A. Artigas, C. Schorr, M. M. Levy, Empiric antibiotic treatment reduces mortality in severe sepsis and septic shock from the first hour: results from a guideline-based performance improvement program*. Crit Care Med 42, 1749-1755 (2014).

6. R. P. Dellinger, M. M. Levy, A. Rhodes, D. Annane, H. Gerlach, S. M. Opal, J. E. Sevransky, C. L. Sprung, I. S. Douglas, R. Jaeschke, T. M. Osborn, M. E. Nunnally, S. R. Townsend, K. Reinhart, R. M. Kleinpell, D. C. Angus, C. S. Deutschman, F. R. Machado, G. D. Rubenfeld, S. Webb, R. J. Beale, J. L. Vincent, R. Moreno, S. S. C. G. C. i. T. P. Subgroup, Surviving Sepsis Campaign: international guidelines for management of severe sepsis and septic shock, 2012. *Intensive Care Med* 39, 165-228 (2013).
7. B. Coburn, A. M. Morris, G. Tomlinson, A. S. Detsky, Does this adult patient with suspected bacteremia require blood cultures? *JAMA* 308, 502-511 (2012).
8. B. M. Tang, G. D. Eslick, J. C. Craig, A. S. McLean, Accuracy of procalcitonin for sepsis diagnosis in critically ill patients: systematic review and meta-analysis. *Lancet Infect Dis* 7, 210-217 (2007).
9. B. Uzzan, R. Cohen, P. Nicolas, M. Cucherat, G. Y. Perret, Procalcitonin as a diagnostic test for sepsis in critically ill adults and after surgery or trauma: a systematic review and meta-analysis. *Crit Care Med* 34, 1996-2003 (2006).
10. C. Cheval, J. F. Timsit, M. Garrouste-Orgeas, M. Assicot, B. De Jonghe, B. Misset, C. Bohuon, J. Carlet, Procalcitonin (PCT) is useful in predicting the bacterial origin of an acute circulatory failure in critically ill patients. *Intensive Care Med* 26 Suppl 2, S153-158 (2000).
11. H. Ugarte, E. Silva, D. Mercan, A. De Mendonca, J. L. Vincent, Procalcitonin used as a marker of infection in the intensive care unit. *Crit Care Med* 27, 498-504 (1999).
12. J. P. Cobb, E. E. Moore, D. L. Hayden, J. P. Minei, J. Cuschieri, J. Yang, Q. Li, N. Lin, B. H. Brownstein, L. Hennessy, P. H. Mason, W. S. Schierding, D. J. Dixon, R. G. Tompkins, H. S. Warren, D. A. Schoenfeld, R. V. Maier, Validation of the riboleukogram to detect ventilator-associated pneumonia after severe injury. *Ann Surg* 250, 531-539 (2009).
13. W. Xiao, M. N. Mindrinos, J. Seok, J. Cuschieri, A. G. Cuenca, H. Gao, D. L. Hayden, L. Hennessy, E.E. Moore, J. P. Minei, P. E. Bankey, J. L. Johnson, J. Sperry, A. B. Nathens, T. R. Billiar, M. A. West, B. H. Brownstein, P. H. Mason, H. V. Baker, C. C. Finnerty, M. G. Jeschke, M. C. Lopez, M. B. Klein, R. L. Gamelli, N. S. Gibran, B. Arnoldo, W. Xu, Y. Zhang, S. E. Calvano, G. P. McDonald-Smith, D. A. Schoenfeld, J. D. Storey, J. P. Cobb, H. S. Warren, L. L. Moldawer, D. N. Herndon, S.E. Lowry, R. V. Maier, R. W. Davis, R. G. Tompkins, I. a. H. R. t. I. L.-S. C. R. Program, A genomic storm in critically injured humans. *J Exp Med* 208, 2581-2590 (2011).
14. R. Pankla, S. Buddhisa, M. Berry, D. M. Blankenship, G. J. Bancroft, J. Banchereau, G. Lertmemongkolchai, D. Chaussabel, Genomic transcriptional profiling identifies a candidate blood biomarker signature for the diagnosis of septicemic melioidosis. *Genome Biol* 10, R127 (2009).
15. B. M. Tang, A. S. McLean, I. W. Dawes, S. J. Huang, R. C. Lin, Gene-expression profiling of peripheral blood mononuclear cells in sepsis. Crit Care Med 37, 882-888 (2009).
16. H. R. Wong, Clinical review: sepsis and septic shock—the potential of gene arrays. *Crit Care* 16, 204 (2012).
17. S. B. Johnson, M. Lissauer, G. V. Bochicchio, R. Moore, A. S. Cross, T. M. Scalea, Gene expression profiles differentiate between sterile SIRS and early sepsis. *Ann Surg* 245, 611-621 (2007).
18. V. L. Vega, A marker for posttraumatic-sepsis: searching for the Holy Grail around intensive care units. *Crit Care Med* 37, 1806-1807 (2009).
19. T. B. Geijtenbeek, S. I. Gringhuis, Signalling through C-type lectin receptors: shaping immune responses. *Nat Rev Immunol* 9, 465-479 (2009).
20. P. R. Crocker, J. C. Paulson, A. Varki, Siglecs and their roles in the immune system. *Nat Rev Immunol* 7, 255-266 (2007).
21. K. Kuespert, S. Pils, C. R. Hauck, CEACAMs: their role in physiology and pathophysiology. *Curr Opin Cell Biol* 18, 565-571 (2006).
22. D. M. Maslove, H. R. Wong, Gene expression profiling in sepsis: timing, tissue, and translational considerations. *Trends Mol Med*, (2014).
23. J. P. Cobb, M. N. Mindrinos, C. Miller-Graziano, S. E. Calvano, H. V. Baker, W. Xiao, K. Laudanski, B. H. Brownstein, C. M. Elson, D. L. Hayden, D. N. Herndon, S. F. Lowry, R. V. Maier, D. A. Schoenfeld, L. L. Moldawer, R. W. Davis, R. G. Tompkins, P. Bankey, T. Billiar, D. Camp, I. Chaudry, B. Freeman, R. Gamelli, N. Gibran, B. Harbrecht, W. Heagy, D. Heimbach, J. Horton, J. Hunt, J. Lederer, J. Mannick, B. McKinley, J. Minei, E. Moore, F. Moore, R. Munford, A. Nathens, G. O'keefe, G. Purdue, L. Rahme, D. Remick, M. Sailors, M. Shapiro, G. Silver, R. Smith, G. Stephanopoulos, G. Stormo, M. Toner, S. Warren, M. West, S. Wolfe, V. Young, I. a. H. R. t. I. L.-S. C. R. Program, Application of genome-wide expression analysis to human health and disease. *Proc Natl Acad Sci USA* 102, 4801-4806 (2005).
24. J. Seok, H. S. Warren, A. G. Cuenca, M. N. Mindrinos, H. V. Baker, W. Xu, D. R. Richards, G. P. McDonald-Smith, H. Gao, L. Hennessy, C. C. Finnerty, C. M. Lopez, S. Honari, E. E. Moore, J. P. Minei, J. Cuschieri, P. E. Bankey, J. L. Johnson, J. Sperry, A. B. Nathens, T. R. Billiar, M. A. West, M. G. Jeschke, M. B. Klein, R. L. Gamelli, N. S. Gibran, B. H. Brownstein, C. Miller-Graziano, S. E. Calvano, P. H. Mason, J. P. Cobb, L. G. Rahme, S. F. Lowry, R. V. Maier, L. L. Moldawer, D. N. Herndon, R. W. Davis, W. Xiao, R. G. Tompkins, L. r. S. C. R. P. Inflammation and Host Response to Injury, Genomic responses in mouse models poorly mimic human inflammatory diseases. *Proc Natl Acad Sci USA* 110, 3507-3512 (2013).
25. K. H. Desai, C. S. Tan, J. T. Leek, R. V. Maier, R. G. Tompkins, J. D. Storey, I. a. t. H. R. t. I. L.-S. C. R. Program, Dissecting inflammatory complications in critically injured patients by within-patient gene expression changes: a longitudinal clinical genomics study. *PLoS Med* 8, e1001093 (2011).
26. H. S. Warren, C. M. Elson, D. L. Hayden, D. A. Schoenfeld, J. P. Cobb, R. V. Maier, L. L. Moldawer, E. E. Moore, B. G. Harbrecht, K. Pelak, J. Cuschieri, D. N. Herndon, M. G. Jeschke, C. C. Finnerty, B. H. Brownstein, L. Hennessy, P. H. Mason, R. G. Tompkins, I. a. H. R. t. I. L. S. C. R. Program, A genomic score prognostic of outcome in trauma patients. *Mol Med* 15, 220-227 (2009).
27. N. Cvijanovich, T. P. Shanley, R. Lin, G. L. Allen, N. J. Thomas, P. Checchia, N. Anas, R. J. Freishtat, M. Monaco, K. Odoms, B. Sakthivel, H. R. Wong, G. o. P. S. S. S. Investigators, Validating the genomic signature of pediatric septic shock. *Physiol Genomics* 34, 127-134 (2008).
28. T. P. Shanley, N. Cvijanovich, R. Lin, G. L. Allen, N. J. Thomas, A. Doctor, M. Kalyanaraman, N. M. Tofil, S. Penfil, M. Monaco, K. Odoms, M. Barnes, B. Sakthivel, B. J. Aronow, H. R. Wong, Genome-level longitudinal expression of signaling pathways and gene networks in pediatric septic shock. *Mol Med* 13, 495-508 (2007).

29. H. R. Wong, T. P. Shanley, B. Sakthivel, N. Cvijanovich, R. Lin, G. L. Allen, N. J. Thomas, A. Doctor, M. Kalyanaraman, N. M. Tofil, S. Penfil, M. Monaco, M. A. Tagavilla, K. Odoms, K. Dunsmore, M. Barnes, B. J. Aronow, G. o. P. S. S. S. Investigators, Genome-level expression profiles in pediatric septic shock indicate a role for altered zinc homeostasis in poor outcome. *Physiol Genomics* 30, 146-155 (2007).

30. H. R. Wong, N. Cvijanovich, G. L. Allen, R. Lin, N. Anas, K. Meyer, R. J. Freishtat, M. Monaco, K. Odoms, B. Sakthivel, T. P. Shanley, G. o. P. S. S. S. Investigators, Genomic expression profiling across the pediatric systemic inflammatory response syndrome, sepsis, and septic shock spectrum. *Crit Care Med* 37, 1558-1566 (2009).

31. H. R. Wong, R. J. Freishtat, M. Monaco, K. Odoms, T. P. Shanley, Leukocyte subset-derived genomewide expression profiles in pediatric septic shock. *Pediatr Crit Care Med* 11, 349-355 (2010).

32. H. R. Wong, N. Z. Cvijanovich, G. L. Allen, N. J. Thomas, R. J. Freishtat, N. Anas, K. Meyer, P. A. Checchia, R. Lin, T. P. Shanley, M. T. Bigham, D. S. Wheeler, L. A. Doughty, K. Tegtmeyer, S. E. Poynter, J. M. Kaplan, R. S. Chima, E. Stalets, R. K. Basu, B. M. Varisco, F. E. Barr, Validation of a gene expression-based subclassification strategy for pediatric septic shock. *Crit Care Med* 39, 2511-2517 (2011).

33. R. Almansa, E. Tamayo, M. Heredia, S. Gutierrez, P. Ruiz, E. Alvarez, E. Gomez-Sanchez, D. Andaluz-Ojeda, R. Celia, L. Rico, V. Iglesias, J. I. Gomez-Herreras, J. F. Bermejo-Martin, Transcriptomic evidence of impaired immunoglobulin G production in fatal septic shock. *J Crit Care* 29, 307-309 (2014).

34. J. F. Bermejo-Martin, I. Martin-Loeches, J. Rello, A. Antón, R. Almansa, L. Xu, G. Lopez-Campos, T. Pumarola, L. Ran, P. Ramirez, D. Banner, D. C. Ng, L. Socias, A. Loza, D. Andaluz, E. Maravi, M. J. Gomez-Sánchez, M. Gordón, M. C. Gallegos, V. Fernandez, S. Aldunate, C. León, P. Merino, J. Blanco, F. Martin-Sanchez, L. Rico, D. Varillas, V. Iglesias, M. Marcos, F. Gandia, F. Bobillo, B. Nogueira, S. Rojo, S. Resino, C. Castro, R. Ortiz de Lejarazu, D. Kelvin, Host adaptive immunity deficiency in severe pandemic influenza. *Crit Care* 14, R167 (2010).

35. I. Martin-Loeches, E. Papiol, R. Almansa, G. López-Campos, J. F. Bermejo-Martin, J. Rello, Intubated patients developing tracheobronchitis or pneumonia have distinctive complement system gene expression signatures in the pre-infection period: a pilot study. *Med Intensiva* 36, 257-263 (2012).

36. E. Tamayo, A. Fernández, R. Almansa, E. Carrasco, L. Goncalves, M. Heredia, D. AndaluzOjeda, G. March, L. Rico, J. I. Gómez-Herreras, R. O. de Lejarazu, J. F. Bermejo-Martin, Beneficial role of endogenous immunoglobulin subclasses and isotypes in septic shock. *J Crit Care* 27, 616-622 (2012).

37. X. Hu, J. Yu, S. D. Crosby, G. A. Storch, Gene expression profiles in febrile children with defined viral and bacterial infection. *Proc Natl Acad SciUS A* 110, 12792-12797 (2013).

38. G. P. Parnell, A. S. McLean, D. R. Booth, N. J. Armstrong, M. Nalos, S. J. Huang, J. Manak, W. Tang, O. Y. Tam, S. Chan, B. M. Tang, A distinct influenza infection signature in the blood transcriptome of patients with severe community-acquired pneumonia. *Crit Care* 16, R157 (2012).

39. A. Sutherland, M. Thomas, R. A. Brandon, R. B. Brandon, J. Lipman, B. Tang, A. McLean, R. Pascoe, G. Price, T. Nguyen, G. Stone, D. Venter, Development and validation of a novel molecular biomarker diagnostic test for the early detection of sepsis. *Crit Care* 15, R149 (2011).

40. Y. Tang, H. Xu, X. Du, L. Lit, W. Walker, A. Lu, R. Ran, J. P. Gregg, M. Reilly, A. Pancioli, J. C. Khoury, L. R. Sauerbeck, J. A. Carrozzella, J. Spilker, J. Clark, K. R. Wagner, E. C. Jauch, D. J. Chang, P. Verro, J. P. Broderick, F. R. Sharp, Gene expression in blood changes rapidly in neutrophils and monocytes after ischemic stroke in humans: a microarray study. *J Cereb Blood Flow Metab* 26, 1089-1102 (2006).

41. B. M. Tang, A. S. McLean, I. W. Dawes, S. J. Huang, R. C. Lin, The use of gene-expression profiling to identify candidate genes in human sepsis. *Am J Respir Crit Care Med* 176, 676-684 (2007).

42. S. H. Ahn, E. L. Tsalik, D. D. Cyr, Y. Zhang, J. C. van Velkinburgh, R. J. Langley, S. W. Glickman, C. B. Cairns, A. K. Zaas, E. P. Rivers, R. M. Otero, T. Veldman, S. F. Kingsmore, J. Lucas, C. W. Woods, G. S. Ginsburg, V. G. Fowler, Gene expression-based classifiers identify Staphylococcus aureus infection in mice and humans. *PLoS One* 8, e48979 (2013).

43. T. Dolinay, Y. S. Kim, J. Howrylak, G. M. Hunninghake, C. H. An, L. Fredenburgh, A. F. Massaro, A. Rogers, L. Gazourian, K. Nakahira, J. A. Haspel, R. Landazury, S. Eppanapally, J. D. Christie, N. J. Meyer, L. B. Ware, D. C. Christiani, S. W. Ryter, R. M. Baron, A. M. Choi, Inflammasome-regulated cytokines are critical mediators of acute lung injury. *Am J Respir Crit Care Med* 185, 1225-1234 (2012).

44. J. E. Berdal, T. E. Mollnes, T. Wæhre, O. K. Olstad, B. Halvorsen, T. Ueland, J. H. Laake, M. T. Furuseth, A. Maagaard, H. Kjekshus, P. Aukrust, C. M. Jonassen, Excessive innate immune response and mutant D222G/N in severe A (H1N1) pandemic influenza. *J Infect* 63, 308-316 (2011).

45. M. P. Berry, C. M. Graham, F. W. McNab, Z. Xu, S. A. Bloch, T. Oni, K. A. Wilkinson, R. Banchereau, J. Skinner, R. J. Wilkinson, C. Quinn, D. Blankenship, R. Dhawan, J. J. Cush, A. Mejias, O. Ramilo, O. M. Kon, V. Pascual, J. Banchereau, D. Chaussabel, A. O'Garra, An interferon-inducible neutrophil-driven blood transcriptional signature in human tuberculosis. *Nature* 466, 973-977 (2010).

46. K. Fredriksson, I. Tjader, P. Keller, N. Petrovic, B. Ahlman, C. Scheele, J. Wernerman, J. A. Timmons, O. Rooyackers, Dysregulation of mitochondrial dynamics and the muscle transcriptome in ICU patients suffering from sepsis induced multiple organ failure. *PLoS One* 3, e3686 (2008).

47. J. E. McDunn, K. D. Husain, A. D. Polpitiya, A. Burykin, J. Ruan, Q. Li, W. Schierding, N. Lin, D. Dixon, W. Zhang, C. M. Coopersmith, W. M. Dunne, M. Colonna, B. K. Ghosh, J. P. Cobb, Plasticity of the systemic inflammatory response to acute infection during critical illness: development of the riboleukogram. *PLoS One* 3, e1564 (2008).

48. T. P. Chung, J. M. Laramie, D. J. Meyer, T. Downey, L. H. Tam, H. Ding, T. G. Buchman, I. Karl, G. D. Stormo, R. S. Hotchkiss, J. P. Cobb, Molecular diagnostics in sepsis: from bedside to bench. *J Am Coll Surg* 203, 585-598 (2006).

49. G. Parnell, A. McLean, D. Booth, S. Huang, M. Nalos, B. Tang, Aberrant cell cycle and apoptotic changes characterise severe influenza A infection—a meta-analysis of genomic signatures in circulating leukocytes. *PLoS One* 6, e17186 (2011).

50. M. Emonts, Ph.D. thesis, Erasmus University Rotterdam, (2008).
51. P. Khatri, S. Roedder, N. Kimura, K. De Vusser, A. A. Morgan, Y. Gong, M. P. Fischbein, R. C. Robbins, M. Naesens, A. J. Butte, M. M. Sarwal, A common rejection module (CRM) for acute rejection across multiple organs identifies novel therapeutics for organ transplantation. *J Exp Med* 210, 2205-2221 (2013).
52. T. M. Osborn, J. K. Tracy, J. R. Dunne, M. Pasquale, L. M. Napolitano, Epidemiology of sepsis in patients with traumatic injury. *Crit Care Med* 32, 2234-2240 (2004).
53. M. J. Pencina, R. B. D'Agostino, O. V. Demler, Novel metrics for evaluating improvement in discrimination: net reclassification and integrated discrimination improvement for normal variables and nested models. *Stat Med* 31, 101-113 (2012).
54. C. L. Smith, P. Dickinson, T. Forster, M. Craigon, A. Ross, M. R. Khondoker, R. France, A. Ivens, D. J. Lynn, J. Orme, A. Jackson, P. Lacaze, K. L. Flanagan, B. J. Stenson, P. Ghazal, Identification of a human neonatal immune-metabolic network associated with bacterial infection. *Nat Commun* 5, 4649 (2014).
55. A. G. Vassiliou, N. A. Maniatis, S. E. Orfanos, Z. Mastora, E. Jahaj, T. Paparountas, A. Armaganidis, C. Roussos, V. Aidinis, A. Kotanidou, Induced expression and functional effects of aquaporin-1 in human leukocytes in sepsis. *Crit Care* 17, R199 (2013).
56. F. Allantaz, D. Chaussabel, D. Stichweh, L. Bennett, W. Allman, A. Mejias, M. Ardura, W. Chung, E. Smith, C. Wise, K. Palucka, O. Ramilo, M. Punaro, J. Banchereau, V. Pascual, Blood leukocyte microarrays to diagnose systemic onset juvenile idiopathic arthritis and follow the response to IL-1 blockade. *J Exp Med* 204, 2131-2144 (2007).
57. K. Newton, V. M. Dixit, Signaling in innate immunity and inflammation. *Cold Spring Harb Perspect Biol* 4, (2012).
58. R. Chen, P. Khatri, P. K. Mazur, M. Polin, Y. Zheng, D. Vaka, C. D. Hoang, J. Shrager, Y. Xu, S. Vicent, A. J. Butte, E. A. Sweet-Cordero, A meta-analysis of lung cancer gene expression identifies PTK7 as a survival gene in lung adenocarcinoma. *Cancer Res* 74, 2892-2902 (2014).
59. F. Hietbrink, L. Koenderman, M. Althuizen, J. Pillay, V. Kamp, L. P. Leenen, Kinetics of the innate immune response after trauma: implications for the development of late onset sepsis. *Shock* 40, 21-27 (2013).
60. S. A. Madsen-Bouterse, R. Romero, A. L. Tarca, J. P. Kusanovic, J. Espinoza, C. J. Kim, J. S. Kim, S. S. Edwin, R. Gomez, S. Draghici, The transcriptome of the fetal inflammatory response syndrome. *Am J Reprod Immunol* 63, 73-92 (2010).
61. H. R. Wong, N. Z. Cvijanovich, M. Hall, G. L. Allen, N. J. Thomas, R. J. Freishtat, N. Anas, K. Meyer, P. A. Checchia, R. Lin, M. T. Bigham, A. Sen, J. Nowak, M. Quasney, J. W. Henricksen, A. Chopra, S. Banschbach, E. Beckman, K. Harmon, P. Lahni, T. P. Shanley, Interleukin-27 is a novel candidate diagnostic biomarker for bacterial infection in critically ill children. *Crit Care* 16, R213 (2012).
62. A. Kwan, M. Hubank, A. Rashid, N. Klein, M. J. Peters, Transcriptional instability during evolving sepsis may limit biomarker based risk stratification. *PLoS One* 8, e60501 (2013).
63. R. Cavallazzi, C. L. Bennin, A. Hirani, C. Gilbert, P. E. Marik, Is the band count useful in the diagnosis of infection? An accuracy study in critically ill patients. *J Intensive Care Med* 25, 353-357 (2010).
64. G. Drifte, I. Dunn-Siegrist, P. Tissières, J. Pugin, Innate immune functions of immature neutrophils in patients with sepsis and severe systemic inflammatory response syndrome. *Crit Care Med* 41, 820-832 (2013).
65. P. J. Cornbleet, Clinical utility of the band count. *Clin Lab Med* 22, 101-136 (2002).
66. W. van der Meer, W. van Gelder, R. de Keijzer, H. Willems, Does the band cell survive the 21st century? *Eur Haematol* 76, 251-254 (2006).
67. K. Saito, T. Wagatsuma, H. Toyama, Y. Ejima, K. Hoshi, M. Shibusawa, M. Kato, S. Kurosawa, Sepsis is characterized by the increases in percentages of circulating CD4+CD25+ regulatory T cells and plasma levels of soluble CD25. *Tohoku J Exp Med* 216, 61-68 (2008).
68. F. Venet, C. S. Chung, G. Monneret, X. Huang, B. Horner, M. Garber, A. Ayala, Regulatory T cell populations in sepsis and trauma. *J Leukoc Biol* 83, 523-535 (2008).
69. D. Grimaldi, S. Louis, F. Pelle, G. Sirgo, C. Rousseau, Y. E. Claessens, L. Vimeux, A. Cariou, J. P. Mira, A. Hosmalin, J. D. Chiche, Profound and persistent decrease of circulating dendritic cells is associated with ICU-acquired infection in patients with septic shock. *Intensive Care Med* 37, 1438-1446 (2011).
70. S. Park, Y. Zhang, S. Lin, T. H. Wang, S. Yang, Advances in microfluidic PCR for point-of-care infectious disease diagnostics. *Biotechnol Adv* 29, 830-839 (2011).
71. M. A. Poritz, A. J. Blaschke, C. L. Byington, L. Meyers, K. Nilsson, D. E. Jones, S. A. Thatcher, T. Robbins, B. Lingenfelter, E. Amiott, A. Herbener, J. Daly, S. F. Dobrowolski, D. H. Teng, K. M. Ririe, FilmArray, an automated nested multiplex PCR system for multi-pathogen detection: development and application to respiratory tract infection. *PLoS One* 6, e26047 (2011).
72. G. Smyth, in *Bioinformatics and Computational Biology Solutions Using R and Bioconductor*, C.V. Gentleman R, Dudoit S, Irizarry R and Huber W (eds.), Ed. (Springer, New York, 2005), pp. pp. 397-420.
73. W. Xu, J. Seok, M. N. Mindrinos, A. C. Schweitzer, H. Jiang, J. Wilhelmy, T. A. Clark, K. Kapur, Y. Xing, M. Faham, J. D. Storey, L. L. Moldawer, R. V. Maier, R. G. Tompkins, W. H. Wong, R. W. Davis, W. Xiao, I. a. H. R. t. I. L.-S. C. R. Program, Human transcriptome array for high-throughput clinical studies. *Proc Natl Acad Sci USA* 108, 3707-3712 (2011).
74. Y. Koren, L. Carmel, Robust linear dimensionality reduction. *IEEE Trans Vis Comput Graph* 10, 459-470 (2004).
75. A. Bodor, I. Csabai, M. W. Mahoney, N. Solymosi, rCUR: an R package for CUR matrix decomposition. *BMC Bioinformatics* 13, 103 (2012).
76. J. Vandesompele, K. De Preter, F. Pattyn, B. Poppe, N. Van Roy, A. De Paepe, F. Speleman, Accurate normalization of real-time quantitative RT-PCR data by geometric averaging of multiple internal control genes. *Genome Biol* 3, RESEARCH0034 (2002).
77. J. T. Leek, W. E. Johnson, H. S. Parker, A. E. Jaffe, J. D. Storey, The sva package for removing batch effects and other unwanted variation in high-throughput experiments. *Bioinformatics* 28, 882-883 (2012).
78. R. K. Auerbach, B. Chen, A. J. Butte, Relating genes to function: identifying enriched transcription factors using the ENCODE ChIP-Seq significance tool. *Bioinformatics* 29, 1922-1924 (2013).

79. H. G. Roider, T. Manke, S. O'Keeffe, M. Vingron, S. A. Haas, PASTAA: identifying transcription factors associated with sets of co-regulated genes. *Bioinformatics* 25, 435-442 (2009).
80. K. L. Jeffrey, T. Brummer, M. S. Rolph, S. M. Liu, N. A. Callejas, R. J. Grumont, C. Gillieron, F. Mackay, S. Grey, M. Camps, C. Rommel, S. D. Gerondakis, C. R. Mackay, Positive regulation of immune cell function and inflammatory responses by phosphatase PAC-1. *Nat Immunol* 7, 274-283 (2006).
81. F. O. Martinez, S. Gordon, M. Locati, A. Mantovani, Transcriptional profiling of the human monocyte-to-macrophage differentiation and polarization: new molecules and patterns of gene expression. *J Immunol* 177, 7303-7311 (2006).
82. S. Radom-Aizik, F. Zaldivar, S. Y. Leu, P. Galassetti, D. M. Cooper, Effects of 30 min of aerobic exercise on gene expression in human neutrophils. *J Appl Physiol* (1985) 104, 236-243 (2008).
83. F. He, H. Chen, M. Probst-Kepper, R. Geffers, S. Eifes, A. Del Sol, K. Schughart, A. P. Zeng, R. Balling, PLAU inferred from a correlation network is critical for suppressor function of regulatory T cells. *Mol Syst Biol* 8, 624 (2012).
84. M. Giefing, S. Winoto-Morbach, J. Sosna, C. Döring, W. Klapper, R. Küppers, S. Böttcher, D. Adam, R. Siebert, S. Schütze, Hodgkin-Reed-Sternberg cells in classical Hodgkin lymphoma show alterations of genes encoding the NADPH oxidase complex and impaired reactive oxygen species synthesis capacity. *PLoS One* 8, e84928 (2013).
85. J. A. Meyers, D. W. Su, A. Lerner, Chronic lymphocytic leukemia and B and T cells differ in their response to cyclic nucleotide phosphodiesterase inhibitors. *J Immunol* 182, 5400-5411 (2009).
86. S. Eckerle, V. Brune, C. Döring, E. Tiacci, V. Bohle, C. Sundström, R. Kodet, M. Paulli, B. Falini, W. Klapper, A. B. Chaubert, K. Willenbrock, D. Metzler, A. Brauninger, R. Küppers, M. L. Hansmann, Gene expression profiling of isolated tumour cells from anaplastic large cell lymphomas: insights into its cellular origin, pathogenesis and relation to Hodgkin lymphoma. *Leukemia* 23, 2129-2138 (2009).
87. K. A. Stegmann, N. K. Bjorkstrom, H. Veber, S. Ciesek, P. Riese, J. Wiegand, J. Hadem, P. V. Suneetha, J. Jaroszewicz, C. Wang, V. Schlaphoff, P. Fytili, M. Cornberg, M. P. Manns, R. Geffers, T. Pietschmann, C. A. Guzman, H. G. Ljunggren, H. Wedemeyer, Interferon-alpha induced TRAIL on natural killer cells is associated with control of hepatitis C virus infection. *Gastroenterology* 138, 1885-1897 (2010).
88. D. C. Vinh, S. Y. Patel, G. Uzel, V. L. Anderson, A. F. Freeman, K. N. Olivier, C. Spalding, S. Hughes, S. Pittaluga, M. Raffeld, L. R. Sorbara, H. Z. Elloumi, D. B. Kuhns, M. L. Turner, E. W. Cowen, D. Fink, D. Long-Priel, A. P. Hsu, L. Ding, M. L. Paulson, A. R. Whitney, E. P. Sampaio, D. M. Frucht, F. R. DeLeo, S. M. Holland, Autosomal dominant and sporadic monocytopenia with susceptibility to mycobacteria, fungi, papillomaviruses, and myelodysplasia. *Blood* 115, 1519-1529 (2010).
89. P. Ancuta, K. Y. Liu, V. Misra, V. S. Wacleche, A. Gosselin, X. Zhou, D. Gabuzda, Transcriptional profiling reveals developmental relationship and distinct biological functions of CD16+ and CD16− monocyte subsets. *BMC Genomics* 10, 403 (2009).
90. N. Novershtern, A. Subramanian, L. N. Lawton, R. H. Mak, W. N. Haining, M. E. McConkey, N. Habib, N. Yosef, C. Y. Chang, T. Shay, G. M. Frampton, A. C. Drake, I. Leskov, B. Nilsson, F. Preffer, D. Dombkowski, J. W. Evans, T. Liefeld, J. S. Smutko, J. Chen, N. Friedman, R. A. Young, T. R. Golub, A. Regev, B. L. Ebert, Densely interconnected transcriptional circuits control cell states in human hematopoiesis. *Cell* 144, 296-309 (2011).
91. F. Allantaz, D. T. Cheng, T. Bergauer, P. Ravindran, M. F. Rossier, M. Ebeling, L. Badi, B. Reis, H. Bitter, M. D'Asaro, A. Chiappe, S. Sridhar, G. D. Pacheco, M. E. Burczynski, D. Hochstrasser, J. Vonderscher, T. Matthes, Expression profiling of human immune cell subsets identifies miRNA-mRNA regulatory relationships correlated with cell type specific expression. *PLoS One* 7, e29979 (2012).
92. E. Tsitsiou, A. E. Williams, S. A. Moschos, K. Patel, C. Rossios, X. Jiang, O. D. Adams, P. Macedo, R. Booton, D. Gibeon, K. F. Chung, M. A. Lindsay, Transcriptome analysis shows activation of circulating CD8+ T cells in patients with severe asthma. *J Allergy Clin Immunol* 129, 95-103 (2012).
93. M. Frankenberger, T. P. Hofer, A. Marei, F. Dayyani, S. Schewe, C. Strasser, A. Aldraihim, F. Stanzel, R. Lang, R. Hoffmann, 0. Prazeres da Costa, T. Buch, L. Ziegler-Heitbrock, Transcript profiling of CD16-positive monocytes reveals a unique molecular fingerprint. *Eur J Immunol* 42, 957-974 (2012).
94. N. Y. Huen, A. L. Pang, J. A. Tucker, T. L. Lee, M. Vergati, C. Jochems, C. Intrivici, V. Cereda, W. Y. Chan, O. M. Rennert, R. A. Madan, J. L. Gulley, J. Schlom, K. Y. Tsang, Up-regulation of proliferative and migratory genes in regulatory T cells from patients with metastatic castration-resistant prostate cancer. *Int J Cancer* 133, 373-382 (2013).
95. K. C. Malcolm, E. M. Nichols, S. M. Caceres, J. E. Kret, S. L. Martiniano, S. D. Sagel, E. D. Chan, L. Caverly, G. M. Solomon, P. Reynolds, D. L. Bratton, J. L. Taylor-Cousar, D. P. Nichols, M. T. Saavedra, J. A. Nick, Mycobacterium abscessus induces a limited pattern of neutrophil activation that promotes pathogen survival. *PLoS One* 8, e57402 (2013).
96. N. Rapin, F. O. Bagger, J. Jendholm, H. Mora-Jensen, A. Krogh, A. Kohlmann, C. Thiede, N. Borregaard, L. Bullinger, 0. Winther, K. Theilgaard-Mönch, B. T. Porse, Comparing cancer vs normal gene expression profiles identifies new disease entities and common transcriptional programs in AML patients. *Blood* 123, 894-904 (2014).
97. N. A. Mabbott, J. K. Baillie, H. Brown, T. C. Freeman, D. A. Hume, An expression atlas of human primary cells: inference of gene function from coexpression networks. *BMC Genomics* 14, 632 (2013).

Example 2

Benchmarking Sepsis Gene Expression Diagnostics Using Public Data

There is no rapidly available gold-standard molecular test that can determine whether a patient with systemic inflammation has an underlying infection. Missed diagnoses of sepsis leads to late treatment and increased mortality, while inappropriate antibiotics increase antibiotic resistance and can lead to complications (Ferrer et al. (2014) Crit Care Med 42(8):1749-1755; McFarland (2008) Future Microbiol 3(5): 563-578; Gaieski et al. (2010) Crit Care Med 38(4):1045-1053). There is thus an urgent and unmet need for new diagnostics that can separate patients with non-infectious inflammation from patients with sepsis (Cohen et al. (2015) Lancet Infect Dis 15(5):581-614).

New diagnostics that can distinguish sepsis from non-infectious inflammation are difficult to derive, as many of the cellular pathways that are activated in response to infections are also activated in response to tissue trauma and non-infectious inflammation. Thus, high-throughput 'omics' technologies, such as gene expression profiling via microarray, are a good way to study sepsis, as they allow for the simultaneous examination of tens of thousands of genes. Statistical techniques can then be used to derive new classifiers that are optimized for diagnosis. However, high-throughput datasets always have more variables than samples, and so are prone to non-reproducible, overfit results (Shi et al. (2008) BMC Bioinformatics 9 Suppl 9:S10; Ioannidis et al. (2001) Nat Genet 29(3):306-309). Moreover, in an effort to increase statistical power, each biomarker dataset is performed in a clinically homogeneous cohort, and often performed using only a single type of microarray. Although this design does result in a greater power to detect differences between the groups being studied, the results are less likely to remain true in different clinical cohorts using different laboratory techniques. As a result, independent validation is absolutely necessary to gauge the generalizability of any new classifier derived from high-throughput studies.

To the best of our knowledge, there are three gene expression diagnostics that have been developed using microarray data specifically to separate patients with sepsis from those with non-infectious inflammation. These are an 11-gene set hereafter referred to as the 'Sepsis MetaScore' (SMS) (Sweeney et al. (2015) Sci Transl Med 7(287): 287ra271), the FAIM3:PLAC8 ratio (Scicluna et al. (2015) Am J Respir Crit Care Med. 192(7):826-835), and the Septicyte Lab (McHugh et al. (2015) PLoS Med 12(12): e1001916). In addition, there are now dozens of publicly available datasets examining patients with sepsis or acute infections. They span a very broad range of clinical conditions, including different age groups, infection types, comorbid conditions, and control (non-infectious) conditions. This relatively untapped public resource can thus be used to estimate the relative strengths and weaknesses of different diagnostics across an enormous number of patient samples. Here we used all available public gene expression data to study and directly compare the diagnostic power of the three sepsis gene expression diagnostics.

Methods

Figure 17:
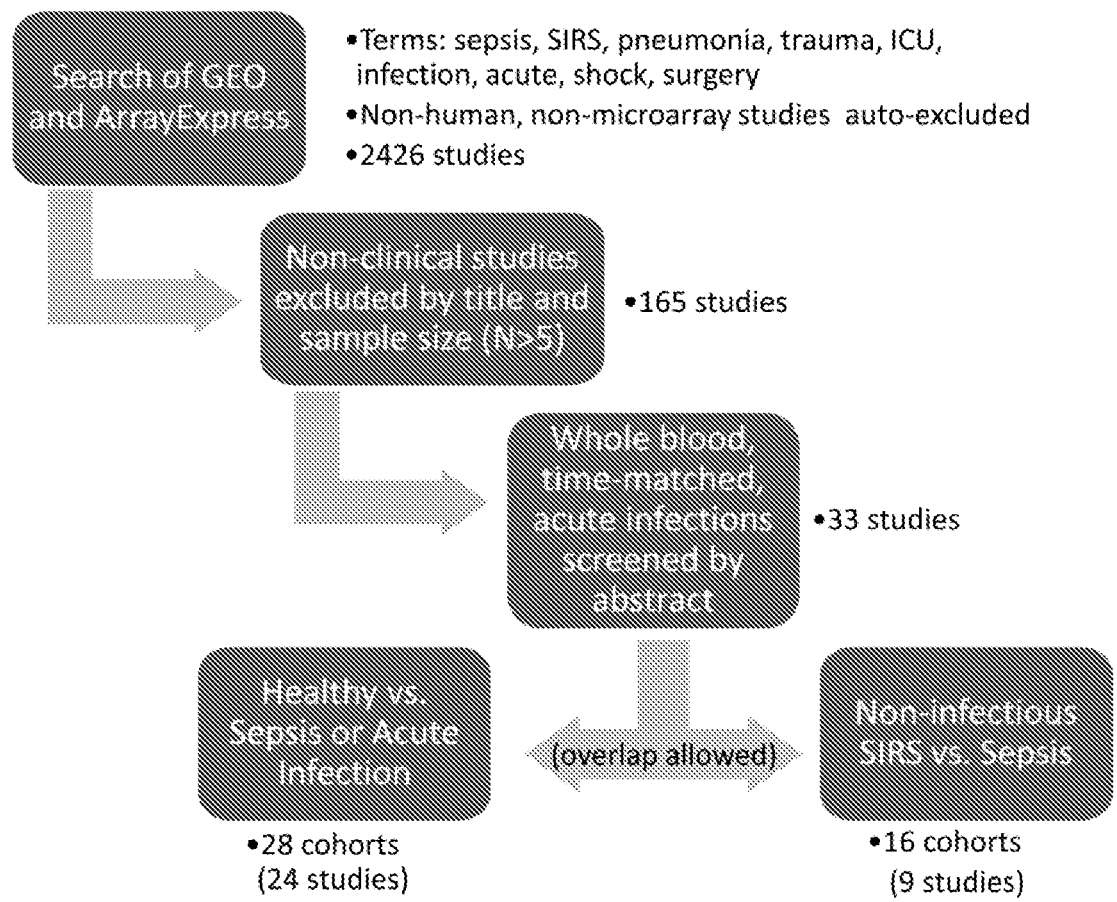
FIG. 17 shows schema for systematic search and selection of clinical sepsis datasets.

We completed a systematic search on Dec. 10, 2015 of two public gene expression repositories (NIH GEO and EBI ArrayExpress) using the following terms: sepsis, SIRS, pneumonia, trauma, ICU, infection, acute, shock, and surgery. We automatically excluded non-microarray, non-human data. Then, using the abstracts of the corresponding manuscripts for screening, we eliminated (1) non-clinical (2) non-time-matched, and (3) non-whole-blood datasets. The remaining datasets were then sorted according to whether the reference group (compared to sepsis) was healthy controls or non-infected SIRS patients. A schematic is shown in FIG. 17. In addition to the data from the systematic search, we included the two longitudinal trauma cohorts from the Inflammation and Host Response to Injury (Glue Grant) cohorts, as described previously (Sweeney et al. (2015) Sci Transl Med 7(287):287ra2717). Cohorts from the same study run on different microarrays were treated as independent.

All datasets for which raw data was available were renormalized if possible. Affymetrix arrays were renormalized using gcRMA (on arrays with perfect-match probes available) or RMA. Illumina, Agilent, GE, and other commercial arrays were renormalized via normal-exponential background correction followed by quantile normalization. Custom arrays were not renormalized. All data were used in log2-transformed state. Probes were summarized to genes within datasets using a fixed-effects model (Ramasamy et al. (2008) PLoS Med 5(9):e184).

A literature review was conducted to search for gene expression signatures specifically optimized for diagnosis of sepsis as compared to non-infected patients. The resulting models were then tested for diagnostic power of sepsis as measured by the area under the receiver operating characteristic curves (AUC). Datasets for which any of the sepsis scores could not be calculated (either all up-regulated or all down-regulated genes were missing) were excluded from final results. For a given comparison (e.g. non-infectious SIRS versus sepsis at admission), means were calculated both for all datasets of that type, as well as for only non-discovery datasets, since discovery datasets are expected to show an overestimate of diagnostic power compared to independent validation datasets. Finally, we compared the overlapping validation sets for each diagnostic score with paired t-tests (e.g., the 11-gene set and the FAIM3:PLAC8 ratio were compared in their ability to diagnose sepsis in GSE74227, E-MEXP-3589, and the Glue Grant neutrophils, as these were the only cohorts that were validated for both datasets).

The patient samples in GSE28750 (11) (N=21) were also used in the later dataset GSE74224 (McHugh et al. (2015) PLoS Med 12(12):e1001916) (N=105), though the two datasets were run using different microarray types (Affymetrix HG 2.0 vs. Affymetrix Exon 1.0 ST). As a result, GSE28750 is not included in the validation calculation for the Septicyte Lab (discovered in GSE74224), while in computing the validation mean for the Sepsis MetaScore, the AUC in GSE74224 was penalized to account for the fact that 20% of the GSE74224 patients were present in discovery (penalized AUC*0.8+actual AUC in GSE28750*0.2) =actual AUC.

To test confounding by infection type, each dataset was screened for presence of either (1) both Gram positive and Gram negative infections, or (2) both bacterial and viral infections. Microbiology determinations as described by the original authors of the data were assumed to be correct. Cases of co-infection were not included in the confounding comparisons. To test confounding, each gene expression score was calculated for datasets which included both classes of interest, and resulting scores between classes were compared via Wilcoxon rank-sum test within the dataset.

Meta-analysis was performed as previously described. Briefly, differential gene expression between non-infectious SIRS and sepsis patients was summarized within datasets using Hedge's g, and then compared between datasets using a DerSimonian-Laird random effects model, followed by Benjamini-Hochberg correction. Forest plots for individual genes show individual effects within each dataset, as well as the summarized 'meta-effect', in log 2 space. All analyses were performed using the R statistical computing language. Significance tests were always two-tailed. The uploaded data are in the renormalized form used here. Glue Grant data is available to researchers who have been approved by the Glue Grant consortium; instructions are on our website. If the results are used in a manuscript, the authors request citations of both this article, and of the articles that described the original datasets.

Results

We performed a systematic search of public gene expression databases (FIG. 17), and also we used the two independent Glue Grant trauma cohorts, broken up into time-matched bins of never-infected patients and patients within +/−24 hours of diagnosis of sepsis, as previously described (Sweeney et al. (2015) Sci Transl Med 7(287):287ra271). This yielded a total of 39 datasets that matched criteria, composed of 3241 patient samples (Scicluna et al., supra; McHugh et al., supra; Dolinay et al. (2012) Am J Respir Crit Care Med 185(11):1225-1234; Parnell et al. (2012) Crit Care 16(4):R157; Wong et al. (2007) Physiol Genomics 30(2): 146-155; Wynn et al. (2011) Mol Med 17(11-12):1146-1156; Wong et al. (2009) Crit Care Med 37(5):1558-1566; Shanley et al. (2007) Mol Med 13(9-10):495-508; Cvijanovich et al. (2008) Physiol Genomics 34(1):127-134; Almansa et al. (2012) BMC Res Notes 5:401; Irwin et al. (2012) BMC Med Genomics 5:13; van de Weg et al. (2015) PLoS Negl Trop Dis 9(3):e0003522; Emonts M. Polymorphisms in Immune Response Genes in Infectious Diseases and Autoimmune Diseases [Ph.D. thesis]: Erasmus University Rotterdam; 2008; Pankla et al. (2009) Genome Biol 10(11):R127; Zaas et al. (2009) Cell Host Microbe 6(3):207-217; Parnell et al. (2011) PLoS One 6(3):e17186; Bermejo-Martin et al. (2010) Crit Care 14(5):R167; Berry et al. (2010) Nature 466(7309): 973-977; Smith et al. (2014) Nat Commun 5:4649; Berdal et al. (2011) J Infect 63(4):308-316; Ahn et al. (2013) PLoS One 8(1):e48979; Mejias et al. (2013) PLoS Med 10(11): e1001549; Hu et al. (2013) Proc Natl Acad Sci USA 110(31):12792-12797; Herberg et al. (2013) J Infect Dis 208(10):1664-1668; Kwissa et al. (2014) Cell Host Microbe 16(1):115-127; Cazalis et al. (2014) Intensive Care Med Exp 2(1):20; Suarez et al. (2015) J Infect Dis. 212(2):213-222; Zhai et al. (2015) PLoS Pathog 11(6):e1004869; Conejero et al. (2015) J Immunol 195(7):3248-3261; Xiao et al. (2011) J Exp Med 208(13):2581-2590; and Warren et al. (2009) Mol Med 15(7-8):220-227).

Our literature review revealed three gene expression classifiers specifically optimized to distinguish non-infectious SIRS from sepsis in whole blood samples. These were: the 11-gene set (SMS) that we published previously (Sweeney et al., Sci Transl Med 2015); the FAIM3:PLAC8 ratio (Scicluna et al., AJRCCM 2015), and the Septicyte Lab (McHugh et al., PLoS Medicine, 2015). For each sample, the 11-gene score is calculated according to the following formula:

$$\sqrt[6]{(CEACAM1 * ZDHHC19 * C9orf95 * GNA15 * BATF * C3AR1)} - 5/6 \sqrt[5]{(KIAA1370 * TGFBI * MTCH1 * RPGRIP1 * HLA-DPB1)}$$

The FAIM3:PLAC8 ratio is calculated as: PLAC8/FAIM3. The Septicyte Lab is calculated as: (PLAC8+LAMP1)−(PLA2G7+CEACAM4). In all cases, the calculations are performed on log2-transformed data.

The robustness and reproducibility of each of the three sepsis scores depends on robust and reproducible change in expression for each of their constituent genes. Therefore, we explored how consistently individual genes in each of the three tests changed across 12 whole-blood cohorts comparing non-infected SIRS/trauma patients to sepsis patients. Our meta-analysis of these datasets revealed that each of the 16 genes included in any of the 3 gene scores (except CEACAM4) changed in the desired direction (FDR <5%). Notably, CEACAM4, one of the genes in the Septicyte Lab, was significantly down-regulated only in its corresponding discovery cohort.

Next, we divided the datasets into two broad types of comparison: patients with non-infectious SIRS or trauma versus sepsis or acute infections (Table 1); and healthy controls vs. patients with sepsis or acute infection (Table 2). For both of these types of comparison, we calculated both the overall mean AUC, as well as the AUC when including only independent validation datasets; for each of the three signatures, we excluded their corresponding discovery datasets.

Figure 18A:
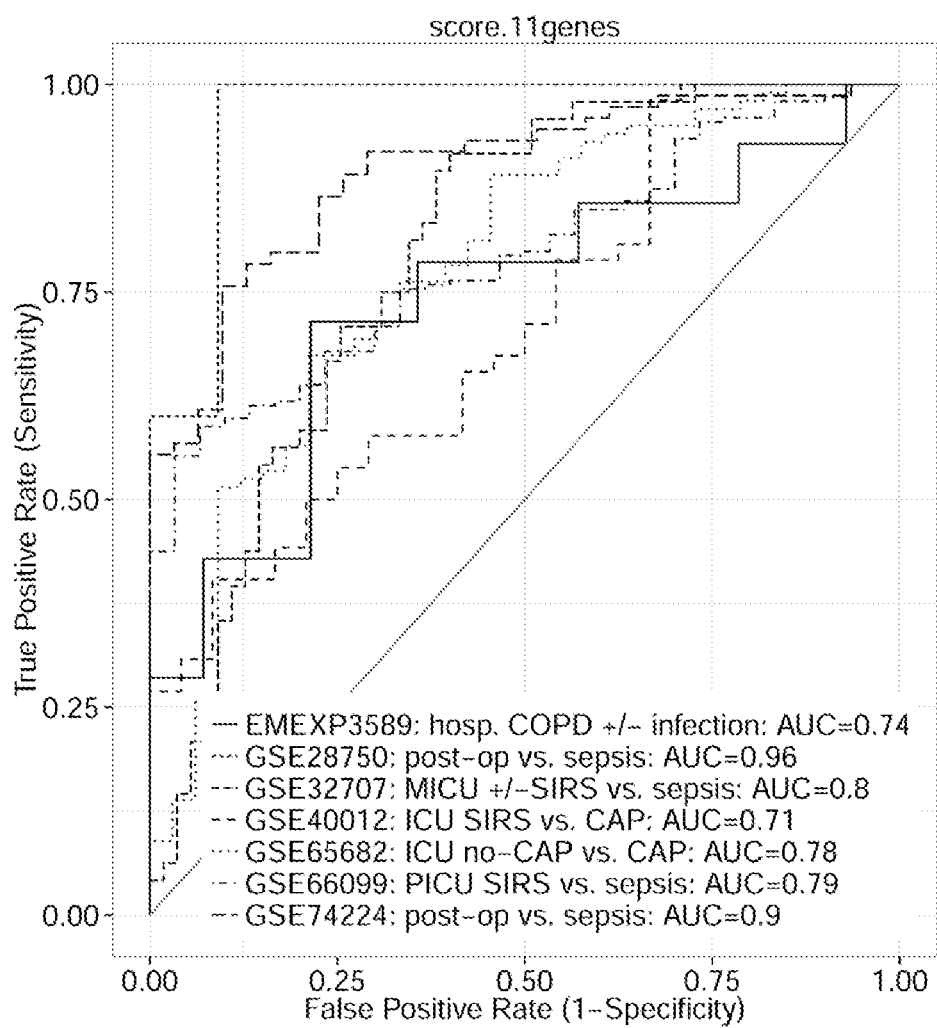
FIGS. 18A-18C show ROC plot discrimination of sepsis/acute infections from patients with non-infectious inflammation at admission.
Figure 18B:
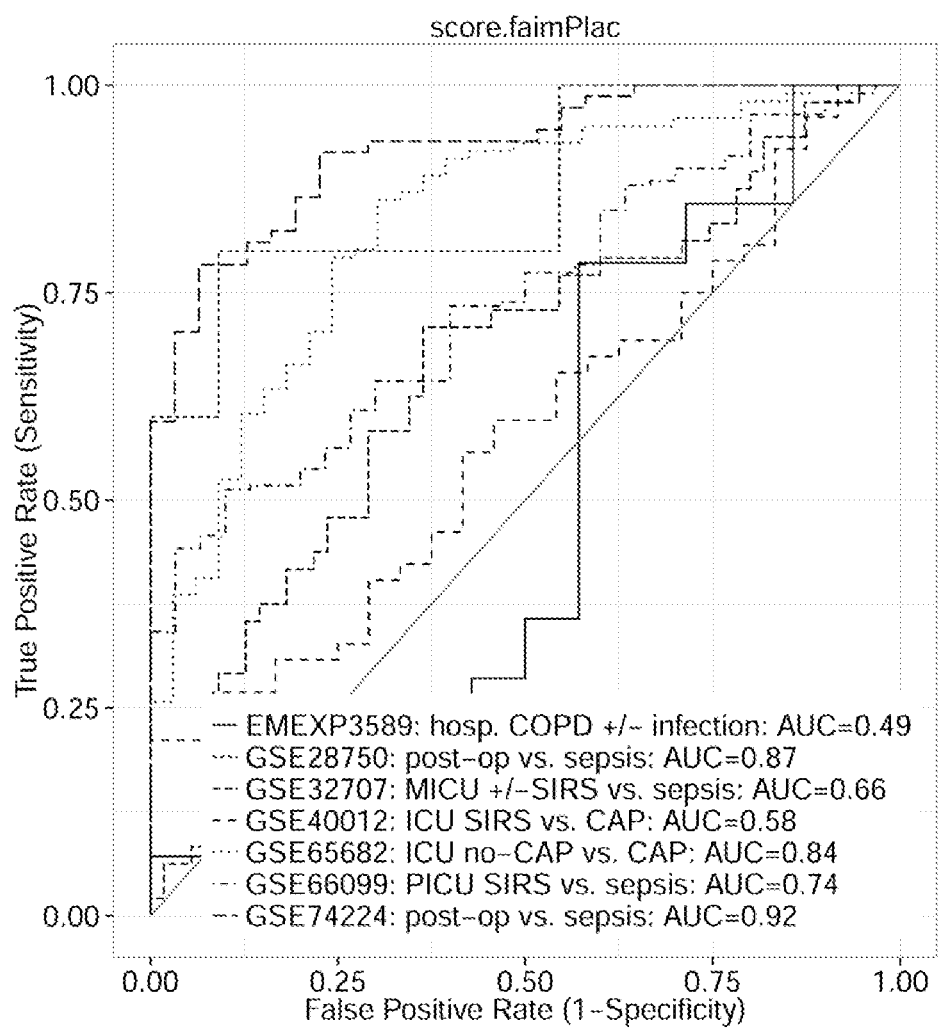
Figure 18C:
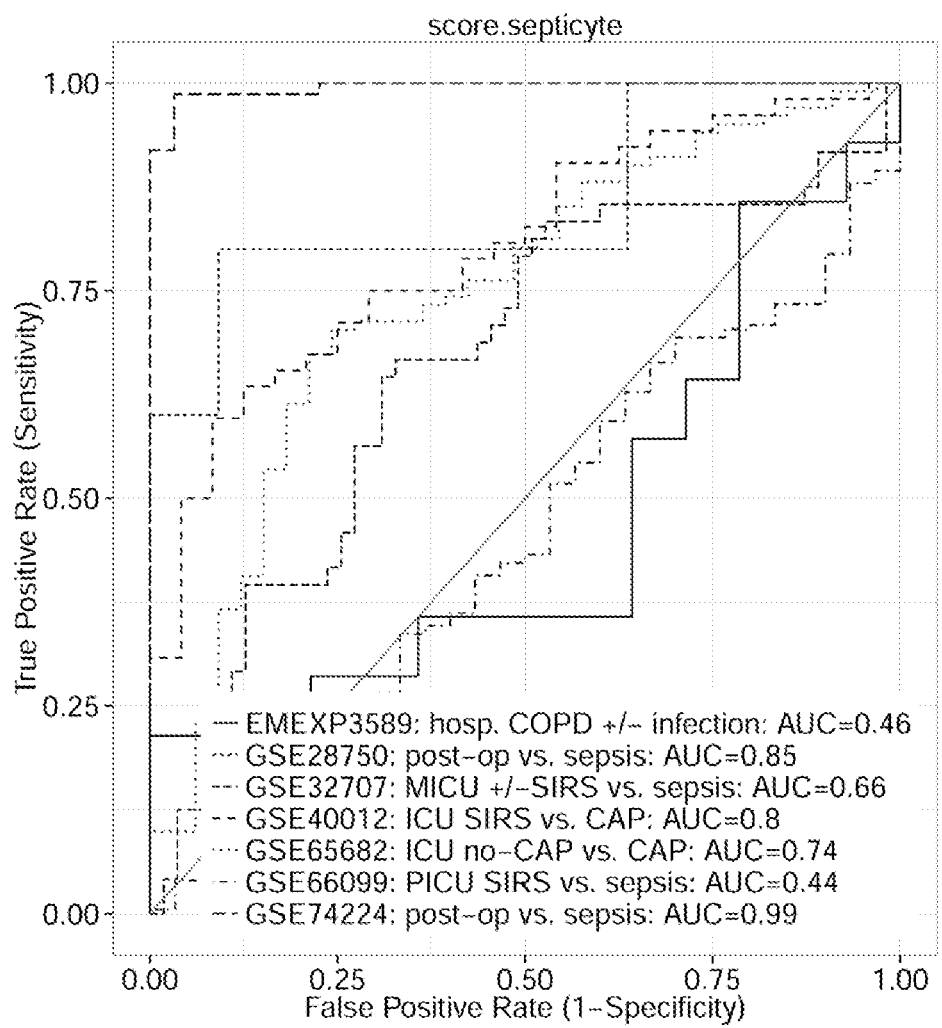
Figure 19A:
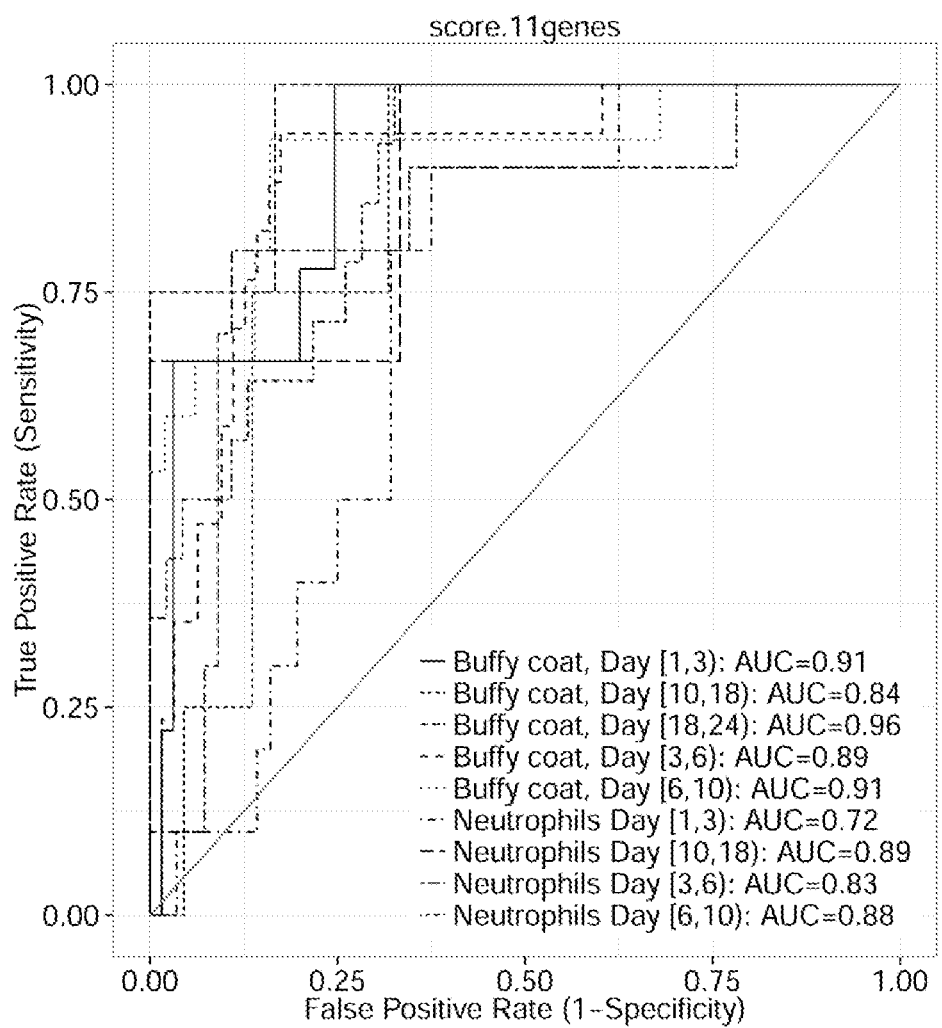
FIGS. 19A-19C show ROC plot discrimination of trauma patients with sepsis/acute infections from time-matched never-infected trauma patients.
Figure 19B:
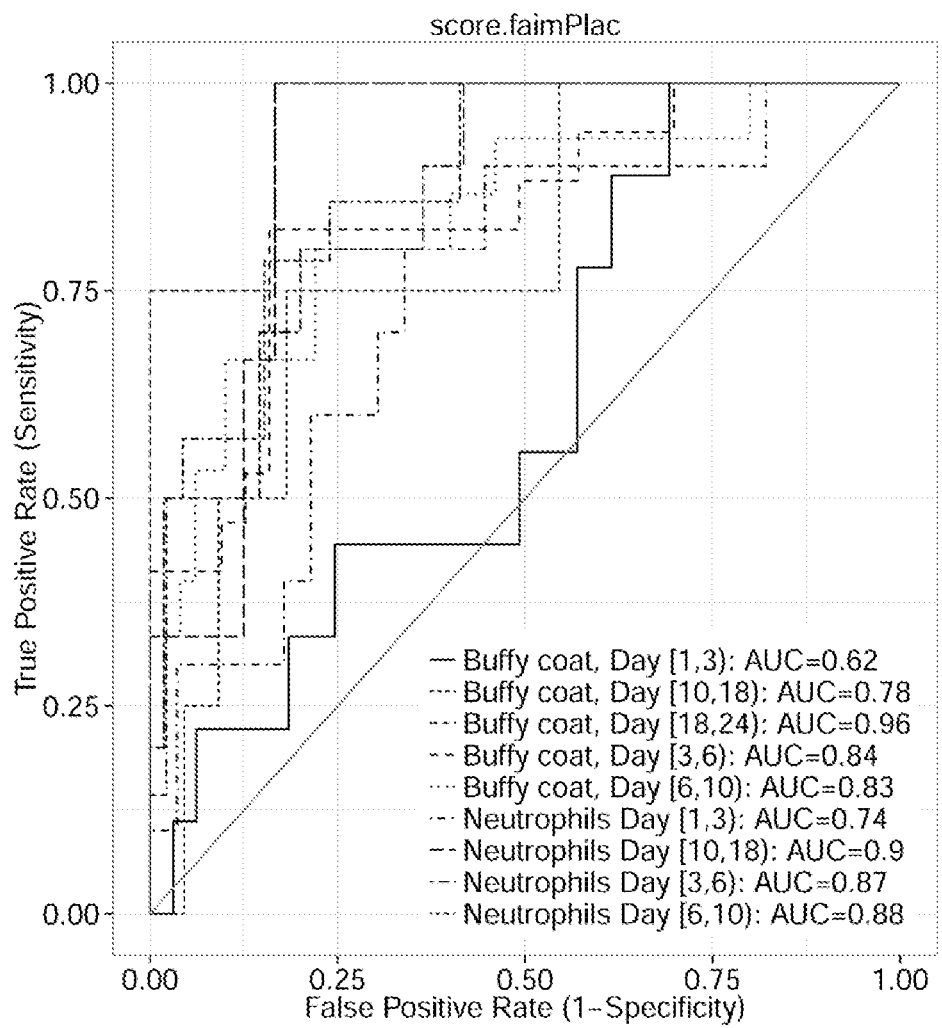
Figure 19C:
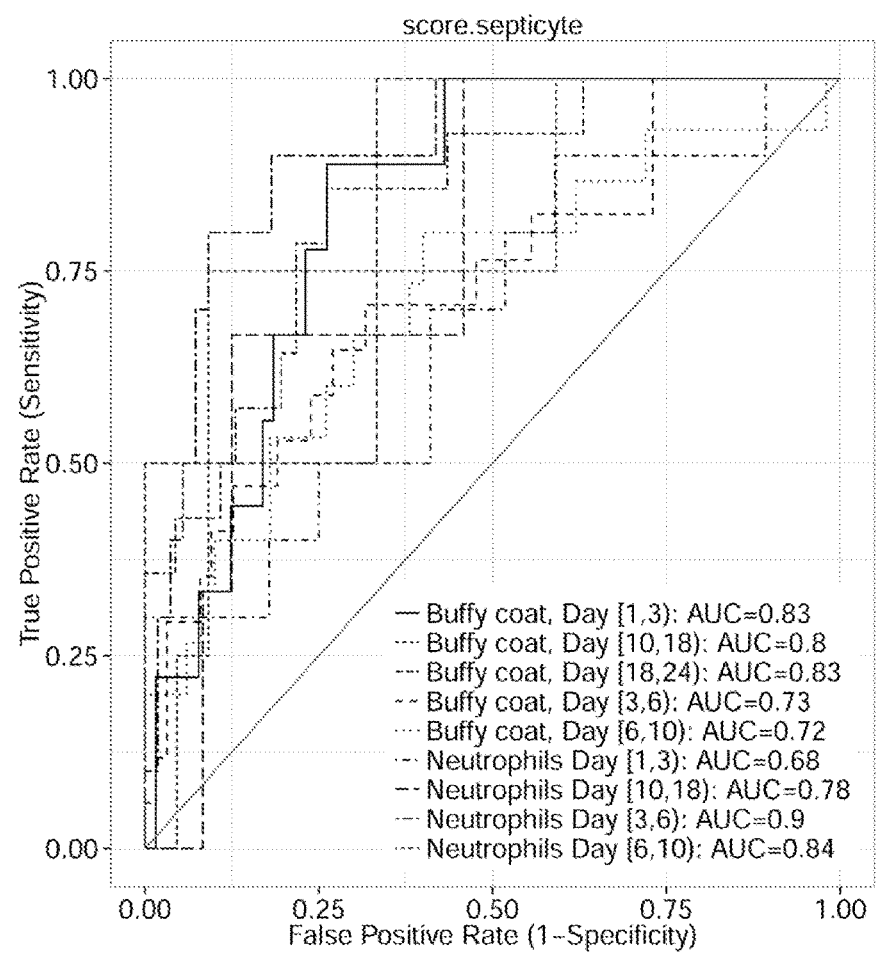

In the non-infectious SIRS/trauma versus sepsis datasets (16 cohorts, 1148 samples, Table 1), there were no significant differences in paired t-tests between the AUCs of the three gene expression diagnostic scores comparing overlapping validation datasets (all p>0.1; FIGS. 18 and 19). When comparing the AUCs from all 16 cohorts (i.e. including the discovery cohorts), the Sepsis MetaScore AUCs were significantly higher than those of the other two gene scores (both p<0.05), with no significant difference between the FAIM3:PLAC8 ratio and the Septicyte Lab. However, these results do not necessarily point to better overall performance of the Sepsis MetaScore, as the Sepsis MetaScore used 9 of these cohorts in discovery. The FAIM3:PLAC8 ratio showed decreased performance in GSE32707 and GSE40012, but as discussed previously, it is specifically designed for testing the presence of CAP and may not be generalizable to other forms of non-infectious inflammation (41, 42). Finally, the Septicyte Lab had significantly reduced performance (AUC<0.5) in separating both pediatric SIRS/sepsis patients, as well as hospitalized COPD patients with and without infections. It possible that this reduction in AUC for the Septicyte Lab is due to the differences in clinical circumstances or microarray types compared to the initial discovery cohort for the Septicyte Lab.

We next examined datasets that compared healthy controls to patients with sepsis or acute infections (26 datasets, 2417 samples, Table 2). Most, but not all, of these patients had sepsis; however, for a sepsis diagnostic test, it is reasonable to expect that it should be able to distinguish most infections from healthy controls. Here, both the Sepsis MetaScore and the FAIM3:PLAC8 ratio performed as expected, with mean validation AUCs of 0.96+/−0.05 and 0.94+/−0.09 (Table 2). However, the Septicyte Lab had an AUC<0.7 in 12 datasets (43% of total datasets) composed of 1562 samples (64% of total samples), resulting in a mean validation AUC=0.71 +/−0.20 (Table 2), significantly lower than both the Sepsis MetaScore and FAIM3:PLAC8 ratio (both P<1e-5). Again, this reduced performance may be due to the Septicyte Lab's inclusion of CEACAM4, which was found to be non-significant in meta-analysis. One could argue that there is no clinical need for a diagnostic to separate healthy controls from those with sepsis; however, poor performance in distinguishing these two groups may be indicative of deeper biases and may increase the risk of non-generalizability.

An ideal sepsis diagnostic would not show varying performance depending on the type of infection present. In order to study whether any of the diagnostics is biased towards a specific type of infection, we searched through all of the included datasets to find those comparing patients with bacterial and viral infections, and those comparing Gram positive and Gram negative infections. We then compared both the diagnostic power in detecting these types of infections (as compared to healthy controls), as well as comparing the distributions of scores. Since a higher score indicates a higher likelihood of infection, a score that is consistently lower in one infection type may indicate decreased diagnostic performance for that type, even if a change in diagnostic performance is not detected as compared to healthy controls.

There were 8 datasets that provided information about whether a patient had bacterial or viral infection. In general, there were few differences between the AUCs for bacterial and viral infections for any of the three scores (Table 3); however, this may be due to small numbers, and the relatively high AUCs in comparing these infections to healthy controls. However, despite these caveats, both the Sepsis MetaScore and the FAIM3:PLAC8 ratio showed higher mean scores in patients with bacterial infections as compared to viral infections in 7/8 datasets tested, both reaching significance in 2/8 datasets (Table 5). The Septicyte Lab, in contrast, did not show a strong trend in comparing bacterial and viral infections, showing a significantly higher mean in viral than in bacterial infections in one dataset.

There were 8 datasets that provided information about whether a patient had Gram positive and Gram negative infection. The comparison of Gram positive and Gram negative infections revealed no differences in AUC for either the Sepsis MetaScore or the FAIM3:PLAC8 ratio; the Septicyte Lab showed some variability, but this may be due to a high variability in diagnostic performance vs. healthy controls rather than differences between Gram positive and Gram negative infections (Table 4). The Sepsis MetaScore, FAIM3:PLAC8 ratio, and Septicyte lab showed 2, 1, and 1 datasets, respectively, for which the score was significantly higher in Gram negative than in Gram positive patients (Table 6).

Discussion

Here we compared three sepsis gene expression diagnostics (the Sepsis MetaScore, the FAIM3:PLAC8 ratio, and the Septicyte Lab) in all available time-matched, whole blood clinical sepsis datasets. There were no significant differences among the distribution of AUCs comparing all validation non-infectious SIRS/trauma and sepsis datasets. However, there were several individual datasets for which the FAIM3:PLAC8 ratio and the Septicyte Lab showed AUCs<0.7. Notably, the Septicyte Lab also had significantly reduced performance in validation cohorts when comparing healthy controls to patients with sepsis or acute infections, with the Septicyte lab showing AUCs<0.7 in 43% of all datasets. The Septicyte Lab was initially validated in a large, independent cohort of patients from the MARS consortium using targeted qPCR, and showed an overall validation AUC of 0.88 (McHugh et al. (2015) PLoS Med 12(12):e1001916); thus, the reduced performance in our analysis may be indicative of either differences in clinical conditions, difference in technology, or both. Forest plots indicate that the effect size of CEACAM4 in GSE74224 (discovery cohort for the Septicyte Lab) may be an outlier, which may be contributing to the relatively worse generalizability. There is some evidence of a trend towards higher scores in bacterial infection as opposed to viral infection for the Sepsis MetaScore and the FAIM3:PLAC8 ratio, while the Septicyte Lab showed some evidence of a higher score in viral infections. There was a statistically non-significant trend towards higher scores in Gram negative as opposed to Gram positive infections for all three scores. However, the differing pathogen types were not matched for illness severity, age, gender, or other clinical confounders in their individual datasets; hence, these trends must be interpreted with caution. For instance, if bacterial infections were generally more severe than viral infections, and Gram negative generally more severe than Gram positive, then these scores might point to a confounding by severity. Further testing against confounders will thus be necessary across all cohorts for all tests compared here. Previously the Sepsis MetaScore was validated in the Glue Grant neutrophils cohort and in a subset of the healthy vs. infections cohorts (Sweeney et al. (2015) Sci Transl Med 7(287):287ra271). In the additional cohorts tested here, the Sepsis MetaScore continues to show results similar to prior validation. The FAIM3:PLAC8 ratio was validated in some of these data in a follow-up publication (Sweeney et al. (2015) Am J Respir Crit Care Med 192(10): 1260-1261), though the authors pointed out that their gene set was initially designed for a very narrow question of determining the presence of CAP in patients admitted to the ICU suspected of having CAP (Scicluna et al. (2015) Am J Respir Crit Care Med 192(10):1261-1262). The Septicyte Lab was tested in cohort E-TABM-1548 (McHugh et al., supra), but we have previously shown that because of expected changes in the baseline gene expression profile due to recovery from surgery, it is not appropriate to use for testing sepsis diagnostics (Sweeney et al. (2015), supra).

The fact that the public data are not used for validation of new diagnostics may reflect the difficulty and knowledge curve that some researchers face in accessing and using these data. Given the difficulty of wrangling the public data into an easily usable form, we have provided a hand-curated, unified repository of these data, along with an R script to easily apply a classifier of interest to the datasets (khatri-lab.stanford.edu/sepsis). We recommend a practice that any new gene expression classifiers for sepsis should be tested in these data to allow for easy benchmarking and comparison between classifiers. We recognize that the simple measure of the AUC does not account for all potential measures of clinical utility. In addition, a score that repeatedly performs well in a single clinical area can still have great clinical utility even if it fails in a different clinical area, and would need to be applied with care. Nevertheless, it is important to elucidate the strengths and weaknesses of any new sepsis diagnostic in order to help focus the resources on further clinical trials in areas that show the most promise.

Each of the diagnostic gene sets tested here has both strengths and weaknesses. In general, for any sepsis diagnostic to become useful clinically, it must retain good diagnostic power in a broad range of patient settings in its final form. The microarray cohorts used here allow for head-to-head comparisons of the different gene expression diagnostics, but may show underestimates of the diagnostic performance of any test when using a targeted assay (i.e., without the technical variation across multiple microarray platforms). Thus, further prospective validation of any gene set will be needed prior to their rollout into clinical practice. Still, it seems likely that given the increasing accuracy of the technique, molecular profiling of the host response will become a valuable part of the clinical toolset in diagnosing, treating, and potentially preventing sepsis.

While the preferred embodiments of the invention have been illustrated and described, it will be appreciated that various changes can be made therein without departing from the spirit and scope of the invention.

TABLE 1

Non-infectious SIRS/trauma vs. sepsis/infections datasets.

| Accession | Microarray Type | Clinical comparison | N Non-infected SIRS | N Sepsis | AUC Sepsis MetaScore | AUC FAIM3:PLAC8 Ratio | AUC Septicyte Lab |
|---|---|---|---|---|---|---|---|
| GSE28750 | GPL570 | post-op vs. sepsis | 11 | 10 | 0.96 (0.92-1) (D) | 0.87 (0.79-0.95) | 0.85 (0.77-0.94)* |
| GSE32707 | GPL10558 | MICU +/− SIRS vs. sepsis | 55 | 48 | 0.8 (0.75-0.84) (D) | 0.66 (0.6-0.71) | 0.66 (0.61-0.71) |
| GSE40012 | GPL6947 | ICU SIRS vs. CAP | 24 | 52 | 0.71 (0.65-0.77) (D) | 0.58 (0.51-0.65) | 0.8 (0.75-0.85) |
| GSE65682 | GPL13667 | ICU non-infected vs. CAP | 33 | 101 | 0.78 (0.74-0.82) | 0.84 (0.8-0.87) (D) | 0.74 (0.7-0.79) |
| GSE66099 | GPL570 | PICU SIRS vs. sepsis | 30 | 199 | 0.79 (0.76-0.83) (D) | 0.74 (0.7-0.78) | 0.44 (0.38-0.5) |
| GSE74224 | GPL5175 | post-op vs. sepsis | 31 | 74 | 0.90 (0.87-0.92)** | 0.92 (0.9-0.95) | 0.99 (0.99-1) (D) |
| E-MEXP-3589 | GPL10332 | Hosp. COPD +/− infection | 14 | 14 | 0.74 (0.65-0.83) | 0.49 (0.38-0.6) | 0.46 (0.36-0.57) |
| Buffy Coat, Day [1, 3] | GPL570 | never-infected trauma vs. trauma with sepsis | 65 | 9 | 0.91 (0.84-0.97) (D) | 0.62 (0.51-0.72) | 0.83 (0.75-0.92) |
| Buffy Coat, Day [3, 6] | GPL570 | never-infected trauma vs. trauma with sepsis | 63 | 17 | 0.89 (0.84-0.94) (D) | 0.84 (0.78-0.9) | 0.73 (0.65-0.8) |
| Buffy Coat, Day [6, 10] | GPL570 | never-infected trauma vs. trauma with sepsis | 50 | 15 | 0.91 (0.86-0.96) (D) | 0.83 (0.77-0.9) | 0.72 (0.64-0.79) |
| Buffy Coat, Day [10, 18] | GPL570 | never-infected trauma vs. trauma with sepsis | 22 | 4 | 0.84 (0.72-0.97) (D) | 0.78 (0.65-0.92) | 0.8 (0.66-0.93) |
| Buffy Coat, Day [18, 24] | GPL570 | never-infected trauma vs. trauma with sepsis | 6 | 4 | 0.96 (0.88-1) (D) | 0.96 (0.88-1) | 0.83 (0.69-0.97) |
| Neutrophils, Day [1, 3] | GGH-1, GGH-2 | never-infected trauma vs. trauma with sepsis | 56 | 10 | 0.72 (0.63-0.82) | 0.74 (0.65-0.83) | 0.68 (0.58-0.77) |
| Neutrophils, Day [3, 6] | GGH-1, GGH-2 | never-infected trauma vs. trauma with sepsis | 55 | 10 | 0.83 (0.75-0.91) | 0.87 (0.79-0.94) | 0.9 (0.84-0.97) |
| Neutrophils, Day [6, 10] | GGH-1, GGH-2 | never-infected trauma vs. trauma with sepsis | 46 | 14 | 0.88 (0.82-0.94) | 0.88 (0.82-0.94) | 0.84 (0.77-0.91) |
| Neutrophils, Day [10, 18] | GGH-1, GGH-2 | never-infected trauma vs. trauma with sepsis | 24 | 3 | 0.89 (0.77-1) | 0.9 (0.79-1) | 0.78 (0.62-0.94) |
| | | Overall mean: | | | 0.844 +/− 0.080 | 0.782 +/− 0.135 | 0.754 +/− 0.145 |
| | | mean in validation only: | | | 0.817 +/− 0.069 | 0.779 +/− 0.139 | 0.729 +/− 0.135 |

(D): Discovery dataset for the given score.
*GSE28750 is a subset of GSE74224, so was counted as discovery for Septicyte Lab.
**GSE28750 is a subset of GSE74224 and is treated as described in Methods.

TABLE 2

Healthy vs. sepsis/acute infections.

| Accession | Microarray Type | Clinical cohort | N Healthy | N Infected | AUC Sepsis MetaScore | AUC FAIM3:PLAC8 Ratio | AUC Septicyte Lab |
|---|---|---|---|---|---|---|---|
| E-MEXP-3567 | GPL96 | children with meningococcal sepsis | 3 | 12 | 0.97 (0.93-1) | 1 (1-1) | 0.94 (0.89-1) |
| E-MEXP-3589 | GPL10332 | hospitalized COPD + infection | 4 | 14 | 0.98 (0.95-1) | 0.95 (0.9-1) | 0.32 (0.16-0.48) |
| E-MTAB-3162 | GPL570 | Dengue, DHF | 15 | 30 | 1 (1-1) | 1 (1-1) | 0.8 (0.73-0.86) |
| GSE11755 | GPL570 | children w/ meningococcal sepsis | 3 | 6 | 1 (1-1) | 1 (1-1) | 0.78 (0.62-0.93) |
| GSE13015 | GPL6106 | sepsis, w/wo burkholderia | 10 | 48 | 1 (0.99-1) | 0.98 (0.97-1) | 0.94 (0.9-0.97) |
| GSE13015 | GPL6947 | sepsis, w/wo burkholderia | 10 | 15 | 1 (1-1) | 1 (1-1) | 0.85 (0.78-0.93) |
| GSE17156 | GPL571 | Viral Challenge Peak symptoms | 56 | 27 | 0.91 (0.87-0.94) | 0.89 (0.85-0.93) | 0.51 (0.45-0.58) |
| GSE20346 | GPL6947 | bacterial or influenza pneumonia | 36 | 20 | 1 (1-1) | 1 (1-1) | 0.95 (0.92-0.99) |
| GSE21802 | GPL6102 | Severe influenza | 4 | 12 | 0.98 (0.95-1) | 1 (1-1) | 0.69 (0.55-0.83) |
| GSE22098 | GPL6947 | children with Staph and Strep infections | 81 | 52 | 0.85 (0.81-0.88) | 0.65 (0.6-0.7) | 0.79 (0.75-0.83) |
| GSE25504 | GPL13667 | neonatal sepsis | 6 | 14 | 0.92 (0.86-0.98) | 0.83 (0.74-0.92) | 0.42 (0.28-0.56) |
| GSE25504 | GPL570 | neonatal sepsis | 3 | 2 | 1 (1-1) | 1 (1-1) | 0.83 (0.62-1) |
| GSE25504 | GPL6947 | neonatal sepsis | 35 | 28 | 0.94 (0.91-0.97) | 0.88 (0.83-0.92) | 0.24 (0.18-0.3) |
| GSE27131 | GPL6244 | Severe Flu A | 7 | 7 | 1 (1-1) | 1 (1-1) | 1 (1-1) |
| GSE28750 | GPL570 | sepsis | 20 | 10 | 1 (1-1) (D) | 1 (1-1) | 0.74 (0.64-0.84) (D) |
| GSE33341 | GPL571 | BSI *S Aureus* or *E* | 43 | 51 | 1 (1-1) | 0.99 (0.98-1) | 0.69 (0.64-0.74) |

TABLE 2-continued

Healthy vs. sepsis/acute infections.

| Accession | Microarray Type | Clinical cohort | N Healthy | N Infected | AUC Sepsis MetaScore | AUC FAIM3:PLAC8 Ratio | AUC Septicyte Lab |
|---|---|---|---|---|---|---|---|
| | | *coli* | | | | | |
| GSE38900 | GPL10558 | Viral infection | 8 | 28 | 0.89 (0.84-0.95) | 0.7 (0.61-0.79) | 0.64 (0.54-0.74) |
| GSE38900 | GPL6884 | Viral infection | 31 | 153 | 0.91 (0.89-0.93) | 0.91 (0.89-0.93) | 0.41 (0.35-0.46) |
| GSE40012 | GPL6947 | ICU-CAP | 18 | 52 | 1 (1-1) (D) | 1 (0.99-1) | 0.89 (0.85-0.93) |
| GSE40396 | GPL10558 | children viral/bacterial infection + fever | 22 | 30 | 0.97 (0.94-0.99) | 0.95 (0.93-0.98) | 0.77 (0.71-0.83) |
| GSE42026 | GPL6947 | Bacterial & viral infection | 33 | 59 | 0.97 (0.95-0.98) | 0.98 (0.97-0.99) | 0.74 (0.7-0.79) |
| GSE51808 | GPL13158 | Dengue, DHF | 9 | 28 | 0.98 (0.95-1) | 1 (1-1) | 1 (0.99-1) |
| GSE57065 | GPL570 | Septic Shock | 25 | 82 | 1 (1-1) | 0.99 (0.99-1) | 0.81 (0.77-0.85) |
| GSE60244 | GPL10558 | Bacterial, Viral, or Both | 40 | 118 | 0.96 (0.95-0.97) | 0.84 (0.81-0.87) | 0.64 (0.59-0.68) |
| GSE65682 | GPL13667 | ICU-CAP | 42 | 101 | 1 (0.99-1) | 0.93 (0.92-0.95) (D) | 0.62 (0.58-0.66) |
| GSE66099 | GPL570 | Pediatric sepsis | 47 | 199 | 1 (1-1) (D) | 0.99 (0.99-1) | 0.54 (0.49-0.59) |
| GSE68310 | GPL10558 | Viral Infection (initial symptoms) | 243 | 258 | 0.87 (0.85-0.88) | 0.92 (0.91-0.93) | 0.66 (0.64-0.69) |
| GSE69528 | GPL10558 | Bacterial infections | 55 | 83 | 0.99 (0.99-1) | 0.97 (0.96-0.98) | 0.72 (0.68-0.76) |
| | | | | Mean Validation AUC: | 0.963 +/- 0.046 | 0.940 +/- 0.092 | 0.711 +/- 0.203 |

(D): Discovery dataset for the given score

TABLE 3

Comparison of AUCs for bacterial and viral infections vs. healthy controls.

| Accession | N Healthy | N Bacterial | N Viral | Bacterial AUC Sepsis MetaScore | Viral AUC Sepsis MetaScore | Bacterial AUC FAIM3:PLAC8 ratio | Viral AUC FAIM3:PLAC8 ratio | Bacterial AUC Septicyte Lab | Viral AUC Septicyte Lab |
|---|---|---|---|---|---|---|---|---|---|
| E-MEXP-3589 | 4 | 4 | 5 | 0.94 (0.84-1) | 1 (1-1) | 1 (1-1) | 1 (1-1) | 0.69 (0.5-0.88) | 0.15 (0.012-0.29) |
| GSE20346 GPL6947 | 36 | 12 | 8 | 1 (1-1) | 1 (1-1) | 1 (1-1) | 1 (1-1) | 0.92 (0.87-0.98) | 1 (1-1) |
| GSE25504 GPL13667 | 6 | 11 | 3 | 0.98 (0.96-1) | 0.67 (0.47-0.87) | 0.91 (0.84-0.98) | 0.56 (0.35-0.76) | 0.35 (0.21-0.49) | 0.67 (0.47-0.87) |
| GSE40012 GPL6947 | 18 | 36 | 11 | 1 (1-1) (D) | 1 (1-1) (D) | 1 (0.99-1) | 1 (1-1) | 0.85 (0.8-0.9) | 0.97 (0.94-1) |
| GSE40396 GPL10558 | 22 | 8 | 22 | 0.97 (0.92-1) | 0.96 (0.94-0.99) | 0.93 (0.87-0.99) | 0.96 (0.93-0.99) | 0.74 (0.63-0.85) | 0.79 (0.72-0.85) |
| GSE42026 GPL6947 | 33 | 18 | 41 | 0.97 (0.95-1) | 0.96 (0.94-0.98) | 1 (1-1) | 0.97 (0.95-0.99) | 0.75 (0.68-0.82) | 0.74 (0.69-0.8) |
| GSE60244 GPL10558 | 40 | 22 | 71 | 0.94 (0.9-0.97) | 0.97 (0.96-0.98) | 0.8 (0.74-0.86) | 0.85 (0.82-0.89) | 0.58 (0.5-0.65) | 0.66 (0.61-0.71) |
| GSE66099 GPL570 | 47 | 109 | 11 | 1 (1-1) (D) | 1 (0.98-1) (D) | 0.94 (0.92-0.95) | 0.96 (0.91-1) | 0.63 (0.58-0.67) | 0.56 (0.47-0.66) |

(D): Discovery dataset for the given score.

TABLE 4

Comparison of AUCs for Gram negative and Gram positive infections vs. healthy controls.

| Accession | N Healthy | N Gram negative | N Gram positive | Gram negative AUC Sepsis MetaScore | Gram positive AUC Sepsis MetaScore | Gram negative AUC FAIM3:PLAC8 ratio | Gram positive AUC FAIM3:PLAC8 ratio | Gram negative AUC Septicyte Lab | Gram positive AUC Septicyte Lab |
|---|---|---|---|---|---|---|---|---|---|
| GSE13015 GPL6106 | 10 | 32 | 13 | 1 (1-1) | 0.98 (0.96-1) | 1 (1-1) | 0.94 (0.89-0.99) | 0.94 (0.91-0.97) | 0.91 (0.85-0.97) |
| GSE13015 GPL6947 | 10 | 11 | 4 | 1 (1-1) | 1 (1-1) | 1 (1-1) | 1 (1-1) | 0.91 (0.84-0.97) | 0.7 (0.54-0.86) |
| GSE25504 GPL13667 | 6 | 4 | 6 | 1 (1-1) | 0.97 (0.92-1) | 1 (1-1) | 0.83 (0.71-0.95) | 0.42 (0.23-0.6) | 0.33 (0.18-0.49) |

TABLE 4-continued

Comparison of AUCs for Gram negative and Gram positive infections vs. healthy controls.

| Accession | N Healthy | N Gram negative | N Gram positive | Gram negative AUC Sepsis MetaScore | Gram positive AUC Sepsis MetaScore | Gram negative AUC FAIM3:PLAC8 ratio | Gram positive AUC FAIM3:PLAC8 ratio | Gram negative AUC Septicyte Lab | Gram positive AUC Septicyte Lab |
|---|---|---|---|---|---|---|---|---|---|
| GSE25504 GPL6947 | 35 | 6 | 19 | 1 (0.98-1) | 0.97 (0.95-1) | 0.9 (0.82-0.98) | 0.91 (0.86-0.95) | 0.31 (0.21-0.41) | 0.17 (0.12-0.23) |
| GSE33341 GPL571 | 43 | 19 | 32 | 1 (1-1) | 1 (1-1) | 0.98 (0.96-1) | 1 (0.99-1) | 0.66 (0.59-0.74) | 0.7 (0.65-0.76) |
| GSE40396 GPL10558 | 22 | 4 | 4 | 0.98 (0.93-1) | 0.95 (0.88-1) | 0.94 (0.86-1) | 0.92 (0.83-1) | 0.89 (0.78-0.99) | 0.59 (0.43-0.75) |
| GSE66099 GPL570 | 47 | 44 | 65 | 1 (1-1) (D) | 1 (1-1) (D) | 0.93 (0.9-0.96) | 0.94 (0.92-0.96) | 0.6 (0.54-0.66) | 0.65 (0.6-0.7) |
| GSE69528 GPL10558 | 55 | 57 | 24 | 1 (0.99-1) | 0.98 (0.96-1) | 1 (0.99-1) | 0.94 (0.91-0.97) | 0.76 (0.72-0.8) | 0.66 (0.59-0.72) |

(D): Discovery dataset for the given score.

TABLE 5

Comparison of score distributions for bacterial and viral infections.

| | EMEXP-3589 | GSE20346 GPL6947 | GSE25504 GPL13667 | GSE40012 GPL6947 | GSE40396 GPL10558 | GSE42026 GPL6947 | GSE60244 GPL10558 | GSE66099 GPL570 |
|---|---|---|---|---|---|---|---|---|
| N Bacterial | 4 | 12 | 11 | 36 | 8 | 18 | 22 | 109 |
| N Viral | 5 | 8 | 3 | 11 | 22 | 41 | 71 | 11 |
| Sepsis MetaScore mean bacterial | 0.372 | −0.0292 | 0.37 | 0.0348 | 0.182 | 0.531 | 0.188 | 0.0595 |
| Sepsis MetaScore mean viral | −0.298 | 0.0438 | −1.36 | −0.114 | −0.0661 | −0.233 | −0.0583 | −0.59 |
| Sepsis MetaScore Wilcoxon statistic | 14 | 43 | 32 | 192 | 95 | 536 | 901 | 792 |
| Sepsis MetaScore Wilcox P-value | 0.413 | 0.734 | 0.011 | 0.892 | 0.765 | 0.00537 | 0.28 | 0.0808 |
| FAIM3:PLAC8 ratio mean bacterial | 1.25 | 1.48 | 1.4 | 1.36 | 1.17 | 1.17 | 1.25 | 1.74 |
| FAIM3:PLAC8 ratio mean viral | 0.998 | 1.18 | 1.19 | 1.19 | 1.26 | 1.09 | 1.23 | 1.55 |
| FAIM3:PLAC8 ratio Wilcoxon statistic | 15 | 84 | 28 | 225 | 54 | 506 | 841 | 726 |
| FAIM3:PLAC8 ratio Wilcox P-value | 0.286 | 0.0041 | 0.0879 | 0.511 | 0.118 | 0.0237 | 0.591 | 0.252 |
| Septicyte Lab mean bacterial | 7.66 | 11.4 | 7.62 | 11.3 | 10.1 | 11.9 | 8.7 | 10.8 |
| Septicyte Lab mean viral | 5.54 | 12.6 | 9.35 | 12.1 | 10.3 | 11.7 | 9.05 | 10.6 |
| Septicyte Lab Wilcoxon statistic | 17 | 25 | 2 | 127 | 69 | 412 | 695 | 679 |
| Septicyte Lab Wilcox P-value | 0.111 | 0.0825 | 0.022 | 0.0763 | 0.393 | 0.488 | 0.44 | 0.472 |

TABLE 6

Comparison of score distributions for Gram negative and Gram positive infections.

| | GSE13015 GPL6106 | GSE13015 GPL6947 | GSE25504 GPL13667 | GSE25504 GPL6947 | GSE33341 GPL571 | GSE40396 GPL10558 | GSE66099 GPL570 | GSE69528 GPL10558 |
|---|---|---|---|---|---|---|---|---|
| N Gram negative | 32 | 11 | 4 | 6 | 19 | 4 | 44 | 57 |
| N Gram positive | 13 | 4 | 6 | 19 | 32 | 4 | 65 | 24 |
| Sepsis MetaScore mean Gram negative | 0.245 | 0.416 | 0.471 | 0.145 | 0.157 | 0.389 | −0.258 | 0.123 |
| Sepsis MetaScore mean Gram positive | −0.602 | 4.14 | −0.314 | −0.0457 | −0.0935 | −0.389 | 0.175 | −0.291 |
| Sepsis MetaScore Wilcoxon statistic | 301 | 42 | 16 | 52 | 341 | 9 | 1050 | 852 |
| Sepsis MetaScore Wilcoxon P-value value | 0.0192 | 0.00586 | 0.476 | 0.78 | 0.481 | 0.886 | 0.0197 | 0.0832 |
| FAIM3:PLAC8 ratio mean Gram negative | 1.51 | 1.57 | 1.42 | 1.28 | 1.46 | 1.22 | 1.72 | 1.35 |
| FAIM3:PLAC8 ratio mean Gram positive | 1.3 | 1.29 | 1.33 | 1.29 | 1.54 | 1.11 | 1.76 | 1.27 |
| FAIM3:PLAC8 ratio Wilcoxon statistic | 310 | 33 | 11 | 52 | 219 | 11 | 1200 | 862 |

TABLE 6-continued

Comparison of score distributions for Gram negative and Gram positive infections.

|  | GSE13015 GPL6106 | GSE13015 GPL6947 | GSE25504 GPL13667 | GSE25504 GPL6947 | GSE33341 GPL571 | GSE40396 GPL10558 | GSE66099 GPL570 | GSE69528 GPL10558 |
|---|---|---|---|---|---|---|---|---|
| FAIM3:PLAC8 ratio Wilcoxon P-value value | 0.00975 | 0.177 | 0.914 | 0.78 | 0.1 | 0.486 | 0.166 | 0.0664 |
| Septicyte Lab mean Gram negative | 11.8 | 12.7 | 7.89 | 10 | 9.47 | 10.4 | 10.7 | 10.2 |
| Septicyte Lab mean Gram positive | 10.7 | 9.95 | 7.66 | 8.95 | 9.48 | 9.86 | 10.9 | 9.6 |
| Septicyte Lab Wilcoxon statistic | 282 | 40 | 15 | 80 | 280 | 13 | 1260 | 795 |
| Septicyte Lab Wilcoxon P-value value | 0.0652 | 0.0176 | 0.61 | 0.156 | 0.65 | 0.2 | 0.307 | 0.253 |

What is claimed is:

1. A method for treating a subject for sepsis, comprising:
   (a) identifying a human subject as having increased levels of expression of CEACAM1, ZDHHC19, C9orf95, GNA15, BATF, and C3AR1 biomarkers and decreased levels of expression of KIAA1370, TGFBI, MTCH1, RPGRIP1, and HLA-DPB1 biomarkers relative to a time-matched, control subject with non-infectious inflammation; and
   (b) administering an antibiotic to the human subject.

2. The method of claim 1, wherein the antibiotic is a broad spectrum antibiotic.

3. The method of claim 1, wherein the levels of expression of the biomarkers are measured by microarray analysis, polymerase chain reaction (PCR), reverse transcriptase polymerase chain reaction (RT-PCR), isothermal amplification, a Northern blot, or a serial analysis of gene expression (SAGE).

4. The method of claim 1, wherein the method comprises identifying the human subject as having increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers in whole blood, buffy coat, plasma, serum, peripheral blood mononucleated cells (PBMCS), band cells, neutrophils, monocytes, or T cells relative to a corresponding sample from the time matched control subject with non-infectious inflammation.

5. The method of claim 1, wherein the method further comprises: receiving values indicating the levels of expression of the CEACAM1, ZDHHC19, C9orf95, GNA15, BATF, C3AR1, KIAA1370, TGFBI, MTCH1, RPGRIP1, and HLA-DPB1 biomarkers in a biological sample from the patient.

6. A method for treating a human subject for sepsis, comprising:

(a) calculating a sepsis score for the human subject based on individual expression levels of CEACAM1, ZDHHC19, C9orf95, GNA15, BATF, C3AR1, KIAA1370, TGFBI, MTCH1, RPGRIP1, and HLA-DPB1;
(b) diagnosing the human subject as having sepsis based on the sepsis score; and
(c) administering an antibiotic to the diagnosed human subject.

* * * * *

UNITED STATES PATENT AND TRADEMARK OFFICE
CERTIFICATE OF CORRECTION

PATENT NO. : 10,533,224 B2
APPLICATION NO. : 15/526306
DATED : January 14, 2020
INVENTOR(S) : Purvesh Khatri et al.

It is certified that error appears in the above-identified patent and that said Letters Patent is hereby corrected as shown below:

In the Specification

In Column 1, Lines 6-9: Please delete the paragraph starting with "This invention" ending with "in the invention." and replace it with the following paragraph:

--This invention was made with Government support under contracts AI057229, AI109662, and LM007033 awarded by the National Institutes of Health. The Government has certain rights in the invention.--

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*